(12) United States Patent
Nazaré et al.

(10) Patent No.: US 6,906,084 B2
(45) Date of Patent: Jun. 14, 2005

(54) INDOLE DERIVATIVES AS FACTOR XA INHIBITORS

(75) Inventors: Marc Nazaré, Idstein (DE); Melanie Essrich, Frankfurt am Main (DE); David William Will, Kriftel (DE); Hans Matter, Langenselbold (DE); Kurt Ritter, Frankfurt am Main (DE); Volkmar Wehner, Sandberg (DE)

(73) Assignee: Aventis Pharma Deutschland GmbH, Frankfurt (DE)

(*) Notice: Subject to any disclaimer, the term of this patent is extended or adjusted under 35 U.S.C. 154(b) by 48 days.

(21) Appl. No.: 10/301,397

(22) Filed: Nov. 21, 2002

(65) Prior Publication Data

US 2003/0199689 A1 Oct. 23, 2003

(30) Foreign Application Priority Data

Nov. 22, 2001 (EP) .............................................. 01127809

(51) Int. Cl.[7] ...................... A61K 31/445; C07D 401/12

(52) U.S. Cl. ........................ 514/323; 514/318; 546/193; 546/201

(58) Field of Search ................................. 514/318, 323; 546/193, 201

(56) References Cited

U.S. PATENT DOCUMENTS

| | | |
|---|---|---|
| 3,317,524 A | 5/1967 | Freed |
| 5,534,530 A | 7/1996 | Frebel et al. |

FOREIGN PATENT DOCUMENTS

| | | |
|---|---|---|
| EP | 0 186 367 | 7/1986 |
| EP | 0432040 A1 | 6/1991 |
| EP | 621221 A1 | 10/1994 |
| EP | 0987274 | 3/2000 |
| FR | 2763337 A1 | 11/1998 |
| JP | 09087282 | 3/1997 |
| WO | WO 92/06711 | 4/1992 |
| WO | WO 93/25524 | 12/1993 |
| WO | WO 95/29189 | 11/1995 |
| WO | WO 96/12800 | 5/1996 |
| WO | WO 97/45119 | * 12/1997 |
| WO | WO 97/47651 | 12/1997 |
| WO | WO 99/33800 | 7/1999 |
| WO | WO99/37304 | 7/1999 |
| WO | WO01/07436 A2 | 2/2001 |
| WO | WO 01/64642 A2 | 9/2001 |
| WO | WO 02/00647 A1 | 1/2002 |

OTHER PUBLICATIONS

Barker et al. "Preparation of substituted indole . . ." CA 130:182354 (1999).*

Shima et al. "Preparation of 1–benzamidopiperazines . . ." CA 129:189343 (1998).*

Adang Anton E P et al., A New Generation of Orally Active Antithrombotics: Comparing Strategies in the GPIIb/IIIa, Thrombin and Factor Xa Areas, Drugs of the Future 2000, vol. 25, pp. 369–383.

Bornstein Joseph et al., Facile Hydrolysis of the Trifluoromethyl Group in the Presence of Base. Some Trifluoromethylated Indoles, J. Amer. Chem. Society, vol. 79, 1957, pp. 1745–1748.

Brennan Mary R et al., The Preparation and Spectral Characterization of 2–Haloindoles, 3–Haloindoles, and 2,3–Dihaloindoles, Heterocycles, 1986, vol. 24, No. 10, pp. 2879–2885.

Bundgaard Hans, Novel Chemical Approaches in Prodrug Design, Drugs of the Future, 1991, vol. 16(5), pp. 443–458.

Burton Harold et al., The Synthesis of 5– and 6–Benzloxyindoles and Attempts to prepare 5– and 6–Hydroxyindoles therefrom, J. Chem. Society, 1937, pp. 1726–1728.

Chan Dominic M T et al., New N– and O–Arylations with Phenylboronic Acids and Cupric Acetate, Tetrahedron Letters, 1998, vol. 39, pp. 2933–2936.

Chen, Cheng–yi et al., Syntheses of Indoles via a Palladium–Catalyzed Annulation between Iodoanllines and Ketones, J. Org. Chem., 1997, vol. 62, pp. 2676–2677.

(Continued)

Primary Examiner—Celia Chang
(74) Attorney, Agent, or Firm—Irving Newman

(57) ABSTRACT

The present invention relates to compounds of formula I, (I)

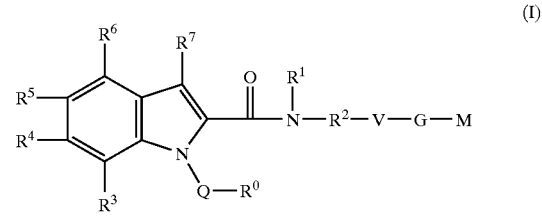

in which $R^0$; $R^1$; $R^2$; $R^3$; $R^4$; $R^5$; $R^6$; $R^7$; Q; V, G and M have the meanings indicated in the claims. The compounds of formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is indicated. The invention furthermore relates to processes for the preparation of compounds of formula I, their use, in particular as pharmaceuticals for treating the foregoing conditions, and pharmaceutical preparations comprising them.

8 Claims, No Drawings

OTHER PUBLICATIONS

Cheng Yung–Chi et al., Relationship Between the inhibition Constant (KI) and the Concentration of inhibitor which causes 50 per cent Inhibition (I 50) of an Enzymatic Reaction, Biochem. Pharmacol., 1973, vol. 22, pp. 3099–3108.

Chikvaidze J Sh et al., Indole Derivatives ,Khim. Geterotsikl. Soedin, 1991, Bol. 11, pp. 1508–1511 (English Abstract attached: full text English translation will be provided when and if obtained.).

Comins Daniel L et al., N–Methyl Lithiation of N–Methylindoles Directed by a–Amino Alkoxides, Tetrahedron Letters, 1989, vol. 30, No. 33, pp. 4337–4340.

Desarbre Eric et al., Synthesis of 2–Susbstituted –1H–Pyrrolo[2,3–b]Pyridines: Preparation of 7–Azaolivacine Analogue and 7–Azaindolopyridopyrimidine Derivatives, Tetrehedron, 1997, vol. 53, No. 10, pp. 3637–3648.

Dormoy Jean–Robert et al., Elaboration d'une nouvelle voie d'accés aux 6H–pyrido[4,3:b]carbazoles et analogues: A. Synthése et étude des précurseurs, Tetrahedron, 1993, vol. 49, No. 14, pp. 2885–2914.

Ezquerra Jesús et al., Efficient Reagents for the Synthesis of 5–, 7–, and 5,7–Substituted Indoles Starting from Aromatic Amines; Scope and Limitations, J. Org. Chem., 1996, vol. 61, pp. 5804–5812.

Fleisher David et al., Improved Oral Drug Delivery: Solubility Limitations Overcome by the Use of Prodrugs, Advanced Drug Delivery Reviews, 1996, vol. 19, pp. 115–130.

Gray Nancy M et al., Novel Indole–2–Carboxylates as Ligands for the Strychnine–Insensitive N–Methyl–D–aspartate–Linked Glycine Receptor, J. Med. Chem., 1991, vol. 34, pp. 1283–1292.

Hartwig John F et al., Room–Temperature Palladium–Catalyzed Amination of Aryl Bromides and Chlorides and Extended Scope of Aromatic C–N Bond Formation with a Commercial Ligand, J. Org. Chem., 1999, vol. 64, pp. 5575–5580.

Hartwig John F, Jüngste Fortschritte bei Palladium–und Nickel–katalysierten Reaktionen eröffnen neue Möglichkelten zur Knüpfung von C–N– und C–O–Bindungen., Angew. Chem., 1998, vol. 110, pp. 2154–2177 (English translation enclosed.).

Hasan Iltifat et al., Synthesis and Reactions of N–Protected 2–Lithiated Pyrroles and Indoles. The tert–Butoxycarbonyl Substituent as a Protecting Group, J. Org. Chem., 1981, vol. 46, pp. 157–164.

Hiremath Shivayogi P et al., Synthesis & Reaction of Indole–1,2–Dicarboxaldehydes with Hydrazine & Hydroxylamine, Indian J. of Chemistry, 1980, vol. 19B, pp. 770–774.

Khanna Ish K et al., 1,2–Diarylimidazoles as Potent, Cyclooxygenase–2 Selective, and Orally Active Antiinflammatory Agents, J. Med. Chem., 1997, vol. 40, pp. 1634–1647.

Kline Toni, Preparation of 2–Iodotryptamine and 2–Iodo–5–methoxytryptamine, J. Heterocycl. Chem., 1985, vol. 22, pp. 505–509.

Lam Patrick Y S et al., New Aryl/Heteroaryl C–N Bond Cross–coupling Reactions via Arylboronic Acid/Cupric Acetate Arylation, Tetrahedron Letters, 1998, vol. 39, pp. 2941–2944.

Larock R C et al., Synthesis of 2,3–Disubstituted Indoles via Palladium–Catalyzed Annulation of Internal Alkynes, J. Org. Chem., 1998, vol. 63, pp. 7652–7662.

Lindwall H G et al., Synthesis and Reactions of Indole Carboxylic Acids; Pyridindolones from Indole–2–Carboxyacetalylbenzylamides, J. Org. Chem., 1953, vol. 18, pp. 345–357.

Mann Grace et al., Palladium–Catalyzed C–N(sp 2) Bond Formation: N–Arylation of Aromatic and Unsaturated Nitrogen and the Reductive Elimination Chemistry of Palladium Azolyl and Methyleneamido Complexes, J. Am. Chem. Soc., 1998, vol. 120, pp. 827–828.

Mederski Werner W K R et al., N–Aryl Heterocycles via Coupling Reactions with Arylboronic Acids, Tetrahedron, 1999, vol. 55, pp. 12757–12770.

Murakami Yasuoki et al., p–Toluenesulfonic Acid and Cation Exchange Resin in Aprotic Solvent: Valuable Catalysis for Fischer Indolization, Heterocycles, 1984, vol. 22, No. 5, pp. 1210–1216.

Nichols David E et al., 1–(2,5–Dimethoxy–4–(trifluoromethyl)phenyl)–2–aminopropane: A Potent Serotonin 5–HT 2A/2C Agonist, J. Med. Chem., 1994, vol. 37, pp. 4346–4351.

Noland Wayland E et al., Ethyl Indole–2–Carboxylate, Org. Synth. 1973, vol. V., J. Wiley New York, pp. 567–571.

Old David W et al., Efficient Palladium–Catalyzed N–Arylation of Indoles, Organic Letters, 2000, vol. 2, No. 10, pp. 1403–1406.

Ostrem James A et al., Discovery of a Novel, Potent, and Specific Family of Factor Xa Inhibitors via Combinatorial Chemistry, Biochemistry, 1998, vol. 37, pp. 1053–1059.

Powers James C, Chloroindoles, J. Org. Chem., 1966, vol. 31, pp. 2627–2631.

Rodriguez Alan Louis et al., Vielseitige Indolsynthese durch eine Kalium–oder Caesiumbasen–vermittette 5–endo–dig–Cyclisierung, Agnew, Chem., 2000, vol. 112, No. 14, pp. 2607–2609 (English Translation enclosed.).

Sakamoto Takao et al., Palladium–Catalyzed Coupling Reaction of 3–Iodoindoles and 3–Iodobenzo[b]thiophene with Terminal Acetylenes, Chem. Pharm. Bull, 1988, vol. 36, No. 6, pp. 2248–2252.

Sakamoto Takao et al., Palladium–catalyzed Cyanation of Aryl and Heteroaryl Iodides with Copper(I) Cyanide, J. Chem. Soc., Perkin Trans:I, 1999, pp. 2323–2326.

Salituro Francesco G et al., 3–(2–Carboxyindol–3–yl)propionic Acid Derivatives: Antagonists of the Strychnine–Insensitive Glycine Receptor Associated with the N–Methyl–D–aspartate Receptor Complex, J. Med. Chem., 1990, vol. 33, pp. 2944–2946.

Sarges Reinhard et al., A Novel Class of "GABAergic" Agents: 1–Aryl–3–(aminoalkylidene)oxindoles, J. Med. Chem., 1989, vol. 32, pp. 437–444.

Segel Irwin H, Behavior and Analysis of Rapid Equilibrium and Steady–State Enzyme Systems, Enzyme Kinetics, 1975, John Wiley & Sons, New York, pp. 100–125.

Stabler S Russell et al., Preparation of N–Arylated Heterocycles by Nucleophilic Aromatic Substitution, Synthetic Communications, 1994, vol. 24(1), pp. 123–129.

Tani Masanobu et al., Regioselective Bromination of Methoxy Derivatives of Ethyl Indole–2–Carboxylate [Synthetic Studies of Indoles and Related Compounds. XXX], Heterocycles, 1992, vol. 34, No. 12, pp. 2349–2362.

Tokmakov Gennadii P et al., Rearrangement of 1–Arylindoles to 5H–Dibenz[b,f]azepines, Tetrahedron, 1995, vol. 51, No. 7, pp. 2091–2098.

Ujjainwalla Feroze et al., Synthesis of 5–, 6– and 7–Azaindoles via Palladium–Catalyzed Heteroannulation of Internal Alkynes, Tetrahedron Lett., 1998, vol. 39, pp. 5355–5358.

Umemoto Teruo et al., Power and Structure–Variable Fluorinating Agents. The N–Fluoropyridinium Salt System, J. Am. Chem. Soc., 1990, vol. 112, pp. 8563–8575.

Unangst Paul C et al., Synthesis of Novel 1–Phenyl–1H–indole–2–carboxylic Acids. I. Utilization of Ullmann and Dieckmann Reactions for the Preparation of 3–Hydroxy, 3–Alkoxy, and 3–Alkyl Derivatives, J. Heterocyclic Chem., 1987, vol. 24, pp. 811–815.

Unangst Paul C et al et al., Novel Indolecarboxamidotetrazoles as Potential Antiallergy Agents, J. Med. Chem., 1989, vol. 32, No. 6, pp. 1360–1366.

Wagaw Seble et al., A Palladium–Catalyzed Method for the Preparation of Indoles via the Fischer Indole Synthesis, J. Am. Chem.Soc., 1999, vol. 121, No. 44, pp. 10251–10263.

Wolfe John P et al., Simple, Efficient Catalyst System for the Palladium–Catalyzed Amination of Aryl Chlorides, Bromides, and Triflates, J. Org. Chem., 2000, vol. 65, pp. 1158–1174.

Yang Bryant H et al., Palladium–catalyzed Amination of Aryl Halides and Sulfonates, J. Organomet. Chem, 1999, vol. 576, pp. 125–146.

* cited by examiner

INDOLE DERIVATIVES AS FACTOR XA INHIBITORS

CROSS-REFERENCE TO RELATED APPLICATIONS

This application claims the benefit of priority from European Patent Application 01127809.0, filed Nov. 22, 2001.

SUMMARY OF THE INVENTION

The present invention relates to compounds of the formula I,

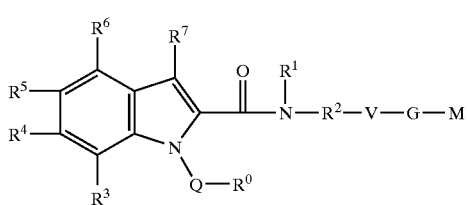

in which $R^0$; $R^1$; $R^2$; $R^3$; $R^4$; $R^5$; $R^6$; $R^7$; Q; V, G and M have the meanings indicated below. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

DETAILED DESCRIPTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369–383).

Low molecular weight, factor Xa-specific blood clotting inhibitors that are effective but do not cause unwanted side effects have been described, for example, in WO-A-95/29189. However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors. WO-A-99/33800 discloses indole derivatives, which inhibit factor Xa activity.

The present invention satisfies the above needs by providing novel compounds of the formula I which exhibit better factor Xa and/or factor VIIa inhibitory activity and are favorable agents with high bioavailability.

Thus, the present invention relates to compounds of the formula I,

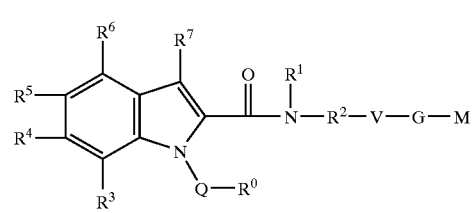

wherein
$R^0$ is selected from the group consisting of
1) monocyclic and bicyclic 6- to 14-membered aryl radicals, said aryl radicals being substituted with one two or three substituents independently selected from the $R^8$ substituents defined below, provided that at least one $R^8$ is halogen, —C(O)—NH$_2$ or —O—(C$_1$–C$_8$)-alkyl;
2) monocyclic and bicyclic 4- to 14-membered heteroaryl radicals selected from the group consisting of pyridyl, pyrimidinyl, indolyl, isoindolyl, indazolyl, phthalazinyl, quinolyl, isoquinolyl, benzothiophen, quinazolinyl and phenylpyridyl radicals, said heteroaryl radicals being unsubstituted or substituted with one two or three substituents independently selected from the $R^8$ substituents defined below;
3) monocyclic or bicyclic 4- to 14-membered heteroaryl radicals containing one, two, three or four heteroatoms selected from the group consisting of nitrogen, sulfur and oxygen, said heteroaryl radicals being unsubstituted or substituted with one two or three substituents independently selected from the $R^8$ substituents defined below, as well as by a monocyclic or bicyclic 4- to 14-membered heteroaryl, containing one, two, three or four heteroatoms selected from the group consisting of nitrogen, sulfur and oxygen, which heteroaryl radical is unsubstituted or substituted with one two or three substituents independently selected from the $R^8$ substituents defined below;

$R^8$ is selected from the group consisting of
halogen, $-NO_2$; $-CN$; $-C(O)-NH_2$; $-OH$; $-NH_2$; $-OCF_3$; monocyclic and bicyclic 4- to 14-membered aryl radicals, said aryl radicals being substituted with one, two, or three substituents independently selected from halogen and $-O-(C_1-C_8)$-alkyl; $-(C_1-C_8)$-alkyl, said alkyl being unsubstituted or substituted with up to three substituents independently selected from halogen, $NH_2$, $-OH$ and methoxy; and $-O-(C_1-C_8)$-alkyl, said alkyl being unsubstituted or substituted with up to three substituents independently selected from halogen, $NH_2$, $-OH$ and methoxy;

Q is selected from the group consisting of
a direct bond; $-C(O)-$; $-(C_0-C_2)$-alkylene-$C(O)-NR^{10}-$; $-NR^{10}-C(O)-NR^{10}-$; $-NR^{10}-C(O)-$; $-SO_2-$; $-(C_1-C_6)$-alkylene, wherein alkylene is unsubstituted or substituted with up to three substituents independently selected from halogen, $-NH_2$ and $-OH$; and $(C_3-C_6)$-cycloalkylene, wherein cycloalkylene is unsubstituted or substituted with up to three substituents independently selected from halogen, $-NH_2$ and $-OH$;

$R^1$ is selected from the group consisting of
hydrogen; $-(C_1-C_4)$-alkyl radicals, said alkyl radicals being unsubstituted or substituted with one two or three substituents independently selected from the $R^{13}$ substituents defined below; and monocyclic or bicyclic 4- to 14-membered heteroaryl radicals said heteroaryl radical is unsubstituted or substituted with one two or three substituents independently selected from the $R^{14}$ substituents defined below;

$R^2$ is a direct bond or $-(C_1-C_4)$-alkylene; provided that:
a) $R^1$ and $R^7$ together with the atoms to which they are bonded can form a 4- to 7-membered cyclic group, which may contain 1, 2, 3 or 4 heteroatoms selected from the group consisting of nitrogen, sulfur and oxygen, said cyclic group being unsubstituted or substituted with one two or three substituents independently selected from the $R^{14}$ substituents defined below;
b) $R^1-N-R^2-V$ can form a 4- to 7-membered cyclic group, which may contain 1, 2, 3 or 4 heteroatoms selected from the group consisting of nitrogen, sulfur and oxygen, said cyclic group being unsubstituted or substituted with one two or three substituents independently selected from the $R^{14}$ substituents defined below;

$R^{14}$ is selected from the group consisting of
halogen, $-OH$, $=O$, $-(C_1-C_8)$-alkyl, $-(C_1-C_4)$-alkoxy, $-NO_2$, $-C(O)-OH$, $-CN$, $-NH_2$, $-C(O)-O-(C_1-C_4)$-alkyl, $-(C_1-C_8)$-alkylsulfonyl, $-SO_2$, $-C(O)-NH-(C_1-C_8)$-alkyl, $-C(O)-N-[(C_1-C_8)$-alkyl]$_2$, $-NR^{10}-C(O)-NH-(C_1-C_8)$-alkyl, $-C(O)-NH_2$, $-SR^{10}$, and $-NR^{10}-C(O)-NH-[(C_1-C_8)$-alkyl]$_2$, said $R^{10}$ being selected from hydrogen, $-(C_1-C_3)$-perfluoroalkyl and $-(C_1-C_6)$-alkyl;

V is selected from the group consisting of
a 3- to 7-membered cyclic group, which may contain 1, 2, 3 or 4 heteroatoms selected from the group consisting of nitrogen, sulfur and oxygen, said cyclic group being unsubstituted or substituted with one two or three substituents independently selected from the $R^{14}$ substituents defined above; a 6- to 14-membered aryl, said aryl being unsubstituted or substituted with one two or three substituents independently selected from the $R^{14}$ substituents defined above; and a monocyclic or bicyclic 4- to 14-membered heteroaryl, said heteroaryl being unsubstituted or substituted with one two or three substituents independently selected from the $R^{14}$ substituents defined above;

G is selected from the group consisting of:
a direct bond, $-(CH_2)_m-NR^{10}-SO_2-NR^{10}-(CH_2)_n-$, $-(CH_2)_m-CH(OH)-(CH_2)_n-$, $-(CH_2)_m-$, $-(CH_2)_m-O-(CH_2)_n-$, $-(CH_2)_m-C(O)-NR^{10}-(CH_2)_n-$, $-(CH_2)-SO_2-(CH_2)_n-$, $-(CH_2)_m-NR^{10}-C(O)-NR^{10}-(CH_2)_n-$, $-(CH_2)_m-NR^{10}-C(O)-(CH_2)_n-$, $-(CH_2)_m-C(O)-(CH_2)_n-$, $-(CH_2)-S-(CH_2)_n-$, $-(CH_2)_m-SO_2-NR^{10}-(CH_2)_n-$, $-(CH_2)_m-NR^{10}-SO_2-(CH_2)_n-$, $-(CH_2)_m-NR^{10}-$, $-(CH_2)_m-O-C(O)-NR^{10}-(CH_2)_n-$ and $-(CH_2)_m-NR^{10}-C(O)-O-(CH_2)_n-$, n and m are independently selected from zero and the integers 1, 2, 3, 4, 5 and 6, $R^{10}$ is hydrogen, $-(C_1-C_3)$-perfluoroalkyl or $-(C_1-C_6)$-alkyl, M is selected from the group consisting of
hydrogen; $-(C_1-C_8)$-alkyl, said alkyl being unsubstituted or substituted with one two or three substituents independently selected from the $R^{14}$ substituents defined above; $-C(O)-NR^{11}R^{12}$; $-(CH_2)_m-NR^{10}$; $-(C_6-C_{14})$-aryl, said aryl being unsubstituted or substituted with one two or three substituents independently selected from the $R^{14}$ substituents defined above; $-(C_4-C_{14})$-heteroaryl, said heteroaryl being unsubstituted or substituted with one two or three substituents independently selected from the $R^{14}$ substituents defined above; $(C_3-C_7)$-cycloalkyl, said cycloalkyl being unsubstituted or substituted with one two or three substituents independently selected from the $R^{14}$ substituents defined above; a 3- to 7-membered cyclic residue, optionally containing 1, 2, 3 or 4 heteroatoms selected from nitrogen, sulfur and oxygen, said cyclic residue being unsubstituted or substituted with one two or three substituents independently selected from the $R^{14}$ substituents defined above;

$R^{11}$ and $R^{12}$ are independently selected from the group consisting of:
hydrogen; $-(C_1-C_6)$-alkyl, said alkyl being unsubstituted or substituted with one two or three substituents independently selected from the $R^{13}$ substituents defined below; $-(C_6-C_{14})$-aryl-$(C_1-C_4)$-alkyl-, wherein said alkyl and said aryl are each independently unsubstituted or substituted with one two or three substituents independently selected from the $R^{13}$ substituents defined below; $-(C_6-C_{14})$-aryl-, said aryl being unsubstituted or substituted with one two or three substituents independently selected from the $R^{13}$ substituents defined below; —$(C_4-C_{14})$-heteroaryl, said heteroaryl being unsubstituted or substituted with one two or three substituents independently selected from the $R^{13}$ substituents defined below; —$(C_4-C_{14})$-heteroaryl-$(C_1-C_4)$-alkyl-, wherein said alkyl and said heteroaryl are each independently unsubstituted or substituted with one two or three substituents independently selected from the $R^{13}$ substituents defined below; or, alternatively, $R^{11}$ and $R^{12}$, together with the nitrogen atom to which they are bonded, form a saturated 5- to 7-membered monocyclic heterocyclic ring which, in addition to said nitrogen atom, may contain one or two identical or different ring heteroatoms selected from oxygen, sulfur and nitrogen; said heterocyclic ring being unsubstituted or substituted with one two or three substituents independently selected from the $R^{13}$ substituents defined below;

$R^{13}$ is selected from the group consisting of:
halogen; —$NO_2$; —CN; =O; —OH; —$(C_1-C_8)$-alkyl; —$(C_1-C_8)$-alkoxy; —$CF_3$; phenyl; phenyloxy-; —C(O)—O—$R^{11}$; phenyl-$(C_1-C_4)$-alkoxy-; —C(O)—N—$R^{11}R^{12}$; —$NR^{11}R^{12}$; —$NR^{10}$—$SO_2$—$R^{10}$; —S—$R^{10}$; —$SO_n$—$R^{10}$; wherein n is 1 or 2; —$SO_2$—$NR^{11}R^{12}$; —C(O)—$R^{10}$; —$(C_0-C_4)$-alkyl-C(O)—O—C($R^{15}R^{16}$)—O—C(O)—$R^{17}$; —$(C_0-C_4)$-alkyl-C(O)—O—C($R^{15}R^{16}$)—O—C(O)O—$R^{17}$, and a residue of formula Va,

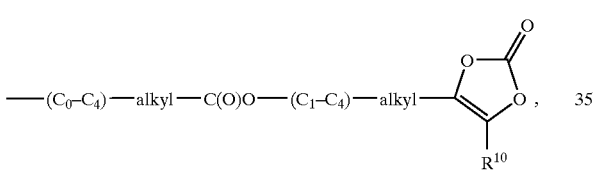

Va wherein $R^{10}$, $R^{11}$, $R^{12}$ are as defined above and $R^{15}$, $R^{16}$ or $R^{17}$ are as defined below;

$R^{15}$ and $R^{16}$ are independently selected from hydrogen, and —$(C_1-C_6)$-alkyl, or, alternatively, together with the carbon atom to which they are bonded, form a 3- to 6 membered carbocyclic ring, said carbocyclic ring being unsubstituted or substituted with one two or three substituents independently selected from the $R^{10}$ substituents defined above;

$R^{17}$ is selected from the group consisting of —$(C_1-C_6)$-alkyl, —$(C_1-C_8)$-cycloalkyl, and —$(C_1-C_6)$-alkyl-$(C_1-C_8)$-cycloalkyl, each said cycloalkyl ring being unsubstituted or substituted with one two or three substituents independently selected from the $R^{10}$ substituents defined above;

$R^3$, $R^4$, $R^5$, $R^6$ and $R^7$ are each independently selected from the group consisting of:
hydrogen; halogen; —$(C_1-C_4)$-alkyl, said alkyl being unsubstituted or substituted with one, two or three substituents independently selected from the $R^{13}$ substituents defined above; —$(C_1-C_3)$-perfluoroalkyl; phenyl, said phenyl being unsubstituted or substituted with one two or three substituents independently selected from the $R^{13}$ substituents defined above; —O—$(C_1-C_4)$-alkyl, said alkyl being unsubstituted or substituted with one two or three substituents selected from the $R^{13}$ substituents defined above; —$NO_2$; —CN; —OH; phenyloxy-, said phenyloxy being unsubstituted or substituted with one two or three substituents independently selected from the $R^{13}$ substituents defined above; benzyloxy-, said benzyloxy being unsubstituted or substituted with one two or three substituents independently selected from the $R^{13}$ substituents defined above; —C(O)—O—$R^{11}$, wherein $R^{11}$ is as defined above; —C(O)—N—$R^{11}R^{12}$, wherein $R^{11}$ and $R^{12}$ are as defined above; —$NR^{11}R^{12}$, wherein $R^{11}$ and $R^{12}$ are as defined above; —$NR^{10}$—$SO_2$—$R^{10}$, wherein $R^{10}$ is as defined above; —$SR^{10}$, wherein $R^{10}$ is as defined above; —$SO_n$—$R^{10}$, wherein n is 1 or 2 and $R^{10}$ is as defined above; —$SO_2$—$NR^{11}R^{12}$, wherein $R^{11}$ and $R^{12}$ are as defined above; —C(O)—$R^{10}$, wherein $R^{10}$ is as defined above; —C(O)—O—C($R^{15}R^{16}$)—O—C(O)—$R^{17}$, wherein $R^{15}$, $R^{16}$ and $R^{17}$ are as defined above; —C(O)—O—C($R^{15}R^{16}$)—O—C(O)O—$R^{17}$, wherein $R^{15}$, $R^{16}$ and $R^{17}$ are as defined above; a residue of formula Va,

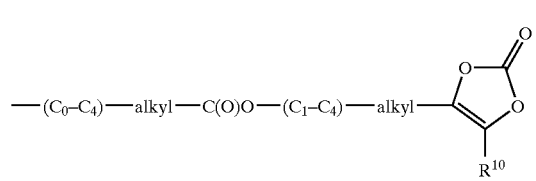

Va wherein $R^{10}$ is as defined above;
a residue of formula Vb or Vc,

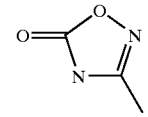

Vb

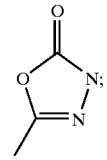

Vc

—$NR^{10}$—$(C_1-C_4)$-alkyl, said alkyl being unsubstituted or substituted with one two or three substituents independently selected from the $R^{13}$ substituents defined above; —O—$CF^3$; and a residue selected from the group consisting of:

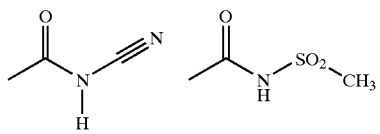

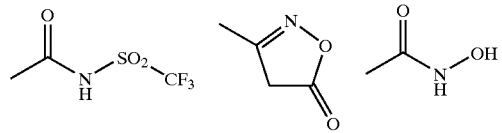

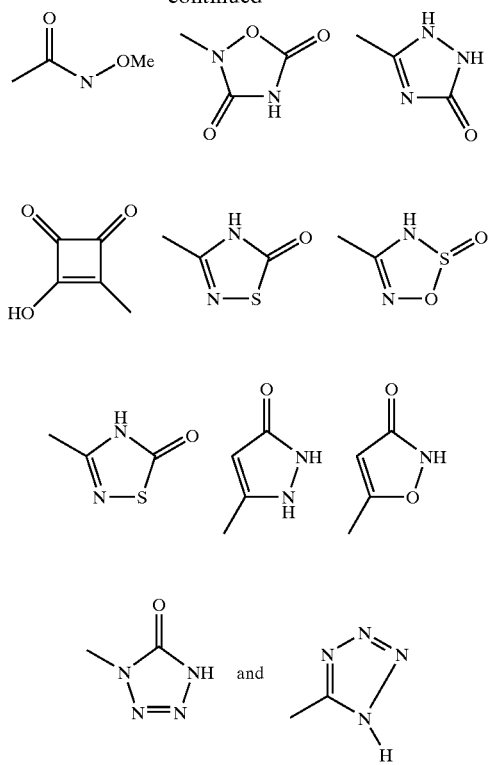

wherein $R^{10}$, $R^{11}$, $R^{12}$ and $R^{13}$ are as defined above, in all its stereoisomeric forms and mixtures thereof in any ratio, and its physiologically tolerable salts.

The present invention also relates to the selected compounds of formula I, wherein $R^0$ is selected from the group consisting of phenyl, said phenyl being unsubstituted or substituted with one, two or three substituents independently selected from the $R^{8'}$ substituents defined below; bicyclic 5- to 14-membered heteroaryl radicals selected from the group consisting of indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, purinyl and pteridinyl, said heteroaryl radicals being unsubstituted or substituted with one, two or three substituents independently selected from the $R^{8'}$ substituents defined below; said heteroaryl radicals being optionally further substituted by an additional residue selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, triazolyl, isothiazolyl, thiadiazolyl, tetrazolyl, pyrimidinyl, pyridazinyl and pyrazinyl, said additional residue being unsubstituted or substituted with one, two or three substituents independently selected from the $R^{8'}$ substituents defined below; a monocyclic 5- to 14-membered heteroaryl radical selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, said heteroaryl radical being unsubstituted or substituted with one, two or three substituents independently selected from the $R^{8'}$ substituents defined below said heteroaryl radical being optionally further substituted by a residue selected from the group consisting of pyridyl, 2-pyridyl, 3-pyridyl, 4-pyridyl, pyrrolyl, 2-pyrrolyl, 3-pyrrolyl, furyl, 2-furyl, 3-furyl, thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, said residue being unsubstituted or substituted with one, two or three substituents independently selected from the $R^{8'}$ substituents defined below $R^{8'}$ is selected from the group consisting of:
halogen, including F, Cl, Br and I; —C(O)—NH$_2$; —(C$_1$–C$_4$)-alkyl, said alkyl being unsubstituted or independently substituted by one, two or three substituents selected from halogen, —OH and methoxy; and —O—(C$_1$–C$_4$)-alkyl, said alkyl being unsubstituted or independently substituted by one, two or three substituents selected from halogen and methoxy, provided that at least one $R^{8'}$ is halogen, —C(O)—NH$_2$ or a —O—(C$_1$–C$_8$)-alkyl residue when $R^0$ is a monocyclic or bicyclic 6- to 14-membered aryl;

Q is selected from the group consisting of:
a direct bond; —C(O)—; —SO$_2$—; —(C$_1$–C$_6$)-alkylen; and —(C$_0$–C$_2$)-alkylen-C(O)—NR$^{10}$—;

$R^1$ is hydrogen or —(C$_1$–C$_2$)-alkyl;

$R^2$ is a direct bond or —(C$_1$–C$_2$)-alkylen; or, alternatively, $R^1$—N—$R^2$—V, together, form a 5- to 7-membered cyclic radical selected from the group consisting of piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, said cyclic radical being unsubstituted or substituted with one, two or three substituents independently selected from the $R^{14}$ substituents defined below;

$R^{14}$ is halogen, —(C$_1$–C$_4$)-alkyl or —NH$_2$,

V is selected from the group consisting of derivatives of 3- to 7-membered cyclic residues selected from the group consisting of aziridine, azirine, azetidine, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, oxazole, isoxazole, 2-isoxazoline, isoxazolidine, morpholine, oxirane, oxaziridine, 1,3-dioxolene, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiopyran, 1,2-thiazine, 1,3-thiazole, 1,3-thiazine, 1,4-thiazine, thiadiazine and thiomorpholine, said cyclic residue being unsubstituted or substituted with one, two or three substituents independently selected from the $R^{14}$ substituents defined above; phenyl, which is unsubstituted or substituted with one, two or three substituents independently selected from the $R^{14}$ substituents defined above; and a bicyclic 5- to 14-membered heteroaryl selected from the group consisting of quinolyl, isoquinolyl and quinoxalinyl, said heteroaryl being unsubstituted or substituted with one, two or three substituents independently selected from the $R^{14}$ substituents defined above;

G is a direct bond, —$(CH_2)_m$—, or —$(CH_2)_m$—$NR^{10}$—;

m is zero or an integer selected from 1, 2, 3 and 4;

$R^{10}$ is hydrogen, —$(C_1-C_3)$-perfluoroalkyl or —$(C_1-C_4)$-alkyl;

M is selected from the group consisting of:
hydrogen; —$(C_6-C_{14})$-heteroaryl, said heteroaryl being a residue selected from the group consisting of the derivatives of piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, thiadiazole and thiomorpholine, which are unsubstituted or substituted with one, two or three substituents independently selected from the $R^{14}$ substituents defined above; —$(C_1-C_6)$-alkyl, said alkyl being unsubstituted or substituted with one, two or three substituents independently selected from the $R^{14}$ substituents defined above; and $(C_3-C_6)$-cycloalkyl;

$R^3$, $R^4$, $R^5$, $R^6$ and $R^7$ are independently selected from the group consisting of
hydrogen; F; Cl; Br; —$(C_1-C_4)$-alkyl, said alkyl being unsubstituted or substituted by $R^{13}$ as defined below; —$CF_3$; phenyl, said phenyl being unsubstituted or substituted with one, two or three substituents independently selected from the $R^{13}$ substituents defined below; —O—$(C_1-C_4)$-alkyl, wherein alkyl is unsubstituted or substituted by $R^{13}$ as defined below; —$NO_2$; —CN; —OH; phenyloxy-, said phenyloxy being unsubstituted or substituted by $R^{13}$, as defined below; benzyloxy-, said benzyloxy being unsubstituted or substituted by $R^{13}$ as defined below; —C(O)—O—$R^{11}$; —C(O)—N—$R^{11}R^{12}$; —$NR^{11}R^{12}$; —$NR^{10}$—$SO_2$—$R^{10}$; —$SO_n$—$R^{10}$, wherein n is 1 or 2; —$SO_2$—$NR^{11}R^{12}$; —C(O)—$R^{10}$; —C(O)—O—C($R^{15}R^{16}$)—O—C(O)—$R^{17}$; —C(O)—O—C($R^{15}R^{16}$)—O—C(O)O—$R^{17}$; a residue of formula Va

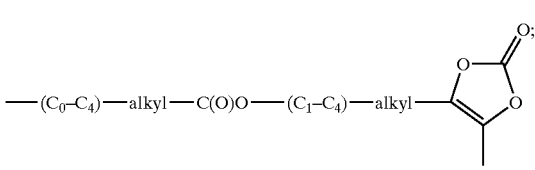

Va a residue of formula Vb or Vc,

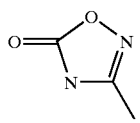

Vb

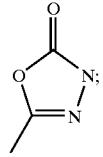

Vc

—O—$CF_3$; and a residue selected from the group consisting of

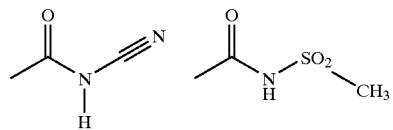

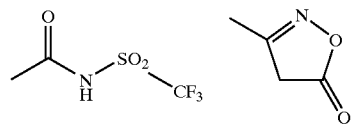

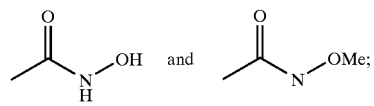

$R^{13}$ is selected from the group consisting of
halogen; —$NO_2$; —CN, =O; —OH; —$(C_1-C_8)$-alkoxy; —$CF_3$; —C(O)—O—$R^{11}$; —C(O)—N—$R^{11}R^{12}$; —$NR^{11}R^{12}$; —$NR^{10}$—$SO_2$—$R^{10}$; —$SO_n$—$R^{10}$, wherein n is 1 or 2; —$SO_2$—$NR^{11}R^{12}$; —C(O)—$R^{10}$; —$(C_0-C_4)$-alkyl-C(O)—O—C($R^{15}R^{16}$)—O—C(O)—$R^{17}$; —$(C_0-C_4)$-alkyl-C(O)—O—C($R^{15}R^{16}$)—O—C(O)O—$R^{17}$; and a residue of formula Va,

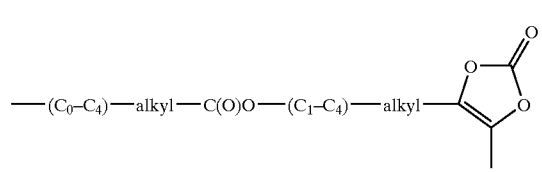

Va and $R^{10}$, $R^{11}$, $R^{12}$, $R^{15}$, $R^{16}$ and $R^{17}$ are as first defined above in the definition of formula I, in all its stereoisomeric forms and mixtures thereof in any ratio, and its physiologically tolerable salts.

The present invention also relates to the preferred compounds of formula I, wherein $R^0$ is phenyl, said phenyl being unsubstituted or substituted with one or two substituents independently selected from the $R^{8''}$ substituents defined below; or a monocyclic 4- to 14-membered heteroaryl radical selected from the group consisting of thienyl, thiadiazolyl, isoxazolyl and thiazolyl, said heteroaryl radical being substituted by a residue selected from the group consisting of thienyl, 2-thienyl and 3-thienyl, wherein said residue is unsubstituted or substituted with one or two substituents independently selected from the $R^{8''}$ substituents defined below;

$R^{8''}$ is selected from the group consisting of F, Cl, Br, —O—CH$_3$, —C(O)—NH$_2$ and —O—CF$_3$, Q is a direct bond, —C(O)—, —SO$_2$—, methylene or ethylene, $R^1$ is hydrogen;

$R^2$ is a direct bond or methylene, or, alternatively, $R^1$—N—$R^2$—V together form a 5- to 7-membered cyclic group selected from the group consisting of pyrrolidine, piperidine and piperazine;

$R^{13}$ is selected from the group consisting of
—C(O)—O—$R^{11}$; —C(O)—N—$R^{11}R^{12}$; —NR$^{11}R^{12}$; —NR$^{10}$—SO$_2$—$R^{10}$; —SO$_n$—$R^{10}$, wherein n is 1 or 2; —SO$_2$—NR$^{11}R^{12}$; —C(O)—$R^{10}$; —(C$_0$-C$_4$)-alkyl-C(O)—O—C(R$^{15}R^{16}$)—O—C(O)—$R^{17}$; —(C$_0$-C$_4$)-alkyl-C(O)—O—C(R$^{15}R^{16}$)—O—C(O) O—$R^{17}$; and a residue of formula Va,

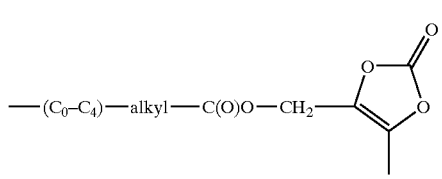

Va wherein $R^{10}$, $R^{11}$, $R^{12}$, $R^{15}$, $R^{16}$ or $R^{17}$ are as first defined above in the definition of formula I;

$R^{14}$ is halogen, methyl, ethyl or —NH$_2$,

V is a cyclic residue selected from the group consisting of compounds derived from isoquinoline, quinoline, quinazoline, piperidine, azetidine, tetrahydropyrane, piperazine and isoxazole, said cyclic residue being substituted with one or two substituents independently selected from the $R^{14}$ substituents defined above; and phenyl, which phenyl is unsubstituted or substituted with one or two substituents independently selected from the $R^{14}$ substituents defined above;

G is a direct bond, —(CH$_2$)$_m$—, or —(CH$_2$)$_m$—NR$^{10}$—, wherein m is zero, 1 or 2, and $R^{10}$ is hydrogen or —(C$_1$-C$_4$)-alkyl;

M is selected from hydrogen, (C$_2$-C$_4$)-alkyl, imidazolyl, pyrazolyl, pyrrolidinyl, tetrahydropyranyl, piperidinyl, pyridinyl, pyrimidyl, pyrazinyl, pyridazinyl, and (C$_3$-C$_6$)-cycloalkyl, which cyclic residues are unsubstituted or substituted with one or two substituents independently selected from the $R^{14}$ substituents defined above; and $R^3$, $R^4$, $R^5$, $R^6$ and $R^7$ are independently selected from the group consisting of
hydrogen; F; Cl; —(C$_1$-C$_4$)-alkyl, wherein alkyl is unsubstituted or substituted by $R^{13}$, as defined above; phenyl, which is unsubstituted or substituted with one, two or three substituents independently selected from the $R^{13}$ substituents defined above; —O—(C$_1$-C$_4$)-alkyl, wherein alkyl is unsubstituted or substituted by $R^{13}$, as defined above; —C(O)—O—$R^{11}$; —C(O)—N—$R^{11}R^{12}$; —NR$^{11}R^{12}$; —NR$^{10}$—SO$_2$—$R^{10}$; —SO$_2$—NR$^{11}R^{12}$; —C(O)—$R^{10}$—C(O)—O—C(R$^{15}R^{16}$)—O—C(O)—$R^{17}$, wherein $R^{15}$, $R^{16}$ and $R^{17}$ are as first defined above in the definition of formula I; —C(O)—O—C(R$^{15}R^{16}$)—O—C(O)O—$R^{17}$, wherein $R^{15}$, $R^{16}$ and $R^{17}$ are as first defined above in the definition of formula I; a residue of formula Va

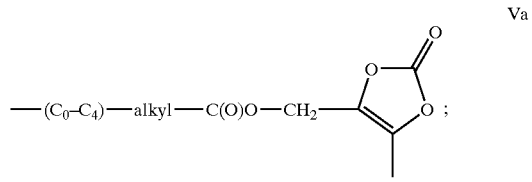

Va a residue of formula Vb or Vc,

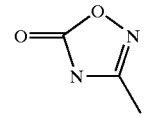

Vb

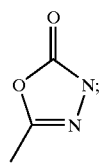

Vc and a residue selected from the group consisting of:

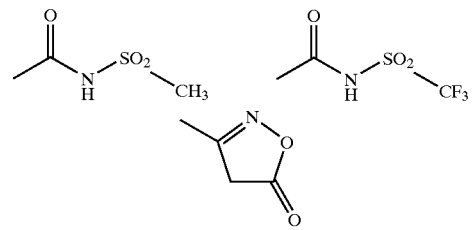

in all its stereoisomeric forms and mixtures thereof in any ratio, and its physiologically acceptable salts.

The present invention also relates to the compounds of formula I, which are selected from the group consisting of:
1-[5-(5-Chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-5-methanesulfonyl-1H-indole-2-carboxyl acid (1-isopropyl-piperidin-4-yl)-amide,
1-[5-(5-Chloro-thiophen-2-yl)-isoxazol-3-ylmethyl]-5-nitro-1H-indole-2-carboxylic acid (1-isopropyl-piperidin-4-yl)-amide,
5-Benzyloxy-1-[5-(5-chloro-thiophen-2-yl)-isoxazol-3-ylmethyl]-1H-indole-2-carboxylic acid (1-isopropyl-piperidin-4-yl)-amide,
5-Chloro-1-[5-(5-chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-5-methoxy-1H-indole-2-carboxylic acid (1-isopropyl-piperidin-4-yl)-amide,
1-[5-(5-Chloro-thiophen-2-yl)-isoxazol-3-ylmethyl]-6-methoxy-1H-indole-2-carboxylic acid (1-isopropyl-piperidin-4-yl)-amide,
1-[5-(5-Chloro-thiophen-2-yl)-isoxazol-3-ylmethyl]-5-methyl-1H-indole-2-carboxylic acid (1-isopropyl-piperidin-4-yl)-amide,
1-[5-(5-Chloro-thiophen-2-yl)-isoxazol-3-ylmethyl]-4,6-dimethoxy-1H-indole-2-carboxylic acid (1-isopropyl-piperidin-4-yl)-amide, 1-[5-(5-Chloro-thiophen-2-yl)-isoxazol-3-ylmethyl]-5,6-dimethoxy-1H-indole-2-carboxylic acid (1-isopropyl-piperidin-4-yl)-amide,
1-[5-(5-Chloro-thiophen-2-yl)-isoxazol-3-ylmethyl]-7-nitro-1H-indole-2-carboxylic acid (1-isopropyl-piperidin-4-yl)-amide,
1-[5-(5-Chloro-thiophen-2-yl)-isoxazol-3-ylmethyl]-5-trifluoromethoxy-1H-indole-2-carboxylic acid (1-isopropyl-piperidin-4-yl)-amide,
1-[5-(5-Chloro-thiophen-2-yl)-isoxazol-3-ylmethyl]-7-methyl-1H-indole-2-carboxylic acid (1-isopropyl-piperidin-4-yl)-amide,
1-[5-(5-Chloro-thiophen-2-yl)-isoxazol-3-ylmethyl]-7-(2,2-dimethyl-propionylamino)-1H-indole-2-carboxylic acid (1-isopropyl-piperidin-4-yl)-amide,
1-[5-(5-Chloro-thiophen-2-yl)-isoxazol-3-ylmethyl]-4-methoxy-1H-indole-2-carboxylic acid (1-isopropyl-piperidin-4-yl)-amide,
1-[5-(5-Chloro-thiophen-2-yl)-isoxazol-3-ylmethyl]-3-phenyl-1H-indole-2-carboxylic acid (1-isopropyl-piperidin-4-yl)-amide,
1-[5-(5-Chloro-thiophen-2-yl)-isoxazol-3-ylmethyl]-6-hydroxy-5-methoxy-1H-indole-2-carboxylic acid (1-isopropyl-piperidin-4-yl)-amide,
1-[5-(5-Chloro-thiophen-2-yl)-isoxazol-3-ylmethyl]-4,6-difluoro-1H-indole-2-carboxylic acid (1-isopropyl-piperidin-4-yl)-amide,
4-Benzyloxy-1-[5-(5-chloro-thiophen-2-yl)-isoxazol-3-ylmethyl]-1H-indole-2-carboxylic acid (1-isopropyl-piperidin-4-yl)-amide,
7-Chloro-1-[5-(5-chloro-thiophen-2-yl)-isoxazol-3-ylmethyl]-1H-indole-2-carboxylic acid (1-isopropyl-piperidin-4-yl)-amide,
6-Chloro-1-[5-(5-chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-5-ethyl-1H-indole-2-carboxylic acid (1-isopropyl-piperidin-4-yl)-amide,
1-[5-(5-Chloro-thiophen-2-yl)-isoxazol-3-ylmethyl]-5-fluoro-1H-indole-2-carboxylic acid (1-isopropyl-piperidin-4-yl)-amide,
1-[5-(5-Chloro-thiophen-2-yl)-isoxazol-3-ylmethyl]-5-nitro-3-phenyl-1H-indole-2-carboxylic acid (1-isopropyl-piperidin-4-yl)-amide,
5-Chloro-1-[5-(5-chloro-thiophen-2-yl)-isoxazol-3-ylmethyl]-3-phenyl-1H-indole-2-carboxylic acid (1-isopropyl-piperidin-4-yl)-amide,
1-[5-(5-Chloro-thiophen-2-yl)-isoxazol-3-ylmethyl]-5,7-difluoro-1H-indole-2-carboxylic acid (1-isopropyl-piperidin-4-yl)-amide,
1-[5-(5-Chloro-thiophen-2-yl)-isoxazol-3-ylmethyl]-5,7-dinitro-1H-indole-2-carboxylic acid (1-isopropyl-piperidin-4-yl)-amide,
1-[5-(5-Chloro-thiophen-2-yl)-isoxazol-3-ylmethyl]-1H-indole-2-carboxylic acid (3,4,5,6-tetrahydro-2H-[1,4']bipyridinyl-4-ylmethyl)-amide,
1-[5-(5-Chloro-thiophen-2-yl)-isoxazol-3-ylmethyl]-7-methyl-1H-indole-2-carboxylic acid (3,4,5,6-tetrahydro-2H-[1,4']bipyridinyl-4-yl)-amide,
1-[5-(5-Chloro-thiophen-2-yl)-isoxazol-3-ylmethyl]-5-nitro-1H-indole-2-carboxylic acid (3,4,5,6-tetrahydro-2H-[1,4']bipyridinyl-4-yl)-amide,
{1-[5-(5-Chloro-thiophen-2-yl)-isoxazol-3-ylmethyl]-1H-indol-2-yl}-[4-(pyridin-4-ylamino)-piperidin-1-yl]-methanone,
{1-[5-(5-Chloro-thiophen-2-yl)-isoxazol-3-ylmethyl]-5-nitro-1H-indol-2-yl}-[4-(pyridin-4-ylamino)-piperidin-1-yl]-methanone,
{1-[5-(5-Chloro-thiophen-2-yl)-isoxazol-3-ylmethyl]-7-methyl-1H-indol-2-yl}-[4-(pyridin-4-ylamino)-piperidin-1-yl]-methanone,
{1-[5-(5-Chloro-thiophen-2-yl)-isoxazol-3-ylmethyl]-1H-indol-2-yl}-(4-isopropylamino-piperidin-1-yl)-methanone,
{1-[5-(5-Chloro-thiophen-2-yl)-isoxazol-3-ylmethyl]-7-methyl-1H-indol-2-yl}-(4-isopropylamino-piperidin-1-yl)-methanone,
1-[5-(5-Chloro-thiophen-2-yl)-isoxazol-3-ylmethyl]-1H-indole-2-carboxylic acid (1-ethyl-piperidin-4-yl)-amide,
1-[5-(5-Chloro-thiophen-2-yl)-isoxazol-3-ylmethyl]-7-methyl-1H-indole-2-carboxylic acid (1-ethyl-piperidin-4-yl)-amide,
{1-[5-(5-Chloro-thiophen-2-yl)-isoxazol-3-ylmethyl]-1H-indol-2-yl}-(4-pyrrolidin-1-yl-piperidin-1-yl)-methanone,
[1,4']Bipiperidinyl-1'-yl-{1-[5-(5-chloro-thiophen-2-yl)-isoxazol-3-ylmethyl]-1H-indol-2-yl}-methanone,
1-[5-(5-Chloro-thiophen-2-yl)-isoxazol-3-ylmethyl]-1H-indole-2-carboxylic acid (3-pyridin-4-yl-4,5-dihydro-isoxazol-5-ylmethyl)-amide,
{1-[5-(5-Chloro-thiophen-2-yl)-isoxazol-3-ylmethyl]-1H-indol-2-yl}-(4-pyridin-4-ylmethyl-piperazin-1-yl)-methanone,
1-[5-(5-Chloro-thiophen-2-yl)-isoxazol-3-ylmethyl]-1H-indole-2-carboxylic acid (1-isopropyl-piperidin-4-ylmethyl)-amide,
1-[5-(5-Chloro-thiophen-2-yl)-isoxazol-3-ylmethyl]-1H-indole-2-carboxylic acid (3,4,5,6-tetrahydro-2H-[1,4']bipyridinyl-4-ylmethyl)-amide,
1-[5-(5-Chloro-thiophen-2-yl)-isoxazol-3-ylmethyl]-1H-indole-2-carboxylic acid (1-cyclopropyl-piperidin-4-yl)-amide,
1-[5-(5-Chloro-thiophen-2-yl)-isoxazol-3-ylmethyl]-1H-indole-2-carboxylic acid [1-(tetrahydro-pyran-4-yl)-piperidin-4-yl]-amide,
1-[5-(5-Chloro-thiophen-2-yl)-isoxazol-3-ylmethyl]-1H-indole-2-carboxylic acid (1-cyclopentyl-piperidin-4-yl)-amide,
1-[5-(5-Chloro-thiophen-2-yl)-isoxazol-3-ylmethyl]-1H-indole-2-carboxylic acid (1-cyclohexyl-piperidin-4-yl)-amide,
1-(3-Methoxy-benzyl)-1H-indole-2-carboxylic acid (1-isopropyl-piperidin-4-yl)-amide,
1-(3-Methoxy-benzyl)-1H-indole-2-carboxylic acid (1-isopropyl-piperidin-4-ylmethyl)-amide,
1-(3-Methoxy-benzyl)-1H-indole-2-carboxylic acid (3,4,5,6-tetrahydro-2H-[1,4']bipyridinyl-4-ylmethyl)-amide,
(4-Isopropylamino-piperidin-1-yl)-[1-(3-methoxy-benzyl)-1H-indol-2-yl]-methanone,
1-(3-Methoxy-benzyl)-1H-indole-2-carboxylic acid (3,4,5,6-tetrahydro-2H-[1,4']bipyridinyl-4-yl)-amide,
[1-(3-Methoxy-benzyl)-1H-indol-2-yl]-[4-(pyridin-4-ylamino)-piperidin-1-yl]-methanone,
4-Methoxy-1-(3-methoxy-benzyl)-1H-indole-2-carboxylic acid (1-isopropyl-piperidin-4-yl)-amide,
5-Chloro-1-(3-methoxy-benzyl)-1H-indole-2-carboxylic acid (1-isopropyl-piperidin-4-yl)-amide,
6-Methoxy-1-(3-methoxy-benzyl)-1H-indole-2-carboxylic acid (1-isopropyl-piperidin-4-yl)-amide,
1-(3-Methoxy-benzyl)-5-methyl-1H-indole-2-carboxylic acid (1-isopropyl-piperidin-4-yl)-amide,
5-Benzyloxy-1-(3-methoxy-benzyl)-1H-indole-2-carboxylic acid (1-isopropyl-piperidin-4-yl)-amide,
1-(3-Methoxy-benzyl)-5-nitro-1H-indole-2-carboxylic acid (1-isopropyl-piperidin-4-yl)-amide, 5-Methoxy-1-(3-methoxy-benzyl)-1H-indole-2-carboxylic acid (1-isopropyl-piperidin-4-yl)-amide,
1-(3-Methoxy-benzoyl)-1H-indole-2-carboxylic acid (1-isopropyl-piperidin-4-yl)-amide,
1-(3-Methoxy-benzenesulfonyl)-1H-indole-2-carboxylic acid (1-isopropyl-piperidin-4-yl)-amide,
1-(4-Methoxy-phenyl)-1H-indole-2-carboxylic acid (1-isopropyl-piperidin-4-yl)-amide,
1-(4-Methoxy-phenyl)-1H-indole-2-carboxylic acid (3,4,5,6-tetrahydro-2H-[1,4']bipyridinyl-4-yl)-amide,
(4-Isopropylamino-piperidin-1-yl)-[1-(4-methoxy-phenyl)-1H-indol-2-yl]-methanone,
1-(3-Methoxy-phenyl)-1H-indole-2-carboxylic acid (1-isopropyl-piperidin-4-yl)-amide,
1-(3-Chloro-phenyl)-1H-indole-2-carboxylic acid (1-isopropyl-piperidin-4-yl)-amide,
1-(3-Chloro-phenyl)-1H-indole-2-carboxylic acid (3,4,5,6-tetrahydro-2H-[1,4']bipyridinyl-4-yl)-amide,
1-(3-Chloro-phenyl)-1H-indole-2-carboxylic acid (1-isopropyl-piperidin-4-ylmethyl)-amide,
1-(3,5-Dichloro-phenyl)-1H-indole-2-carboxylic acid (1-isopropyl-piperidin-4-yl)-amide,
1-(4-Chloro-phenyl)-1H-indole-2-carboxylic acid (1-isopropyl-piperidin-4-yl)-amide,
1-(6-Chloro-benzo[b]thiophen-2-ylmethyl)-1H-indole-2-carboxylic acid (1-isopropyl-piperidin-4-yl)-amide,
1-[5-(5-Chloro-thiophen-2-yl)-[1,3,4]thiadiazol-2-ylmethyl]-1H-indole-2-carboxylic acid (1-isopropyl-piperidin-4-yl)-amide,
1-[3-(5-Chloro-thiophen-2-yl)-isoxazol-5-ylmethyl]-1H-indole-2-carboxylic acid (1-isopropyl-piperidin-4-yl)-amide,
3-Chloro-1-[5-(5-chloro-thiophen-2-yl)-isoxazol-3-ylmethyl]-1H-indole-2-carboxylic acid (1-isopropyl-piperidin-4-yl)-amide,
3-Bromo-1-[5-(5-chloro-thiophen-2-yl)-isoxazol-3-ylmethyl]-1H-indole-2-carboxylic acid (1-isopropyl-piperidin-4-yl)-amide,
1-(4-Chloro-benzyl)-1H-indole-2-carboxylic acid (1-isopropyl-piperidin-4-yl)-amide
1-(4-Chloro-benzyl)-1H-indole-2-carboxylic acid (3,4,5,6-tetrahydro-2H-[1,4']bipyridinyl-4-yl)-amide,
1-(2,4-Dichloro-benzyl)-1H-indole-2-carboxylic acid (1-isopropyl-piperidin-4-yl)-amide,
1-(4-Methoxy-benzyl)-1H-indole-2-carboxylic acid (1-isopropyl-piperidin-4-yl)-amide,
(4-Isopropylamino-piperidin-1-yl)-[1-(4-methoxy-benzyl)-1H-indol-2-yl]-methanone,
1-(4-Trifluoromethoxy-benzyl)-1H-indole-2-carboxylic acid (1-isopropyl-piperidin-4-yl)-amide,
1-(2-Chloro-benzyl)-1H-indole-2-carboxylic acid (1-isopropyl-piperidin-4-yl)-amide
1-(2-Chloro-benzyl)-1H-indole-2-carboxylic acid (3,4,5,6-tetrahydro-2H-[1,4']bipyridinyl-4)-amide,
1-(2-Chloro-benzyl)-1H-indole-2-carboxylic acid (3,4,5,6-tetrahydro-2H-[1,4']bipyridinyl-4-ylmethyl)-amide,
1-(3,5-Dichloro-benzyl)-1H-indole-2-carboxylic acid (1-isopropyl-piperidin-4-yl)-amide,
[1-(3,5-Dichloro-benzyl)-1H-indol-2-yl]-(4-isopropylamino-piperidin-1-yl)-methanone,
3-Fluoro-1-[5-(5-chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-3-cyano-1H-indole-2-carboxylic acid (1-isopropyl-piperidin-4-yl)-amide,
1-[5-(5-Chloro-thiophen-2-yl)-isoxazol-3-ylmethyl]-3-cyano-7-methyl-1H-indole-2-carboxylic acid (1-isopropyl-piperidin-4-yl)-amide,
1-[2-(5-Chloro-thiophen-2-yl)-thiazol-5-ylmethyl]-1H-indole-2-carboxylic acid (1-isopropyl-piperidin-4-yl)-amide,
1-(3-Chloro-benzyl)-1H-indole-2-carboxylic acid (1-isopropyl-piperidin-4-yl)-amide,
[1-(3-Chloro-benzyl)-1H-indol-2-yl]-(4-isopropylamino-piperidin-1-yl)-methanone,
1-[2-(4-Chloro-phenyl)-ethyl]-1H-indole-2-carboxylic acid (1-isopropyl-piperidin-4-yl)-amide,
1-[2-(2,4-Dichloro-phenyl)-ethyl]-1H-indole-2-carboxylic acid (1-isopropyl-piperidin-4-yl)-amide,
1-[2-(3-Methoxy-phenyl)-ethyl]-1H-indole-2-carboxylic acid (1-isopropyl-piperidin-4-yl)-amide,
1-[2-(4-Chloro-phenyl)-ethyl]-4-methoxy-1H-indole-2-carboxylic acid (1-isopropyl-piperidin-4-yl)-amide,
4-Bromo-1-[5-(5-chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-4-methyl-1H-indole-2-carboxylic acid (1-isopropyl-piperidin-4-yl)-amide,
5-Bromo-1-[5-(5-chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-5-cyano-1H-indole-2-carboxylic acid (1-isopropyl-piperidin-4-yl)-amide,
1-[5-(5-Chloro-thiophen-2-yl)-isoxazol-3-ylmethyl]-4-trifluoromethyl-1H-indole-2-carboxylic acid (1-isopropyl-piperidin-4-yl)-amide,
1-[5-(5-Chloro-thiophen-2-yl)-isoxazol-3-ylmethyl]-4,7-dimethyl-1H-indole-2-carboxylic acid (1-isopropyl-piperidin-4-yl)-amide,
1-[5-(5-Chloro-thiophen-2-yl)-isoxazol-3-ylmethyl]-4,7-dimethoxy-1H-indole-2-carboxylic acid (1-isopropyl-piperidin-4-yl)-amide,
4,7-Dichloro-1-[5-(5-chloro-thiophen-2-yl)-isoxazol-3-ylmethyl]-1H-indole-2-carboxylic acid (1-isopropyl-piperidin-4-yl)-amide,
5,7-Dichloro-1-[5-(5-chloro-thiophen-2-yl)-isoxazol-3-ylmethyl]-1H-indole-2-carboxylic acid (1-isopropyl-piperidin-4-yl)-amide,
4-Chloro-1-[5-(5-chloro-thiophen-2-yl)-isoxazol-3-ylmethyl]-1H-indole-2-carboxylic acid (1-isopropyl-piperidin-4-yl)-amide,
1-[5-(5-Chloro-thiophen-2-yl)-isoxazol-3-ylmethyl]-1H-indole-2-carboxylic acid (4-methyl-piperazin-1-yl)-amide,
[{1-[5-(5-Chloro-thiophen-2-yl)-isoxazol-3-ylmethyl]-7-methyl-1H-indole-2-carbonyl}-1-isopropyl-piperidin-4-yl)-amino]-acetic acid ethyl ester,
[{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid,
1-[5-(5-Chloro-thiophen-2-yl)-isoxazol-3-ylmethyl]-1H-indole-2-carboxylic acid [1-(1-ethyl-propyl)-piperidin-4-yl]-amide,
1-[5-(5-Chloro-thiophen-2-yl)-isoxazol-3-ylmethyl]-1H-indole-2-carboxylic acid (1-methyl-piperidin-4-yl)-amide,
1-[5-(5-Chloro-thiophen-2-yl)-isoxazol-3-ylmethyl]-1H-indole-2-carboxylic acid [1-(2,2,2-trifluoro-ethyl)-piperidin-4-yl]-amide,
1-[5-(5-Chloro-thiophen-2-yl)-isoxazol-3-ylmethyl]-1H-indole-2-carboxylic acid (1-formyl-piperidin-4-yl)-amide,
1-[5-(5-Chloro-thiophen-2-yl)-isoxazol-3-ylmethyl]-1H-indole-2-carboxylic acid (1-carbamoyl-piperidin-4-yl)-amide, 1-[5-(5-Chloro-thiophen-2-yl)-isoxazol-3-ylmethyl]-1H-indole-2-carboxylic acid (1-methanesulfonyl-piperidin-4-yl)-amide,
1-[5-(5-Chloro-thiophen-2-yl)-isoxazol-3-ylmethyl]-1H-indole-2-carboxylic acid (1-acetyl-piperidin-4-yl)-amide,
1-[5-(5-Chloro-thiophen-2-yl)-isoxazol-3-ylmethyl]-1H-indole-2-carboxylic acid [1-(2-chloro-pyrimidin-4-yl)-piperidin-4-yl]-amide,
1-[5-(5-Chloro-thiophen-2-yl)-isoxazol-3-ylmethyl]-1H-indole-2-carboxylic acid (1-pyrimidin-4-yl-piperidin-4-yl)-amide,
{1-[5-(5-Chloro-thiophen-2-yl)-isoxazol-3-ylmethyl]-1H-indol-2-yl}-[4-(pyridin-4-yloxy)-piperidin-1-yl]-methanone,
1-[5-(5-Chloro-thiophen-2-yl)-isoxazol-3-ylmethyl]-1H-indole-2-carboxylic acid [4-(1H-imidazol-4-yl)-phenyl]-amide,
1-[5-(5-Chloro-thiophen-2-yl)-isoxazol-3-ylmethyl]-1H-indole-2-carboxylic acid (4-pyridin-3-yl-thiazol-2-yl)-amide,
1-[5-(5-Chloro-thiophen-2-yl)-isoxazol-3-ylmethyl]-1H-indole-2-carboxylic acid [3-(pyrrolidine-1-carbonyl)-4,5-dihydro-isoxazol-5-ylmethyl]-amide,
1-[5-(5-Chloro-thiophen-2-yl)-isoxazol-3-ylmethyl]-1H-indole-2-carboxylic acid (1-isobutyl-piperidin-4-yl)-amide,
1-[5-(5-Chloro-thiophen-2-yl)-isoxazol-3-ylmethyl]-1H-indole-2-carboxylic acid (1-propyl-piperidin-4-yl)-amide,
4-({1-[5-(5-Chloro-thiophen-2-yl)-isoxazol-3-ylmethyl]-1H-indole-2-carbonyl}-amino)-piperidine-1-carboxylic acid methyl ester,
1-[5-(5-Chloro-thiophen-2-yl)-isoxazol-3-ylmethyl]-1H-indole-2-carboxylic acid (4-isopropyl-piperazin-1-yl)-amide,
1-[5-(5-Chloro-thiophen-2-yl)-isoxazol-3-ylmethyl]-1H-indole-2-carboxylic acid (4-ethyl-piperazin-1-yl)-amide,
1-[5-(5-Chloro-thiophen-2-yl)-isoxazol-3-ylmethyl]-1H-indole-2-carboxylic acid pyridin-4-yl-(3,4,5,6-tetrahydro-2H-[1,4']bipyridinyl-4-yl)-amide,
1-[5-(5-Chloro-thiophen-2-yl)-isoxazol-3-ylmethyl]-5-nitro-1H-indole-2-carboxylic acid pyridin-4-yl-(3,4,5,6-tetrahydro-2H-[1,4']bipyridinyl-4-yl)-amide,
1-[5-(5-Chloro-thiophen-2-yl)-isoxazol-3-ylmethyl]-3-cyano-1H-indole-2-carboxylic acid (3,4,5,6-tetrahydro-2H-[1,4']bipyridinyl-4-yl)-amide,
1-[5-(5-Chloro-thiophen-2-yl)-isoxazol-3-ylmethyl]-3,7-diiodo-4-methoxy-1H-indole-2-carboxylic acid (1-isopropyl-piperidin-4-yl)-amide,
1-[5-(5-Chloro-thiophen-2-yl)-isoxazol-3-ylmethyl]-3,7-dicyano-4-methoxy-1H-indole-2-carboxylic acid (1-isopropyl-piperidin-4-yl)-amide,
1-[2-(4-Chloro-phenyl)-thiazol-4-ylmethyl]-1H-indole-2-carboxylic acid (1-isopropyl-piperidin-4-yl)-amide,
1-(1,7-Dichloro-isoquinolin-3-ylmethyl)-1H-indole-2-carboxylic acid (1-isopropyl-piperidin-4-yl)-amide,
1-[3-(4-Chloro-phenyl)-isoxazol-5-ylmethyl]-1H-indole-2-carboxylic acid (1-isopropyl-piperidin-4-yl)-amide,
1-[5-(4-Chloro-phenyl)-isoxazol-3-ylmethyl]-1H-indole-2-carboxylic acid (1-isopropyl-piperidin-4-yl)-amide,
1-[3-(4-Chloro-phenyl)-[1,2,4]oxadiazol-5-ylmethyl]-1H-indole-2-carboxylic acid (1-isopropyl-piperidin-4-yl)-amide,
1-[(5-Chloro-pyridin-2-ylcarbamoyl)-methyl]-5-methanesulfonyl-1H-indole-2-carboxylic acid (1-isopropyl-piperidin-4-yl)-amide,
1-[(4-Chloro-phenylcarbamoyl)-methyl]-5-methanesulfonyl-1H-indole-2-carboxylic acid (1-isopropyl-piperidin-4-yl)-amide,
5-Chloro-1-[(5-chloro-pyridin-2-ylcarbamoyl)-methyl]-1H-indole-2-carboxylic acid (1-isopropyl-piperidin-4-yl)-amide,
1-[(5-Chloro-pyridin-2-ylcarbamoyl)-methyl]-5-fluoro-1H-indole-2-carboxylic acid (1-isopropyl-piperidin-4-yl)-amide,
1-[(5-Chloro-pyridin-2-ylcarbamoyl)-methyl]-5,7-difluoro-1H-indole-2-carboxylic acid (1-isopropyl-piperidin-4-yl)-amide,
S-1-[5-(5-Chloro-thiophen-2-yl)-isoxazol-3-ylmethyl]-1H-indole-2-carboxylic acid (1-ethyl-pyrrolidin-3-yl)-amide,
R-1-[5-(5-Chloro-thiophen-2-yl)-isoxazol-3-ylmethyl]-1H-indole-2-carboxylic acid (1-ethyl-pyrrolidin-3-yl)-amide,
R-1-[5-(5-Chloro-thiophen-2-yl)-isoxazol-3-ylmethyl]-1H-indole-2-carboxylic acid (1-isopropyl-pyrrolidin-3-yl)-amide,
S-1-[5-(5-Chloro-thiophen-2-yl)-isoxazol-3-ylmethyl]-1H-indole-2-carboxylic acid (1-isopropyl-pyrrolidin-3-yl)-amide,
[{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid ethyl ester,
[{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid ethyl ester,
[{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid ethyl ester,
[{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester,
[{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester,
[{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester,
[{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid,
[{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid,
[{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid,
[{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid,
[{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid,
[{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid,
1-[5-(5-Chloro-thiophen-2-yl)-isoxazol-3-ylmethyl]-2-(1-isopropyl-piperidin-4-ylcarbamoyl)-1H-indole-5-carboxylic acid isopropyl ester,
1-[5-(5-Chloro-thiophen-2-yl)-isoxazol-3-ylmethyl]-2-(1-isopropyl-piperidin-4-ylcarbamoyl)-1H-indole-5-carboxylic acid,
1-[5-(5-Chloro-thiophen-2-yl)-isoxazol-3-ylmethyl]-5-hydroxymethyl-1H-indole-2-carboxylic acid (1-isopropyl-piperidin-4-yl)-amide,
1-[5-(5-Chloro-thiophen-2-yl)-isoxazol-3-ylmethyl]-2-(1-isopropyl-piperidin-4-ylcarbamoyl)-1H-indole-5-carboxylic acid ethyl ester, 1-[5-(5-Chloro-thiophen-2-yl)-isoxazol-3-ylmethyl]-2-(1-isopropyl-piperidin-4-ylcarbamoyl)-1H-indole-5-carboxylic acid methyl ester,
1-[5-(5-Chloro-thiophen-2-yl)-isoxazol-3-ylmethyl]-2-(1-isopropyl-piperidin-4-ylcarbamoyl)-1H-indole-5-carboxylic acid 2,2-dimethyl-propionyloxymethyl ester,
1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid isopropyl ester,
1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid,
1-[(4-Chloro-phenylcarbamoyl)-methyl]-2-(1-isopropyl-piperidin-4-ylcarbamoyl)-1H-indole-5-carboxylic acid isopropyl ester,
1-[(4-Chloro-phenylcarbamoyl)-methyl]-2-(1-isopropyl-piperidin-4-ylcarbamoyl)-1H-indole-5-carboxylic acid,
1-[5-(5-Chloro-thiophen-2-yl)-isoxazol-3-ylmethyl]-2-(1-isopropyl-piperidin-4-ylcarbamoyl)-1H-indole-4-carboxylic acid methyl ester,
1-[5-(5-Chloro-thiophen-2-yl)-isoxazol-3-ylmethyl]-2-(1-isopropyl-piperidin-4-ylcarbamoyl)-1H-indole-4-carboxylic acid,
1-[5-(5-Chloro-thiophen-2-yl)-isoxazol-3-ylmethyl]-1H-indole-2,5-dicarboxylic acid 5-amide 2-[(1-isopropyl-piperidin-4-yl)-amide],
1-[(4-chloro-phenylcarbamoyl)-methyl]-1H-indole-2-carboxylic acid 1-isopropyl-piperidin-4-yl)-amide,
1-[(5-chloro-thiophen-2-ylcarbamoyl)-methyl]-1H-indole-2-carboxylic acid (1-isopropyl-piperidin-4-yl)-amide,
1-[(4-chloro-2-fluoro-phenylcarbamoyl)-methyl]-1H-indole-2-carboxylic acid (1-isopropyl-piperidin-4-yl)-amide,
1-[(5-chloro-pyridin-2-ylcarbamoyl)-methyl]-1H-indole-2-carboxylic acid (1-isopropyl-piperidin-4-yl)-amide,
1-[(4-chloro-phenylcarbamoyl)-methyl]-1H-indole-2-carboxylic acid (3,4,5,6-tetrahydro-2H-[1,4']bipyridinyl-4-ylmethyl)-amide,
1-[(4-chloro-phenylcarbamoyl)-methyl]-1H-indole-2-carboxylic acid (3,4,5,6-tetrahydro-2H-[1,4']bipyridinyl-4-ylmethyl)-amide,
N-(4-chloro-phenyl)-2-{2-[4-(pyridin-4-ylamino)-piperidine-1-carbonyl]-indol-1-yl}-acetamide,
1-[(4-chloro-phenylcarbamoyl)-methyl]-1H-indole-2-carboxylic acid (1-cyclopropyl-piperidin-4-yl)-amide,
N-(4-chloro-phenyl)-2-[2-(4-pyrrolidin-1-yl-piperidine-1-carbonyl)-indol-1-yl]-acetamide,
1-[(4-chloro-phenylcarbamoyl)-methyl]-5-nitro-1H-indole-2-carboxylic acid (1-isopropyl-piperidin-4-yl)-amide,
5-amino-4-chloro-1-[5-(5-chloro-thiophen-2-yl)-isoxazol-3-ylmethyl]-1H-indole-2-carboxylic acid (1-isopropyl-piperidin-4-yl)-amide,
1-[5-(5-chloro-thiophen-2-yl)-isoxazol-3-ylmethyl]-1H-indole-2-carboxylic acid (1-cyanomethyl-piperidin-4-yl)-amide,
1-[5-(5-chloro-thiophen-2-yl)-isoxazol-3-ylmethyl]-1H-indole-2-carboxylic acid [1-(2-hydroxy-ethyl)-piperidin-4-yl]-amide,
1-[5-(5-chloro-thiophen-2-yl)-isoxazol-3-ylmethyl]-1H-indole-2-carboxylic acid [1-(2-methoxy-ethyl)-piperidin-4-yl]-amide,
1-[5-(5-chloro-thiophen-2-yl)-isoxazol-3-ylmethyl]-1H-indole-2-carboxylic acid (1-carbamoylmethyl-piperidin-4-yl)-amide,
1-[5-(5-chloro-thiophen-2-yl)-isoxazol-3-ylmethyl]-1H-indole-2-carboxylic acid (1-methylcarbamoylmethyl-piperidin-4-yl)-amide,
1-[5-(5-chloro-thiophen-2-yl)-isoxazol-3-ylmethyl]-1H-indole-2-carboxylic acid [1-(1H-imidazol-2-ylmethyl)-piperidin-4-yl]-amide,
1-[5-(5-chloro-thiophen-2-yl)-isoxazol-3-ylmethyl]-1H-indole-2-carboxylic acid [1-(2-dimethylamino-acetyl)-piperidin-4-yl]-amide,
1-[5-(5-Chloro-thiophen-2-yl)-isoxazol-3-ylmethyl]-2-(1-isopropyl-piperidin-4-ylcarbamoyl)-1H-indole-5-carboxylic acid 1-ethoxycarbonyloxy-ethyl ester,
1[-5-(5-Chloro-thiophen-2-yl)-isoxazol-3-ylmethyl]-2-(1-isopropyl-piperidin-4-ylcarbamoyl)-1H-indole-4-carboxylic acid 1-ethoxycarbonyloxy-ethyl ester,
1-[5-(5-Chloro-thiophen-2-yl)-isoxazol-3-ylmethyl]-2-(1-isopropyl-piperidin-4-ylcarbamoyl)-1H-indole-4-carboxylic acid 2,2-dimethyl-propionyloxymethyl ester,
1-[5-(5-Chloro-thiophen-2-yl)-isoxazol-3-ylmethyl]-2-(1-isopropyl-piperidin-4-ylcarbamoyl)-1H-indole-5-carboxylic acid 1-(2,2-dimethyl-propionyloxy)-ethyl ester,
1-[5-(5-Chloro-thiophen-2-yl)-isoxazol-3-ylmethyl]-2-(1-isopropyl-piperidin-4-ylcarbamoyl)-1H-indole-4-carboxylic acid 1-(2,2-dimethyl-propionyloxy)-ethyl ester,
1-[5-(5-Chloro-thiophen-2-yl)-isoxazol-3-ylmethyl]-2-(1-isopropyl-piperidin-4-ylcarbamoyl)-1H-indole-5-carboxylic acid 5-methyl-2-oxo-[1,3]dioxol-4-ylmethyl,
1-[5-(5-Chloro-thiophen-2-yl)-isoxazol-3-ylmethyl]-2-(1-isopropyl-piperidin-4-ylcarbamoyl)-1H-indole-4-carboxylic acid 5-methyl-2-oxo-[1,3]dioxol-4-ylmethyl,
1-[5-(5-Chloro-thiophen-2-yl)-isoxazol-3-ylmethyl]-2-(1-isopropyl-piperidin-4-ylcarbamoyl)-1H-indole-5-carboxylic acid 1-cyclohexyloxycarbonyloxy-ethyl ester and
1-[5-(5-Chloro-thiophen-2-yl)-isoxazol-3-ylmethyl]-2-(1-isopropyl-piperidin-4-ylcarbamoyl)-1H-indole-4-carboxylic acid 1-cyclohexyloxycarbonyloxy-ethyl ester.

In addition, the present invention further relates to a process for the preparation of a compound of formula I which comprises condensing a compound of formula 14

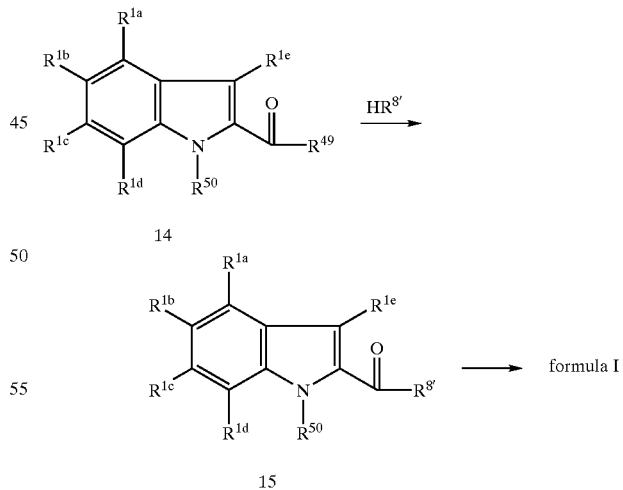

with a compound of the formula $HR^{8'}$ to give a compound of formula 15 and optionally converting the compound of the formula 15 into a compound of formula I, wherein the residue $R^{8'}$ is $—N(R^1)—R^2—V\text{-}G\text{-}M$, wherein each of $R^1$, $R^2$, V, G, and M are as first defined above in the definition formula I, but wherein said $R^{8'}$ functional groups can also be present in the form of precursor groups that are subsequently transformed into the final functional groups present in —N(R¹)—R²—V-G-M; wherein the residue R⁵⁰ denotes the group -Q-R⁰, as Q and R⁰ are first defined above in the definition of formula I, or a precursor group which is subsequently transformed into the group -Q-R⁰; the group —C(O)R⁴⁹ is a carboxylic acid group or derivative thereof; and the groups R¹ᵉ, R¹ᵃ, R¹ᵇ, R¹ᶜ and R¹ᵈ in the formulae 14 and 15 have the meanings corresponding to the definitions of R⁷, R⁶, R⁵, R⁴, and R³, respectively, in the definition of formula I as first defined above, or contain such functional groups in protected form or in the form of precursor groups.

It relates, also, to a pharmaceutical preparation, comprising at least one compound of formula I as defined above, as well as to methods for inhibition of factor Xa and/or factor VIIa or for influencing blood coagulation or fibrinolysis comprising administering to a patient in need thereof an effective amount of such pharmaceutical preparation, more particularly, to the use of such preparation for influencing a condition selected from the group consisting of blood coagulation, inflammatory response, fibrinolysis, cardiovascular disorders, thromboembolic diseases, restenoses, abnormal thrombus formation, acute myocardial infarction, unstable angina, acute vessel closure associated with thrombolytic therapy, thromboembolism, percutaneous, pathologic thrombus formation occurring in the veins of the lower extremities following abdominal, knee and hip surgery, transluminal coronary angioplasty, transient ischemic attacks, stroke, disseminated systemic intravascular coagulatopathy occurring in vascular systems during septic shock, a risk of pulmonary thromboembolism, certain viral infections or cancer, intravascular coagulatopathy occurring in vascular systems during septic shock, coronary heart disease, myocardial infarction, angina pectoris, vascular restenosis, for example, restenosis following angioplasty like PTCA, adult respiratory distress syndrome, multi-organ failure, stroke and disseminated intravascular clotting disorder, and thromboses such as deep vein and proximal vein thrombosis which can occur following surgery.

In general, the meaning of any group, residue, heteroatom, number etc., which can occur more than once in the compounds of formula I, is independent of the meaning of this group, residue, heteroatom, number etc. in any other occurrence. All groups, residues, heteroatoms, numbers etc., which can occur more than once in the compounds of the formula I can be identical or different.

As used herein, the term alkyl is to be understood in the broadest sense to mean hydrocarbon residues which can be linear, i.e. straight-chain, or branched and which can be acyclic or cyclic residues or comprise any combination of acyclic and cyclic subunits. Further, the term alkyl as used herein expressly includes saturated groups as well as unsaturated groups, which latter groups contain one or more, for example, one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of alkyl residues containing 1, 2, 3, 4, 5, 6, 7 or 8 carbon atoms are methyl, ethyl, propyl, butyl, pentyl, hexyl, heptyl, octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl and tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of cyclic alkyl residues are cycloalkyl residues containing 3, 4, 5 or 6 ring carbon atoms like cyclopropyl, cyclobutyl, cyclopentyl or cyclohexyl, which can also be substituted and/or unsaturated. Unsaturated cyclic alkyl groups and unsaturated cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like $(C_1-C_8)$-alkyl is to be understood as comprising, among others, saturated acyclic $(C_1-C_8)$-alkyl, $(C_3-C_6)$-cycloalkyl, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, and unsaturated $(C_2-C_4)$-alkyl like $(C_2-C_4)$-alkenyl or $(C_2-C_4)$-alkynyl.

Unless stated otherwise, the term alkyl preferably comprises acyclic saturated hydrocarbon residues which have from one to six carbon atoms and which can be linear or branched. A particular group of interest comprises such saturated acyclic alkyl residues as $(C_1-C_4)$-alkyl residues like methyl, ethyl, n-propyl, isopropyl, n-butyl, isobutyl, sec-butyl and tBu.

Unless stated otherwise, and irrespective of any specific substituents bonded to alkyl groups which are indicated in the definition of the compounds of formula I, alkyl groups can in general be unsubstituted or substituted by one or more, for example one, two or three, identical or different substituents. Any kind of substituents generally present in substituted alkyl residues can be present in any desired position provided that the substitution does not lead to an unstable molecule. Examples of substituted alkyl residues are alkyl residues in which one or more, for example, 1, 2 or 3, hydrogen atoms are replaced with halogen atoms, in particular, fluorine atoms.

The term "mono- or bicyclic 4- to 14-membered heteroaryl" refers to $(C_4-C_{14})$-aryl in which one or more of the 5 to 14 ring carbon atoms are replaced by heteroatoms such as nitrogen, oxygen or sulfur. Examples are azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydrochinolinyl, 2H,6H-1,5,2-dithiazinyl, dihydrofuro[2,3-b]-tetrahydrofuran, fuanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 6H-1,2,5-thiadazinyl, 1,2,3-thiadiazolyl, 1,2,4-thiadiazolyl, 1,2,5-thiadiazolyl, 1,3,4-thiadiazolyl and xanthenyl. Preferred are pyridyl; such as 2-pyridyl, 3-pyridyl or 4-pyridyl; pyrrolyl; such as 2-pyrrolyl and 3-pyrrolyl; furyl; such as 2-furyl and 3-furyl; thienyl; such as 2-thienyl and 3-thienyl; imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, purinyl and pteridinyl.

The term "$R^1$ and $R^2$ together with the nitrogen atom and V to which they are bonded form a 5- to 7-membered cyclic group" refers to structures of heterocycles which can be derived from compounds such as piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole and thiomorpholine.

The term "a 3- to 7-membered cyclic residue, containing up to 1, 2, 3 or 4 heteroatoms" refers to structures of heterocycles which can be derived from compounds such as, aziridine, azirine, azetidine, pyrrole, pyrrolidine, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine,furan, pyran, dioxole, oxazole, isoxazole, 2-isoxazoline, isoxazolidine, morpholine, oxirane, oxaziridine, 1,3-dioxolene, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiopyran, 1,2-thiazine, 1,3-thiazole, 1,3-thiazine, 1,4-thiazine, thiadiazine and thiomorpholine.

The term "$R^{11}$ and $R^{12}$ together with the nitrogen atom to which they are bonded form a saturated or unsaturated 5- to 7-membered monocyclic heterocyclic ring" refers to residues which can be derived from compounds such as piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole and thiomorpholine.

The fact that many of the before-listed names of heterocycles are the chemical names of unsaturated or aromatic ring systems does not imply that the 4–15 membered mono- or polycyclic group could only be derived from the respective unsaturated ring system. The names here only serve to describe the ring system with respect to ring size and the number of the heteroatoms and their relative positions. As explained above, the 4–15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The 4–15 membered mono- or polycyclic group may be bonded via any ring carbon atom, and, in the case of nitrogen heterocycles, via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly, benzimidazolyl, benzoxazolyl and benzothiazol residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to the 4–15 membered mono- or polycyclic group or any other heterocyclic groups which are indicated in the definition of the compounds of formula I, the 4–15 membered mono- or polycyclic group can be unsubstituted or substituted on ring carbon atoms with one or more, for example one, two, three, four or five, identical or different substituents, such as ($C_1$–$C_8$)-alkyl, in particular ($C_1$–$C_4$)-alkyl, ($C_1$–$C_8$)-alkyloxy, in particular ($C_1$–$C_4$)-alkyloxy, ($C_1$–$C_4$)-alkylthio, halogen, nitro, amino, (($C_1$–$C_4$)-alkyl)carbonylamino like acetylamino, trifluoromethyl, trifluoromethoxy, hydroxy, oxo, hydroxy-($C_1$–$C_4$)-alkyl, such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, ($C_1$–$C_4$)-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course, an oxo group cannot be present in an aromatic ring. Each suitable ring nitrogen atom in the 4–15 membered mono- or polycyclic group can independently be unsubstituted, i.e. carry a hydrogen atom, or can be substituted, i.e., carry a substituent like ($C_1$–$C_8$)-alkyl, for example ($C_1$–$C_4$)-alkyl such as methyl or ethyl, optionally substituted phenyl, phenyl-($C_1$–$C_4$)-alkyl, for example benzyl, optionally substituted in the phenyl group, hydroxy-($C_2$–$C_4$)-alkyl, such as, for example, 2-hydroxyethyl, acetyl or another acyl group, methylsulfonyl or another sulfonyl group, aminocarbonyl, ($C_1$–$C_4$)-alkyloxycarbonyl, etc. In general, in the compounds of the formula I nitrogen heterocycles can also be present as N-oxides or as quaternary salts. Ring sulfur atoms can be oxidized to the sulfoxide or to the sulfone. Thus, for example, a tetrahydrothienyl residue may be present as S,S-dioxotetrahydro-thienyl residue or a thiomorpholinyl residue like thiomorpholin-4-yl may be present as 1-oxo-thiomorpholin-4-yl or 1,1-dioxo-thiomorpholin-4-yl. A substituted 4–15 membered mono- or polycyclic group that can be present in a specific position of the compounds of formula I can independently of other groups be substituted by substituents selected from any desired subgroup of the substituents listed before and/or in the definition of that group.

The 3–7 membered monocyclic group may be bonded via any ring carbon atom, and, in the case of nitrogen heterocycles, via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Unless stated otherwise, and, irrespective of any specific substituents bonded to the 3–7 membered monocyclic group, or any other heterocyclic groups which are indicated in the definition of the compounds of the formula I, can be unsubstituted or substituted on ring carbon atoms with one or more, for example, one, two, three, four or five, identical or different substituents like ($C_1$–$C_8$)-alkyl, in particular, ($C_1$–$C_4$)-alkyl, ($C_1$–$C_8$)-alkyloxy, in particular, ($C_1$–$C_4$)-alkyloxy, ($C_1$–$C_4$)-alkylthio, halogen, nitro, amino, (($C_1$–$C_4$)-alkyl)carbonylamino like acetylamino, trifluoromethyl, trifluoromethoxy, hydroxy, oxo, hydroxy-($C_1$–$C_4$)-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, ($C_1$–$C_4$)-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course, an oxo group cannot be present in an aromatic ring. Each suitable ring nitrogen atom in the 3–7 membered monocyclic group can independently be unsubstituted, i.e. carry a hydrogen atom, or can be substituted, i.e. carry a substituent like ($C_1$–$C_8$)-alkyl, for example, ($C_1$–$C_4$)-alkyl such as methyl or ethyl, optionally substituted phenyl, phenyl-($C_1$–$C_4$)-alkyl, for example benzyl, optionally substituted in the phenyl group, hydroxy-($C_2$–$C_4$)-alkyl such as, for example 2-hydroxyethyl, acetyl or another acyl group, methylsulfonyl or another sulfonyl group, aminocarbonyl, ($C_1$–$C_4$)-alkyloxycarbonyl, etc. In general, in the compounds of formula I, nitrogen heterocycles can also be present as N-oxides or as quaternary salts. Ring sulfur atoms can be oxidized to the sulfoxide or to the sulfone. Thus, for example, a tetrahydrothienyl residue may be present as S,S-dioxotetrahydrothienyl residue or a thiomorpholinyl residue like thiomorpholin-4-yl may be present as 1-oxo-thiomorpholin-4-yl or 1,1-dioxo-thiomorpholin-4-yl. A substituted 3–7 membered monocyclic group that can be present in a specific position of the compounds of formula I can independently of other groups be substituted by substituents selected from any desired subgroup of the substituents listed before and/or in the definition of that group.

Halogen is fluorine, chlorine, bromine or iodine, preferably fluorine, chlorine or bromine, particularly preferably chlorine or bromine.

Optically active carbon atoms present in the compounds of formula I can, independently of each other, have R configuration or S configuration. The compounds of formula I can be present in the form of pure enantiomers or pure diastereomers or in the form of mixtures of enantiomers and/or diastereomers, for example, in the form of racemates. The present invention relates to pure enantiomers and mixtures of enantiomers as well as to pure diastereomers and mixtures of diastereomers. The invention comprises mixtures of two or of more than two stereoisomers of formula I, and it also comprises all ratios of the stereoisomers in the mixtures. When the compounds of formula I can be present as E isomers or Z isomers (or cis isomers or trans isomers), the invention relates to pure E isomers and pure Z isomers as well as to E/Z mixtures in all ratios. The invention also comprises all tautomeric forms of the compounds of formula I.

Diastereomers, including E/Z isomers, can be separated into the individual isomers, for example, by chromatography. Racemates can be separated into the two enantiomers by customary methods, for example, by chromatography on chiral phases or by resolution, for example, by crystallization of diastereomeric salts obtained with optically active acids or bases. Stereochemically uniform compounds of formula I can also be obtained by employing stereochemically uniform starting materials or by using stereoselective reactions.

Physiologically tolerable salts of the compounds of formula I are nontoxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention.

Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiologically tolerability, are not directly suitable for use in pharmaceuticals but are suitable, for example, as intermediates for carrying out further chemical modifications of the compounds of formula I or as starting materials for the preparation of physiologically tolerable salts.

The present invention furthermore includes all solvates of compounds of formula I, for example, hydrates or adducts with alcohols.

The invention also includes derivatives and modifications of the compounds of formula I, for example, prodrugs, protected forms and other physiologically tolerable derivatives, as well as active metabolites of the compounds of formula I. The invention relates, in particular, to prodrugs and protected forms of compounds of the formula I which can be converted into compounds of formula I under physiological conditions. Suitable prodrugs for the compounds of the formula I, i.e. chemically modified derivatives of the compounds of the formula I having properties which are improved in a desired manner, for example, with respect to solubility, bioavailability or duration of action, are known to those skilled in the art. More detailed information relating to prod rugs is found in standard literature like, for example, Design of Prodrugs, H. Bundgaard (ed.), Elsevier, 1985; Fleisher et al., Advanced Drug Delivery Reviews 19 (1996) 115–130; or H. Bundgaard, Drugs of the Future 16 (1991) 443, the contents of all of which are hereby incorporated herein by reference. Suitable prodrugs for the compounds of the formula I are especially acyl prodrugs and carbamate prodrugs of acylatable nitrogen-containing groups, such as amino groups and the guanidino group and also ester prodrugs and amide prodrugs of carboxylic acid groups which may be present in compounds of formula I. In the acyl prodrugs and carbamate prod rugs, one or more, for example, one or two, hydrogen atoms on nitrogen atoms in such groups are replaced with an acyl group or a carbamate, preferably a $(C_1-C_6)$-alkyloxycarbonyl group. Suitable acyl groups and carbamate groups for acyl prodrugs and carbamate prodrugs are, for example, the groups $R^{P1}$—CO— and $R^{P2}$O—CO—, in which $R^{P1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, Het-, $(C_6-C_{14})$-aryl-$(C_1-C_4)$-alkyl- or Het-$(C_1-C_4)$-alkyl- and in which $R^{P2}$ has the meanings indicated for $R^{P1}$ with the exception of hydrogen.

Especially preferred compounds of formula I are those wherein two or more residues are defined as indicated before for preferred compounds of formula I, or contain residues that have one or more of the specific definitions of the residues given in their general definitions or in the definitions of preferred compounds above.

Also, with respect to all preferred compounds of formula I, all their stereoisomeric forms and mixtures thereof in any ratio and their physiologically acceptable salts explicitly are a subject of the present invention, as well as are their prodrugs. Similarly, also in all preferred compounds of formula I, all residues that are present more than one time in the molecule are independent of each other and can be identical or different.

The compounds of formula I can be prepared by utilizing procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases, they are commercially available or have been described in the literature. Otherwise, they can be prepared from readily available precursor compounds analogously to procedures described in the literature, or by procedures or analogously to procedures described in this application.

In general, compounds of formula I can be prepared, for example, in the course of a convergent synthesis, by linking two or more fragments which can be derived retrosynthetically from formula I. More specifically, suitably substituted starting indole derivatives are employed as building blocks in the preparation of the compounds of formula I. If not commercially available, such indole derivatives can be prepared according to the well-known standard procedures for the formation of the indole ring system such as, for example, the Fischer indole synthesis, the Madelung indole synthesis, the indole synthesis starting from N-chloroanilines and э-ketosulfides described by Gassman et al., the Bischler indole synthesis, the Reissert indole synthesis, or the Nenitzescu indole synthesis. By choosing suitable precursor molecules, these indole syntheses allow the introduction of a variety of substituents into the various positions of the indole system which can then be chemically modified in order to finally arrive at the molecule of the formula I having the desired substituent pattern. As one of the comprehensive reviews in which numerous details and literature references on the chemistry of indoles and on synthetic procedures for their preparation can be found, W. J. Houlihan (ed.), "Indoles, Part One", volume 25, 1972, out of the series "The Chemistry of Heterocyclic Compounds", A. Weissberger and E. C. Taylor (ed.), John Wiley & Sons, is preferred.

Examples of the many commercially available indole derivatives that are suitable as starting materials for the preparation of the compounds of formula I, are the following (the acids listed are commercially available as the free acids themselves and/or as the methyl or ethyl esters): indole-2-carboxylic acid, indole-3-carboxylic acid, indole-3-acetic acid, 3-(3-indolyl)-propionic acid, indole-2,3-dicarboxylic acid, 3-ethoxycarbonylmethyl-indole-2-carboxylic acid, 3-methyl-indole-2-carboxylic acid, 5-fluoroindole-2-carboxylic acid, 5-chloro-indole-2-carboxylic acid, 5-bromo-indole-2-carboxylic acid, 5-methoxy-indole-2-carboxylic acid, 5-hydroxy-indole-2-carboxylic acid, 5,6-dimethoxy-indole-2-carboxylic acid, 4-benzyloxy-indole-2-carboxylic acid, 5-benzyloxy-indole-2-carboxylic acid, 6-benzyloxy-5-methoxy-indole-2-carboxylic acid, 5-methyl-indole-2-carboxylic acid, 5-ethyl-indole-2-carboxylic acid, 7-methyl-indole-2-carboxylic acid, 4-methoxy-indole-2-carboxylic acid, 6-methoxy-indole-2-carboxylic acid, 4,6-dimethoxy-indole-2-carboxylic acid, 4,6-dichloro-indole-2-carboxylic acid, 5-nitro-indole-2-carboxylic acid, 5-methylsulfonyl-indole-2-carboxylic acid, 7-nitro-indole-2-carboxylic acid, 7-tert-butylcarbonylamino-indole-2-carboxylic acid, 7-(3-trifluoro-methylbenzoylamino)-indole-2-carboxylic acid, 7-(4-methoxyphenylsulfonylamino)-indole-2-carboxylic acid, 5-bromo-3-methyl-indole-2-carboxylic acid, 3-(2-carboxyethyl)-6-chloroindole-2-carboxylic acid.

If starting indole derivatives are to be synthesized this can be done, for example, according to the well known indole syntheses mentioned above. In the following they are explained briefly, however, they are standard procedures comprehensively discussed in the literature, and are well known to one skilled in the art.

The Fischer indole synthesis comprises the acid cyclization of phenylhydrazones, for example of the general formula 2,

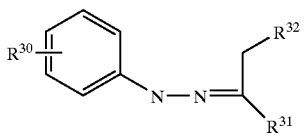

2 which can be obtained by various methods and in which $R^{30}$, $R^{31}$ and $R^{32}$ and n can have a wide variety of denotations. Besides hydrogen and alkyl, $R^{31}$ and $R^{32}$ can especially denote ester groups or methyl or ethyl groups or 2,2,2-trifluoroethyl groups carrying an ester group as substituent thus allowing the introduction into the indole molecule of the $(CH_2)_p$—CO moiety occurring in the groups $R^2$ and/or $R^3$ in the compounds of the formula I. As examples of the many literature references describing the synthesis of indole derivatives according to the Fischer synthesis, besides the above-mentioned book edited by Houlihan, the following articles are mentioned: F. G. Salituro et al., J. Med. Chem. 33 (1990) 2944; N. M. Gray et al., J. Med. Chem. 34 (1991) 1283; J. Sh. Chikvaidze et al., Khim. Geterotsikl. Soedin. (1991) 1508; S. P. Hiremath et al., Indian J. Chem. 19 (1980) 770; J. Bornstein, J. Amer. Chem. Soc. 79 (1957) 1745; S. Wagaw, B. Yang and S. Buchwald, J. Am. Chem. Soc. 121 (1999) 10251 or by Y. Murakami, Y. Yokoyama, T. Miura, H. Hirasawa Y. Kamimura and M. Izaki, Heterocycles 22 (1984) 1211.

The Reissert indole synthesis comprises the reductive cyclization of o-nitrophenylpyruvic acids or esters thereof, for example of the general formula 3,

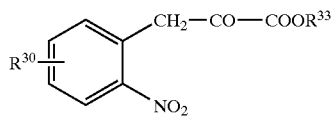

3 in which the groups $R^{30}$ can have a wide variety of denotations and can be present in all positions of the benzene ring. The Reissert indole synthesis leads to derivatives of indole-2-carboxylic acids. The pyruvic acid derivatives of the formula 3 can be obtained by condensation of oxalic acid esters with substituted o-nitrotoluenes. As literature references, besides the above-mentioned book edited by Houlihan and the literature articles mentioned therein, for example the articles by H. G. Lindwall and G. J. Mantell, J. Org. Chem. 18 (1953) 345 or by H. Burton and J. L. Stoves, J. Chem. Soc. (1937) 1726 or by W. Noland, F. Baude, Org. Synth Coll. Vol. V, J. Wiley, New York, (1973) 567 are mentioned. Another method to gain regioselective access to the indole structure involves palladium catalysis, for example o-haloanilines (X=Cl, Br, I) or o-trifluoromethanesufonyloxyanilines (X=OTf) of the general formula 4 can be cyclized to indoles utilizing several alkynes by adopting procedures described by J. Ezquerra, C. Pedregal. C. Lamas, J. Barluenga, M. Pérez, M. Garcia-Martin, J. Gonzalez, J. Org. Chem. 61 (1996) 5805; or F. Ujjainwalla, D. Warner, Tetrahedron Lett. 39 (1998) 5355 and furthermore A. Rodriguez, C. Koradin, W. Dohle, P. Knochel, Angew. Chem. 112 (2000) 2607; or R. Larock, E. Yum, M. Refvik, J. Org. Chem. 63 (1998) 7653; R. Larock, E. Yum, J. Am. Chem. Soc. 113 (1991) 6689; K. Roesch; R. Larock, J. Org. Chem. 66 (2001) 412

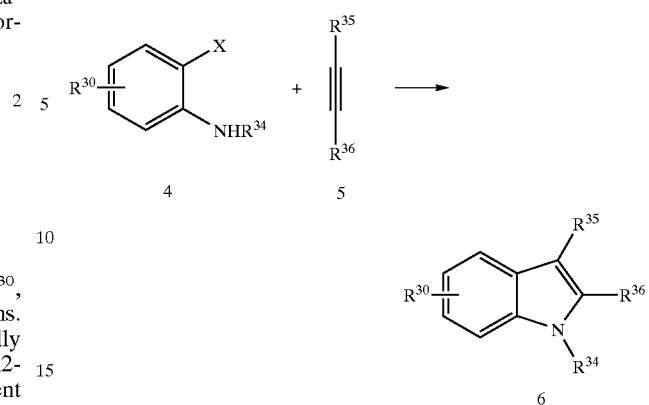

Alternatively the indole structure can be built up by employment of a variety of ketones under palladium catalysis by adopting and modifying a procedure described by C. Chen, D. Liebermann, R. Larsen, T. Verhoeven and P. Reider J. Org. Chem. 62 (1997) 2676 as indicated below:

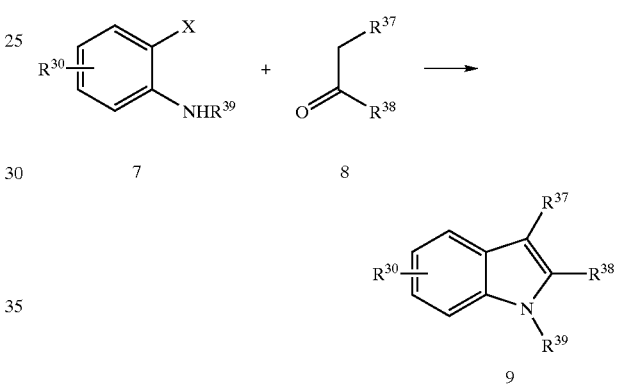

According to the Bischler indole synthesis ∀-anilinoketones, for example of the general formula 10,

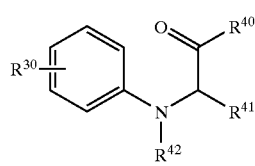

10 can be cyclized to indole derivatives.

The Nenitzescu indole synthesis provides a valuable route to indole-3-carboxylic acid derivatives carrying a hydroxy group in the 5-position. It comprises the reaction of a para-benzoquinone with a ∃-aminocrotonate, for example of the compounds of the formulae 11 and 12.

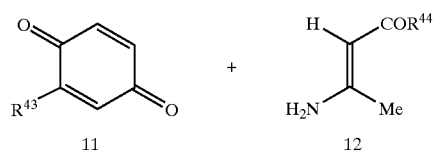

A further route to specifically substituted indole derivatives proceeds via 2,3-dihydroindoles (indolines) which can be easily obtained by reduction of indoles, for example by hydrogenation, or by cyclization of suitable phenylethylamine derivatives. Indolines can undergo a variety of electrophilic aromatic substitution reaction allowing the introduction of various substituents into the benzene nucleus which cannot directly be introduced by such reactions into the benzene nucleus of the indole molecule. The indolines can then be dehydrogenated to the corresponding indoles, for example with reagents like chloranil, or palladium together with a hydrogen acceptor. Again, details on these syntheses can be found in the above-mentioned book edited by Houlihan.

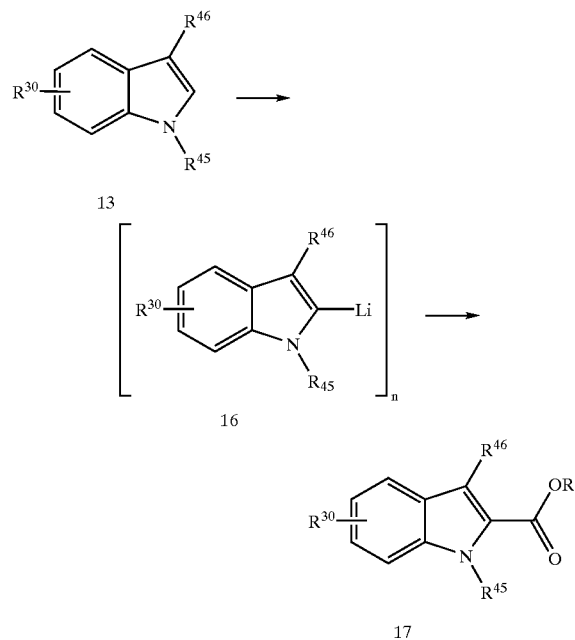

Moreover 2-H-indoles can be converted into the corresponding carboxylic acids or carboxylic esters by lithiation of the 2-position of the indoles of the general formula 13 and subsequent reaction with carbon dioxide or alkylchloroformate according to I. Hasan, E. Marinelli, L. Lin, F. Fowler, A. Levy, J. Org. Chem. 46 (1981)157; T. Kline J. Heterocycl. Chem. 22 (1985) 505; J. -R. Dormoy, A. Heymes, Tetrahedron 49, (1993) 2885; E. Desarbre, S. Coudret, C. Meheust, J. -Y. Mérour, Tetrahedron 53 (1997) 3637 as indicated below:

$R^{45}$ represents hydrogen or a protecting group like, for example, benzenesulfonyl or tert-butoxycarbonyl.

Depending on the substituents in the starting materials, in certain indole syntheses, mixtures of positional isomers may be obtained which, however, can be separated by modern separation techniques like, for example, preparative HPLC.

Further, in order to obtain the desired substituents in the benzene nucleus and in the heterocyclic nucleus of the indole ring system in the formula I, the functional groups introduced into the ring system during the indole synthesis can be chemically modified. For example, indoles carrying a hydrogen atom in the 2-position or the 3-position can also be obtained by saponification and subsequent decarboxylation of indoles carrying an ester group in the respective position. Carboxylic acid groups and acetic acid groups in the 2-position and the 3-position can be converted into their homologues by usual reactions for chain elongation of carboxylic acids. Halogen atoms can be introduced into the 2-position or the 3-position, for example by reacting the respective indolinone with a halogenating agent such as phosphorus pentachloride analogously to the method described by J. C. Powers, J. Org. Chem. 31 (1966) 2627. The starting indolinones for such a synthesis can be obtained from 2-aminophenyl acetic acids. Starting indole derivatives for the preparation of compounds of the formula I carrying a halogen substituent in the 3-position can also be obtained according to procedures described in the literature like the following. For the fluorination of 1 H-indole-2-carboxylic acid ethyl ester derivatives in the 3-position N-fluoro-2,4, 6-trimethylpyridinium triflate is the reagent of choice (T. Umemoto, S. Fukami, G. Tomizawa, K. Harasawa, K. Kawada, K. Tomita J. Am. Chem. Soc. 112 (1990) 8563). Chlorination of 1 H-indole-2-carboxylic acid ethyl ester derivatives in the 3-position by reaction with sulfuryl chloride in benzene yields 3-chloro-1H-indole-2-carboxylic acid ethyl ester (Chem. Abstr. 1962, 3441i-3442b); the same result can obtained by means of NCS (D. Comins, M. Killpack, Tetrahedron Lett. 33 (1989) 4337; M. Brennan, K. Erickson, F. Szmlac, M. Tansey, J. Thornton, Heterocycles 24 (1986) 2879). Bromination of 1H-indole-2-carboxylic acid ethyl ester derivatives in the 3-position can be achieved by reaction with NBS (M. Tani, H. Ikegami, M. Tashiro, T. Hiura, H. Tsukioka, Heterocycles 34 (1992) 2349). Analogously to the procedures described above NIS can be used efficiently for the iodination in the of 1H-indole-2-carboxylic acid ethyl ester derivatives in the 3-position. Furthermore the iodination of 1H-indole-2-carboxylic acid ethyl ester derivatives in the 3-position the use of iodine is efficient (T. Sakamoto, T. Nagano, Y. Kondo, H. Yamanaka Chem. Pharm. Bull. 36 (1988) 2248). Especially the groups present in the indole ring system can be modified by a variety of reactions and thus the desired residues $R^{1a}$, $R^{1b}$, $R^{1c}$, $R^{1d}$ and $R^{1e}$ be obtained. For example, nitro groups can be reduced to amino group with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce or derive the residues $R^{1a-e}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides. Carboxylic acids, carboxylic acid chlorides or carboxylic acid esters can be introduced by procedures described by F. Santangelo, C. Casagrande, G. Norcini, F. Gerli, Synth. Commun. 23 (1993) 2717; P. Beswick, C. Greenwood, T. Mowlem, G. Nechvatal, D. Widdowson, Tetrahedron 44 (1988) 7325; V. Collot, M. Schmitt, P. Marwah, J. Bourguignon, Heterocylces 51 (1999) 2823. Halogens or hydroxy groups—via the triflate or nonaflate—or primary amines—via its diazonium salt—or after interconversion to the corresponding stannane, or boronic acid—present in the indole structure can be converted into a variety of other functional groups like for example —CN, —CF$_3$, Ethers, acids, esters, amides, amines, alkyl- or aryl groups mediated by means of transition metals, namely palladium or nickel catalysts or copper salts and reagents for example referred to below (F.

Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 110 (1998) 2154; B. Yang, S. Buchwald, J. Organomet. Chem. 576 (1999) 125; T. Sakamoto, K. Ohsawa, J. Chem. Soc. Perkin Trans I, (1999), 2323; D. Nichols, S. Frescas, D. Marona-Lewicka, X. Huang, B. Roth, G. Gudelsky, J. Nash, J. Med. Chem, 37 (1994), 4347; P. Lam, C. Clark, S. Saubern, J. Adams, M. Winters, D. Chan, A. Combs, Tetrahedron Lett., 39 (1998) 2941; D. Chan, K. Monaco, R. Wang, M. Winters, Tetrahedron Lett. 39 (1998) 2933; V. Farina, V. Krishnamurthy, W. Scott, The Stille Reaction, Wiley, 1994; A. Klaspars, X. Huang, S. Buchwald, J. Am. Chem. Soc. 124 (2002) 7421; F. Kwong, A. Klapars, S. Buchwald, Org. Lett. 4 (2002) 581; M Wolter, G. Nordmann, G. Job, S. Buchwald, 4 (2002) 973).

Ester groups present in the benzene nucleus can be hydrolyzed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{50}$ or $R^{8'}$ attached to the indole ring system by application of parallel synthesis methodology, beside a variety of reactions, palladium or copper salt catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 110 (1998), 2154; B. Yang, S. Buchwald, J. Organomet. Chem. 576 (1999) 125; P. Lam, C. Clark, S. Saubern, J. Adams, M. Winters, D. Chan, A. Combs, Tetrahedron Lett. 39 (1998) 2941; D. Chan, K. Monaco, R. Wang, M. Winters, Tetrahedron Lett. 39 (1998) 2933; J. Wolfe, H. Tomori, J. Sadight, J. Yin, S. Buchwald, J. Org. Chem. 65 (2000) 1158; V. Farina, V. Krishnamurthy, W. Scott, The Stille Reaction, Wiley, 1994; A. Klaspars, X. Huang, S. Buchwald, J. Am. Chem. Soc. 124 (2002) 7421; F. Kwong, A. Klapars, S. Buchwald, Org. Lett. 4 (2002) 581; M Wolter, G. Nordmann, G. Job, S. Buchwald, 4 (2002) 973).

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to an indole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art. The structural elements present in the residues in the 1-position of the indole ring in the compounds of the formula I and in the $COR^8$ group present in the 2-position and/or in the 3-position of the indole ring can be introduced into the starting indole derivative obtainable as outlined above by consecutive reaction steps using parallel synthesis methodologies like those outlines below using procedures which per se are well known to one skilled in the art.

The residues $R^{8'}$ that can be introduced in formula 14, for example, by condensing a corresponding carboxylic acid of the formula 14 with a compound of the formula $HR^{8'}$, i.e. with an amine of the formula $HN(R^1)R^{2'}$—V-G-M to give a compound of the formula 15. The compound of the formula 15 thus obtained can already contain the desired final groups, i.e. the groups $R^{8'}$ and $R^{50}$ can be the groups —$N(R^1)R^2$—V-G-M and $R^0$-Q- as defined in the formula I, or optionally in the compound of the formula 15 thus obtained subsequently the residue or the residues $R^{8'}$ and the residue $R^{50}$ are converted into the residues —$N(R^1)R^2$—V-G-M and $R^0$-Q-, respectively, to give the desired compound of the formula I.

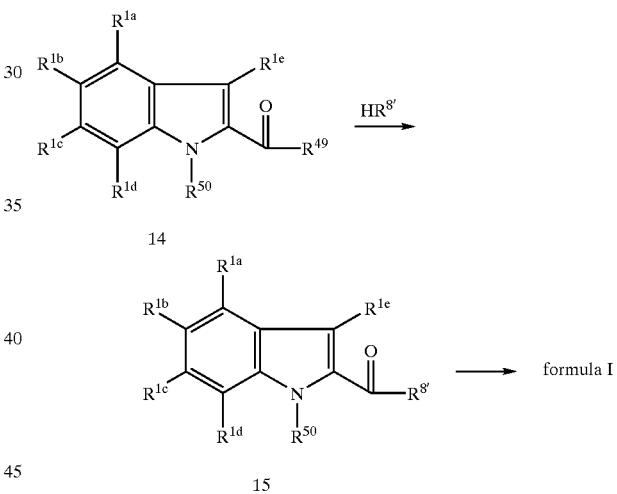

Thus, the residues $R^{8'}$ and the residues $R^{1'}$ and $R^{2'}$—V-G-M contained therein can have the denotations of $R^1$ and $R^2$—V-G-M, respectively, given above or in addition in the residues $R^{1'}$ and $R^{2'}$—V-G-M functional groups can also be present in the form of groups that can subsequently be transformed into the final groups $R^1$ and $R^2$—V-G-M, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As examples of precursor groups nitro groups and cyano groups may be mentioned which can in a later step be transformed into carboxylic acid derivatives or by reduction into aminomethyl groups, or nitro groups which may be transformed by reduction like catalytic hydrogenation into amino groups by reduction. Protective groups can also have the meaning of a solid phase, and cleavage from the solid phase stands for the removal of the protective group. The use of such techniques is known to those skilled in the art (Burgess K (Ed.) Solid Phase Organic Synthesis ,New York: Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{50}$ in the compounds of the formulae 14 and 15 can denote the group $-Q-R^0$ as defined above which finally is to be present in the desired target molecule of the formula I, or it can denote a group which can subsequently be transformed into the group $-Q-R^0$, for example a precursor group or a derivative of the group $-Q-R^0$ in which functional groups are present in protected form, or $R^{50}$ can denote a hydrogen atom or a protective group for the nitrogen atom of the indole ring. Similarly, the residues $R^{1e}$, $R^{1a}$, $R^{1b}$, $R^{1c}$ and $R^{1d}$ in the formulae 14 and 15 have the corresponding definitions of $R^7$, $R^6$, $R^5$, $R^4$, and $R^3$ in formula I as defined above, however, for the synthesis of the compounds of the formula I these residues, too, can in principle be present at the stage of the condensation of a compound of the formula 14 with a compound of the formula $HR^{8'}$ giving a compound of the formula 15 in the form of precursor groups or in protected form.

The residues $R^{49}$ in the compounds of the formula 14 which can be identical or different, can be, for example, hydroxy or $(C_1-C_4)$-alkoxy, i.e., the groups $COR^{49}$ present in the compounds of the formula 14 can be, for example, the free carboxylic acids or esters thereof like alkyl esters as can be the groups $COR^8$ in the compounds of the formula I. The groups $COR^{49}$ can also be any other activated derivative of a carboxylic acid which allows amide formation, ester formation or thioester formation with a compound of the formula $HR^{8'}$. The group $COR^{49}$ can be, for example, an acid chloride, an activated ester like a substituted phenyl ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing $COR^{49}$ in a compound of the formula 14 can be obtained, for example, from an ester group introduced into the indole system during an indole synthesis by standard hydrolysis procedures.

Compounds of the formula I in which a group $COR^8$ is an ester group can also be prepared from compounds of the formula 14 in which $COR^{49}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formula I in which a group $COR^8$ is an amide group can be prepared from amines and compounds of the formula 14 in which $COR^{49}$ is a carboxylic acid group or an ester thereof by common amination reactions. Especially for the preparation of amides the compounds of the formula 14 in which $COR^{49}$ is a carboxylic acid group can be condensed under standard conditions with compounds of the formula $HR^{8'}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyidiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others.

If the residue $-Q-R^0$ present in an indole of the formula I or the residue $R^{50}$ present in an indole of the formula 14, or a residue in which functional groups within the residue $-Q-R^0$ or $R^{50}$ are present in protected form or in the form of a precursor group, have not already been introduced during a preceding step, for example during a synthesis of the indole nucleus, these residues can, for example, be introduced into the 1-position of the indole system by conventional literature procedures well known to one skilled in the art for N-alkylation, reductive amination, N-arylation, N-acylation or N-sulfonylation of ring nitrogen atoms of heterocycles. The starting indole derivative that is to be employed in such a reaction carries a hydrogen atom in the 1-position. N-Alkylation of a ring nitrogen atom can, for example, be performed under standard conditions, preferably in the presence of a base, using an alkylating compound of the formula $LG-Q-R^0$ or of the formula $R^{50}$-LG, wherein the atom in the group Q or in the group $R^{50}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated by a conventional activating agent. For the preparation of compounds in which A is a direct linkage and an aromatic group is directly bonded to the 1-position of the indole system, conventional arylation procedures can be used. For example aryl fluorides like alkyl fluorobonzoates or 4-fluorophenyl methyl sulfones can be employed as arylating agents. Such processes are described, for example, By S. Stabler, Jahangir, Synth. Commun. 24 (1994) 123; I. Khanna, R. Weier, Y. Yu, X. Xu. F. Koszyk, J. Med. Chem. 40 (1997) 1634. Alternatively a wide variety of substituted aryl iodides, aryl bromides or aryl triflates can serve as arylating agents at the 1-position of the indole system in a copper salt or palladium mediated reaction according to R. Sarges, H. Howard, K. Koe, A. Weissmann, J. Med. Chem, 32 (1989) 437; P. Unangst, D. Connor, R. Stabler, R. Weikert, J. Heterocycl. Chem, 24 (1987) 811; G. Tokmakov, I. Grandberg, Tetrahedron 51 (1995) 2091; D. Old, M. Harris, S. Buchwald, Org. Lett. 2 (2000) 1403, G. Mann, J. Hartwig, M. Driver, C. Fernandez-Rivas, J. Am. Chem. Soc. 120 (1998) 827; J. Hartwig, M. Kawatsura, S. Hauk, K. Shaughnessy, L. J. Org. Chem. 64 (1999) 5575. Moreover such arylations can also be accomplished by reaction of a wide range of substituted aryl boronic acids as demonstrated for example by W. Mederski, M. Lefort, M. Germann, D. Kux, Tetrahedron 55(1999) 12757.

In the course of the synthesis the employment of microwave assistance for speeding-up, facilitating or enabling reactions may be beneficial or even required in many cases. Some reactions are for example described by J. L. Krstenansky, I. Cotteril, Curr. Opin. Drug. Disc. & Development., 4(2000), 454; P. Lidstrom, J. Tierney, B. Wathey, J. Westman, Tetrahedron, 57(2001), 9225; M. Larhed, A. Hallberg, Drug Discovery Today, 8 (2001) 406; S. Caddick, Tetrahedron, 51 (1995) 10403.

Preferred methods include, but are not limited to those described in the examples.

The compounds of the present invention are serine protease inhibitors, which inhibit the activity of the blood coagulation enzyme factors Xa and/or factor VIIa. In particular, they are highly active inhibitors of factor Xa. They are specific serine protease inhibitors inasmuch as they do not substantially inhibit the activity of other proteases whose inhibition is not desired. The activity of the compounds of the formula I can be determined, for example, in the assays described below or in other assays known to those skilled in the art. With respect to factor Xa inhibition, a preferred embodiment of the invention comprises compounds which have a Ki☐1 for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty, transient ischemic attacks, stroke, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. In case a pharmaceutical preparation contains two or more compounds of the formula I the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or its physiologically tolerable salts and/or its prodrugs, the pharmaceutical preparations can also contain one or more other therapeutically or prophylactically active ingredients.

As inhibitors of factor Xa and/or factor VIIa the compounds of the formula I and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician.

A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

Conditions in which a compound of the formula I can be favorably used include, for example, cardiovascular disorders, thromboembolic diseases or complications associated, for example, with infection or surgery. The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure, stroke and disseminated intravascular clotting disorder. Examples of related complications associated with surgery are thromboses like deep vein and proximal vein thrombosis, which can occur following surgery. In view of their pharmacological activity the compounds of the invention can replace or supplement other anticoagulant agents such as heparin. The use of a compound of the invention can result, for example, in a cost saving as compared to other anticoagulants.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I and its salts can be used for diagnostic purposes, for example in in vitro diagnoses, and as an auxiliary in biochemical investigations. For example, a compound of the formula I can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formula I or a salt thereof can be used as a probe to detect the location or amount of factor Xa and/or factor VIIa activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

| Abbreviations used: | |
| --- | --- |
| tert-Butyl | tBu |
| 2,2'-bis(diphenylphoshino-1,1'-binaphthyl | Binap |
| Bis-(oxo-3-oxazolidinyl)-phosphoryl chloride | BOP—Cl |
| dibenzylidenacetone | dba |
| Dicyclohexyl-carbodiimide | DCC |
| Dichloromethane | DCM |
| Diethylphosphoryl cyanide | DEPC |
| 4-Dimethyaminopyridine | DMAP |
| N,N-Dimethylformamide | DMF |
| Dimethylsulfoxide | DMSO |
| Ethyl-diisopropyl-amine | DIPEA |
| 1,1'-Bis(diphenylphosphino)ferrocene | DPPF |
| O-(7-Azabenzotriazol-1-yl)-N,N,N',N'-tetramethyluronium-Hexafluorophosphate | HATU |
| N-Bromosuccinimide | NBS |
| N-Chlorosuccinimide | NCS |
| N-Iodosuccinimide | NIS |

-continued

| Abbreviations used: | |
|---|---|
| N-Ethylmorpholine | NEM |
| Methanol | MeOH |
| Room temperature | RT |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

1-[5-(5-Chloro-thiophen-2-yl)-isoxazol-3-ylmethyl]-1H-indole-2-carboxylic acid (1-isopropyl-piperidin-4-yl)-amide

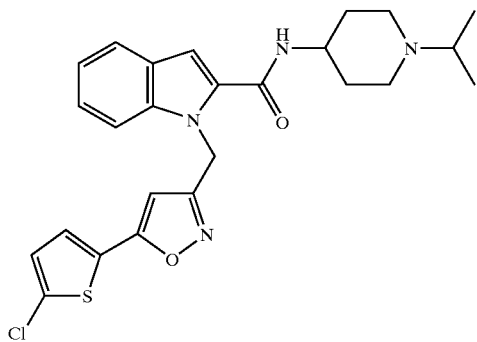

(i) (1-Isopropyl-piperidin-4-yl)-carbamic acid tert-butyl ester

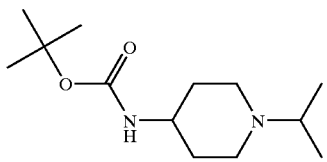

To a solution of 5.0 g Piperidin-4-yl-carbamic acid tert-butyl ester in 15 ml methanol, 7.34 ml acetone, 3.14 g Na(CN)BH₃ and 0.3 ml acetic acid were added. After stirring for 16 h at room temperature the solvent was removed under reduced pressure and the residue was partitioned between 30 ml of water and 30 ml ethyl acetate. The organic layer was washed with saturated Na₂CO₃ solution, water and then dried over Na₂SO₄. The solvent was removed under reduced pressure to give the product as a white solid. Yield: 4.8 g MS (ES⁺): m/e=243.

(ii) 1-Isopropyl-piperidin-4-ylamine

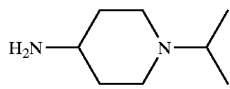

To 4.8 g (1-Isopropyl-piperidin-4-yl)-carbamic acid tert-butyl ester in 15 ml methanol, 20 ml methanolic hydrochloric acid (8M) were added and the mixture was stirred for 16 h. Removal of the solvent under reduced pressure, followed by removal of residual volatiles by twice coevaporating with toluene, gave the product. Yield: 5.42 g MS (ES⁺): m/e=143.

(iii) 1H-Indole-2-carboxylic acid methyl ester 2 g of 1H-Indole-2-carboxylic acid was dissolved in 15 ml of methanolic hydrochloric acid (8M) and the mixture was stirred at RT for 16 h. After removal of the solvent under reduced pressure, reisidual volatiles were removed by codistillation twice with 10 ml toluene. The remaining slightly yellow solid was subjected to the subsequent reaction without further purification.
Yield: 2.3 g.

(iv) 1-[5-(5-Chloro-thiophen-2-yl)-isoxazol-3-ylmethyl]-1H-indole-2-carboxylic acid methyl ester

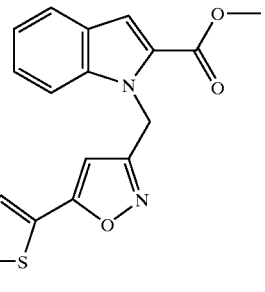

To a solution of 244.2 mg 1H-Indole-2-carboxylic acid methyl ester in 2 ml DMF, 52.2 mg sodium hydride (60% in oil) were added at RT. After stirring for 30 min 500 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2] were added and the mixture was heated for 1 h at 80° C. After subsequent cooling of the reaction to RT and addition of 5 ml water the mixture was filtered through a chem elut® cartridge by elution with ethyl acetate. After concentration under reduced pressure the residue was directly subjected to the subsequent saponification reaction without further purification.
Yield: 288 mg MS (ES⁺): m/e=373.

(v) 1-[5-(5-Chloro-thiophen-2-yl)-isoxazol-3-ylmethyl]-1H-indole-2-carboxylic acid To a solution of 288 mg 1-[5-(5-Chloro-thiophen-2-yl)-isoxazol-3-ylmethyl]-1H-indole-2-carboxylic acid methyl ester in 10 ml THF, 3 ml water and 57.0 mg lithium hydroxide monohydrate were added. After stirring for 2 h at 60° C. the reaction was cooled to RT. The mixture was acidified with half concentrated hydrochloric acid. The resulting precipitate was collected by filtration and washed with 3 ml water. The product was obtained as a white solid which was dried under reduced pressure.
Yield: 253 mg MS (ES⁺): m/e=359, chloro pattern.

(vi) 1-[5-(5-Chloro-thiophen-2-yl)-isoxazol-3-ylmethyl]-1H-indole-2-carboxylic acid (1-isopropyl-piperidin-4-yl)-amide.

To a solution of 117 mg 1-[5-(5-Chloro-thiophen-2-yl)-isoxazol-3-ylmethyl]-1H-indole-2-carboxylic acid in 1 ml DCM and 0.17 ml NEt₃, 76 mg BOP-Cl were added at RT and the mixture was stirred for 30 min. After addition of 81 mg 1-Isopropyl-piperidin-4-ylamine hydrochloride the mixture was stirred over night. After removal of the solvent under reduced pressure the residue was purified by preparative HPLC (C18 reverse phase column, elution with a H₂O/MeCN gradient with 0.1% TFA). The fractions containing the product were evaporated and lyophilized to yield a white solid. The product was obtained as its trifluoroacetate salt.
Yield: 93 mg MS (ES⁺): m/e=483, chloro pattern.

Analogously to example 1 the following compounds were prepared by a similar procedure:

| Example | Structure | MS (ESI+) |
|---|---|---|
| 2 | 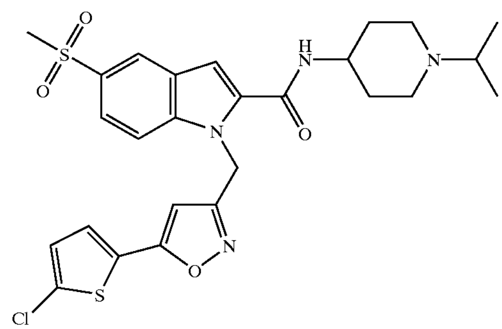 | 561, chloro pattern |
| 3 | 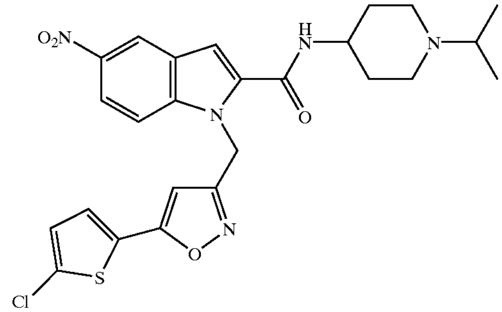 | 528, chloro pattern |
| 4 | 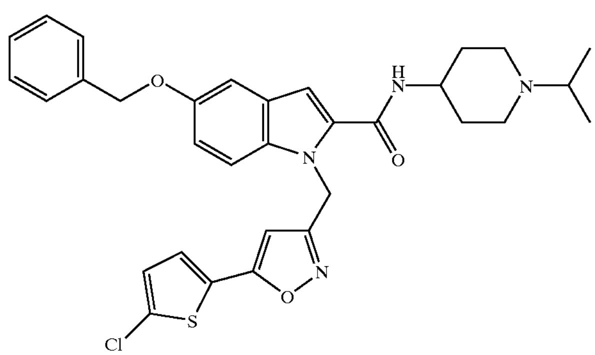 | 589, chloro pattern |
| 5 | 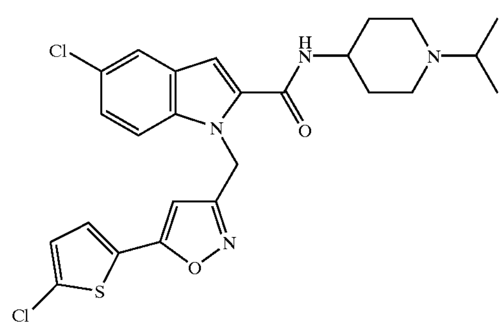 | 517, chloro pattern |

-continued
| Example | Structure | MS (ESI+) |
|---------|-----------|-----------|
| 6 | 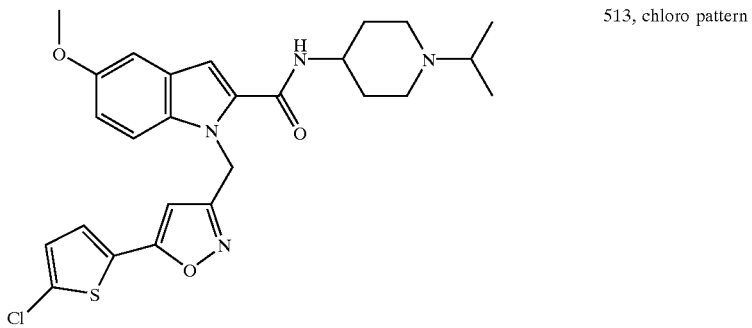 | 513, chloro pattern |
| 7 | 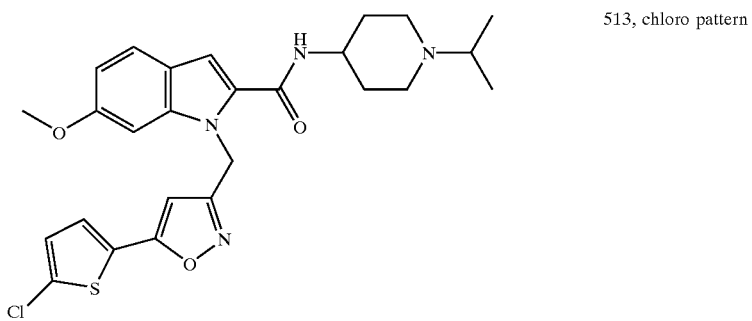 | 513, chloro pattern |
| 8 | 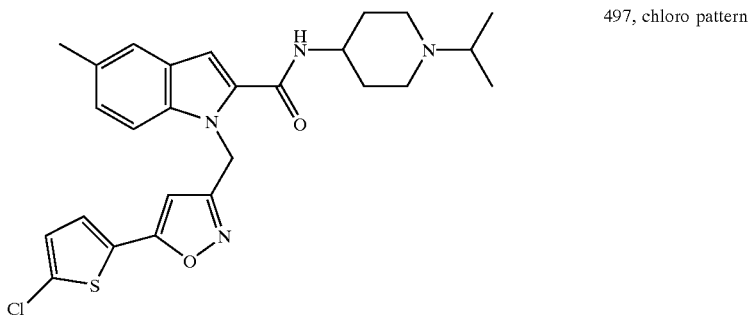 | 497, chloro pattern |
| 9 | 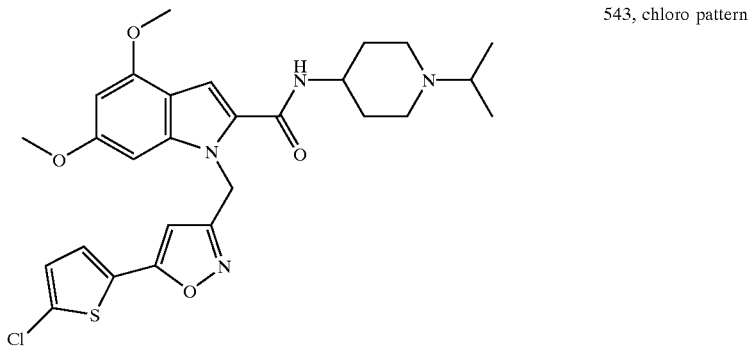 | 543, chloro pattern |

-continued

| Example | Structure | MS (ESI+) |
|---|---|---|
| 10 | 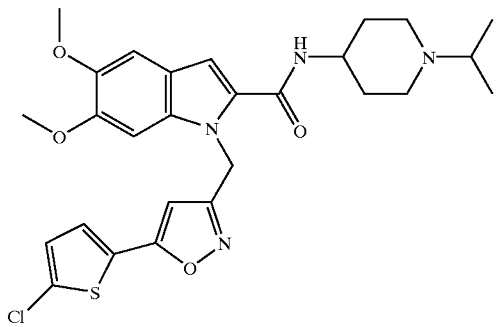 | 543, chloro pattern |
| 11 | 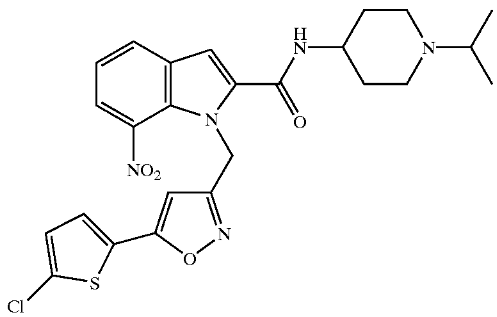 | 528, chloro pattern |
| 12 | 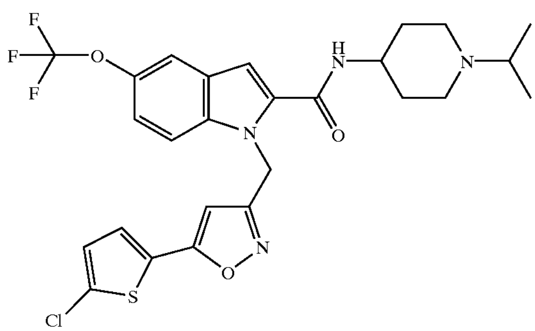 | 567, chloro pattern |
| 13 | 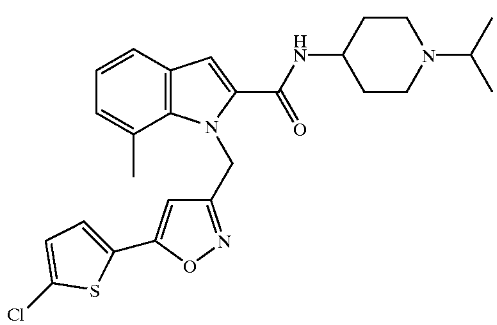 | 497, chloro pattern |
| 14 | 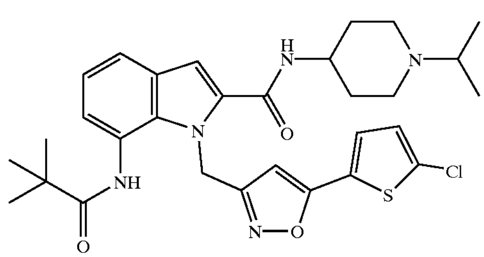 | 582, chloro pattern |

-continued

| Example | Structure | MS (ESI+) |
|---|---|---|
| 15 | 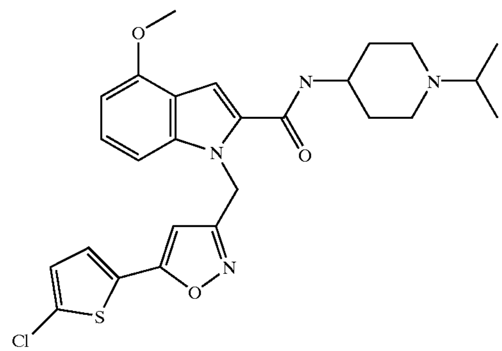 | 513, chloro pattern |
| 16 | 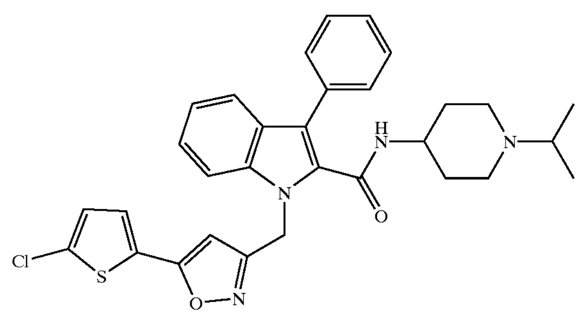 | 559, chloro pattern |
| 17 | 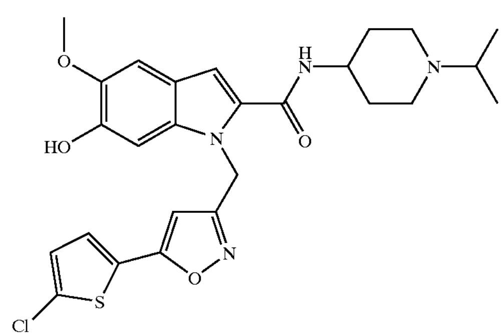 | 529, chloro pattern |
| 18 | 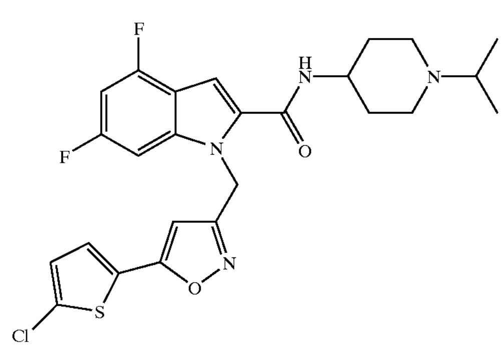 | 519, chloro pattern |

-continued

| Example | Structure | MS (ESI+) |
|---|---|---|
| 19 | 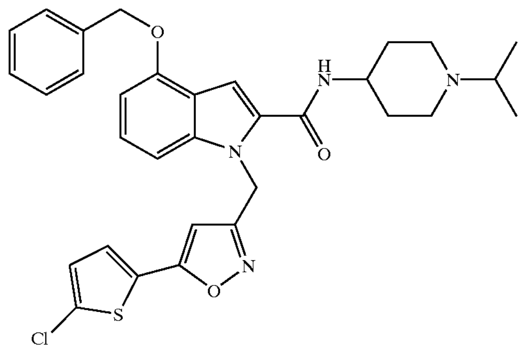 | 589, chloro pattern |
| 20 | 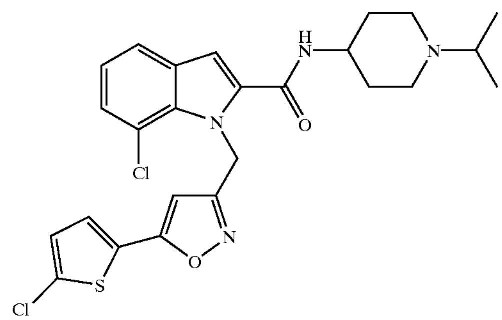 | 517, chloro pattern |
| 21 | 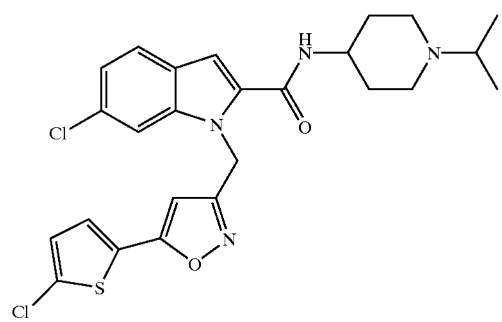 | 517, chloro pattern |
| 22 | 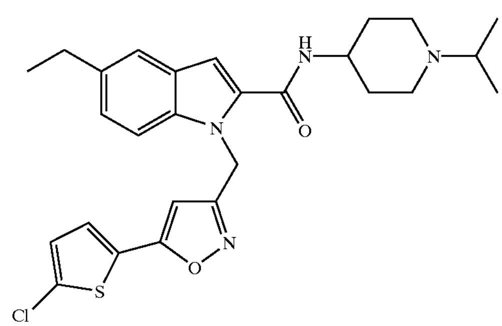 | 511, chloro pattern |

-continued
| Example | Structure | MS (ESI+) |
|---|---|---|
| 23 | 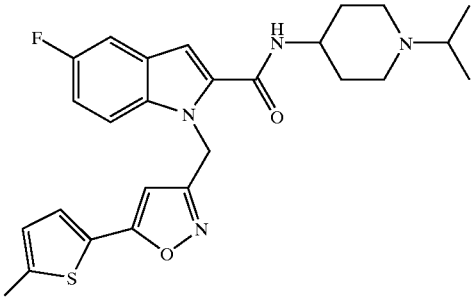 | 501, chloro pattern |
| 24 | 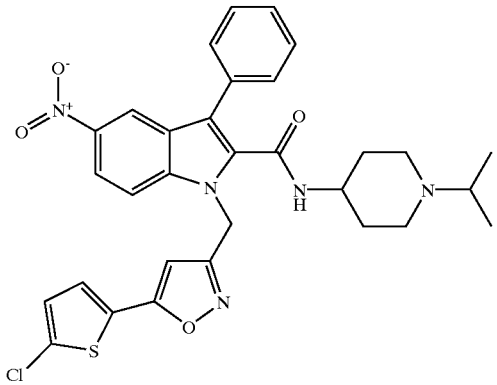 | 604, chloro pattern |
| 25 | 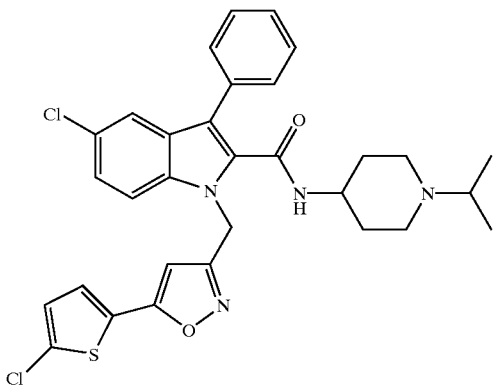 | 593, chloro pattern |
| 26 | 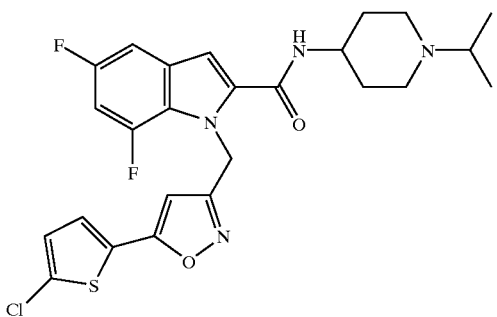 | 519, chloro pattern |

| Example | Structure | MS (ESI+) |
|---|---|---|
| 27 | 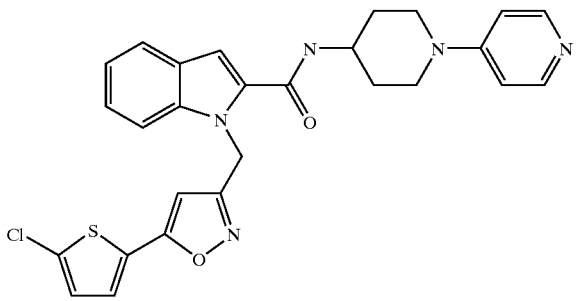 | 573, chloro pattern |

Example 28

1-[5-(5-Chloro-thiophen-2-yl)-isoxazol-3-ylmethyl]-1H-indole-2-carboxylic acid (3,4,5,6-tetrahydro-2H-[1,4']bipyridinyl-4-yl)-amide

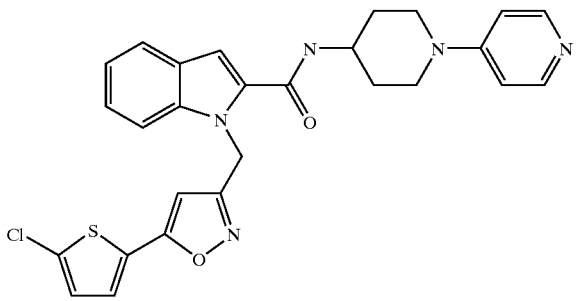

(i) (3,4,5,6-Tetrahydro-2H-[1,4']bipyridinyl-4-yl)-carbamic acid tert-butyl ester

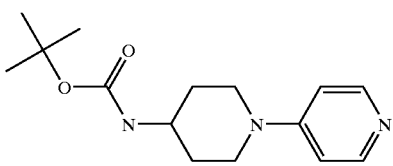

A solution of 3 g Piperidin-4-yl-carbamic acid tert-butyl ester and 2.5 g 4-Chloropyridine in 9 ml n-butanol/water/NEt₃ 1:1:1 was heated at 100° C. for 48 h. The solution was cooled to RT, diluted with DCM and was washed with NaHCO₃ solution and then with water. The organic layer was dried over Na₂SO₄ and the solvent was removed under reduced pressure. Chromatographic purification of the residue on silica gel with DCM as eluent gave after evaporation of the fractions containing the product a white foam. Yield 1.7 g.

(ii) 3,4,5,6-Tetrahydro-2H-[1,4']bipyridinyl-4-ylamine

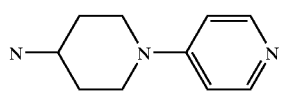

To a solution of 4 g (3,4,5,6-Tetrahydro-2H-[1,4']bipyridinyl-4-yl)-carbamic acid tert-butyl ester in 4 ml DCM, 12 ml TFA was added at RT. After stirring for 20 h the solution was diluted with 20 ml of toluene and was evaporated under reduced pressure. The residue was codistilled twice with toluene and was used in the subsequent reactions without further purification. The product was obtained as its trifluoroacetate salt.

Yield: 2.7 g.

(iii) 1-[5-(5-Chloro-thiophen-2-yl)-isoxazol-3-ylmethyl]-1H-indole-2-carboxylic acid (3,4,5,6-tetrahydro-2H-[1,4']bipyridinyl-4-yl)-amide.

The title compound was prepared analogously to example 1 with the difference that 3,4,5,6-Tetrahydro-2H-[1,4']bipyridinyl-4-ylamine was used instead of 1-Isopropyl-piperidin-4-ylamine.

MS (ESI+): m/e=518, chloro pattern.

Example 29

1-[5-(5-Chloro-thiophen-2-yl)-isoxazol-3-ylmethyl]-7-methyl-1H-indole-2-carboxylic acid (3,4,5,6-tetrahydro-2H-[1,4']bipyridinyl-4-yl)-amide

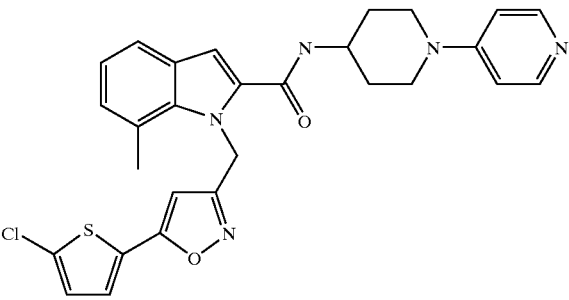

The title compound was prepared analogously to example 28 with the difference that 7-Methyl-1H-indole-2-carboxylic acid was used instead of 1H-Indole-2-carboxylic acid.

MS (ESI+): m/e=532, chloro pattern.

Example 30

1-[5-(5-Chloro-thiophen-2-yl)-isoxazol-3-ylmethyl]-5-nitro-1H-indole-2-carboxylic acid (3,4,5,6-tetrahydro-2H-[1,4']bipyridinyl-4-yl)-amide

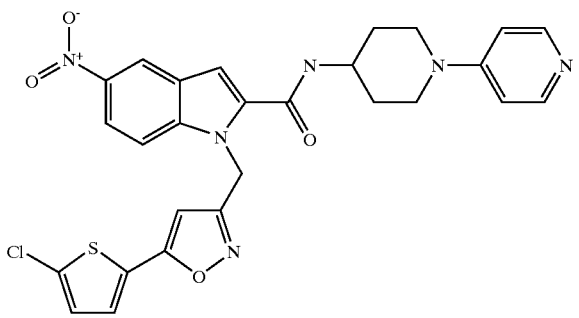

The title compound was prepared analogously to example 28 with the difference that 5-Nitro-1H-indole-2-carboxylic acid was used instead of 1H-Indole-2-carboxylic acid.

MS (ESI+): m/e=563, chloro pattern.

Example 31

{1-[5-(5-Chloro-thiophen-2-yl)-isoxazol-3-ylmethyl]-1H-indol-2-yl}-[4-(pyridin-4-ylamino)-piperidin-1-yl]-methanone

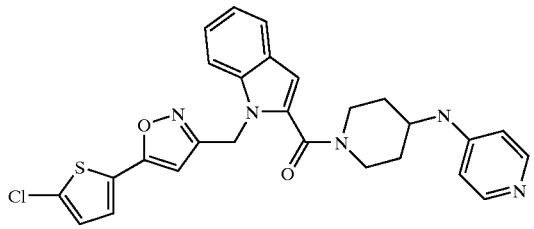

(i) 4-(Pyridin-4-ylamino)-piperidine-1-carboxylic acid tert-butyl ester

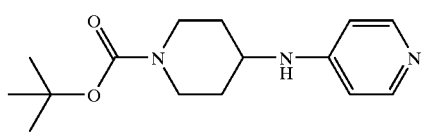

A solution of 2.5 g 4-Amino-piperidine-1-carboxylic acid tert-butyl ester and 2.5 g 4-chloropyridine in 9 ml n-butanol/water/NEt₃ 1:1:1 was heated at 100° C. for 85 h. Then the solution was cooled to RT was diluted with DCM and was washed with NaHCO₃ solution and water. The organic layer was dried over Na₂SO₄ and the solvent was removed under reduced pressure. Chromatographic purification of the residue on silica gel with DCM as eluent gave after evaporation of the fractions containing the product, a white foam. Yield 1.7 g.

(ii) Piperidin-4-yl-pyridin-4-yl-amine

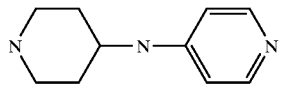

To a solution of 1.7 4-(Pyridin-4-ylamino)-piperidine-1-carboxylic acid tert-butyl ester in 4 ml DCM, 12 ml TFA was added at RT. After stirring for 20 h the solution was diluted with 20 ml of toluene and was evaporated under reduced pressure. The residue was codistilled twice with toluene and was used in the subsequent reactions without further purification. The product was obtained as its trifluoroacetate salt. Yield: 4.0 g.

(iii) {1-[5-(5-Chloro-thiophen-2-yl)-isoxazol-3-ylmethyl]-1H-indol-2-yl}-[4-(pyridin-4-ylamino)-piperidin-1-yl]-methanone The title compound was prepared analogously to example 1 with the difference that Piperidin-4-yl-pyridin-4-yl-amine was used instead of 1-Isopropyl-piperidin-4-ylamine.

MS (ESI+): m/e=518, chloro pattern.

Example 32

{1-[5-(5-Chloro-thiophen-2-yl)-isoxazol-3-ylmethyl]-5-nitro-1H-indol-2-yl}-[4-(pyridin-4-ylamino)-piperidin-1-yl]-methanone

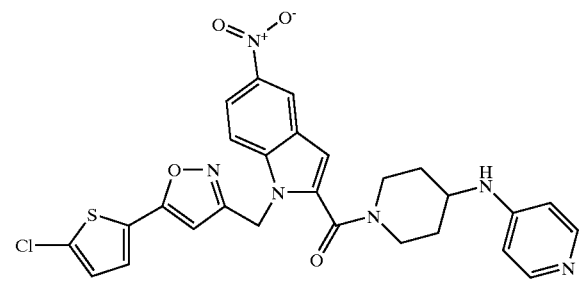

The title compound was prepared analogously to example 31 with the difference that 5-Nitro-1H-indole-2-carboxylic acid was used instead of 1H-Indole-2-carboxylic acid.

MS (ESI+): m/e=563, chloro pattern.

Example 33

{1-[5-(5-Chloro-thiophen-2-yl)-isoxazol-3-ylmethyl]-7-methyl-1H-indol-2-yl}-[4-(pyridin-4-ylamino)-piperidin-1-yl]-methanone

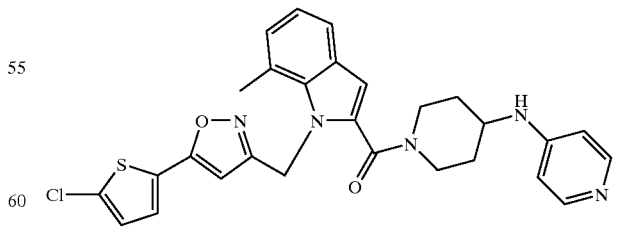

The title compound was prepared analogously to example 31 with the difference that 7-Methyl-1H-indole-2-carboxylic acid was used instead of 1H-Indole-2-carboxylic acid.

MS (ESI+): m/e=532, chloro pattern.

Example 34

{1-[5-(5-Chloro-thiophen-2-yl)-isoxazol-3-ylmethyl]-1H-indol-2-yl}-(4-isopropylamino-piperidin-1-yl)-methanone

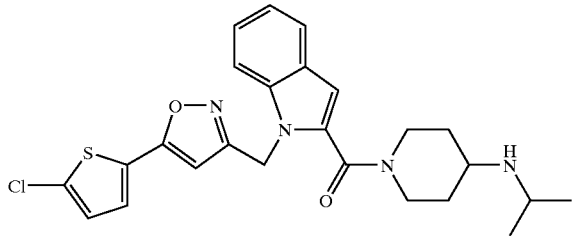

(i) 4-Isopropylamino-piperidine-1-carboxylic acid tert-butyl ester

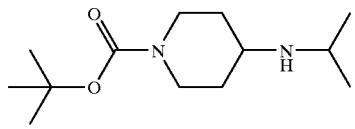

To a solution of 1.5 g 4-Amino-piperidine-1-carboxylic acid tert-butyl ester in 20 ml acetonitrile, 2.6 ml acetone, 0.94 g Na(CN)BH$_3$ and 0.3 ml acetic acid were added. After stirring for 16 h at RT the solvent was removed under reduced pressure and the residue was partitioned between 30 ml of water and 30 ml of ethyl acetate. The organic layer was washed with saturated Na$_2$CO$_3$ solution, water and was dried over Na$_2$SO$_4$. Removal of the solvent under reduced pressure yields a white solid. Yield: 2.8 g MS (ES$^+$): m/e=243.

(ii) Isopropyl-piperidin-4-yl-amine

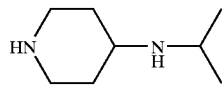

To a solution of 2.8 g 4-Isopropylamino-piperidine-1-carboxylic acid tert-butyl ester in 8 ml DCM, 4 ml TFA was added at RT. After stirring for 20 h the solution was diluted with 20 ml of toluene and was evaporated under reduced pressure. The residue was codistilled twice with toluene and was used in the subsequent reactions without further purification. The product was obtained as its trifluoroacetate salt. Yield: 4.4 g MS (ES$^+$): m/e=143.

(iii) {1-[5-(5-Chloro-thiophen-2-yl)-isoxazol-3-ylmethyl]-1H-indol-2-yl}-(4-isopropylamino-piperidin-1-yl)-methanone The title compound was prepared analogously to example 1 with the difference that Isopropyl-piperidin-4-yl-amine was used instead of 1-Isopropyl-piperidin-4-ylamine.

MS (ESI+): m/e=483, chloro pattern.

Example 35

{1-[5-(5-Chloro-thiophen-2-yl)-isoxazol-3-ylmethyl]-7-methyl-1H-indol-2-yl}-(4-isopropylamino-piperidin-1-yl)-methanone

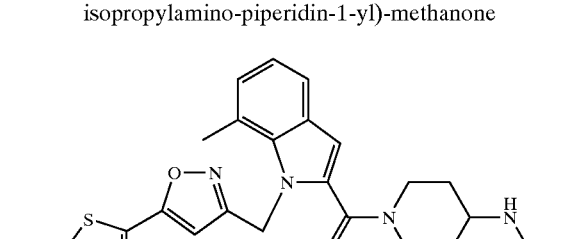

The title compound was prepared analogously to example 34 with the difference that 7-Methyl-1H-indole-2-carboxylic acid was used instead of 1H-Indole-2-carboxylic acid.

MS (ESI+): m/e=497, chloro pattern.

Example 36

1-[5-(5-Chloro-thiophen-2-yl)-isoxazol-3-ylmethyl]-1H-indole-2-carboxylic acid (1-ethyl-piperidin-4-yl)-amide

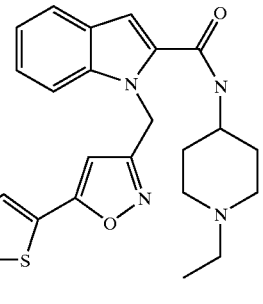

(i) (1-Ethyl-piperidin-4-yl)-carbamic acid tert-butyl ester

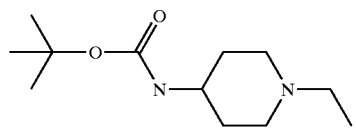

To a solution of 5 g Piperidin-4-yl-carbamic acid tert-butyl ester in 20 ml methanol, 5.6 ml acetaldehyde, 3.2 g Na(CN)BH$_3$ and 3.2 g acetic acid were added. After stirring for 16 h at RT the solvent was removed under reduced pressure and the residue was partitioned between 30 ml of water and 200 ml of ethyl acetate. The organic layer was washed with saturated Na$_2$CO$_3$ solution, water and then it was dried over Na$_2$SO$_4$. Removal of the solvent under reduced pressure gave a white solid. Yield: 4.4 g.

(ii) 1-Ethyl-piperidin-4-ylamine

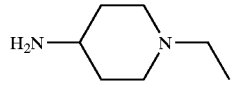

To 4.4 g (1-Ethyl-piperidin-4-yl)-carbamic acid tert-butyl ester in 15 ml methanol, 20 ml of methanolic hydrochloric acid (8M) was added and the mixture was stirred for 16 h.

Removal of the solvent under reduced pressure gave a white solid, which was coevaporated twice with 20 ml toluene. The product was obtained as its hydrochloride.

Yield: 4.3 g.

(iii) 1-[5-(5-Chloro-thiophen-2-yl)-isoxazol-3-ylmethyl]-1H-indole-2-carboxylic acid (1-ethyl-piperidin-4-yl)-amide The title compound was prepared analogously to example 1 with the difference that 1-Ethyl-piperidin-4-ylamine was used instead of 1-Isopropyl-piperidin-4-ylamine.

MS (ESI+): m/e=469, chloro pattern.

Example 37

1-[5-(5-Chloro-thiophen-2-yl)-isoxazol-3-ylmethyl]-7-methyl-1H-indole-2-carboxylic acid (1-ethyl-piperidin-4-yl)-amide

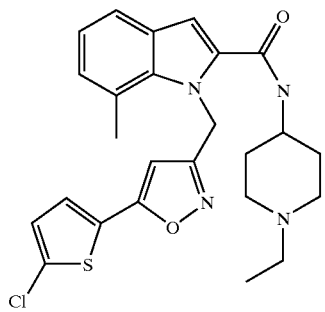

The title compound was prepared analogously to example 36 with the difference that 7-methyl-1H-indole-2-carboxylic acid was used instead of 1H-Indole-2-carboxylic acid.

MS (ESI+): m/e=483, chloro pattern.

Example 38

{1-[5-(5-Chloro-thiophen-2-yl)-isoxazol-3-ylmethyl]-1H-indol-2-yl}-(4-pyrrolidin-1-yl-piperidin-1-yl)-methanone

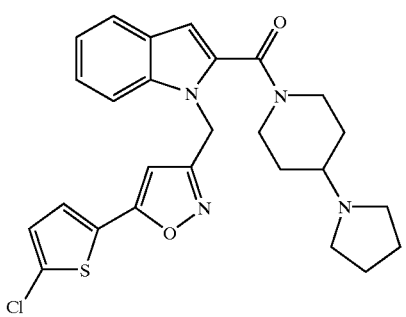

The title compound was prepared analogously to example 1 with the difference that 4-Pyrrolidin-1-yl-piperidine was used instead of 1-Isopropyl-piperidin-4-ylamine.

MS (ESI+): m/e=509, chloro pattern.

Example 39

{1-[5-(5-Chloro-thiophen-2-yl)-isoxazol-3-ylmethyl]-1H-indol-2-yl}-[4-(1-methyl-piperidin-4-yl)-piperazin-1-yl]-methanone

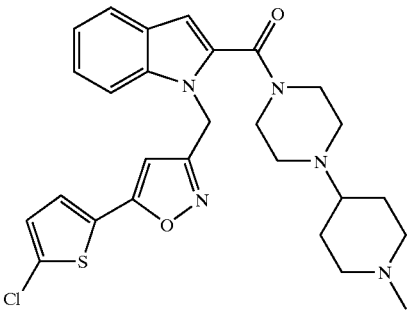

The title compound was prepared analogously to example 1 with the difference that 1-(1-Methyl-piperidin-4-yl)-piperazine was used instead of 1-Isopropyl-piperidin-4-ylamine.

MS (ESI+): m/e=524, chloro pattern.

Example 40

[1,4']Bipiperidinyl-1'-yl-{1-[5-(5-chloro-thiophen-2-yl)-isoxazol-3-ylmethyl]-1H-indol-2-yl}-methanone

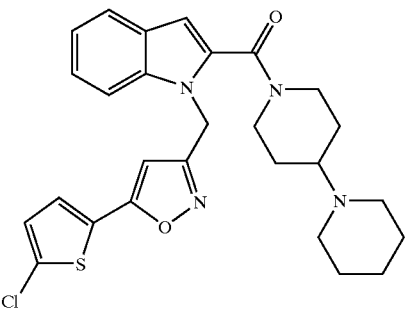

The title compound was prepared analogously to example 1 with the difference that [1,4']bipiperidinyl was used instead of 1-Isopropyl-piperidin-4-ylamine.

MS (ESI+): m/e=523, chloro pattern.

Example 41

1-[5-(5-Chloro-thiophen-2-yl)-isoxazol-3-ylmethyl]-1H-indole-2-carboxylic acid (3-pyridin-4-yl-4,5-dihydro-isoxazol-5-ylmethyl)-amide

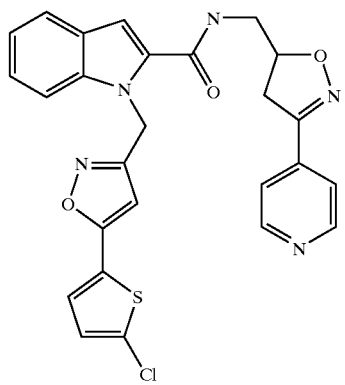

The title compound was prepared analogously to example 1 with the difference that C-(3-Pyridin-4-yl-4,5-dihydro-isoxazol-5-yl)-methylamine was used instead of 1-Isopropyl-piperidin-4-ylamine. MS (ESI+): m/e=518, chloro pattern.

Example 42

1-[5-(5-Chloro-thiophen-2-yl)-isoxazol-3-ylmethyl]-1H-indole-2-carboxylic acid (4-amino-quinazolin-7-ylmethyl)-amide

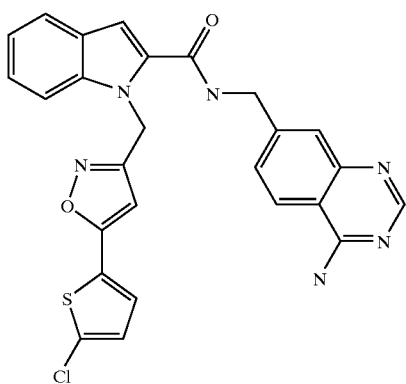

The title compound was prepared analogously to example 1 with the difference that 7-Aminomethyl-quinazolin-4-ylamine [Ewing, William R. et al. PCT Int. Appl. (2001), 460 pp. WO 0107436 A2] was used instead of 1-Isopropyl-piperidin-4-ylamine.

MS (ESI+): m/e=515, chloro pattern.

Example 43

{1-[5-(5-Chloro-thiophen-2-yl)-isoxazol-3-ylmethyl]-1H-indol-2-yl}-(4-pyridin-4-ylmethyl-piperazin-1-yl)-methanone

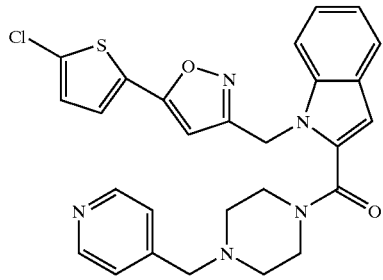

The title compound was prepared analogously to example 1 with the difference that 1-Pyridin-4-ylmethyl-piperazine was used instead of 1-Isopropyl-piperidin-4-ylamine.

MS (ESI+): m/e=518, chloro pattern.

Example 44

1-[5-(5-Chloro-thiophen-2-yl)-isoxazol-3-ylmethyl]-1H-indole-2-carboxylic acid 3,5-dichloro-benzylamide

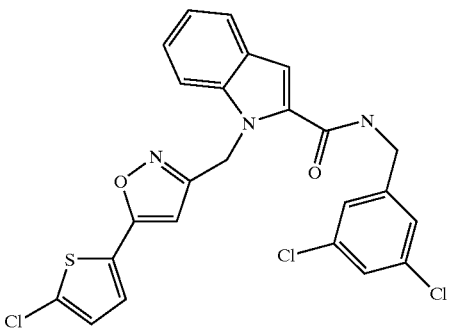

The title compound was prepared analogously to example 1 with the difference that 3,5-Dichloro-benzylamine was used instead of 1-Isopropyl-piperidin-4-ylamine.

MS (ESI+): m/e=516, chloro pattern.

Example 45

1-[5-(5-Chloro-thiophen-2-yl)-isoxazol-3-ylmethyl]-1H-indole-2-carboxylic acid (4-tert-butyl-phenyl)-amide

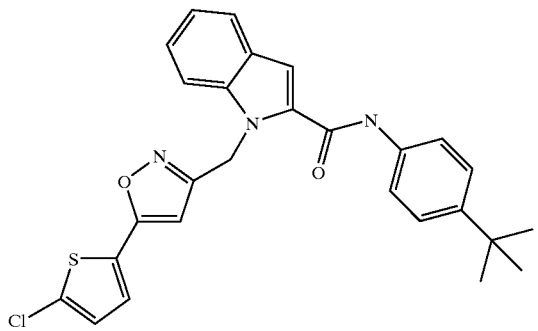

The title compound was prepared analogously to example 1 with the difference that 4-tert-Butyl-phenylamine was used instead of 1-Isopropyl-piperidin-4-ylamine.

MS (ESI+): m/e=490, chloro pattern.

Example 46

1-[5-(5-Chloro-thiophen-2-yl)-isoxazol-3-ylmethyl]-1H-indole-2-carboxylic acid (1-isopropyl-piperidin-4-ylmethyl)-amide

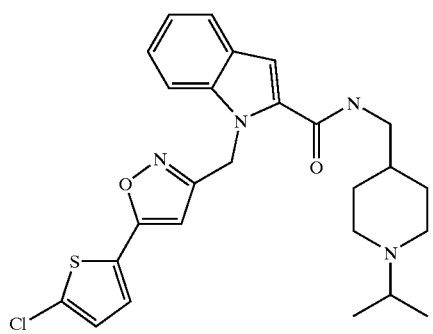

(i) (1-Isopropyl-piperidin-4-ylmethyl)-carbamic acid tert-butyl ester

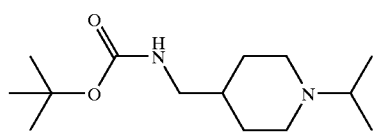

To a solution of 1.0 g Piperidin-4-ylmethyl-carbamic acid tert-butyl ester in 20 ml acetonitrile, 2.6 ml acetone and 586 mg Na(CN)BH$_3$ were added. After stirring for 16 h at RT the solvent was removed under reduced pressure and the residue was partitioned between 30 ml of water and 30 ml of ethyl acetate. The organic layer was washed with saturated Na$_2$CO$_3$ solution, water and was dried over Na$_2$SO$_4$. Removal of the solvent under reduced pressure gave a white solid.

Yield: 802 mg.

(ii) C-(1-Isopropyl-piperidin-4-yl)-methylamine

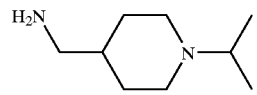

To a solution of 802 mg (1-Isopropyl-piperidin-4-ylmethyl)-carbamic acid tert-butyl ester in 5 ml DCM, 4 ml TFA was added at RT. After stirring for 20 h the solution was diluted with 20 ml of toluene and was evaporated under reduced pressure. The residue was codistilled twice with toluene and was used in the subsequent reactions without further purification. The product was obtained as its trifluoroacetate salt. Yield: 1.7 g (iii) 1-[5-(5-Chloro-thiophen-2-yl)-isoxazol-3-ylmethyl]-1H-indole-2-carboxylic acid (1-isopropyl-piperidin-4-ylmethyl)-amide.

The title compound was prepared analogously to example 1 with the difference that C-(1-Isopropyl-piperidin-4-yl)-methylamine was used instead of 1-Isopropyl-piperidin-4-ylamine.

MS (ESI+): m/e=496, chloro pattern.

Example 47

1-[5-(5-Chloro-thiophen-2-yl)-isoxazol-3-ylmethyl]-1H-indole-2-carboxylic acid (3,4,5,6-tetrahydro-2H-[1,4']bipyridinyl-4-ylmethyl)-amide

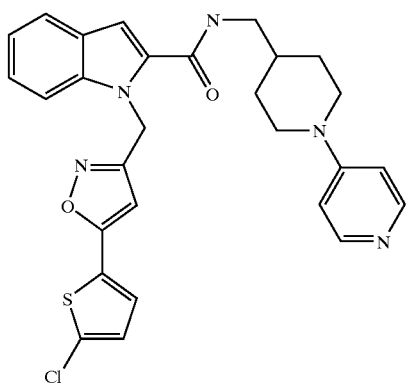

(i) (3,4,5,6-Tetrahydro-2H-[1,4']bipyridinyl-4-ylmethyl)-carbamic acid tBu ester

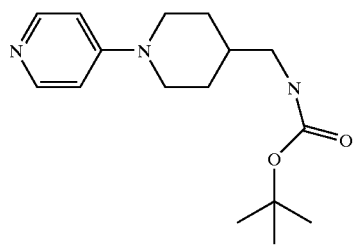

A suspension of 5 g (23.3 mmol) Piperidin-4-ylmethyl-carbamic acid tBu ester 3.85 g (25.7 mmol) and 4-Chloropyridine hydrochloride in 15 ml n-BuOH/H₂O/ NEt₃ 1:1:1 was boiled under reflux for 3 days. After removal of the solvent under reduced pressure the residue was purified by chromatography on silica gel with DCM/MeOH 100:1→50:1→10:1–5:1. The product was obtained as a white solid. Yield: 4.3 g.

(ii) C-(3,4,5,6-Tetrahydro-2H-[1,4']bipyridinyl-4-yl)-methylamine

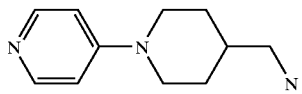

To a solution of 4.58 g (3,4,5,6-Tetrahydro-2H-[1,4'] bipyridinyl-4-ylmethyl)-carbamic acid tBu ester in 12 ml DCM, 12 ml TFA was added at RT. After stirring for 30 min the solution was diluted with 20 ml of toluene and was evaporated under reduced pressure. The residue was codistilled twice with toluene and was used in the subsequent reactions without further purification. The product was obtained as its trifluoroacetate salt.

Yield: 3.3 g.

(iii) 1-[5-(5-Chloro-thiophen-2-yl)-isoxazol-3-ylmethyl]-1H-indole-2-carboxylic acid (3,4,5,6-tetrahydro-2H-[1,4'] bipyridinyl-4-ylmethyl)-amide The title compound was prepared analogously to example 1 with the difference that C-(3,4,5,6-Tetrahydro-2H-[1,4'] bipyridinyl-4-yl)-methylamine was used instead of 1-Isopropyl-piperidin-4-ylamine. MS (ESI+): m/e=532, chloro pattern.

Example 48

1-[5-(5-Chloro-thiophen-2-yl)-isoxazol-3-ylmethyl]-1H-indole-2-carboxylic acid (1-cyclopropyl-piperidin-4-yl)-amide

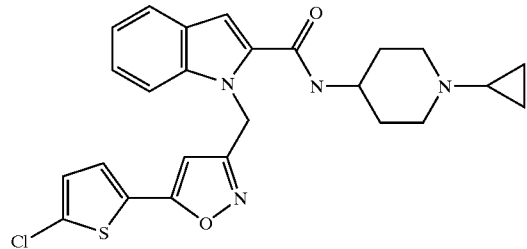

(i) (1-Cyclopropyl-piperidin-4-yl)-carbamic acid tert-butyl ester

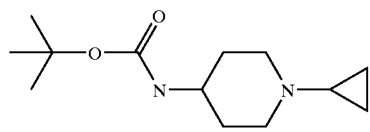

To a suspension of 1 g Piperidin-4-yl-carbamic acid tert-butyl ester, 2 g freshly activated 3 Å molecular sieve, 1 ml acetic acid, 6 ml 1-Ethoxycyclopropyl-oxy-trimethylsilane in 25 ml methanol, 22.5 ml Na(CN)BH₃ (1M in THF) were added and the mixture was heated under reflux for 2 h. The reaction mixture was filtered through a plug of celite, concentrated under reduced pressure and the residue was taken-up in ethyl acetate. The organic layer was washed with 1 M NaOH and saturated NaCl solution and finally was dried over Na₂SO₄. Evaporation of the solvents under reduced pressure gave a clear oil. Yield: 1.44 g.

(ii) 1-Cyclopropyl-piperidin-4-ylamine

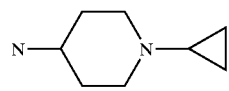

To a solution of 0.72 g (1-Cyclopropyl-piperidin-4-yl)-carbamic acid tert-butyl ester in 5 ml DCM, 3 ml TFA was added at RT. After stirring for 20 h the solution was diluted with 20 ml of toluene and evaporated under reduced pressure. The residue was codistilled twice with toluene and used in the subsequent reactions without further purification. The product was obtained as its trifluoroacetate salt. Yield: 870 mg.

(iii) 1-[5-(5-Chloro-thiophen-2-yl)-isoxazol-3-ylmethyl]-1H-indole-2-carboxylic acid (1-cyclopropyl-piperidin-4-yl)-amide The title compound was prepared analogously to example 1 with the difference that 1-Cyclopropyl-piperidin-4-ylamine was used instead of 1-Isopropyl-piperidin-4-ylamine.

MS (ESI+): m/e=481, chloro pattern.

Example 49

1-[5-(5-Chloro-thiophen-2-yl)-isoxazol-3-ylmethyl]-1H-indole-2-carboxylic acid [1-(tetrahydro-pyran-4-yl)-piperidin-4-yl]-amide

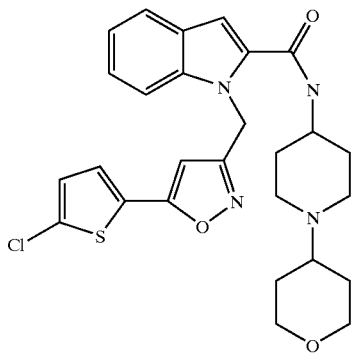

(i) 4-({1-[5-(5-Chloro-thiophen-2-yl)-isoxazol-3-ylmethyl]-1H-indole-2-carbonyl}-amino)-piperidine-1-carboxylic acid tert-butyl ester

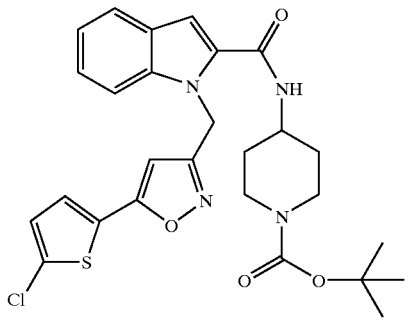

To a solution of 1 g 1-[5-(5-Chloro-thiophen-2-yl)-isoxazol-3-ylmethyl]-1H-indole-2-carboxylic acid and 1.4 ml NEM in 5 ml DCM, 0.9 g TOTU were added and the mixture was stirred for 30 min at RT. Then 0.7 g 4-Amino-piperidine-1-carboxylic acid tert-butyl ester were added and the reaction as stirred for 16 h. After removal of the solvent under reduced pressure the residue was purified by chromatography on silica gel with ethyl acetate/heptane 4:1 as eluent. The fractions containing the product were evaporated to give a white foam. Yield: 1 g.

(ii) 1-[5-(5-Chloro-thiophen-2-yl)-isoxazol-3-ylmethyl]-1H-indole-2-carboxylic acid piperidin-4-ylamide

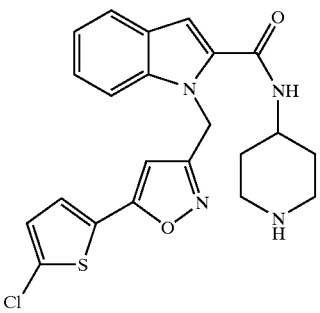

To 1 g of 4-({1-[5-(5-Chloro-thiophen-2-yl)-isoxazol-3-ylmethyl]-1H-indole-2-carbonyl}-amino)-piperidine-1-carboxylic acid tert-butyl ester, 10 ml of methanolic hydrochloric acid (8M) were added and the mixture was stirred at RT for 2 h. After removal of the solvent under reduced pressure the residue was codistilled twice with 10 ml toluene. The resulting slightly yellow solid was used in the subsequent reaction without further purification. Yield: 0.85 g.

(iii) 1-[5-(5-Chloro-thiophen-2-yl)-isoxazol-3-ylmethyl]-1H-indole-2-carboxylic acid [1-(tetrahydro-pyran-4-yl)-piperidin-4-yl]-amide.

To a solution of 50 mg 1-[5-(5-Chloro-thiophen-2-yl)-isoxazol-3-ylmethyl]-1H-indole-2-carboxylic acid piperidin-4-ylamide and 35 mg Tetrahydro-pyran-4-one in 2 ml acetonitrile, 14 mg Na(CN)BH$_3$ was introduced. After stirring at RT for 16 h the reaction mixture was concentrated under reduced pressure and was purified by preparative HPLC (C$_{18}$ reverse phase column, elution with a H$_2$O/MeCN gradient with 0.5% TFA). The fractions containing the product were evaporated and lyophilized. The product was obtained as its trifluoroacetate salt.

Yield: 14 mg MS (ES$^+$): m/e=525, chloro pattern.

According to example 49 the following compounds were prepared by a similar procedure:

| Example | Structure | MS (ESI+) |
|---|---|---|
| 50 | 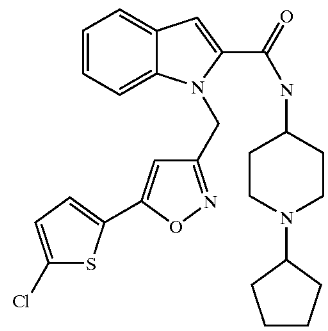 | 495, chloro pattern |
| 51 | 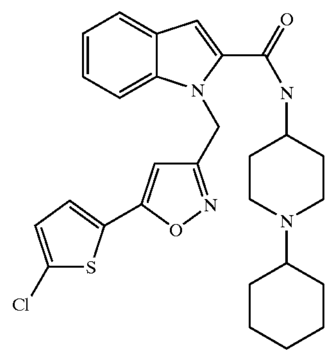 | 509, chloro pattern |

Example 52

1-(3-Methoxy-benzyl)-1H-indole-2-carboxylic acid (1-isopropyl-piperidin-4-yl)-amide

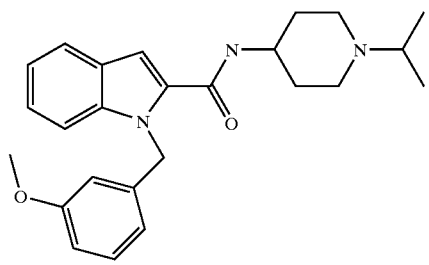

The title compound was prepared analogously to example 1 with the difference that 1-Bromomethyl-3-methoxy-benzene was used instead of 3-Bromomethyl-5-(5-chloro-thiophen-2-yl)-isoxazole. MS (ESI+): m/e=406.

According to example 52 the following compounds were prepared by a similar procedure:

| Example | Structure | MS (ESI+) |
|---------|-----------|-----------|
| 53 | 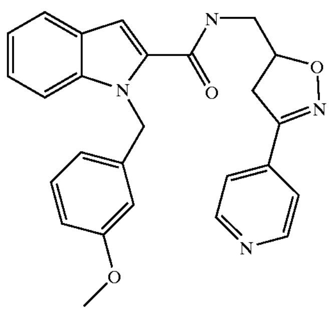 | 441 |
| 54 | 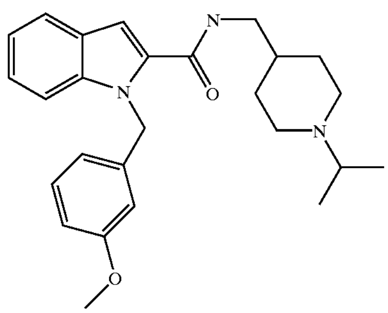 | 420 |
| 55 | 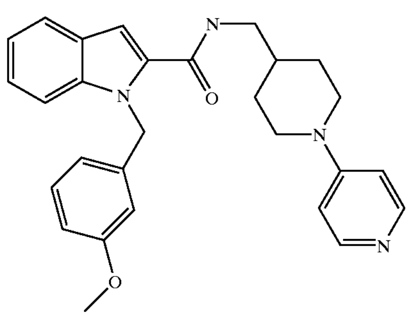 | 455 |
| 56 | 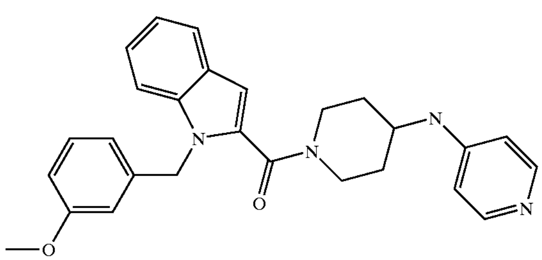 | 441 |
| 57 | 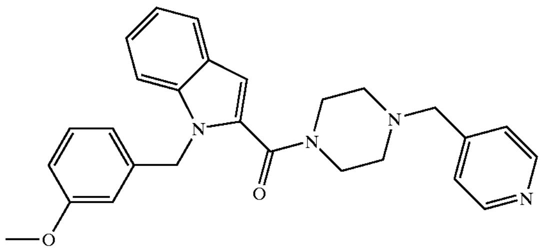 | 441 |

-continued

| Example | Structure | MS (ESI+) |
|---|---|---|
| 58 | 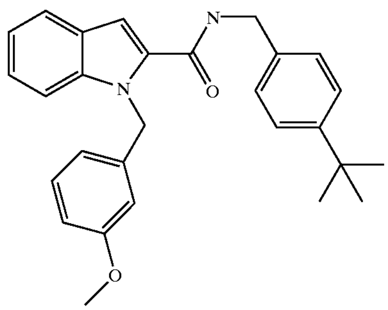 | 427 |
| 59 | 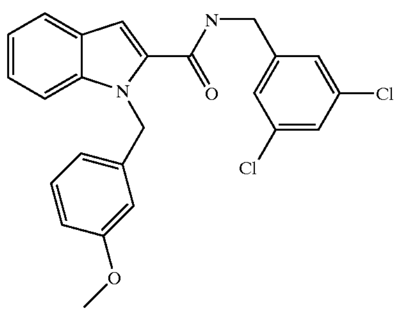 | 439, chloro pattern |
| 60 | 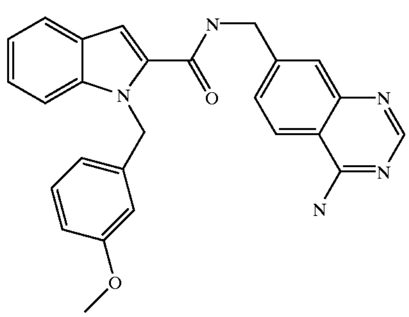 | 438 |
| 61 | 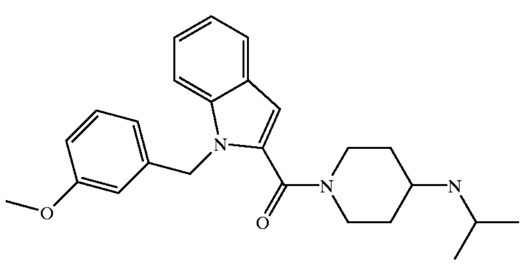 | 405 |
| 62 | 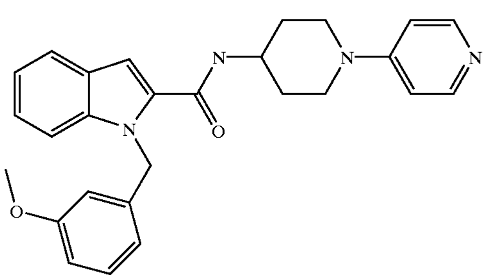 | 441 |

| Example | Structure | MS (ESI+) |
|---|---|---|
| 63 | 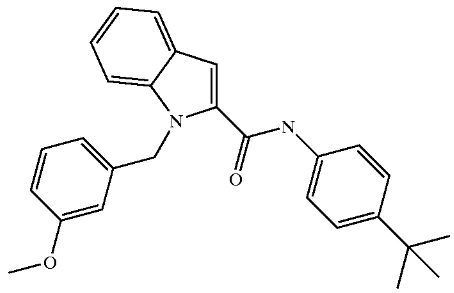 | 413 |
| 64 | 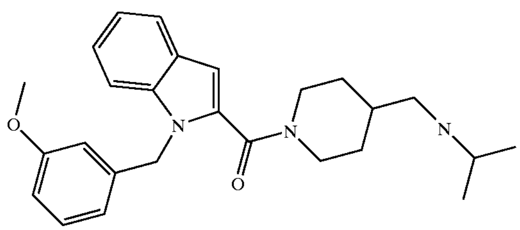 | 420 |

Example 65

1-(3-Methoxy-benzyl)-1H-indole-2-carboxylic acid (4-pyridin-4-yl-phenyl)-amide

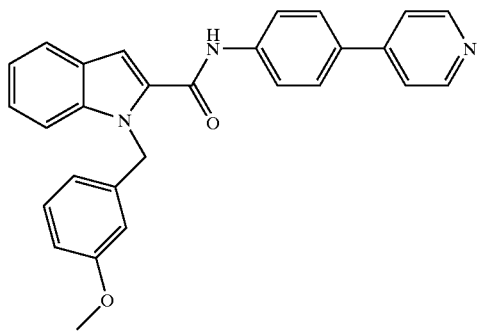

(i) 1-(3-Methoxy-benzyl)-1H-indole-2-carboxylic acid (4-iodo-phenyl)-amide

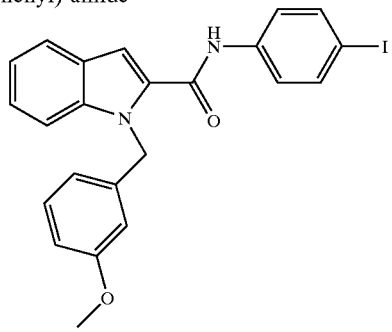

To a solution of 500 mg 1-(3-Methoxy-benzyl)-1H-indole-2-carboxylic acid in 8 ml DCM and 0.9 NEt₃ 452 mg, BOP-Cl was added at RT and the mixture was stirred for 30 min. After addition of 583 mg 4-Iodo-phenylamine the mixture was stirred for 16 h. Then the solvent was removed under reduced pressure to yield a white precipitate, which was washed with 1 ml MeOH/DCM 1:1.

Yield: 380 mg.

(ii) 1-(3-Methoxy-benzyl)-1H-indole-2-carboxylic acid (4-pyridin-4-yl-phenyl)-amide A solution of 100 mg 1-(3-Methoxy-benzyl)-1H-indole-2-carboxylic acid (4-iodo-phenyl)-amide, 31 mg 4-Pyridyl boronic acid and 200 µl aqueous Na₂CO₃ solution (2M) in 5 ml dimethoxyethane (dme) was purged with argon for 15 min. Then 20 mg Pd(PPh₃)₄ was added and the mixture was heated to 80° C. for 16 h. Finally, 3 ml saturated NaHCO₃ solution were added and the mixture was filtered through a chem elut® cartridge by elution with ethyl acetate. After subsequent removal of the solvent under reduced pressure the residue was purified by preparative HPLC (C18 reverse phase column, elution with a H₂O/MeCN gradient with 0.1% TFA). The fractions containing the product were evaporated and lyophilized to yield a white solid. The product was obtained as its trifluoroacetate salt. Yield: 15 mg MS (ESI+): m/e=434.

Example 66

4-Methoxy-1-(3-methoxy-benzyl)-1H-indole-2-carboxylic acid (1-isopropyl-piperidin-4-yl)-amide

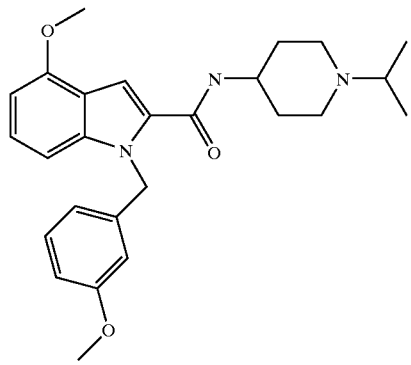

The title compound was prepared analogously to example 52 with the difference that 4-Methoxy-1H-indole-2-carboxylic acid was used instead of 1H-Indole-2-carboxylic acid.

MS (ESI+): m/e=436.

Example 67

5-Chloro-1-(3-methoxy-benzyl)-1H-indole-2-carboxylic acid (1-isopropyl-piperidin-4-yl)-amide

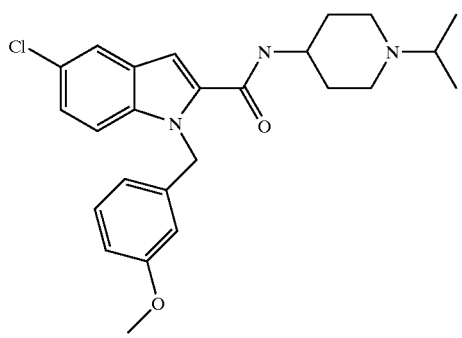

The title compound was prepared analogously to example 57 with the difference that 5-Chloro-1H-indole-2-carboxylic acid was used instead of 1H-indole-2-carboxylic acid.

MS (ESI+): m/e=440, chloro pattern.

Example 68

6-Methoxy-1-(3-methoxy-benzyl)-1H-indole-2-carboxylic acid 1-isopropyl-piperidin-4-yl)-amide

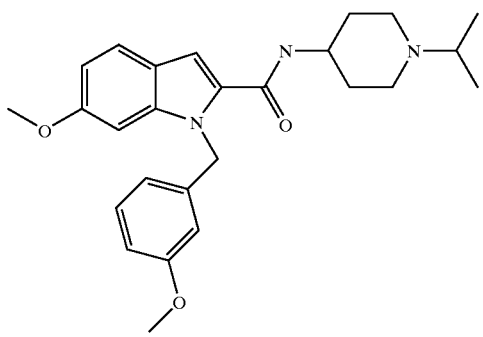

The title compound was prepared analogously to example 52 with the difference that 6-Methoxy-1H-indole-2-carboxylic acid was used instead of 1H-indole-2-carboxylic acid.

MS (ESI+): m/e=436.

Example 69

1-(3-Methoxy-benzyl)-5-methyl-1H-indole-2-carboxylic acid (1-isopropyl-piperidin-4-yl)-amide

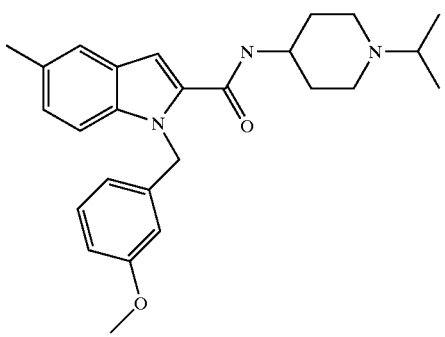

The title compound was prepared analogously to example 52 with the difference that 5-Methyl-1H-indole-2-carboxylic acid was used instead of 1H-indole-2-carboxylic acid.

MS (ESI+): m/e=420.

Example 70

5-Benzyloxy-1-(3-methoxy-benzyl)-1H-indole-2-carboxylic acid (1-isopropyl-piperidin-4-yl)-amide

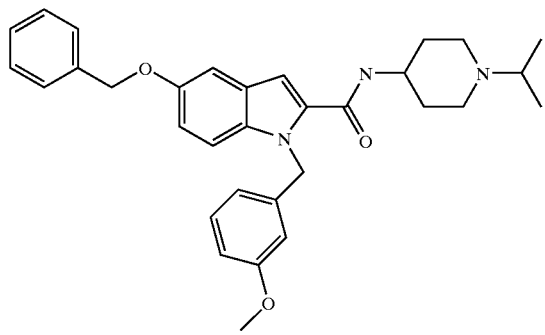

The title compound was prepared analogously to example 52 with the difference that 5-Benzyloxy-1H-indole-2-carboxylic acid was used instead of 1H-indole-2-carboxylic acid.

MS (ESI+): m/e=512.

Example 71

1-(3-Methoxy-benzyl)-5-nitro-1H-indole-2-carboxylic acid (1-isopropyl-piperidin-4-yl)-amide

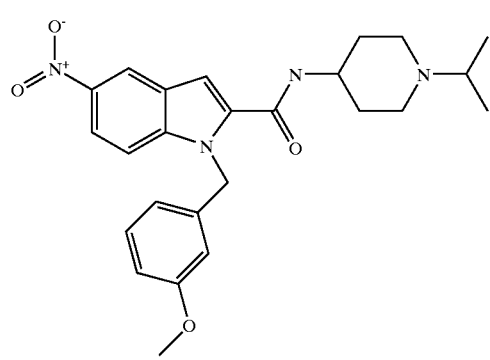

The title compound was prepared analogously to example 52 with the difference that 5-Nitro-1H-indole-2-carboxylic acid was used instead of 1H-indole-2-carboxylic acid.

MS (ESI+): m/e=451.

Example 72

5-Methoxy-1-(3-methoxy-benzyl)-1H-indole-2-carboxylic acid (1-isopropyl-piperidin-4-yl)-amide

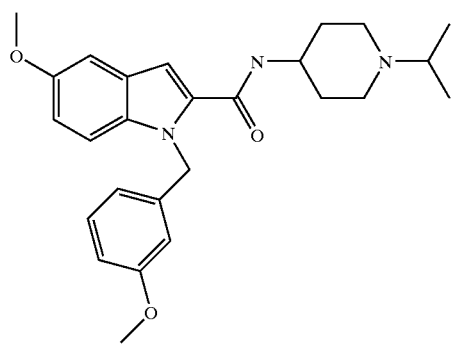

The title compound was prepared analogously to example 52 with the difference that 5-Methoxy-1H-indole-2-carboxylic acid was used instead of 1H-indole-2-carboxylic acid.

MS (ESI+): m/e=436.

Example 73

1-(3-Methoxy-benzoyl)-1H-indole-2-carboxylic acid 1-isopropyl-piperidin-4-yl)-amide

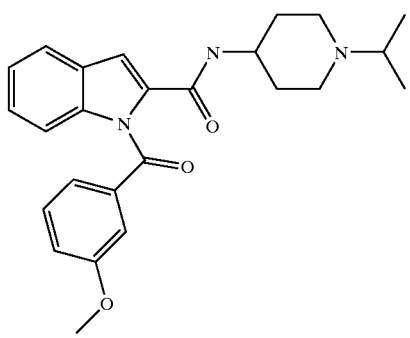

The title compound was prepared analogously to example 1 with the difference that 3-Methoxy-benzoyl chloride was used instead of 3-Bromomethyl-5-(5-chloro-thiophen-2-yl)-isoxazole. MS (ESI+): m/e=420.

Example 74

1-(3-Methoxy-benzenesulfonyl)-1H-indole-2-carboxylic acid (1-isopropyl-piperidin-4-yl)-amide

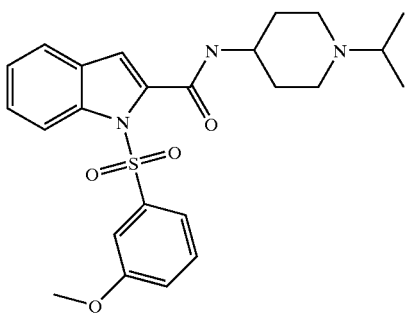

The title compound was prepared analogously to example 1 with the difference that 3-Methoxy-benzenesulfonyl chloride was used instead of 3-Bromomethyl-5-(5-chloro-thiophen-2-yl)-isoxazole. MS (ESI+): m/e=456.

Example 75

1-(4-Methoxy-phenyl)-1H-indole-2-carboxylic acid (1-isopropyl-piperidin-4-yl)-amide

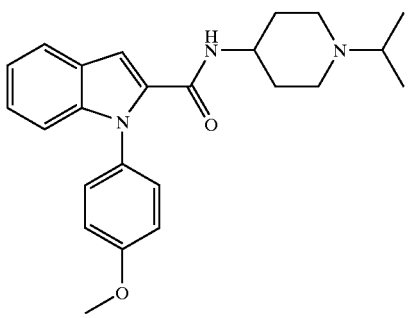

(i) 1-(4-Methoxy-phenyl)-1H-indole-2-carboxylic acid methyl ester.

To a suspension of 2 g 1H-Indole-2-carboxylic acid methyl ester, 3.2 g 4-Methoxyphenyl boronic acid, 2 g molecular sieve (4 Å), 1.7 ml pyridine, 3 ml NEt₃ in 40 ml DCM, 3.9 g Cu(OAc)₂ were added. The suspension was stirred for 3 d at RT and for 2 d at 50° C. then 3 ml saturated NaHCO₃ solution was added and the mixture filtered through a chem elut® cartridge by elution with ethyl acetate. After concentration under reduced pressure and chromatographic purification on silica gel with ethyl acetate/heptane 4:1 the fractions containing the product were evaporated.

Yield: 3 g.

(ii) 1-(4-Methoxy-phenyl)-1H-indole-2-carboxylic acid.

To a solution of 3 g 1-(4-Methoxy-phenyl)-1H-indole-2-carboxylic acid methyl ester in 50 ml THF, 10 ml water and 0.58 g lithium hydroxide monohydrate were added. After stirring for 2 h at 60° C. the reaction was cooled to RT. The mixture was acidified with half concentrated hydrochloric acid and the precipitate was collected by filtration and was washed with 10 ml water The product was obtained as a white solid which was dried under reduced pressure. Yield: 520 mg.

(vi) 1-(4-Methoxy-phenyl)-1H-indole-2-carboxylic acid (1-isopropyl-piperidin-4-yl)-amide To a solution of 36 mg 1-(4-Methoxy-phenyl)-1H-indole-2-carboxylic acid in 1 ml DCM and 0.17 ml NEt₃, 34 mg BOP-Cl were added at RT and the mixture was stirred for 30 min. After addition of 57 mg 1-Isopropyl-piperidin-4-ylamine hydrochloride the mixture was stirred over night. Subsequently the solvent was removed under reduced pressure and the residue was purified by preparative HPLC (C18 reverse phase column, elution with a H₂O/MeCN gradient with 0.1% TFA). The fractions containing the product were evaporated and lyophilized to yield a white solid. The product was obtained as its trifluoroacetate salt.

Yield: 14 mg MS (ES+): m/e=329.

According to example 75 the following compounds were prepared by a similar procedure:

| Example | Structure | MS (ESI+) |
|---|---|---|
| 76 | 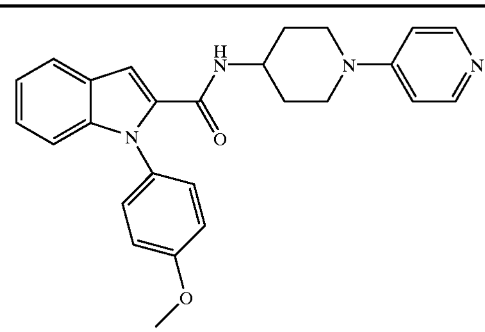 | 427 |

-continued

| Example | Structure | MS (ESI+) |
|---------|-----------|-----------|
| 77 | 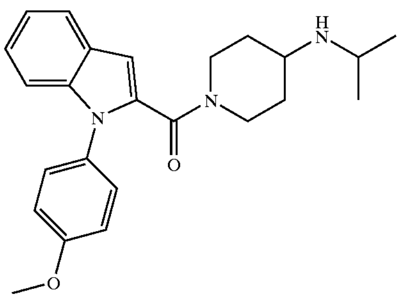 | 391 |
| 78 | 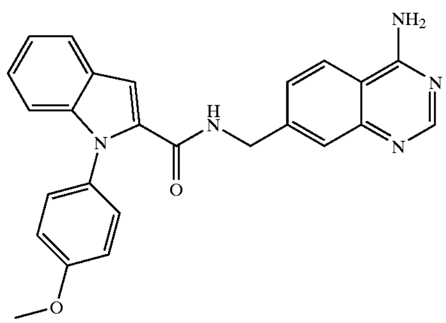 | 424 |
| 79 | 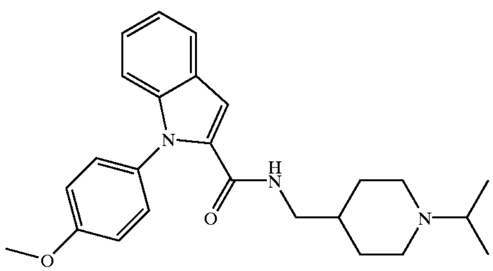 | 405 |
| 80 | 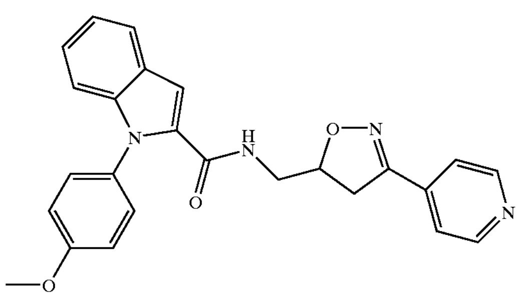 | 424 |
| 81 | 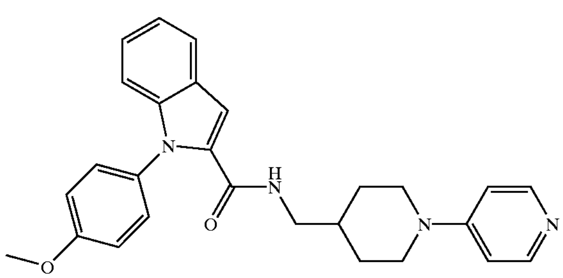 | 441 |

-continued

| Example | Structure | MS (ESI+) |
|---------|-----------|-----------|
| 82 | 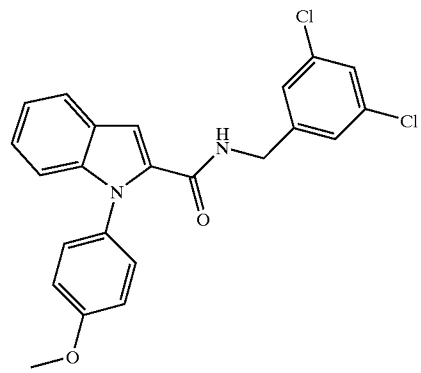 | 425, chloro pattern |
| 83 | 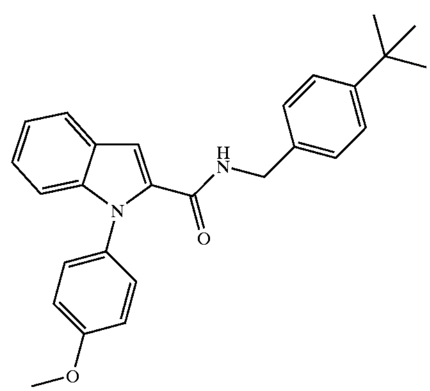 | 413 |
| 84 | 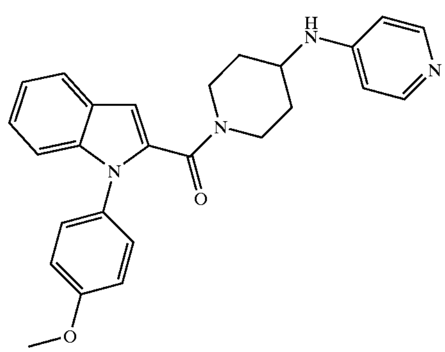 | 427 |
| 85 | 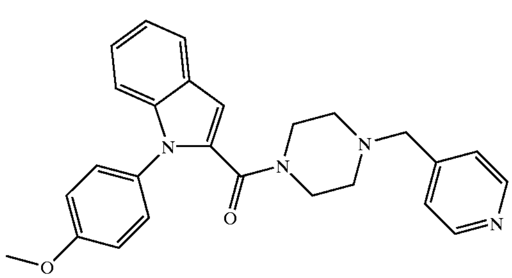 | 427 |

Example 86

1-(4-Methoxy-phenyl)-1H-indole-2-carboxylic acid 4-pyridin-4-yl-benzylamide

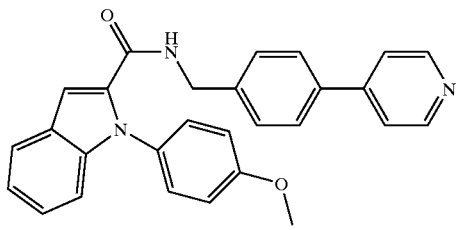

(i) (4-Bromo-benzyl)-carbamic acid tert-butyl ester.

To a solution of 5 g 4-Bromo-benzylamine and 7 ml NEt$_3$ in 30 ml DCM 5.4 g Boc$_2$O were added. After stirring for 16 h at RT the reaction mixture was concentrated and the precipitate was collected by filtration. The solid product was dried under reduced pressure and was used in the subsequent reaction without further purification. Yield: 6.5 g.

(ii) (4-Pyridin-4-yl-benzyl)-carbamic acid tert-butyl ester

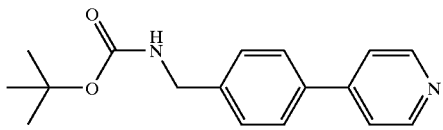

A solution of 500 mg (4-Bromo-benzyl)-carbamic acid tert-butyl ester, 213 mg 4-Pyridyl boronic acid and 500 µl aqueous Na$_2$CO$_3$ solution (2M) in 5 ml dimethoxyethane was purged with argon for 15 min. Then 60 mg Pd(PPh$_3$)$_4$ were added and the mixture was heated to 100° C. for 16 h. Finally, 10 ml saturated NaHCO$_3$ solution was added and the mixture was filtered through a chem elut® cartridge by elution with ethyl acetate. After subsequent removal of the solvent under reduced pressure the residue was purified by chromatography on silica gel with ethyl acetate as eluent. The fractions containing the product were evaporated to yield a white solid.

Yield: 490 mg.

(iii) 4-Pyridin-4-yl-benzylamine

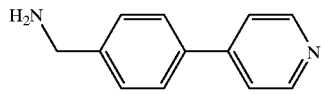

To a solution of 490 mg (4-Pyridin-4-yl-benzyl)-carbamic acid tert-butyl ester in 2 ml DCM, 3 ml TFA were added at RT. After stirring for 12 h the reaction mixture was diluted with 10 ml toluene and was evaporated under reduced pressure to yield a brown foam. The product was obtained as its trifluoro acetate salt. Yield: 330 mg (iii) 1-(4-Methoxy-phenyl)-1H-indole-2-carboxylic acid 4-pyridin-4-yl-benzylamide.

To solution of 50 mg 1-(4-Methoxy-phenyl)-1H-indole-2-carboxylic acid and 100 µl NEt$_3$ in 2 ml DCM, 47 mg BOP-Cl were added at RT. After 1 h, 51 mg 4-Pyridin-4-yl-benzylamine were added and the reaction mixture was stirred for 16 h. After removal of the solvent under reduced pressure the residue was purified by preparative HPLC (C18 reverse phase column, elution with a H$_2$O/MeCN gradient with 0.1% TFA). The fractions containing the product were evaporated and were lyophilized to yield a white solid. The product was obtained as its trifluoroacetate salt.

Yield: 27 mg MS (ESI+): m/e=434.

Example 87

1-(3-Methoxy-phenyl)-1H-indole-2-carboxylic acid (1-isopropyl-piperidin-4-yl)-amide

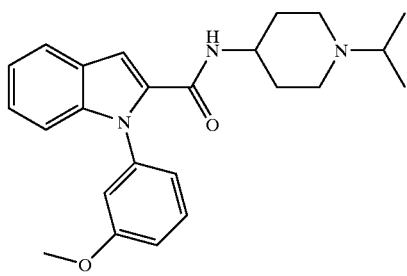

The title compound was prepared analogously to example 75 with the difference that 3-Methoxyphenyl boronic acid was used instead of 4-Methoxyphenyl boronic acid.

MS (ESI+): m/e=392.

Example 88

1-(3-Chloro-phenyl)-1H-indole-2-carboxylic acid (1-isopropyl-piperidin-4-yl)-amide

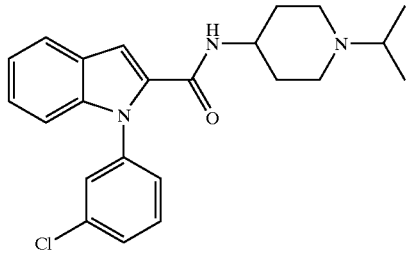

The title compound was prepared analogously to example 75 with the difference that 3-Chlorophenyl boronic acid was used instead of 4-Methoxyphenyl boronic acid.

MS (ESI+): m/e=396, chloro pattern.

Analogously to example 88 the following compounds were prepared by a similar procedure:

| Example | Structure | MS (ESI+) |
|---|---|---|
| 89 | 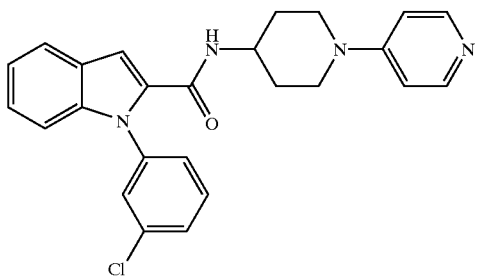 | 431, chloro pattern |
| 90 | 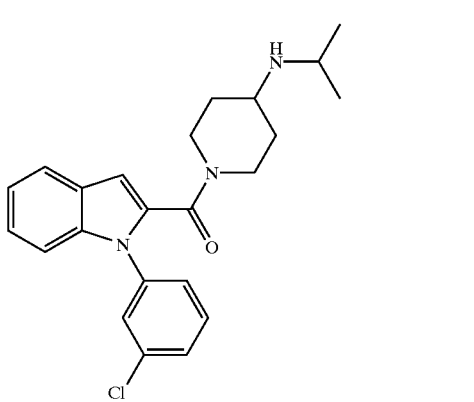 | 396, chloro pattern |
| 91 | 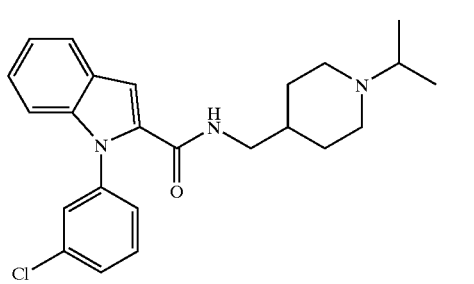 | 409, chloro pattern |
| 92 | 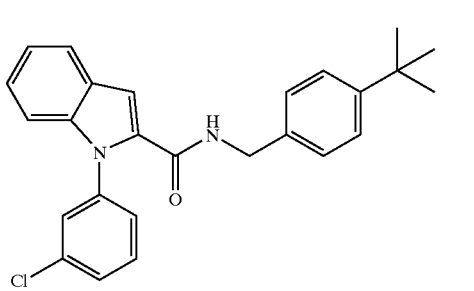 | 417, chloro pattern |
| 93 | 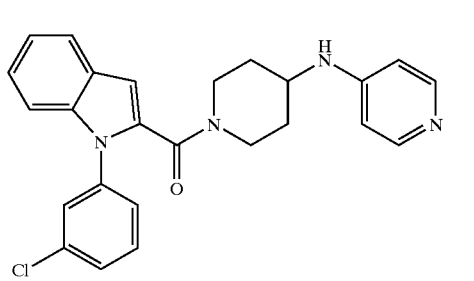 | 431, chloro pattern |

-continued
| Example | Structure | MS (ESI+) |
|---|---|---|
| 94 | 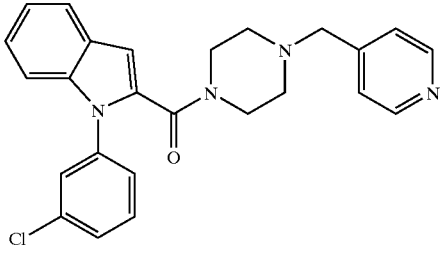 | 431, chloro pattern |
| 95 | 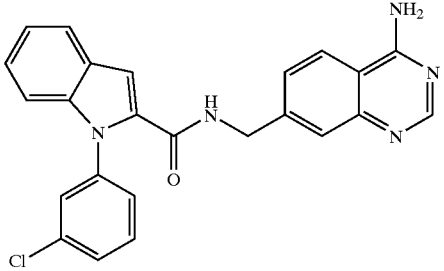 | 428, chloro pattern |
| 96 | 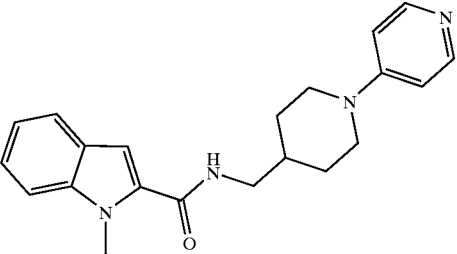 | 445, chloro pattern |
| 97 | 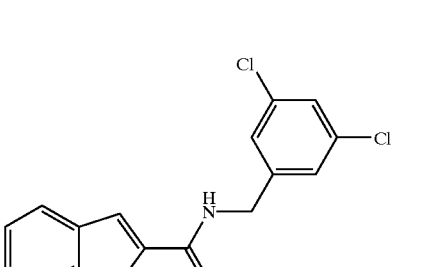 | 429, chloro pattern |

Example 98

1-(3-Chloro-phenyl)-1H-indole-2-carboxylic acid 4-pyridin-4-yl-benzylamide

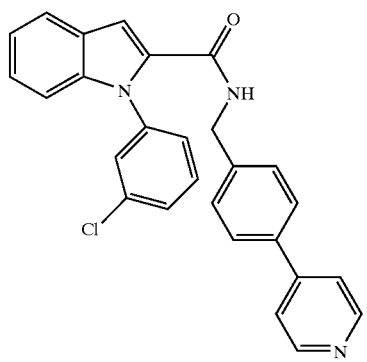

The title compound was prepared analogously to example 86 with the difference that 1-(3-Chloro-phenyl)-1H-indole-2-carboxylic acid was used instead of 1-(4-Methoxyphenyl)-1H-indole-2-carboxylic acid.

MS (ESI+): m/e=438, chloro pattern.

Example 99

1-(3,5-Dichloro-phenyl)-1H-indole-2-carboxylic acid (1-isopropyl-piperidin-4-yl)-amide

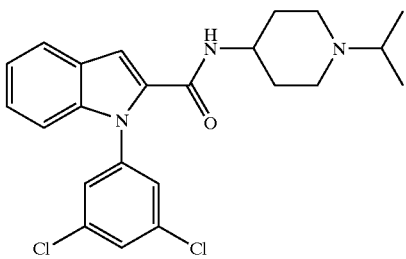

The title compound was prepared analogously to example 75 with the difference that 3,5-Dichlorophenyl boronic acid was used instead of 4-Methoxyphenyl boronic acid.

MS (ESI+): m/e=430, chloro pattern.

Analogously to example 99 the following compounds were prepared by a similar procedure:

| Example | Structure | MS (ESI+) |
|---|---|---|
| 100 | 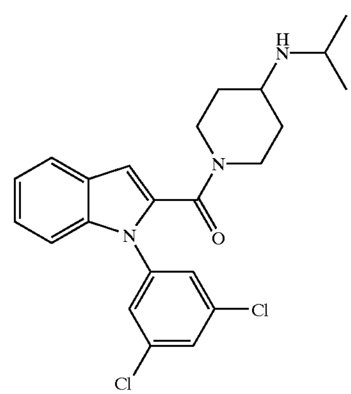 | 430, chloro pattern |
| 101 | 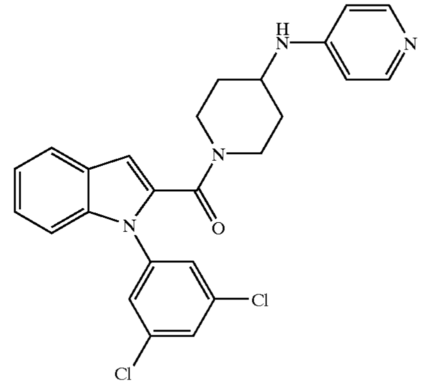 | 465, chloro pattern |

-continued
| Example | Structure | MS (ESI+) |
|---|---|---|
| 102 | 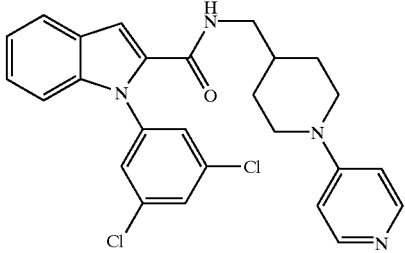 | 479, chloro pattern |
| 103 | 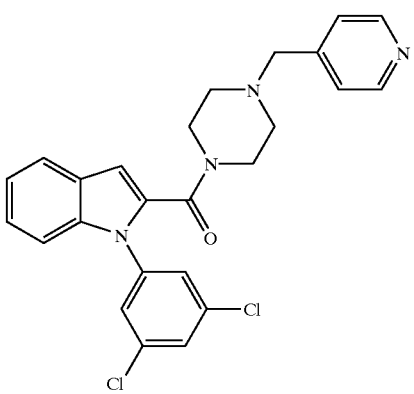 | 465, chloro pattern |
| 104 | 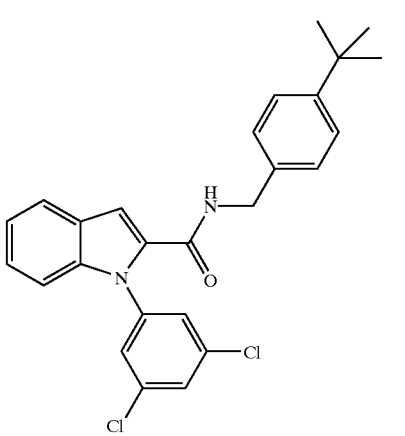 | 451, chloro pattern |

| Example | Structure | MS (ESI+) |
|---|---|---|
| 105 | 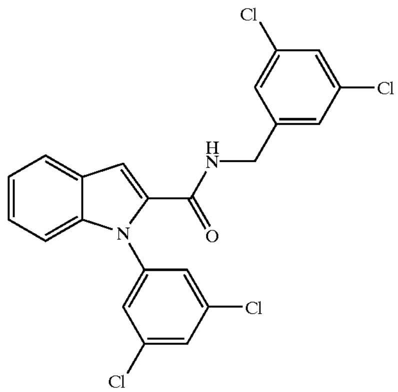 | 465, chloro pattern |

Example 106

1-(4-Chloro-phenyl)-1H-indole-2-carboxylic acid (1-isopropyl-piperidin-4-yl)-amide

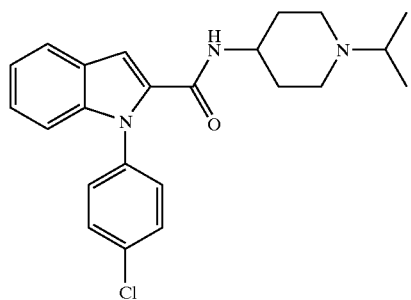

The title compound was prepared analogously to example 75 with the difference 4-Chlorophenyl boronic acid was used instead of 4-Methoxyphenyl boronic acid.

MS (ESI+): m/e=396, chloro pattern.

Analogously to example 107 the following compounds were prepared by a similar procedure:

| Example | Structure | MS (ESI+) |
|---|---|---|
| 108 | 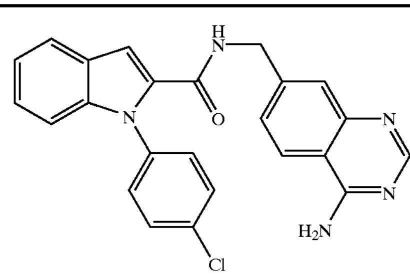 | 428, chloro pattern |
| 109 | 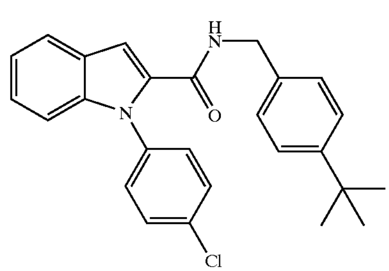 | 415, chloro pattern |

-continued
| Example | Structure | MS (ESI+) |
|---------|-----------|-----------|
| 110 | 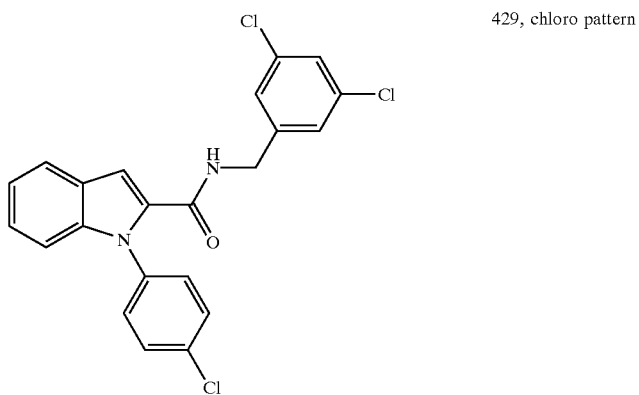 | 429, chloro pattern |
| 111 | 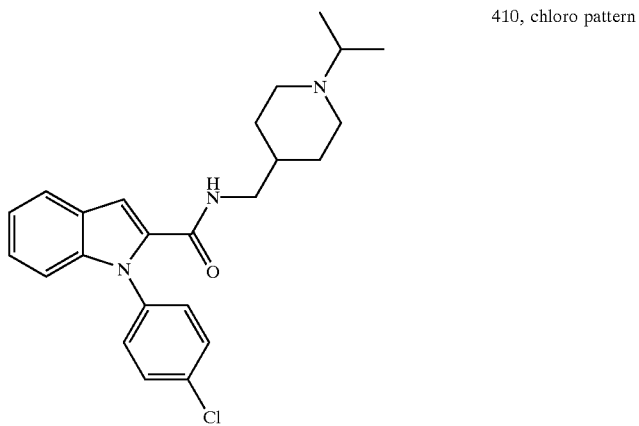 | 410, chloro pattern |
| 112 | 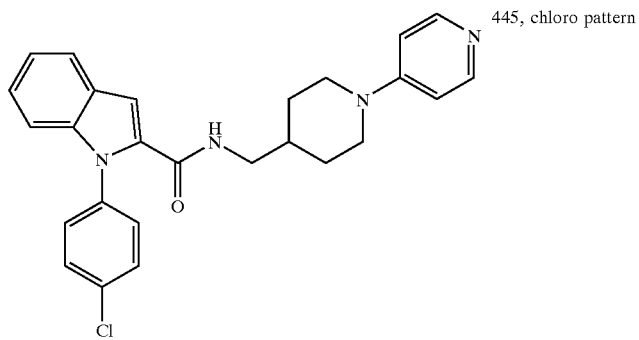 | 445, chloro pattern |

-continued
| Example | Structure | MS (ESI+) |
|---|---|---|
| 113 | 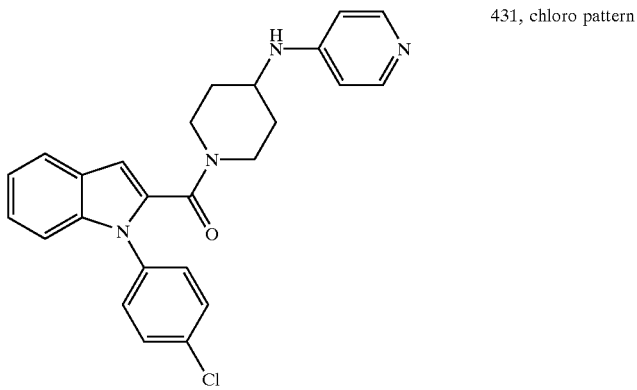 | 431, chloro pattern |
| 114 | 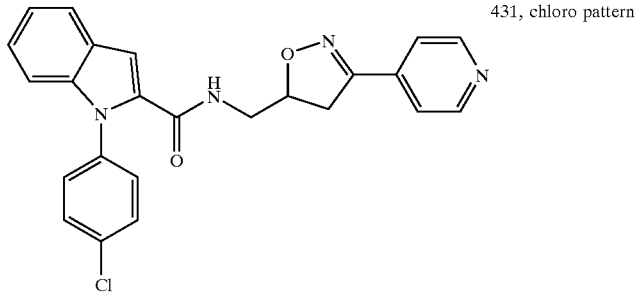 | 431, chloro pattern |
| 115 | 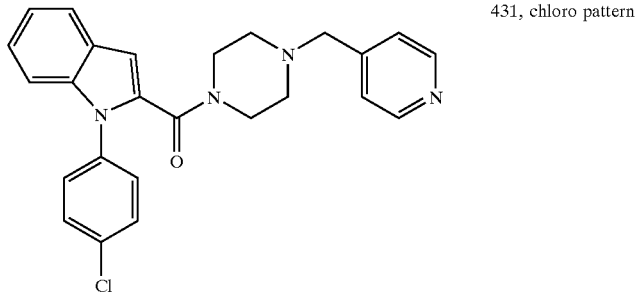 | 431, chloro pattern |
| 116 | 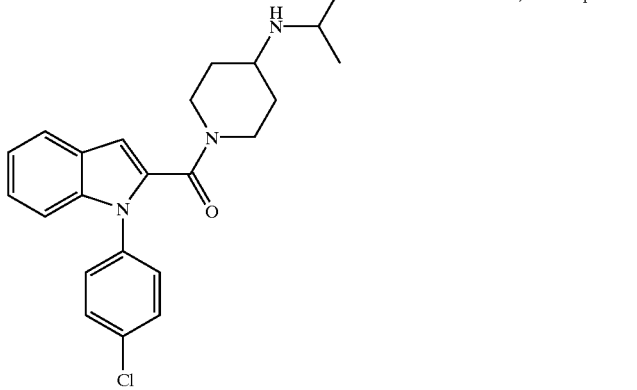 | 396, chloro pattern |

Example 117

1-(4-Chloro-phenyl)-1H-indole-2-carboxylic acid 4-pyridin-4-yl-benzylamide

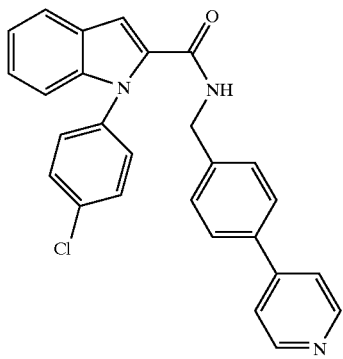

The title compound was prepared analogously to example 86 with the difference that 1-(4-Chloro-phenyl)-1H-indole-2-carboxylic acid was used instead of 1-(4-Methoxy-phenyl)-1H-indole-2-carboxylic acid.

MS (ESI+): m/e 438, chloro pattern.

Example 118

1-(4-Amino-quinazolin-7-ylmethyl)-1H-indole-2-carboxylic acid (1-isopropyl-piperidin-4-yl)-amide

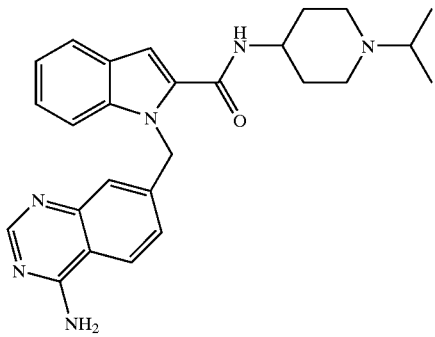

The title compound was prepared analogously to example 1 with the difference that 7-Bromomethyl-quinazolin-4-ylamine [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B. PCT Int. Appl. (2001), 460 pp. WO 0107436 A2] was used instead of 3-Bromomethyl-5-(5-chloro-thiophen-2-yl)-isoxazole.

MS (ESI+): m/e=443.

Example 119

1-(6-Chloro-benzo[b]thiophen-2-ylmethyl)-1H-indole-2-carboxylic acid (1-isopropyl-piperidin-4-yl)-amide

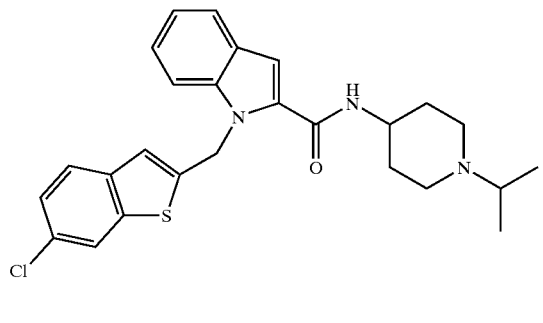

The title compound was prepared analogously to example 1 with the difference that 2-Bromomethyl-6-chloro-benzo[b]thiophene [prepared by adopting a procedure described by Ewing, William R. et al. in ;PCT Int. Appl. (1999), 300 pp. WO 9937304 A1; and Ewing, William R. et al. PCT Int. Appl. (2001), 460 pp. WO 0107436 A2] was used instead of 3-Bromomethyl-5-(5-chloro-thiophen-2-yl)-isoxazole.

MS (ESI+): m/e=466, chloro pattern.

Example: 120

1-[5-(5-Chloro-thiophen-2-yl)-[1,3,4]thiadiazol-2-ylmethyl]-1H-indole-2-carboxylic acid (1-isopropyl-piperidin-4-yl)-amide

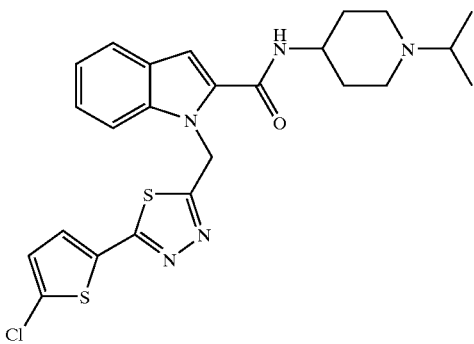

The title compound was prepared analogously to example 1 with the difference that 2-Bromomethyl-5-(5-chloro-thiophen-2-yl)-[1,3,4]thiadiazole [prepared by adopting a procedure described by Ewing, William R. et al. PCT Int. Appl. (2001), 460 pp. WO 0107436 A2] was used instead of 3-Bromomethyl-5-(5-chloro-thiophen-2-yl)-isoxazole.

MS (ESI+): m/e=500, chloro pattern.

Example: 121

1-[3-(5-Chloro-thiophen-2-yl)-isoxazol-5-ylmethyl]-1H-indole-2-carboxylic acid (1-isopropyl-piperidin-4-yl)-amide

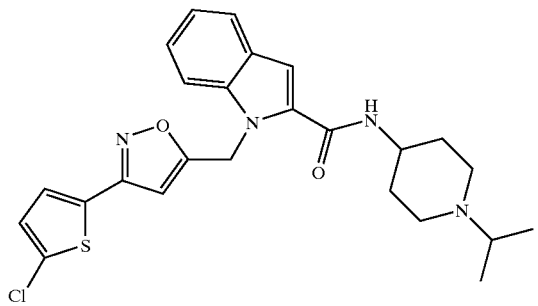

The title compound was prepared analogously to example 1 with the difference that 5-Bromomethyl-3-(5-chloro-thiophen-2-yl)-isoxazole [Ewing, William R. et al. PCT Int. Appl. (2001), 460 pp. WO 0107436 A2] was used instead of 3-Bromomethyl-5-(5-chloro-thiophen-2-yl)-isoxazole.

MS (ESI+): m/e=483, chloro pattern.

Example 122

3-Chloro-1-[5-(5-chloro-thiophen-2-yl)-isoxazol-3-ylmethyl]-1H-indole-2-carboxylic acid (1-isopropyl-piperidin-4-yl)-amide

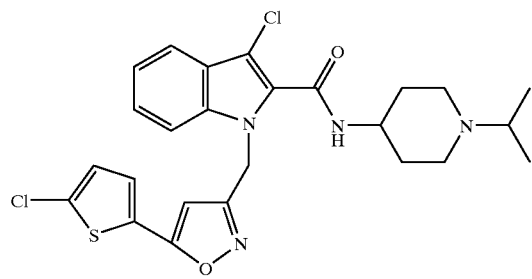

To a solution of 40 mg 1-[5-(5-Chloro-thiophen-2-yl)-isoxazol-3-ylmethyl]-1H-indole-2-carboxylic acid (1-isopropyl-piperidin-4-yl)-amide in 1 ml DCM, 17 mg NCS were added and the mixture was stirred at RT for 16 h. Finally, the reaction mixture was directly purified by preparative RP-HPLC eluting with a gradient of 0–100% acetonitrile in water (+0.01% trifluoroacetic acid). After lyophilization the product was obtained as its trifluoroacetate salt.

Yield: 15 mg MS (ESI+): m/e=517, chloro pattern.

Example 123

3-Bromo-1-[5-(5-chloro-thiophen-2-yl)-isoxazol-3-ylmethyl]-1H-indole-2-carboxylic acid (1-isopropyl-piperidin-4-yl)-amide

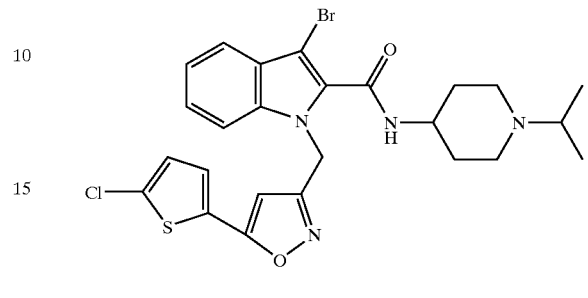

To a solution of 40 mg 1-[5-(5-Chloro-thiophen-2-yl)-isoxazol-3-ylmethyl]-1H-indole-2-carboxylic acid (1-isopropyl-piperidin-4-yl)-amide in 1 ml DCM, 22 mg NBS were added and the mixture was stirred at RT over night. Finally, the reaction mixture was directly purified by preparative RP-HPLC eluting with a gradient of 0–100% acetonitrile in water (+0.01% trifluoroacetic acid). After lyophilization the product was obtained as its trifluoroacetate salt.

Yield: 18 mg MS (ESI+): m/e=562, chloro pattern.

Example 124

1-(4-Chloro-benzyl)-1H-indole-2-carboxylic acid (1-isopropyl-piperidin-4-yl)-amide

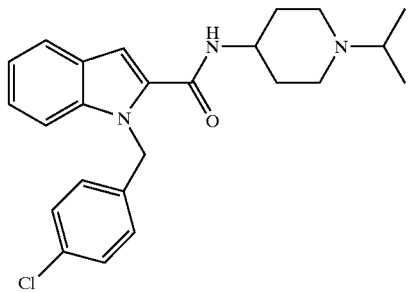

The title compound was prepared analogously to example 1 with the difference that 1-Chloromethyl-4-chloro-benzene was used instead of 3-Bromomethyl-5-(5-chloro-thiophen-2-yl)-isoxazole.

MS (ESI+): m/e=410, chloro pattern.

Analogously to example 124 the following compounds were prepared by a similar procedure:

| Example | Structure | MS (ESI+) |
|---|---|---|
| 125 | 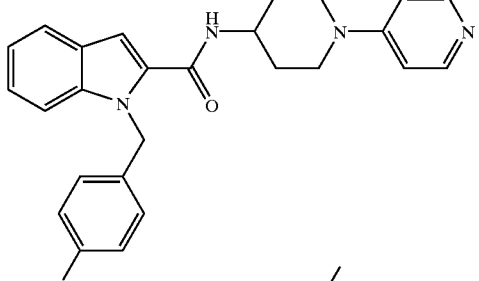 | 445, chloro pattern |
| 126 | 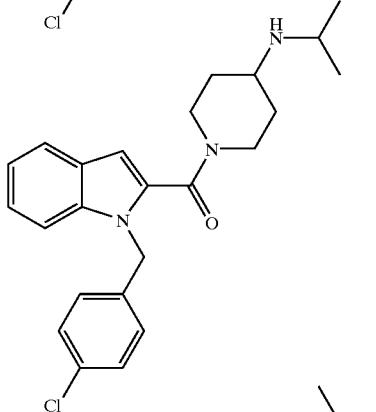 | 409, chloro pattern |
| 127 | 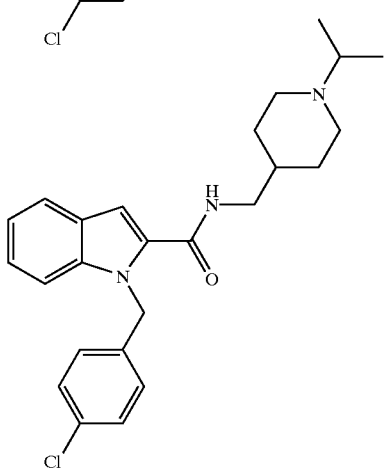 | 423, chloro pattern |
| 128 | 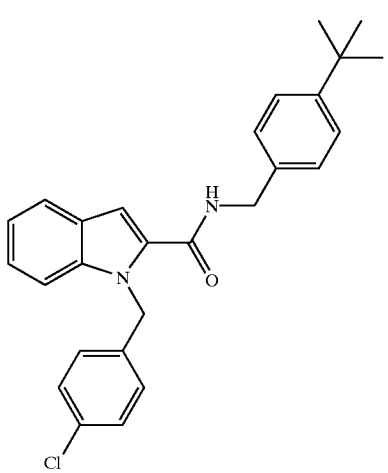 | 431, chloro pattern |

-continued
| Example | Structure | MS (ESI+) |
|---|---|---|
| 129 | 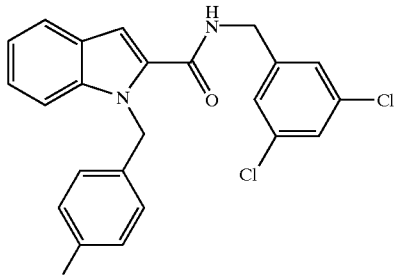 | 443, chloro pattern |
| 130 | 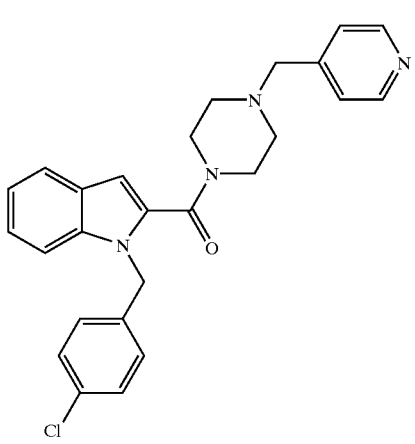 | 445, chloro pattern |
| 131 | 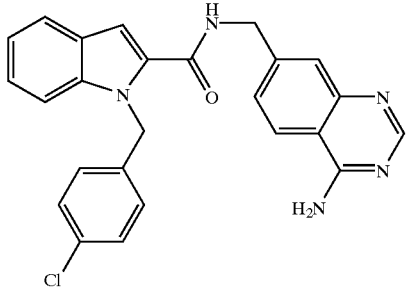 | 442, chloro pattern |
| 132 | 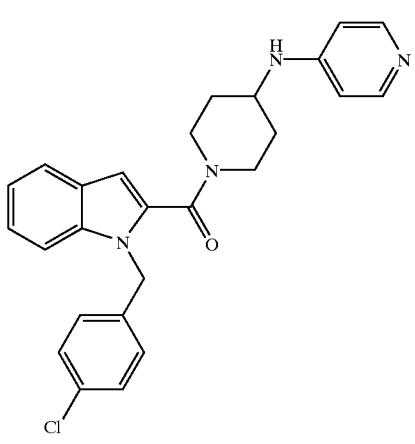 | 445, chloro pattern |

-continued

| Example | Structure | MS (ESI+) |
|---|---|---|
| 133 | 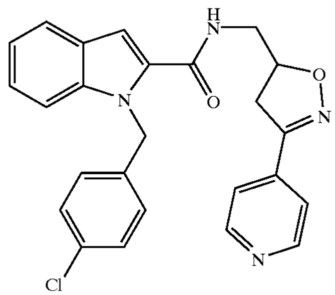 | 445, chloro pattern |
| 134 | 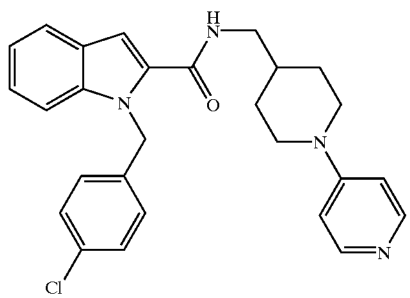 | 459, chloro pattern |

Example 135

1-(2,4-Dichloro-benzyl)-1H-indole-2-carboxylic acid (1-isopropyl-piperidin-4-yl)-amide

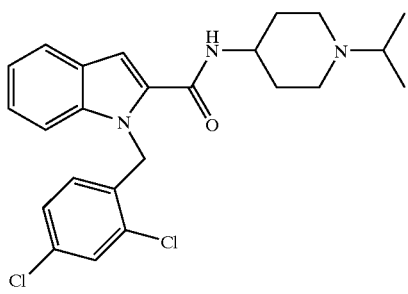

The title compound was prepared analogously to example 1 with the difference that 1-Chloromethyl-2,4-dichlorobenzene was used instead of 3-Bromomethyl-5-(5-chlorothiophen-2-yl)-isoxazole.

MS (ESI+): m/e=444, chloro pattern.

According to example 135 the following compounds were prepared by a similar procedure:

| Example | Structure | MS (ESI+) |
|---|---|---|
| 136 | 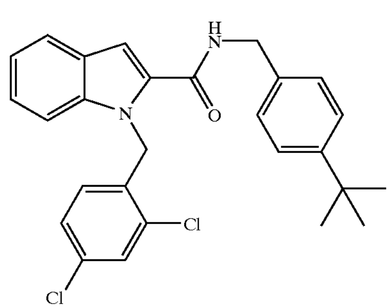 | 465, chloro pattern |

-continued

| Example | Structure | MS (ESI+) |
|---------|-----------|-----------|
| 137 | 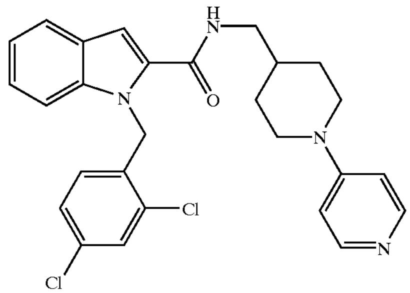 | 493, chloro pattern |
| 138 | 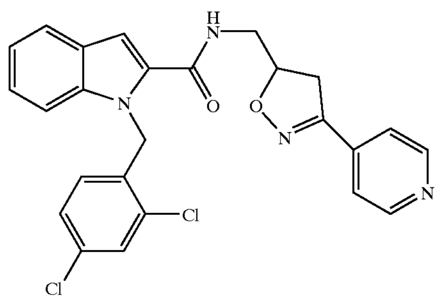 | 479, chloro pattern |
| 139 | 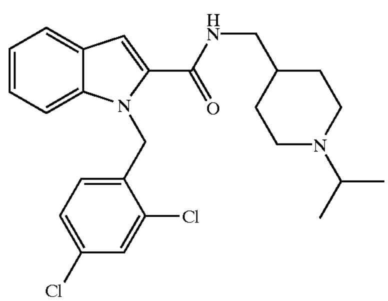 | 457, chloro pattern |
| 140 | 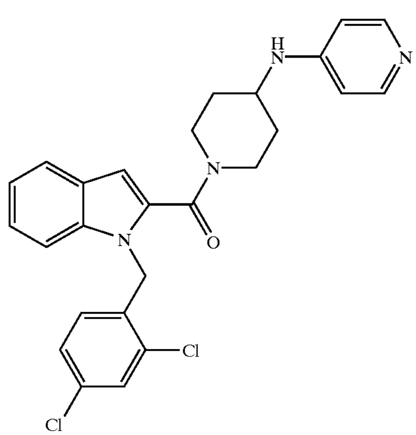 | 479, chloro pattern |

-continued

| Example | Structure | MS (ESI+) |
|---|---|---|
| 141 | 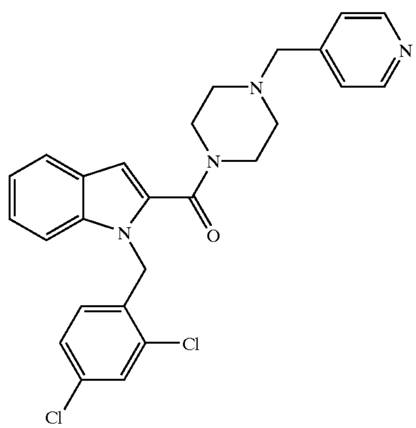 | 479, chloro pattern |
| 142 | 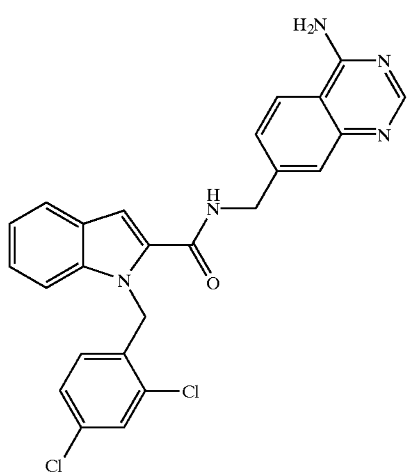 | 476, chloro pattern |
| 143 | 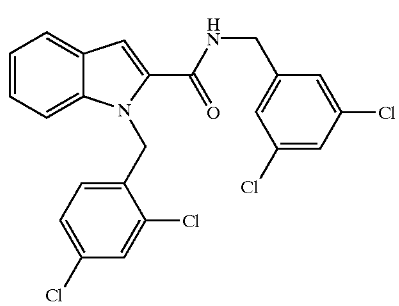 | 478, chloro pattern |

Example 144

1-(4-Methoxy-benzyl)-1H-indole-2-carboxylic acid (1-isopropyl-piperidin-4-yl)-amide

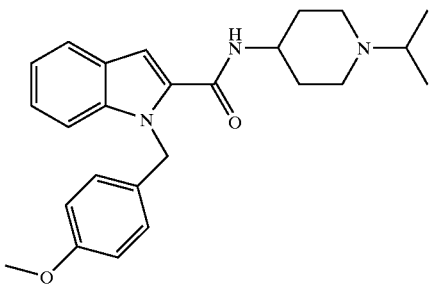

The title compound was prepared analogously to example 1 with the difference that 1-Chloromethyl-4-methoxy-benzene was used instead of 3-Bromomethyl-5-(5-chloro-thiophen-2-yl)-isoxazole. MS (ESI+): m/e=406.

Example 145

(4-Isopropylamino-piperidin-1-yl)-[1-(4-methoxy-benzyl)-1H-indol-2-yl]-methanone

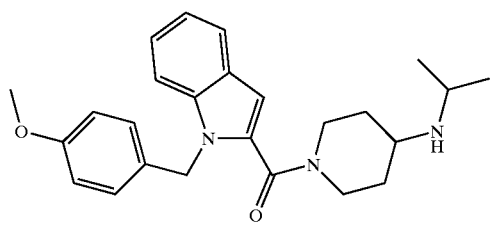

The title compound was prepared analogously to example 144 with the difference that 4-Isopropyl-piperidin-1-yl-amine was used instead of 1-Isopropyl-piperidin-4-ylamine.
MS (ESI+): m/e=406.

Example 146

1-(4-Trifluoromethoxy-benzyl)-1H-indole-2-carboxylic acid (1-isopropyl-piperidin-4-yl)-amide

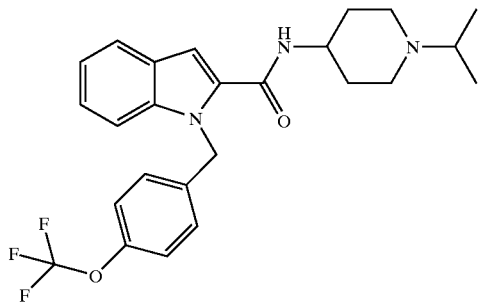

The title compound was prepared analogously to example 1 with the difference that 1-Bromomethyl-4-trifluoromethoxy-benzene was used instead of 3-Bromomethyl-5-(5-chloro-thiophen-2-yl)-isoxazole. MS (ESI+): m/e=459.

Example 147

(4-Isopropylamino-piperidin-1-yl)-[1-(4-trifluoromethoxy-benzyl)-1H-indol-2-yl]-methanone

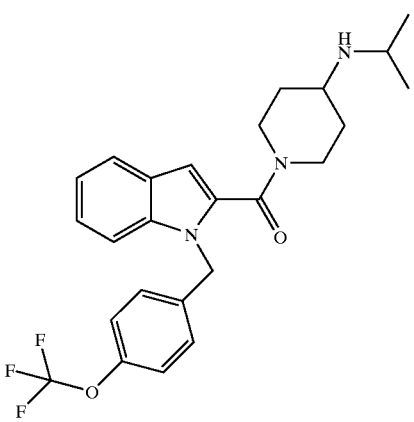

The title compound was prepared analogously to example 146 with the difference that Isopropyl-piperidin-4-yl-amine was used instead of 1-Isopropyl-piperidin-4-ylamine.

MS (ESI+): m/e=459.

Example 148

1-(2-Chloro-benzyl)-1H-indole-2-carboxylic acid (1-isopropyl-piperidin-4-yl)-amide

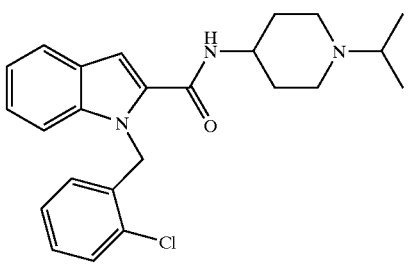

The title compound was prepared analogously to example 1 with the difference that 1-Bromomethyl-2-chloro-benzene was used instead of 3-Bromomethyl-5-(5-chloro-thiophen-2-yl)-isoxazole.

MS (ESI+): m/e=410, chloro pattern.

According to example 148 the following compounds were prepared by a similar procedure:

| Example | Structure | MS (ESI+) |
|---|---|---|
| 149 | 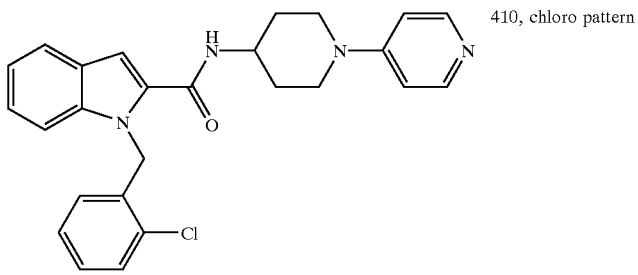 | 410, chloro pattern |
| 150 | 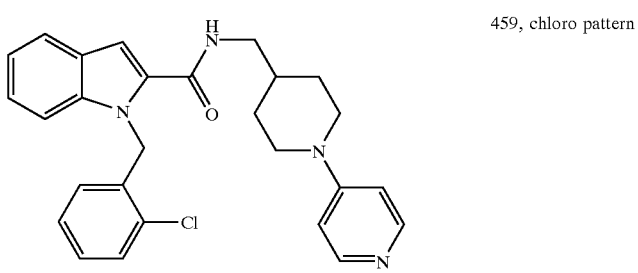 | 459, chloro pattern |
| 151 | 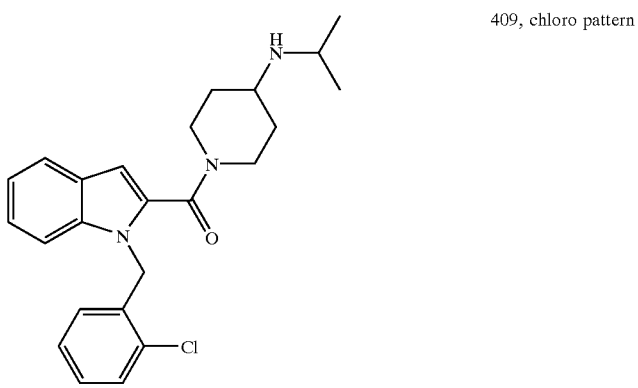 | 409, chloro pattern |
| 152 | 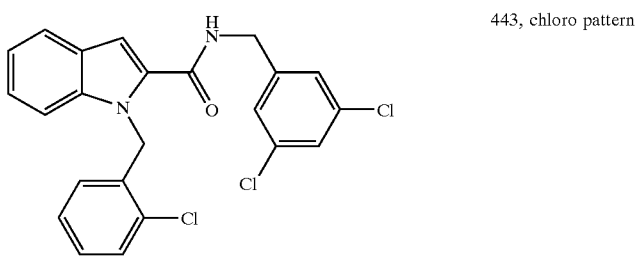 | 443, chloro pattern |

-continued
| Example | Structure | MS (ESI+) |
|---|---|---|
| 153 | 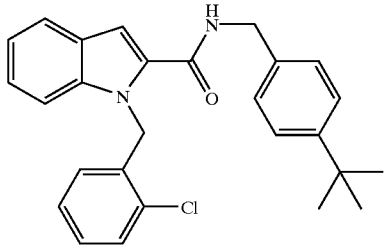 | 431, chloro pattern |
| 154 | 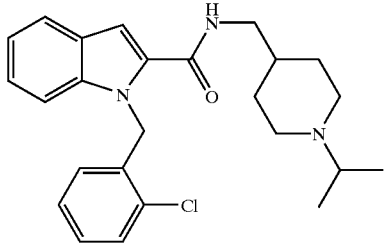 | 423, chloro pattern |
| 155 | 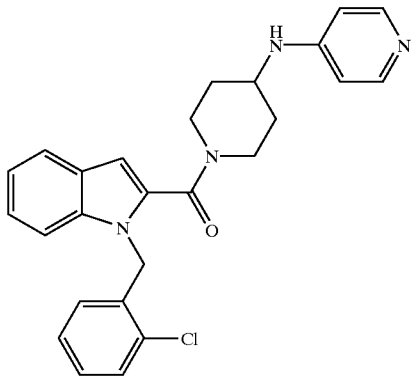 | 445, chloro pattern |
| 156 | 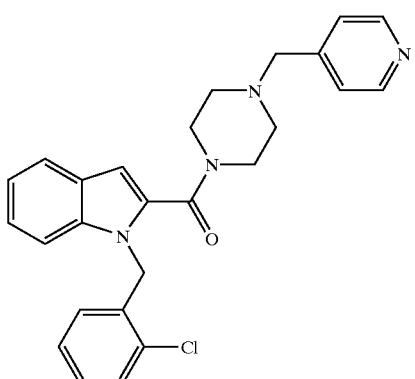 | 445, chloro pattern |

Example 157

1-(3,5-Dicloro-benzyl)-1H-indole-2-carboxylic acid (1-isopropyl-piperidin-4-yl)-amide

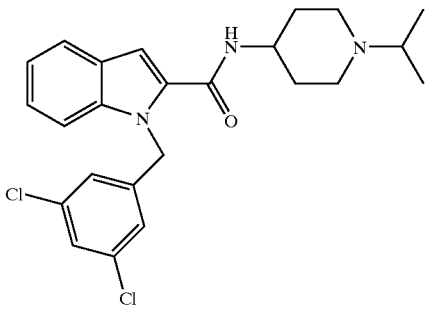

The title compound was prepared analogously to example 1 with the difference that 1-Chloromethyl-3,5-dichloro-benzene was used instead of 3-Bromomethyl-5-(5-chloro-thiophen-2-yl)-isoxazole.

MS (ESI+): m/e=444, chloro pattern.

Example 158

[1-(3,5-Dichloro-benzyl)-1H-indol-2-yl]-(4-isopropylamino-piperidin-1-yl)-methanone

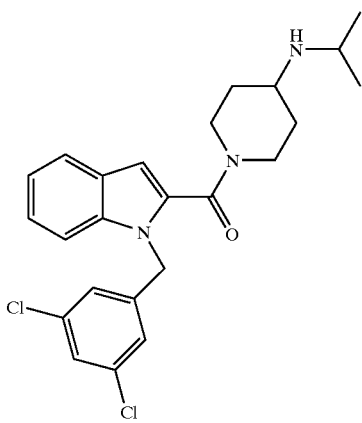

The title compound was prepared analogously to example 157 with the difference that Isopropyl-piperidin-4-yl-amine was used instead of 1-Isopropyl-piperidin-4-ylamine.

MS (ESI+): m/e=443, chloro pattern.

Example 159

3-Fluoro-1-[5-(5-chloro-thiophen-2-yl)-isoxazol-3-ylmethyl]-1H-indole-2-carboxylic acid (1-isopropyl-piperidin-4-yl)-amide

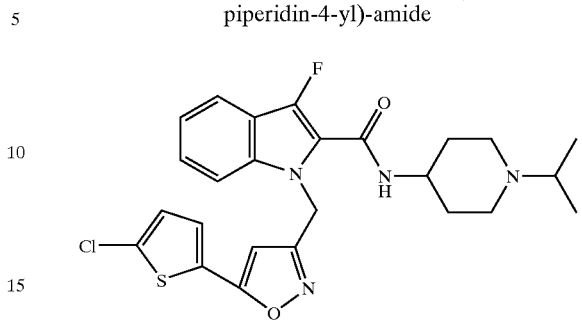

To a solution of 40 mg 1-[5-(5-Chloro-thiophen-2-yl)-isoxazol-3-ylmethyl]-1H-indole-2-carboxylic acid (1-isopropyl-piperidin-4-yl)-amide in 1 ml DCM 22 mg N-Fluoropyridinium triflate were added and the mixture was stirred at RT for 4 days. Finally, the reaction mixture was directly purified by preparative RP-HPLC eluting with a gradient of 0–100% acetonitrile in water (+0.01% trifluoroacetic acid). After lyophilization the product was obtained as its trifluoroacetate salt.

Yield: 22 mg MS (ES+): m/e=501, chloro pattern.

Example 160

1-[5-(5-Chloro-thiophen-2-yl)-isoxazol-3-ylmethyl]-3-cyano-1H-indole-2-carboxylic acid (1-isopropyl-piperidin-4-yl)-amide

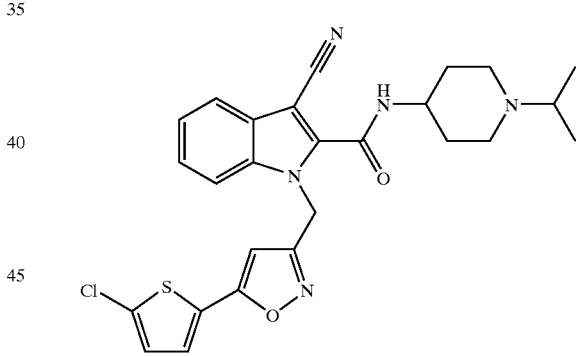

(i) 3-Iodo-1H-indole-2-carboxylic acid methyl ester.

To a solution of 2 g 1H-Indole-2-carboxylic acid methyl ester and 2.1 g KOH in 20 ml DMF a solution of 2.7 g $I_2$ in 10 ml DMF were added dropwise at RT. After 30 min the reaction mixture was diluted with a solution of 2.5 g $NaHSO_3$ in 100 ml water. The product was collected as a white precipitate by filtration and was washed with 10 ml water. Yield: 3 g.

(ii) 3-Cyano-1H-indole-2-carboxylic acid methyl ester.

To a solution of 2 g 3-Iodo-1H-indole-2-carboxylic acid methyl ester in 10 ml DMF and 20 ml THF, 1.5 g CuCN, 434 mg $Et_4NCN$ and 461 mg DPPF were added and the mixture was purged with argon for 15 min. Then, 254 mg $Pd_2(dba)_3$ were introduced and the reaction was heated to 80° C. for 5 h. Finally, 10 ml saturated $NaHCO_3$ solution were added and the mixture was filtered through a chem elut® cartridge by elution with DCM. After subsequent removal of the solvent under reduced pressure the residue was purified by chromatography on silica gel with ethylacetate as eluent. The fractions containing the product were evaporated to yield a white solid. Yield: 1.2 g.

(iii) 1-[5-(5-Chloro-thiophen-2-yl)-isoxazol-3-ylmethyl]-3-cyano-1H-indole-2-carboxylic acid methyl ester.

This compound was prepared using a procedure analogous to that described for the preparation of Example 1 (iv), using 3-Cyano-1H-indole-2-carboxylic acid methyl ester as the starting material.

(iv) 1-[5-(5-Chloro-thiophen-2-yl)-isoxazol-3-ylmethyl]-3-cyano-1H-indole-2-carboxylic acid This compound was prepared using a procedure analogous to that described for the preparation of Example 1 (v), using 1-[5-(5-Chloro-thiophen-2-yl)-isoxazol-3-ylmethyl]-3-cyano-1H-indol-2-carboxylic acid methyl ester as the starting material.

(v) 1-[5-(5-Chloro-thiophen-2-yl)-isoxazol-3-ylmethyl]-3-cyano-1H-indole-2-carboxylic acid (1-isopropyl-piperidin-4-yl)-amide.

This compound was prepared using a procedure analogous to that described for the preparation of Example 1 (vi), using 1-[5-(5-Chloro-thiophen-2-yl)-isoxazol-3-ylmethyl]-3-cyano-1H-indole-2-carboxylic acid as the starting material.

MS (ES$^+$): m/e=508, chloro pattern.

Example 161

1-[5-(5-Chloro-thiophen-2-yl)-isoxazol-3-ylmethyl]-3-cyano-7-methyl-1H-indole-2-carboxylic acid (1-isopropyl-piperidin-4-yl)-amide

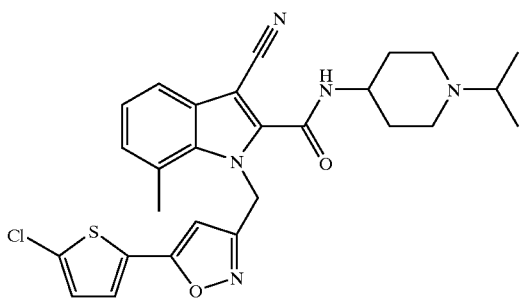

The title compound was prepared analogously to example 186 with the difference that 7-Methyl-1H-indole-2-carboxylic acid methyl ester was used instead of 1H-Indole-2-carboxylic acid methyl ester. MS (ESI+): m/e=522, chloro pattern.

Example 162

1-[2-(5-Chloro-thiophen-2-yl)-thiazol-5-ylmethyl]-1H-indole-2-carboxylic acid 1-isopropyl-piperidin-4-yl)-amide

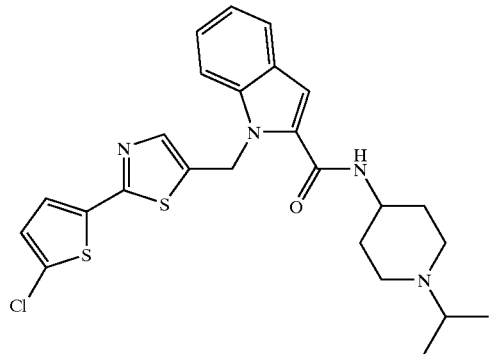

The title compound was prepared analogously to example 1 with the difference that 5-Bromomethyl-2-(5-chloro-thiophen-2-yl)-thiazole [prepared by adopting a procedure described by Ewing, William R. et al.; PCT Int. Appl. (2001), 460 pp. WO 0107436 A2] was used instead 3-Bromomethyl-5-(5-chloro-thiophen-2-yl)-isoxazole.

MS (ESI+): m/e=499, chloro pattern.

Example 163

1-(3-Chloro-benzyl)-1H-indole-2-carboxylic acid (1-isopropyl-piperidin-4-yl)-amide

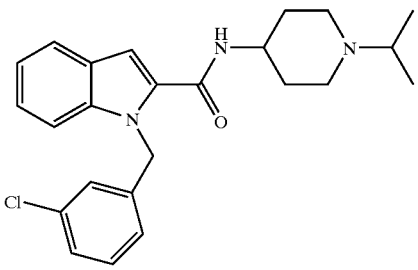

The title compound was prepared analogously to example 1 with the difference that 1-Bromomethyl-3-chloro-benzene was used instead of 3-Bromomethyl-5-(5-chloro-thiophen-2-yl)-isoxazole.

MS (ESI+): m/e=410, chloro pattern.

Example 164

[1-(3-Chloro-benzyl)-1H-indol-2-yl]-(4-isopropylamino-piperidin-1-yl)-methanone

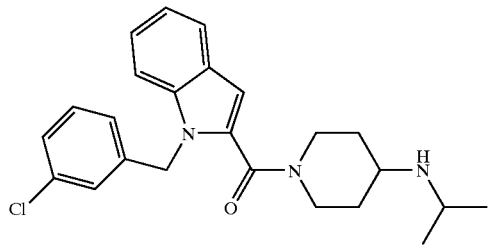

The title compound was prepared analogously to example 163 with the difference that Isopropyl-piperidin-4-yl-amine was used instead of 1-Isopropyl-piperidin-4-ylamine.
MS (ESI+): m/e=409, chloro pattern.

Example 165

1-(3-Carbamoyl-benzyl)-1H-indole-2-carboxylic acid (1-isopropyl-piperidin-4-yl)-amide

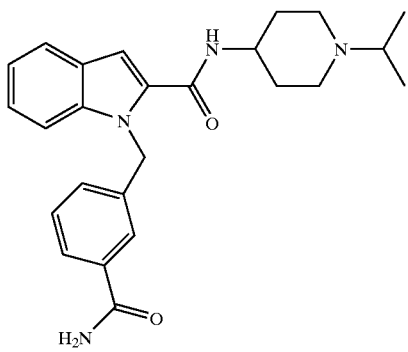

The title compound was prepared analogously to example 1 with the difference that 3-Bromomethyl-benzamide was used instead of 3-Bromomethyl-5-(5-chloro-thiophen-2-yl)-isoxazole. MS (ESI+): m/e=419.

Example 166

3-[2-(4-Isopropylamino-piperidine-1-carbonyl)-indol-1-ylmethyl]-benzamide

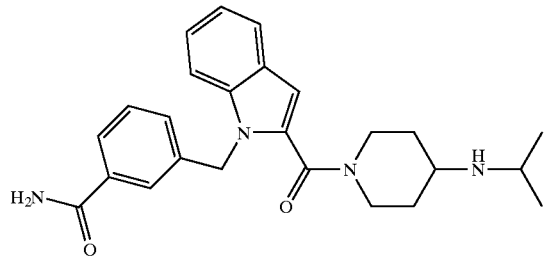

The title compound was prepared analogously to example 165 with the difference that Isopropyl-piperidin-4-yl-amine was used instead of 1-Isopropyl-piperidin-4-ylamine.
MS (ESI+): m/e=419.

Example 167

1-(3,5-Dimethoxy-benzyl)-1H-indole-2-carboxylic acid (1-isopropyl-piperidin-4-yl)-amide

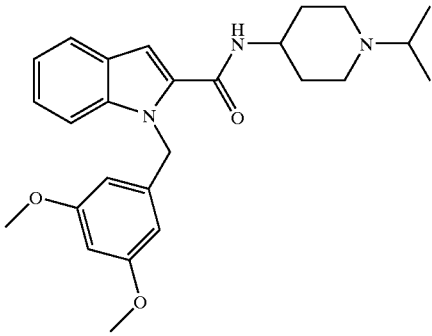

The title compound was prepared analogously to example 1 with the difference that 1-Chloromethyl-3,5-dimethoxy-benzene was used instead of 3-Bromomethyl-5-(5-chloro-thiophen-2-yl)-isoxazole. MS (ESI+): m/e 435.

Example 168

[1-(3,5-Dimethoxy-benzyl)-1H-indol-2-yl]-(4-isopropylamino-piperidin-1-yl)-methanone

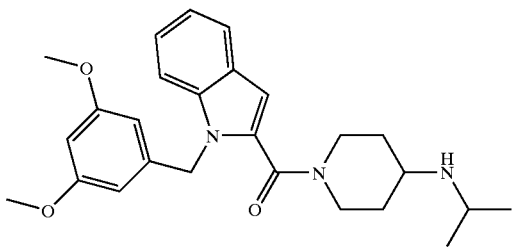

The title compound was prepared analogously to example 167 with the difference that Isopropyl-piperidin-4-yl-amine was used instead of 1-Isopropyl-piperidin-4-ylamine.
MS (ESI+): m/e=435.

Example 169

1-[2-(4-Chloro-phenyl)-ethyl]-1H-indole-2-carboxylic acid (1-isopropyl-piperidin-4-yl)-amide.

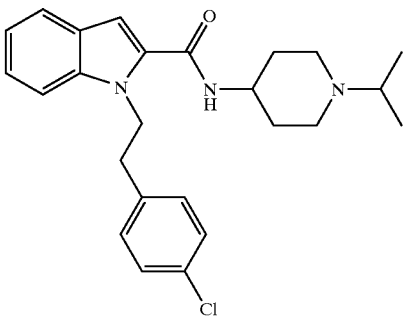

(i) Toluene-4-sulfonic acid 2-(4-chloro-phenyl)-ethyl ester
5 g (31.9 mmol) of 2-(4-Chloro-phenyl)-ethanol was dissolved in 100 ml of pyridine and the solution was cooled to 0° C. 6.09 g (31.9 mmol) of para-toluene sulfonyl chloride was added to this solution and the reaction was stirred at 0° C. for 2 h, then at room temperature for 16 h. The solvent was removed under reduced pressure, the residue was taken-up in ethyl acetate and the solution was washed once with saturated aqueous sodium bicarbonate, once with water, and once with saturated aqueous sodium chloride. The organic phase was dried with sodium sulfate, filtered and the solvent was removed under reduced pressure. The compound was recrystallised from n-heptane/ethyl acetate. Yield: 6.23 g MS (Cl$^+$): m/e=311, chloro pattern.

(ii) 1-[2-(4-Chloro-phenyl)-ethyl]-1H-indole-2-carboxylic acid ethyl ester 0.5 g (2.6 mmol) of 1H-Indole-2-carboxylic acid ethyl ester was dissolved in DMF and 116 mg (2.9 mmol) of sodium hydride (60% dispersion in mineral oil) was added. The solution was stirred for 30 min at room temperature, then cooled to −78° C. A solution of 0.82 g (2.6 mmol) of toluene-4-sulfonic acid 2-(4-chloro-phenyl)-ethyl ester in DMF was added to this cooled solution. The solution was warmed to RT and was stirred for 16 h. The solvent was removed under reduced pressure, the residue was taken-up in ethyl acetate and the solution was washed once with saturated aqueous sodium bicarbonate, once with water, and once with saturated aqueous sodium chloride. The organic phase was dried with magnesium sulfate, filtered and the solvent was removed under reduced pressure. The residue was chromatographed on silica gel eluting with a gradient of n-heptane/ethyl acetate.

Yield: 480 mg MS (Cl$^+$): m/e=328, chloro pattern.

(iii) 1-[2-(4-Chloro-phenyl)-ethyl]-1H-indole-2-carboxylic acid.

480 mg (1.5 mmol) of 1-[2-(4-Chloro-phenyl)-ethyl]-1H-indole-2-carboxylic acid ethyl ester was dissolved in 5 ml of dioxan and 5 ml of 2N aqueous sodium hydroxide was added. The reaction was heated to 60° C. for 2 h, then was cooled to 0° C. The solution was diluted with 10 ml of water and the pH of the solution was adjusted to between 2 and 3 by the addition of concentrated aqueous HCl, whereupon the product precipitates. The product was filtered off and dried under reduced pressure. Yield: 390 mg MS (Cl$^+$): m/e=300, chloro pattern.

(iv) 1-[2-(4-Chloro-phenyl)-ethyl]-1H-indole-2-carboxylic acid (1-isopropyl-piperidin-4-yl)-amide.

50 mg (0.2 mmol) of 1-[2-(4-Chloro-phenyl)-ethyl]-1H-indole-2-carboxylic acid was dissolved in 2 ml of DMF and 54.7 mg (0.2 mmol) of TOTU and 0.21 ml (1.7 mmol) of NEM was added. This solution was stirred at room temperature for 30 min. 35.9 mg (0.2 mmol) of 1-isopropyl-piperidin-4-ylamine dihydrochloride was added and the resulting solution was stirred at room temperature for 16 h. The product was purified by preparative RP-HPLC eluting with a gradient of 0–100% acetonitrile in water (+0.01% trifluoroacetic acid). After lyophilization the product was obtained as its trifluoroacetate salt. Yield: 46.9 mg MS (TOF-ES$^+$): m/e=424, chloro pattern.

Example 170

1-[2-(2,4-Dichloro-phenyl)-ethyl]-1H-indole-2-carboxylic acid (1-isopropyl-piperidin-4-yl)-amide

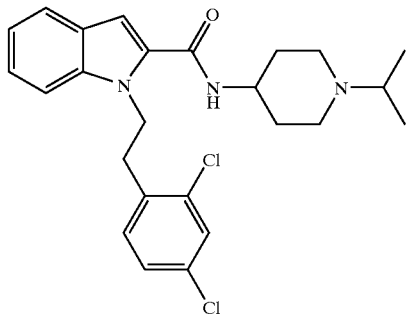

(i) Toluene-4-sulfonic acid 2-(2,4-dichloro-phenyl)-ethyl ester.

This compound was prepared using a procedure analogous to that described for the preparation of Example 169 (i), using 2-(2,4-dichloro-phenyl)-ethanol as the starting material. The compound was recrystallised from n-heptane/ethyl acetate.

Yield: 7.12 g MS (Cl$^+$): m/e=345, chloro pattern.

(ii) 1-[2-(2,4-Dichlorophenyl)-ethyl]-1H-indole-2-carboxylic acid ethyl ester.

This compound was prepared using a procedure analogous to that described for the preparation of Example 169 (ii), and using toluene-4-sulfonic acid 2-(2,4-dichloro-phenyl)-ethyl ester as the starting material. Yield: 91 mg MS (LC-MS-ES$^+$): m/e=362, chloro pattern.

(iii) 1-[2-(2,4-Dichlorophenyl)-ethyl]-1H-indole-2-carboxylic acid.

This compound was prepared using a procedure analogous to that described for the preparation of Example 169 (iii), using 1-[2-(2,4-Dichlorophenyl)-1H-indole-2-carboxylic acid ethyl ester as the starting material. Yield: 69 mg MS (Cl$^+$): m/e=334, chloro pattern.

(iv) 1-[2-(2,4-Dichlorophenyl)-ethyl]-1H-indole-2-carboxylic acid (1-isopropyl-piperidin-4-yl)-amide This compound was prepared using a procedure analogous to that described for the preparation of Example 169 (iv), using 1-[2-(2,4-Dichlorophenyl)-ethyl]-1H-indole-2-carboxylic acid as the starting material. Yield: 69 mg MS (Cl$^+$): m/e=334, chloro pattern.

Example 171

1-[2-(3-Methoxy-phenyl)-ethyl]-1H-indole-2-carboxylic acid (1-isopropyl-piperidin-4-yl)-amide

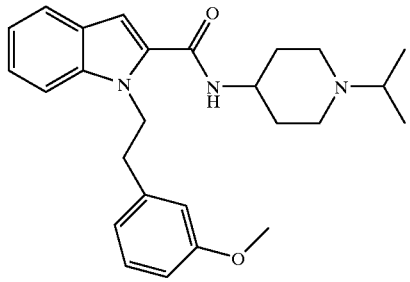

(i) Toluene-4-sulfonic acid 2-(3-methoxyphenyl)-ethyl ester.

This compound was prepared using a procedure analogous to that described for the preparation of Example 169

(i), using 2-(3-methoxyphenyl)-ethanol as the starting material. The compound was chromatographed on silica gel eluting with n-heptane/ethyl acetate (4/1).

Yield: 5.13 g. MS (Cl$^+$): m/e=306 (M$^+$).

(ii) 1-[2-(3-Methoxy-phenyl)-ethyl]-1H-indole-2-carboxylic acid ethyl ester.

This compound was prepared using a procedure analogous to that described for the preparation of Example 169 (ii), using toluene-4-sulfonic acid 2-(3-methoxyphenyl)-ethyl ester as the starting material. Yield: 554 mg. MS (LC-MS-ES$^+$): m/e=324 (M+H$^+$).

(iii) 1-[2-(3-Methoxy-phenyl)-ethyl]-1H-indole-2-carboxylic acid.

This compound was prepared using a procedure analogous to that described for the preparation of Example 169 (iii), using 1-[2-(3-Methoxy-phenyl)-ethyl]-1H-indole-2-carboxylic acid ethyl as the starting material. Yield: 384 mg. MS (Cl$^+$): m/e=296 (M+H$^+$).

(iv) 1-[2-(3-Methoxy-phenyl)-ethyl]-1H-indole-2-carboxylic acid (1-isopropyl-piperidin-4-yl)-amide This compound was prepared using a procedure analogous to that described for the preparation of Example 169 (iv), using 1-[2-(3-Methoxy-phenyl)-ethyl]-1H-indole-2-carboxylic acid as the starting material. Yield: 44 mg MS (LC-MS-ES$^+$): m/e=419 (M$^+$).

Example 172

1-[2-(4-Chloro-phenyl)-ethyl]-4-methoxy-1H-indole-2-carboxylic acid (1-isopropyl-piperidin-4-yl)-amide

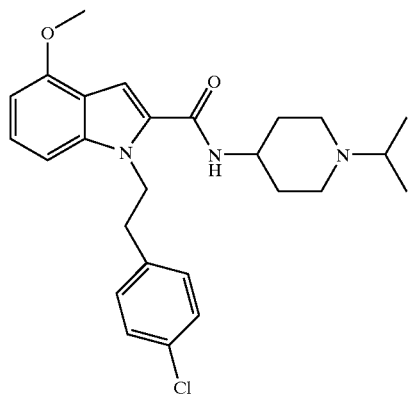

This compound was prepared using a procedure analogous to that described for the preparation of Example 169, using 4-methoxy-1H-indole-2-carboxylic acid methyl ester as the starting material. Yield: 67 mg. MS (ES$^+$): m/e=454 (M$^+$), chloro pattern.

Example 173

4-Bromo-1-[5-(5-chloro-thiophen-2-yl)-isoxazol-3-ylmethyl]-1H-indole-2-carboxylic acid (1-isopropyl-piperidin-4-yl)-amide

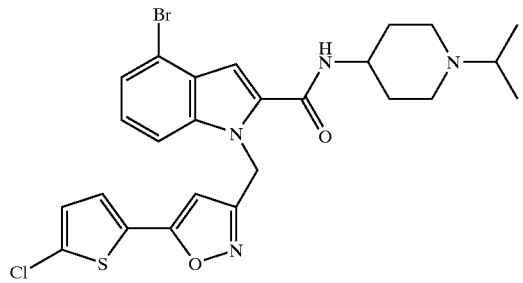

The title compound was prepared analogously to example 1 with the difference that 4-Bromo-1H-indole-2-carboxylic acid was used instead of 1H-Indole-2-carboxylic acid.

MS (ESI+): m/e=562, chloro pattern.

Example 174

1-[5-(5-Chloro-thiophen-2-yl)-isoxazol-3-ylmethyl]-4-methyl-1H-indole-2-carboxylic acid (1-isopropyl-piperidin-4-yl)-amide

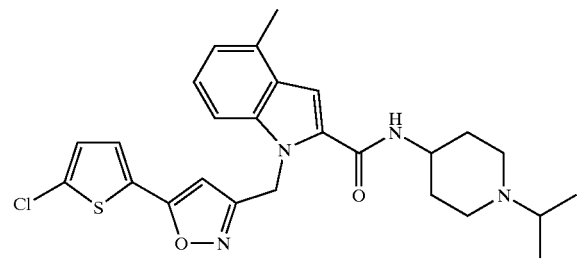

The title compound was prepared analogously to example 1 with the difference that 4-Methyl-1H-indole-2-carboxylic acid was used instead of 1H-Indole-2-carboxylic acid.

MS (ESI+): m/e=497, chloro pattern.

Example 175

5-Bromo-1-[5-(5-chloro-thiophen-2-yl)-isoxazol-3-ylmethyl]-1H-indole-2-carboxylic acid (1-isopropyl-piperidin-4-yl)-amide

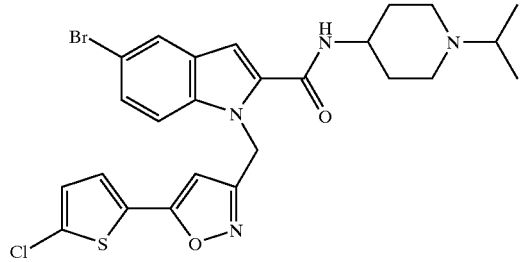

The title compound was prepared analogously to example 1 with the difference that 5-Bromo-1H-indole-2-carboxylic acid was used instead of 1H-Indole-2-carboxylic acid.

MS (ESI+): m/e=562, chloro pattern.

Example 176

1-[5-(5-Chloro-thiophen-2-yl)-isoxazol-3-ylmethyl]-5-cyano-1H-indole-2-carboxylic acid (1-isopropyl-piperidin-4-yl)-amide

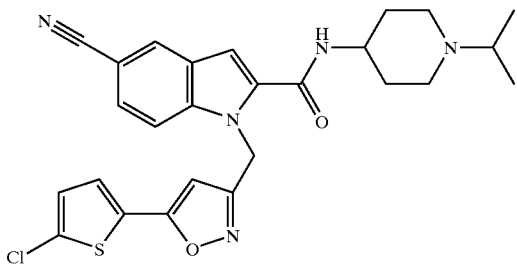

The title compound was prepared analogously to example 1 with the difference that 5-Cyano-1H-indole-2-carboxylic acid was used instead of 1H-Indole-2-carboxylic acid.

MS (ESI+): m/e=508, chloro pattern.

Example 177

1-[5-(5-Chloro-thiophen-2-yl)-isoxazol-3-ylmethyl]-4-trifluoromethyl-1H-indole-2-carboxylic acid (1-isopropyl-piperidin-4-yl)-amide

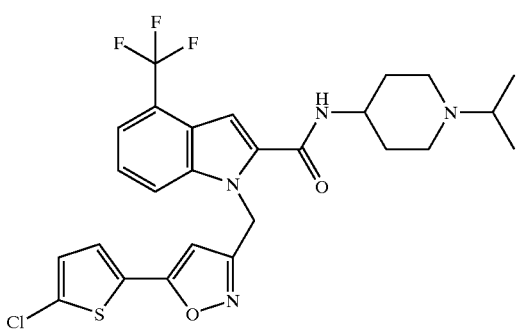

The title compound was prepared analogously to example 1 with the difference that 4-Trifluoromethyl-1H-indole-2-carboxylic acid was used instead of 1H-Indole-2-carboxylic acid.

MS (ESI+): m/e=551, chloro pattern.

Example 178

1-[5-(5-Chloro-thiophen-2-yl)-isoxazol-3-ylmethyl]-4,7-dimethyl-1H-indole-2-carboxylic acid (1-isopropyl-piperidin-4-yl)-amide

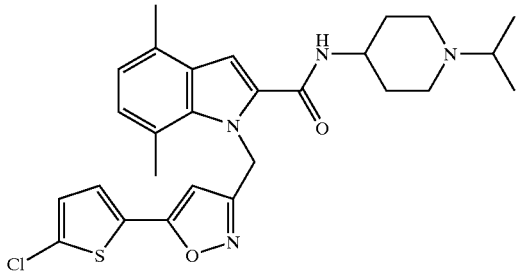

The title compound was prepared analogously to example 1 with the difference that 4,7-Dimethyl-1H-indole-2-carboxylic acid was used instead of 1H-Indole-2-carboxylic acid.

MS (ESI+): m/e=511, chloro pattern.

Example: 179

1-[5-(5-Chloro-thiophen-2-yl)-isoxazol-3-ylmethyl]-4,7-dimethoxy-1H-indole-2-carboxylic acid (1-isopropyl-piperidin-4-yl)-amide

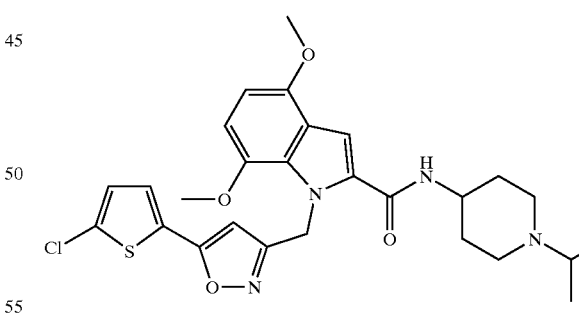

The title compound was prepared analogously to example 1 with the difference that 4,7-Dimethoxy-1H-indole-2-carboxylic acid was used instead of 1H-Indole-2-carboxylic acid.

MS (ESI+): m/e=543, chloro pattern.

Example: 180

4,7-Dichloro-1-[5-(5-chloro-thiophen-2-yl)-isoxazol-3-ylmethyl]-1H-indole-2-carboxylic acid (1-isopropyl-piperidin-4-yl)-amide

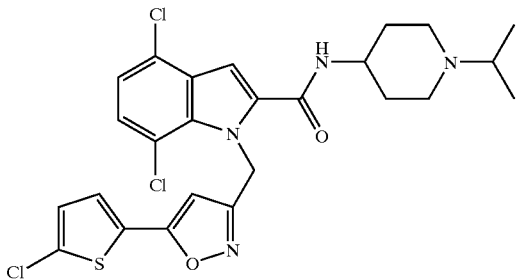

The title compound was prepared analogously to example 1 with the difference that 4,7-Dichloro-1H-indole-2-carboxylic acid was used instead of 1H-Indole-2-carboxylic acid.

MS (ESI+): m/e=551, chloro pattern.

Example 181

5,7-Dichloro-1-[5-(5-chloro-thiophen-2-yl)-isoxazol-3-ylmethyl]-1H-indole-2-carboxylic acid (1-isopropyl-piperidin-4-yl)-amide

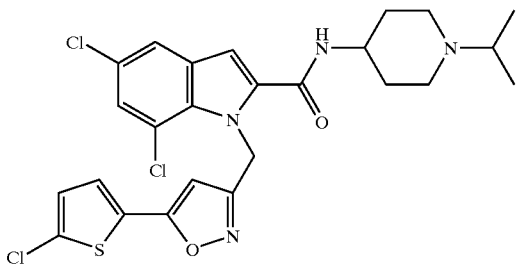

The title compound was prepared analogously to example 1 with the difference that 5,7-Dichloro-1H-indole-2-carboxylic acid was used instead of 1H-Indole-2-carboxylic acid.

MS (ESI+): m/e=551, chloro pattern.

Example 182

4-Chloro-1-[5-(5-chloro-thiophen-2-yl)-isoxazol-3-ylmethyl]-1H-indole-2-carboxylic acid (1-isopropyl-piperidin-4-yl)-amide

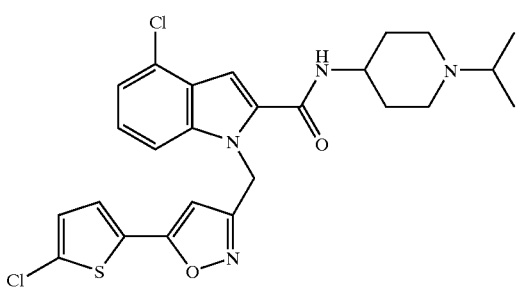

The title compound was prepared analogously to example 1 with the difference that 4-Chloro-1H-indole-2-carboxylic acid was used instead of 1H-Indole-2-carboxylic acid.

MS (ESI+): m/e=517, chloro pattern.

Example 183

1-[5-(5-Chloro-thiophen-2-yl)-isoxazol-3-ylmethyl]-1H-indole-2-carboxylic acid (4-methyl-piperazin-1-yl)-amide

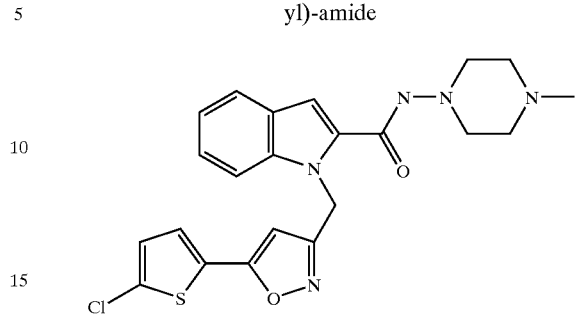

The title compound was prepared analogously to example 1 with the difference that 4-Methyl-piperazin-1-ylamine was used instead of 1-Isopropyl-piperidin-4-ylamine.

MS (ESI+): m/e=456, chloro pattern.

Example 184

[{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester

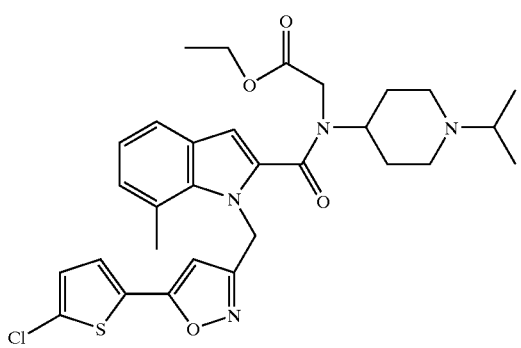

(i) (1-Isopropyl-piperidin-4-ylamino)-acetic acid ethyl ester.

To a solution of 1 g 1-Isopropyl-piperidin-4-ylamine hydrochloride in 10 ml DMF, 1.2 g 2-Bromoacetic acid ethyl ester, 2.3 g $Cs_2CO_3$, and 2 ml $NEt_3$, were added and the reaction mixture was stirred for 2 h at RT. Finally, 10 ml saturated $NaHCO_3$ solution were added and the mixture was filtered through a chem elut® cartridge by elution with DCM. After evaporation of the solvent under reduced pressure the product was obtained as a white foam and employed in the following reaction without further purification.

Yield: 1.3 g.

(ii) [{1-[5-(5-chloro-thiophen-2-yl)-isoxazol-3-ylmethyl]-7-methyl-1H-indole-2-carbonyl}-(1-isopropyl-piperidin-4-yl)-amino]-acetic acid ethyl ester.

To a solution of 70 mg 1-[5-(5-Chloro-thiophen-2-yl)-isoxazol-3-ylmethyl]-7-methyl-1H-indole-2-carboxylic acid in 1 ml DMF, 0.1 ml $NEt_3$, 47 mg BOP-Cl and 81 mg (1-Isopropyl-piperidin-4-ylamino)-acetic acid ethyl ester were added and the mixture was stirred for 16 h. After removal of the solvent under reduced pressure the residue was filtered through a chem elut® cartridge by elution with ethyl acetate and then purified by preparative HPLC (C18

Example 185

[{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid

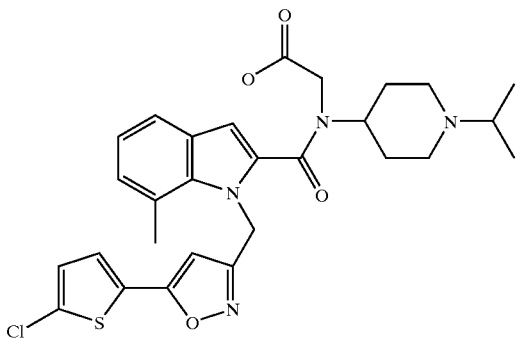

To a solution of 15 mg [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester in 2 ml water/THF 1:2, 25 µl aqueous NaOH solution (2M) were added and the reaction stirred for 16 h at RT. The reaction mixture was acidified by addition of hydrochloric acid (5M), concentrated under reduced pressure and the residue taken-up in DCM. The inorganic salts were filtered off, the filtrate was concentrated under reduced pressure, taken-up in 1 ml water and lyophilized to yield a white solid. The product was obtained as its HCl salt. Yield: 5 mg MS (ES$^+$): m/e=555, chloro pattern.

Example 186

1-[5-(5-Chloro-thiophen-2-yl)-isoxazol-3-ylmethyl]-1H-indole-2-carboxylic acid [1-(1-ethyl-propyl)-piperidin-4-yl]-amide

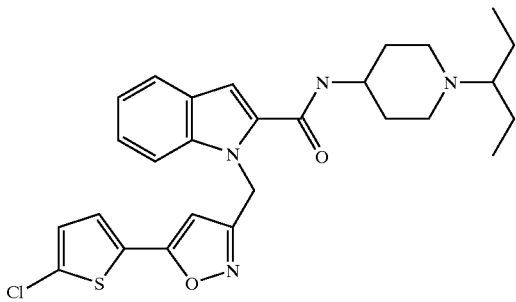

The title compound was prepared analogously to example 49 with the difference that Pentan-3-one was used instead of Tetrahydro-pyran-4-one. MS (ESI+): m/e=511, chloro pattern.

Example 187

1-[5-(5-Chloro-thiophen-2-yl)-isoxazol-3-ylmethyl]-1H-indole-2-carboxylic acid (1-methyl-piperidin-4-yl)-amide

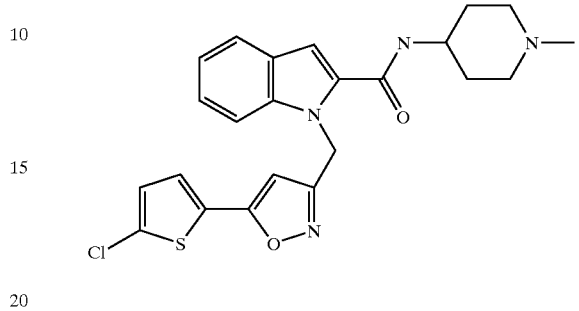

To a solution of 50 mg 1-[5-(5-Chloro-thiophen-2-yl)-isoxazol-3-ylmethyl]-1H-indole-2-carboxylic acid piperidin-4-ylamide in 1 ml DMF and 40 µl NEt$_3$, 24 mg methyl iodide were added at RT and the reaction mixture stirred for 4 h. After removal of the solvent under reduced pressure the residue was directly purified by preparative RP-HPLC eluting with a gradient of 0–100% acetonitrile in water (+0.01% trifluoroacetic acid). After lyophilization the product was obtained as its trifluoroacetate salt.

Yield: 32 mg MS (ES$^+$): m/e=455, chloro pattern.

Example 188

1-[5-(5-Chloro-thiophen-2-yl)-isoxazol-3-ylmethyl]-1H-indole-2-carboxylic acid [1-(2,2,2-trifluoro-ethyl)-piperidin-4-yl]-amide

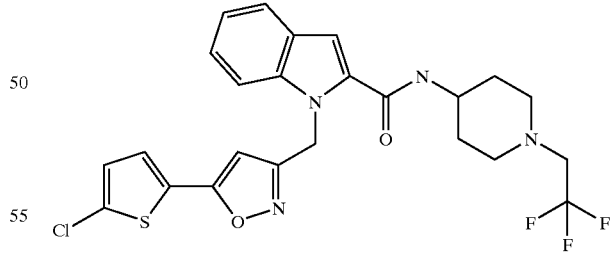

The title compound was prepared analogously to example 187 with the difference that 2-Iodo1,1,1-trifluoroethane was used instead of methyl iodide.

MS (ESI+): m/e=523, chloro pattern.

--- reverse phase column, elution with a H$_2$O/MeCN gradient with 0.1% TFA). The fractions containing the product were evaporated and lyophilized to yield a white solid. The product was obtained as its trifluoroacetate salt. Yield: 9.3 mg MS (ES$^+$): m/e=583, chloro pattern.

Example 189

1-[5-(5-Chloro-thiophen-2-yl)-isoxazol-3-ylmethyl]-1H-indole-2-carboxylic acid (1-formyl-piperidin-4-yl)-amide

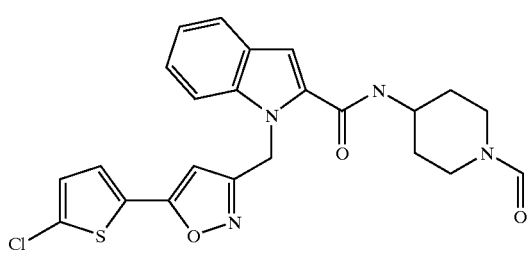

A solution of 50 mg 1-[5-(5-Chloro-thiophen-2-yl)-isoxazol-3-ylmethyl]-1H-indole-2-carboxylic acid piperidin-4-ylamide in 2 ml formic acid was heated to 100° C. for 5 h. After removal of the solvent under reduced pressure the residue directly purified by preparative RP-HPLC eluting with a gradient of 0–100% acetonitrile in water (+0.01% trifluoroacetic acid). After lyophilization the product was obtained as a white solid. Yield: 14 mg MS (ES$^+$): m/e=469, chloro pattern.

Example 190

1-[5-(5-Chloro-thiophen-2-yl)-isoxazol-3-ylmethyl]-1H-indole-2-carboxylic acid (1-carbamoyl-piperidin-4-yl)-amide

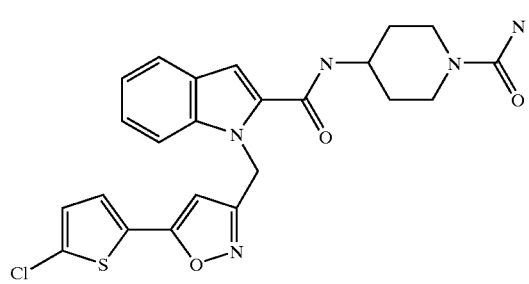

To a solution of 50 mg 1-[5-(5-Chloro-thiophen-2-yl)-isoxazol-3-ylmethyl]-1H-indole-2-carboxylic acid piperidin-4-ylamide in 2 ml acetic acid, 14 mg KOCN were added at RT and stirred over night. After removal of the solvent under reduced pressure the residue directly purified by preparative RP-HPLC eluting with a gradient of 0–100% acetonitrile in water (+0.01% trifluoroacetic acid). After lyophilization the product was obtained as a white solid.

Yield: 31 mg MS (ES$^+$): m/e=484, chloro pattern.

Example 191

1-[5-(5-Chloro-thiophen-2-yl)-isoxazol-3-ylmethyl]-1H-indole-2-carboxylic acid (1-methanesulfonyl-piperidin-4-yl)-amide

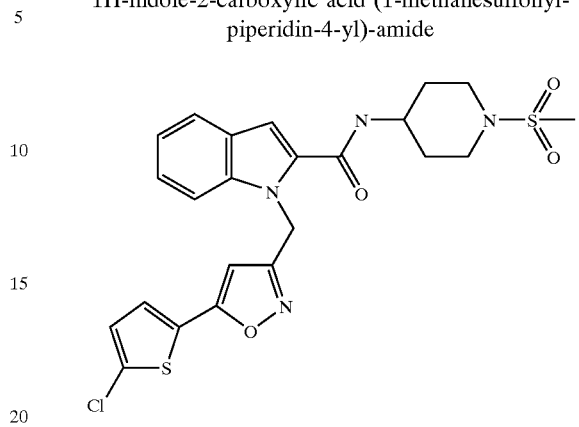

To a solution of 50 mg 1-[5-(5-Chloro-thiophen-2-yl)-isoxazol-3-ylmethyl]-1H-indole-2-carboxylic acid piperidin-4-ylamide in 2 ml DCM, 0.3 ml NEt$_3$ and 20 mg Methanesulfonyl chloride were added at RT and stirred for 16 h. After removal of the solvent under reduced pressure the residue was directly purified by preparative RP-HPLC eluting with a gradient of 0–100% acetonitrile in water (+0.01% trifluoroacetic acid). After lyophilization the product was obtained as a white solid.

Yield: 23 mg MS (ES$^+$): m/e=519, chloro pattern.

Example 192

1-[5-(5-Chloro-thiophen-2-yl)-isoxazol-3-ylmethyl]-1H-indole-2-carboxylic acid (1-acetyl-piperidin-4-yl)-amide

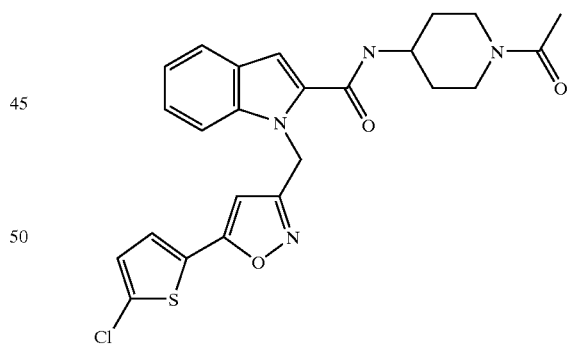

To a solution of 50 mg 1-[5-(5-Chloro-thiophen-2-yl)-isoxazol-3-ylmethyl]-1H-indole-2-carboxylic acid piperidin-4-ylamide in 2 ml DCM, 0.3 ml NEt$_3$ and 11 mg acetic acid anhydride were added at RT and stirred over night. After removal of the solvent under reduced pressure the residue was directly purified by preparative RP-HPLC eluting with a gradient of 0–100% acetonitrile in water (+0.01% trifluoroacetic acid). After lyophilization the product was obtained as a white solid.

Yield: 24 mg MS (ES$^+$): m/e=483, chloro pattern.

Example 193

1-[5-(5-Chloro-thiophen-2-yl)-isoxazol-3-ylmethyl]-1H-indole-2-carboxylic acid [1-(2-chloro-pyrimidin-4-yl)-piperidin-4-yl]-amide

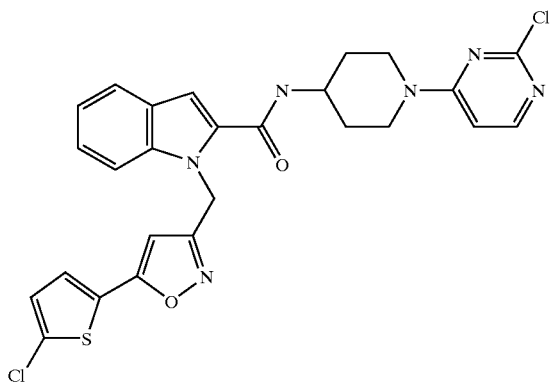

(i) [1-(2-Chloro-pyrimidin-4-yl)-piperidin-4-yl]-carbamic acid tert-butyl ester.

To a solution of 500 mg Piperidin-4-yl-carbamic acid tert-butyl ester in 6 ml n-BuOH/water/NEt₃ 1:1:1, 557 mg 2,4-Dichloro-pyrimidine were added and the reaction mixture was heated to 100° C. over night. After cooling the reaction to RT, the solvent was evaporated under reduced pressure and the residue was taken-up in ethyl acetate washed twice with water and then with brine. The organic layer was dried over Na₂SO₄ and the solvent removed under reduced pressure. The residue was purified by chromatography on silica gel eluting with ethyl acetate/heptane 2:1. The fractions containing the product were evaporated under reduced pressure to give a white solid.

Yield: 630 mg.

(ii) 1-(2-Chloro-pyrimidin-4-yl)-piperidin-4-ylamine.

To a solution of 250 mg [1-(2-Chloro-pyrimidin-4-yl)-piperidin-4-yl]-carbamic acid tert-butyl ester in 1 ml DCM, 1 ml TFA was added and the mixture was stirred for 2 h at RT. Then, 10 ml toluene was added and the solvents were removed under reduced pressure. The residue was codistilled twice with toluene to yield a yellow oil. The product was obtained as its trifluoroacetate salt.

Yield: 367 mg (iii) 1-[5-(5-Chloro-thiophen-2-yl)-isoxazol-3-ylmethyl]-1H-indole-2-carboxylic acid [1-(2-chloro-pyrimidin-4-yl)-piperidin-4-yl]-amide.

To a solution of 100 mg 1-[5-(5-Chloro-thiophen-2-yl)-isoxazol-3-ylmethyl]-1H-indole-2-carboxylic acid in 3 ml of DCM 91 mg TOTU and 0.13 ml NEM were added. This solution was stirred at room temperature for 30 min. Then 148 mg 1-(2-Chloro-pyrimidin-4-yl)-piperidin-4-ylamine trifluoro acetate was added and the resulting solution was stirred at room temperature for 16 h. The product was purified by preparative RP-HPLC eluting with a gradient of 0–100% acetonitrile in water (+0.01% trifluoroacetic acid). After lyophilization the product was obtained as its trifluoroacetate salt.

Yield: 71 mg MS (ES⁺): m/e=553, chloro pattern.

Example 194

1-[5-(5-Chloro-thiophen-2-yl)-isoxazol-3-ylmethyl]-1H-indole-2-carboxylic acid (1-pyrimidin-4-yl-piperidin-4-yl)-amide

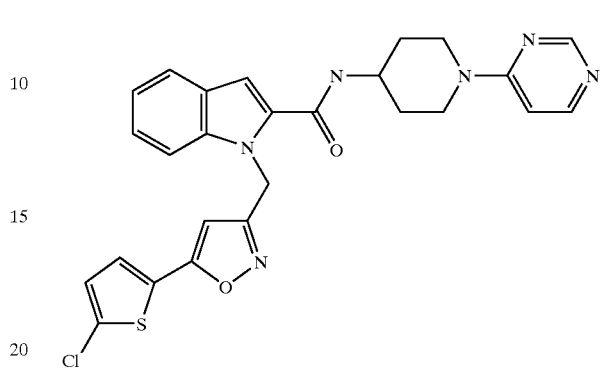

(i) (1-Pyrimidin-4-yl-piperidin-4-yl)-carbamic acid tert-butyl ester.

To a solution of 395 mg [1-(2-Chloro-pyrimidin-4-yl)-piperidin-4-yl]-carbamic acid tert-butyl ester in 10 ml ethanol and 0.3 ml acetic acid, 20 mg Pd/C (10%) were added and the mixture purged with argon for 10 min. Then the flask was stirred under a hydrogen atmosphere for 5 h at RT. After addition of 10 ml ethyl acetate the reaction mixture was filtered through a pad of celite. The solvent was evaporated under reduced pressure and the residue codistilled twice with toluene to give the product as a white solid. Yield: 468 mg.

(ii) 1-Pyrimidin-4-yl-piperidin-4-ylamine.

To a solution of 468 mg (1-Pyrimidin-4-yl-piperidin-4-yl)-carbamic acid tert-butyl ester in 2 ml DCM, 2 ml TFA were added and the mixture was stirred for 2 h at RT. Then, 10 ml toluene was added and the solvents were removed under reduced pressure. The residue was codistilled twice with toluene to yield a yellow oil. The product was obtained as its trifluoroacetate salt.

Yield: 703 mg.

(iii) 1-[5-(5-Chloro-thiophen-2-yl)-isoxazol-3-ylmethyl]-1H-indole-2-carboxylic acid (1-pyrimidin-4-yl-piperidin-4-yl)-amide.

To a solution of 100 mg 1-[5-(5-Chloro-thiophen-2-yl)-isoxazol-3-ylmethyl]-1H-indole-2-carboxylic acid in 3 ml of DCM, 91 mg TOTU and 0.13 ml NEM were added. This solution was stirred at room temperature for 30 min. Then 135 mg 1-Pyrimidin-4-yl-piperidin-4-ylamine trifluoroacetate was added and the resulting solution was stirred at room temperature for 16 h. The product was purified by preparative RP-HPLC eluting with a gradient of 0–100% acetonitrile in water (+0.01% trifluoroacetic acid). After lyophilization the product was obtained as its trifluoroacetate salt.

Yield: 52 mg MS (ES⁺): m/e=519, chloro pattern.

Example 195

{1-[5-(5-Chloro-thiophen-2-yl)-isoxazol-3-ylmethyl]-1H-indol-2-yl}-[4-(pyridin-4-yloxy)-piperidin-1-yl]-methanone

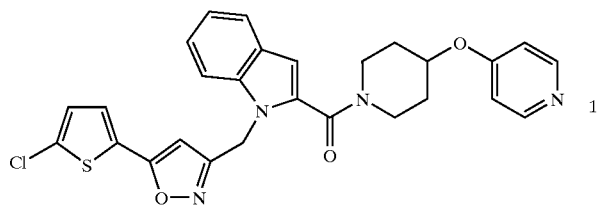

The title compound was prepared analogously to example 1 with the difference that 4-(Piperidin-4-yloxy)-pyridine [prepared by adopting a procedure described Baxter, Andrew Douglas; Owen, David Alan; Montana, John Gary; Watson, Robert John PCT Int. Appl. (1999), 44 pp. WO 9924399 A1] was used instead of 1-Isopropyl-piperidin-4-ylamine.

MS (ESI+): m/e=519, chloro pattern.

Example 196

1-[5-(5-Chloro-thiophen-2-yl)-isoxazol-3-ylmethyl]-1H-indole-2-carboxylic acid [4-(1H-imidazol-4-yl)-phenyl]-amide

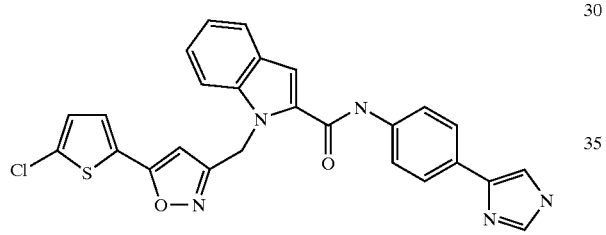

The title compound was prepared analogously to example 1 with the difference that 4-(1H-Imidazol-4-yl)-phenylamine was used instead of 1-Isopropyl-piperidin-4-ylamine.

MS (ESI+): m/e=500, chloro pattern.

Example 197

1-[5-(5-Chloro-thiophen-2-yl)-isoxazol-3-ylmethyl]-1H-indole-2-carboxylic acid (4-pyridin-3-yl-thiazol-2-yl)-amide

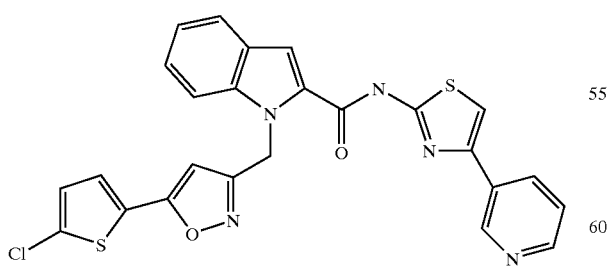

The title compound was prepared analogously to example 1 with the difference that 4-Pyridin-3-yl-thiazol-2-ylamine was used instead of 1-Isopropyl-piperidin-4-ylamine.

MS (ESI+): m/e=518, chloro pattern.

Example 198

1-[5-(5-Chloro-thiophen-2-yl)-isoxazol-3-ylmethyl]-1H-indole-2-carboxylic acid [3-(pyrrolidine-1-carbonyl)-4,5-dihydro-isoxazol-5-ylmethyl]-amide

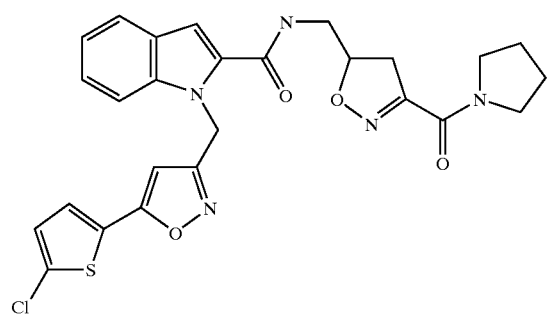

The title compound was prepared analogously to example 1 with the difference that (5-Aminomethyl-4,5-dihydro-isoxazol-3-yl)-pyrrolidin-1-yl-methanone was used instead of 1-Isopropyl-piperidin-4-ylamine. MS (ESI+): m/e=538, chloro pattern.

Example 199

1-[5-(5-Chloro-thiophen-2-yl)-isoxazol-3-ylmethyl]-1H-indole-2-carboxylic acid (1-isobutyl-piperidin-4-yl)-amide

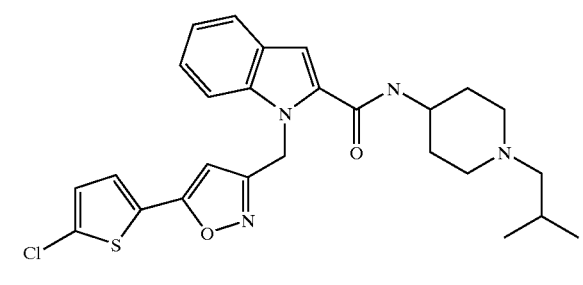

The title compound was prepared analogously to example 187 with the difference that 1-Iodo-2-methylpropane was used instead of methyl iodide.

MS (ESI+): m/e=497, chloro pattern.

Example 200

1-[5-(5-Chloro-thiophen-2-yl)-isoxazol-3-ylmethyl]-1H-indole-2-carboxylic acid (1-propyl-piperidin-4-yl)-amide

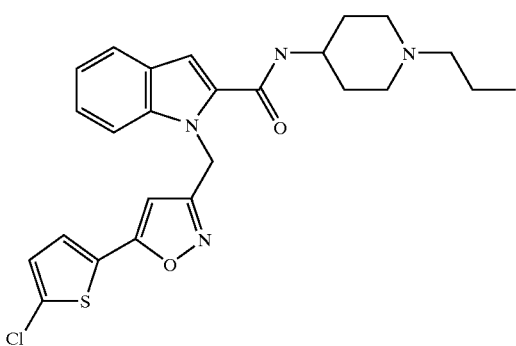

The title compound was prepared analogously to example 187 with the difference that 1-Iodopropane was used instead of methyl iodide. MS (ESI+): m/e=483, chloro pattern.

Example 201

4-({1-[5-(5-Chloro-thiophen-2-yl)-isoxazol-3-ylmethyl]-1H-indole-2-carbonyl})-amino)-piperidine-1-carboxylic acid methyl ester

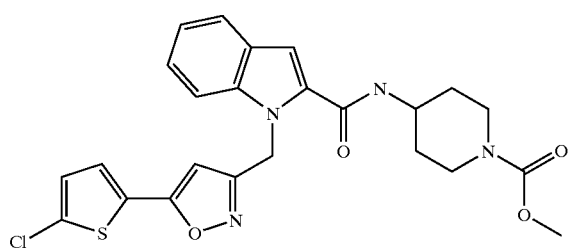

To a solution of 50 mg 1-[5-(5-Chloro-thiophen-2-yl)-isoxazol-3-ylmethyl]-1H-indole-2-carboxylic acid piperidin-4-ylamide in 2 ml DCM, 0.3 ml NEt$_3$ and 20 mg Methyl chloroformate were added at RT and stirred over night. After removal of the solvent under reduced pressure the residue was directly purified by preparative RP-HPLC eluting with a gradient of 0–100% acetonitrile in water (+0.01% trifluoroacetic acid). After lyophilization the product was obtained as its trifluoroacetate salt a white solid. Yield: 24 mg MS (ES+): m/e=499, chloro pattern.

Example 202

1-[5-(5-Chloro-thiophen-2-yl)-isoxazol-3-ylmethyl]-1H-indole-2-carboxylic acid (4-isopropyl-piperazin-1-yl)-amide

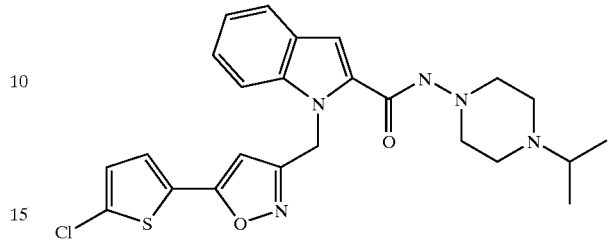

(i) 4-Amino-piperazine-1-carboxylic acid tert-butyl ester.

To a solution of Piperazin-1-ylamine in 20 ml THF and 1.37 ml NEt$_3$, 2.2 g Boc$_2$O in 5 ml THF were added dropwise at 0° C. The reaction mixture was stirred for 16 h at RT then 50 ml ethyl acetate and 20 ml water were added. The organic layer was separated, washed with brine and dried over Na$_2$SO$_4$. After removal of the solvent under reduced pressure the product was obtained as a white solid.

Yield: 1.53 g.

(ii) 4-({1-[5-(5-Chloro-thiophen-2-yl)-isoxazol-3-ylmethyl]-1H-indole-2-carbonyl}-amino)-piperazine-1-carboxylic acid tert-butyl ester.

To a solution of 1 g 1-[5-(5-Chloro-thiophen-2-yl)-isoxazol-3-ylmethyl]-1H-indole-2-carboxylic acid and 1.3 ml NEM in 8 ml DCM, 914 mg TOTU were added and the mixture was stirred for 30 min at RT. Then 673 mg 4-Amino-piperazine-1-carboxylic acid tert-butyl ester were added and the reaction was stirred over night. After removal of the solvent under reduced pressure the residue was directly purified by chromatography on silica gel eluting with an ethyl acetate/heptane gradient. Yield: 1.1 g.

(iv) 1-[5-(5-Chloro-thiophen-2-yl)-isoxazol-3-ylmethyl]-1H-indole-2-carboxylic acid piperazin-1-ylamide.

To 1.1 g 4-({1-[5-(5-Chloro-thiopn-2-yl)-isoxazol-3-ylmethyl]-1H-indole-2-carbonyl}-amino)-piperazine-1-carboxylic acid tert-butyl ester in 5 ml MeOH, 20 ml sat. methanolic HCl were added and the reaction was stirred for 5 h at RT. Then, 70 ml toluene were added and the solvents were evaporated under reduced pressure to yield a yellow solid. The product was obtained as its hydrochloride salt. Yield: 941 mg.

(v) 1-[5-(5-Chloro-thiophen-2-yl)-isoxazol-3-ylmethyl]-1H-indole-2-carboxylic acid (4-isopropyl-piperazin-1-yl)-amide.

To 100 mg 1-[5-(5-Chloro-thiophen-2-yl)-isoxazol-3-ylmethyl]-1H-indole-2-carboxylic acid piperazin-1-ylamide in 2 ml methanol and 2 ml DMF and 0.2 ml acetone, 0.42 ml of Na(CN)BH$_3$ in THF (1M) were added and the mixture was heated to 80° C. for 30 min. After cooling the reaction to RT the solvent was removed under reduced pressure and the residue was directly purified by preparative RP-HPLC eluting with a gradient of 0–100% acetonitrile in water (+0.01% trifluoroacetic acid). After lyophilization the product was obtained as its trifluoroacetate salt.

Yield: 39 mg MS (ESI+): m/e=484, chloro pattern.

Example 203

1-[5-(5-Chloro-thiophen-2-yl)-isoxazol-3-ylmethyl]-1H-indole-2-carboxylic acid (4-ethyl-piperazin-1-yl)-amide

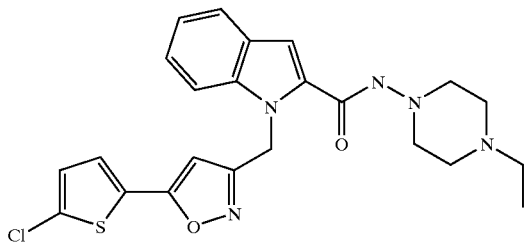

The title compound was prepared analogously to example 202 with the difference that acetaldehyde was used instead of acetone in the reductive amination step.

MS (ESI+): m/e=470, chloro pattern.

Example 204

1-[5-(5-Chloro-thiophen-2-yl)-isoxazol-3-ylmethyl]-1H-indole-2-carboxylic acid pyridin-4-yl-(3,4,5,6-tetrahydro-2H-[1,4']bipyridinyl-4-yl)-amide

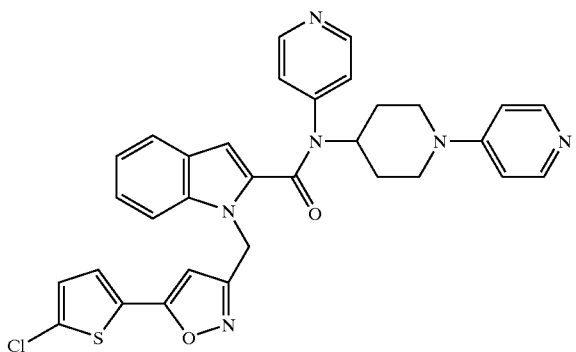

(i) Pyridin-4-yl-(3,4,5,6-tetrahydro-2H-[1,4']bipyridinyl-4-yl)-carbamic acid tert-butyl ester.

A solution of 5 g Piperidin-4-yl-carbamic acid tert-butyl ester and 8 g 4-Chloropyridine hydrochloride in 9 ml n-butanol/water/NEt$_3$ 1:1:1 was heated at 100° C. for 48 h. Then the reaction mixture was cooled to RT, concentrated under reduced pressure and directly purified by chromatography on silica gel eluting with DCM. The fractions containing the product were evaporated under reduced pressure to yield a white foam. Yield: 7 g.

(ii) Pyridin-4-yl-(3,4,5,6-tetrahydro-2H-[1,4']bipyridinyl-4-yl)-amine.

To 2 g Pyridin-4-yl-(3,4,5,6-tetrahydro-2H-[1,4'] bipyridinyl-4-yl)-carbamic acid tert-butyl ester in 10 ml MeOH, 30 ml sat. methanolic HCl was added and stirred for 5 h at RT. Then, 70 ml toluene were added and the solvents were evaporated under reduced pressure to give a yellow solid. The product was obtained as its hydrochloride salt. Yield: 1.6 g.

(ii) 1-[5-(5-Chloro-thiophen-2-yl)-isoxazol-3-ylmethyl]-1H-indole-2-carboxylic acid pyridin-4-yl-(3,4,5,6-tetrahydro-2H-[1,4']bipyridinyl-4-yl)-amide.

To a solution of 200 mg 1-[5-(5-Chloro-thiophen-2-yl)-isoxazol-3-ylmethyl]-1H-indole-2-carboxylic acid and 0.3 ml NEM in 2 ml DCM, 182 mg TOTU were added and the mixture was stirred for 30 min at RT. Then 170 mg Pyridin-4-yl-(3,4,5,6-tetrahydro-2H-[1,4']bipyridinyl-4-yl)-amine were added and the reaction was stirred for 16 h. After removal of the solvent under reduced pressure the residue was directly purified by preparative RP-HPLC eluting with a gradient of 0–100% acetonitrile in water (+0.01% trifluoroacetic acid). After lyophilization the product was obtained as its trifluoroacetate salt. Yield: 39 mg MS (ESI+): m/e=595, chloro pattern.

Example 205

1-[5-(5-Chloro-thiophen-2-yl)-isoxazol-3-ylmethyl]-5-nitro-1H-indole-2-carboxylic acid pyridin-4-yl-(3,4,5,6-tetrahydro-2H-[1,4']bipyridinyl-4-yl)-amide

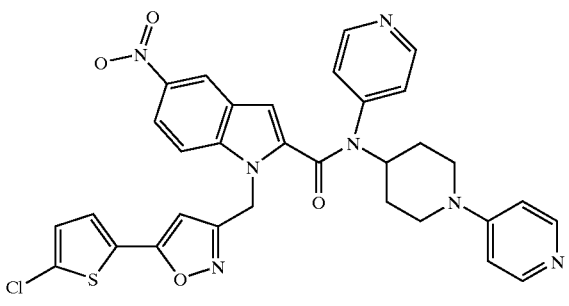

The title compound was prepared analogously to example 204 with the difference that 1-[5-(5-Chloro-thiophen-2-yl)-isoxazol-3-ylmethyl]-5-nitro-1H-indole-2-carboxylic acid was used instead of 1-[5-(5-Chloro-thiophen-2-yl)-isoxazol-3-ylmethyl]-1H-indole-2-carboxylic acid.

MS (ESI+): m/e=642, chloro pattern.

Example 206

1-[5-(5-Chloro-thiophen-2-yl)-isoxazol-3-ylmethyl]-3-cyano-1H-indole-2-carboxylic acid (3,4,5,6-tetrahydro-2H-[1,4']bipyridinyl-4-yl)-amide

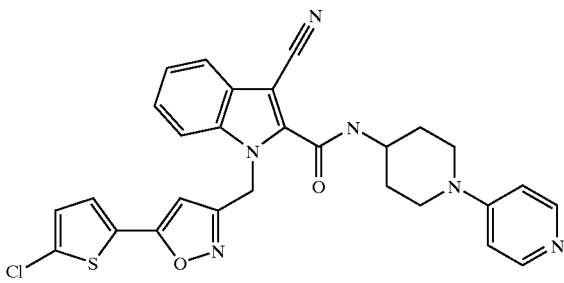

The title compound was prepared analogously to example 160 with the difference that 3,4,5,6-Tetrahydro-2H-[1,4'] bipyridinyl-4-ylamine was used instead of 1-Isopropyl-piperidin-4-ylamine.

MS (ESI+): m/e=543, chloro pattern.

Example 207

1-[5-(5-Chloro-thiophen-2-yl)-isoxazol-3-ylmethyl]-3,7-diiodo-4-methoxy-H-indole-2-carboxylic acid (1-isopropyl-piperidin-4-yl)-amide

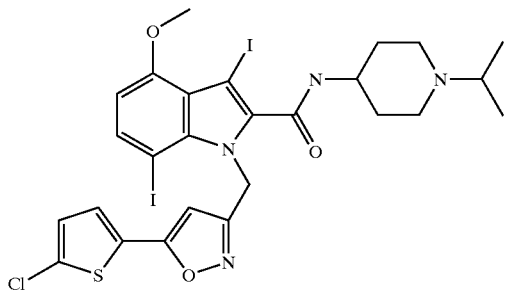

(i) 3,7-Diiodo-4-methoxy-1H-indole-2-carboxylic acid methyl ester.

To a solution of 1 g 4-Methoxy-1H-indole-2-carboxylic acid methyl ester in 15 ml DCM, 5.4 g Bis(pyridine) iodonium(I) tetrafluoroborate were added at RT and the reaction was stirred over night. Then, the reaction mixture was diluted with 20 ml DCM and washed with sat. $Na_2S_2O_3$ solution and water. The organic layer was separated and dried over $Na_2SO_4$ and the solvent removed under reduced pressure. The residue was used in the subsequent reaction without further purification. Yield: 1.6 g.

(ii) 1-[5-(5-Chloro-thiophen-2-yl)-isoxazol-3-ylmethyl]-3,7-diiodo-4-methoxy-1H-indole-2-carboxylic acid.

To a solution of 200 mg 3,7-Diiodo-4-methoxy-1H-indole-2-carboxylic acid methyl ester in 2 ml DMF 20 mg (60% in oil) sodium hydride were added at RT. After stirring for 30 min 121 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, ChristopherJ.; Jiang, John Z.; Li, Aiwen; Myers, Michael R.; Lau, Wan F.; Poli, Gregory B; PCT Int. Appl. (2001), 460 pp. WO 0107436 A2] were added and the mixture was heated for 1 h at 60° C. After subsequent cooling of the reaction to RT and addition of 5 ml water the mixture was filtered through a chem elut® cartridge by elution with ethyl acetate. After concentration under reduced pressure the residue was treated with 30 mg lithium hydroxide monohydrate in THF/water 2:1. After stirring for 2 h at 60° C. the reaction was cooled to RT. The mixture was acidified with half concentrated hydrochloric acid to pH 2 and the precipitate collected by filtration and washed with 3 ml water The product was obtained as a white solid which was dried under reduced pressure. Yield: 200 mg.

(iv) 1-[5-(5-Chloro-thiophen-2-yl)-isoxazol-3-ylmethyl]-3,7-diiodo-4-methoxy-1H-indole-2-carboxylic acid (1-isopropyl-piperidin-4-yl)-amide.

To a solution of 100 mg 1-[5-(5-Chloro-thiophen-2-yl)-isoxazol-3-ylmethyl]-3,7-diiodo-4-methoxy-1H-indole-2-carboxylic acid and 0.1 ml NEM in 2 ml DCM, 63 mg TOTU were added and the mixture was stirred for 30 min at RT. Then 41 mg 1-Isopropyl-piperidin-4-ylamine hydrochloride were added and the reaction was stirred for 2 h. After removal of the solvent under reduced pressure the residue was directly purified by preparative RP-HPLC eluting with a gradient of 0–100% acetonitrile in water (+0.01% trifluoroacetic acid). After lyophilization the product was obtained as its trifluoroacetate salt.

Yield: 67 mg MS (ESI+): m/e=765, chloro pattern.

Example 208

1-[5-(5-Chloro-thiophen-2-yl)-isoxazol-3-ylmethyl]-3,7-dicyano-4-methoxy-1H-indole-2-carboxylic acid (1-isopropyl-piperidin-4-yl)-amide

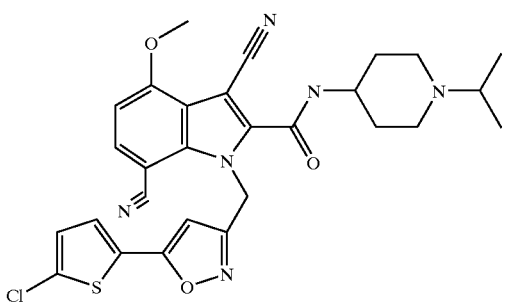

To a solution of 20 mg 1-[5-(5-Chloro-thiophen-2-yl)-isoxazol-3-ylmethyl]-3,7-diiodo-4-methoxy-1H-indole-2-carboxylic acid (1-isopropyl-piperidin-4-yl)-amide in 1 ml DMF and 1 ml THF, 14 mg CuCN, 4 mg $Et_4NCN$, 5 mg DPPF were added and the mixture was purged with argon for 15 min. Then, 3 mg $Pd_2(dba)_3$ were introduced and the reaction was heated for 5 min to 120° C. under microwave irradiation (150 W, CEM Discover™ apparatus). Finally, 10 ml saturated $NaHCO_3$ solution were added and the mixture was filtered through a chem elut® cartridge by elution with DCM. After removal of the solvent under reduced pressure the residue was directly purified by preparative RP-HPLC eluting with a gradient of 0–100% acetonitrile in water (+0.01% trifluoroacetic acid). After lyophilization the product was obtained as its trifluoroacetate salt.

Yield: 3 mg MS (ESI+): m/e=563, chloro pattern.

Example 209

1-[2-(4-Chloro-phenyl)-thiazol-4-ylmethyl]-1H-indole-2-carboxylic acid (1-isopropyl-piperidin-4-yl)-amide

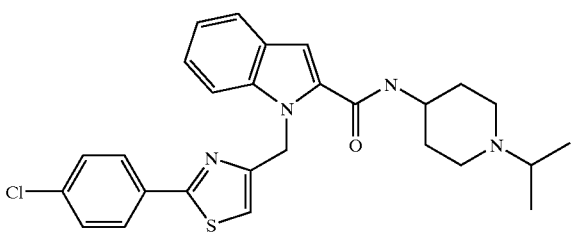

The title compound was prepared analogously to example 1 with the difference that 4-Chloromethyl-2-(4-chloro-phenyl)-thiazole was used in the alkylation step instead of 3-Bromomethyl-5-(5-chloro-thiophen-2-yl)-isoxazole. MS (ESI+): m/e=493, chloro pattern.

Example 210

1-(1,7-Dichloro-isoquinolin-3-ylmethyl)-1H-indole-2-carboxylic acid (1-isopropyl-piperidin-4-yl)-amide

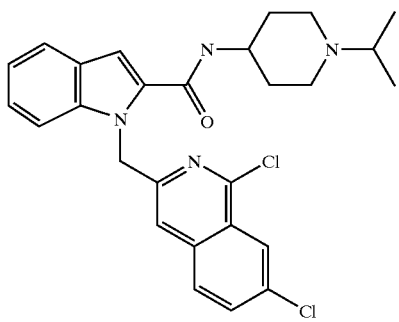

The title compound was prepared analogously to example 1 with the difference that 3-Bromomethyl-1,7-dichloro-isoquinoline [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (1999), 300 pp. WO 9937304 A1] was used in the alkylation step instead of 3-Bromomethyl-5-(5-chloro-thiophen-2-yl)-isoxazole. MS (ESI+): m/e=495, chloro pattern.

Example 211

1-[3-(4-Chloro-phenyl)-isoxazol-5-ylmethyl]-1H-indole-2-carboxylic acid (1-isopropyl-piperidin-4-yl)-amide

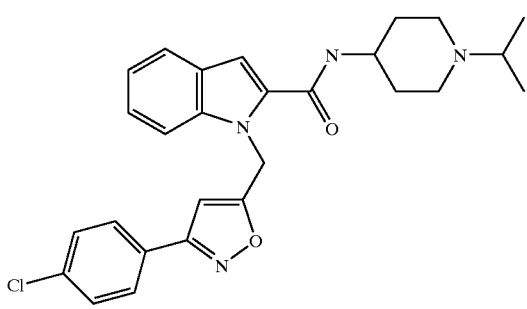

The title compound was prepared analogously to example 1 with the difference that 5-Chloromethyl-3-(4-chloro-phenyl)-isoxazole was used in the alkylation step instead of 3-Bromomethyl-5-(5-chloro-thiophen-2-yl)-isoxazole. MS (ESI+): m/e=477, chloro pattern.

Example 212

1-[5-(4-Chloro-phenyl)-isoxazol-3-ylmethyl]-1H-indole-2-carboxylic acid (1-isopropyl-piperidin-4-yl)-amide

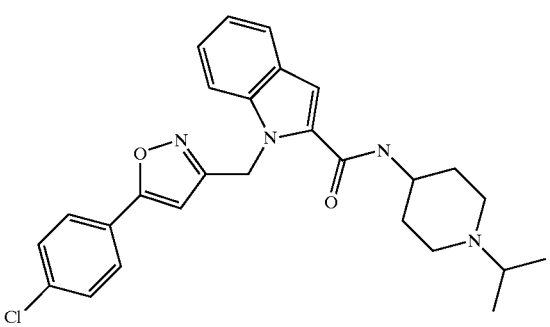

The title compound was prepared analogously to example 1 with the difference that 3-Chloromethyl-5-(4-chloro-phenyl)-isoxazole was used in the alkylation step instead of 3-Bromomethyl-5-(5-chloro-thiophen-2-yl)-isoxazole. MS (ESI+): m/e=477, chloro pattern.

Example 213

1-[3-(4-Chloro-phenyl)-[1,2,4]oxadiazol-5-ylmethyl]-1H-indole-2-carboxylic acid (1-isopropyl-piperidin-4-yl)-amide

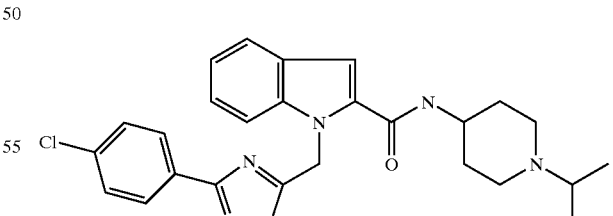

The title compound was prepared analogously to example 1 with the difference that 5-Chloromethyl-3-(4-chloro-phenyl)-[1,2,4]oxadiazole was used in the alkylation step instead of 3-Bromomethyl-5-(5-chloro-thiophen-2-yl)-isoxazole. MS (ESI+): m/e=478, chloro pattern.

Example 214

1-[(5-Chloro-pyridin-2-ylcarbamoyl)-methyl]-5-methanesulfonyl-1H-indole-2-carboxylic acid (1-isopropyl-piperidin-4-yl)-amide

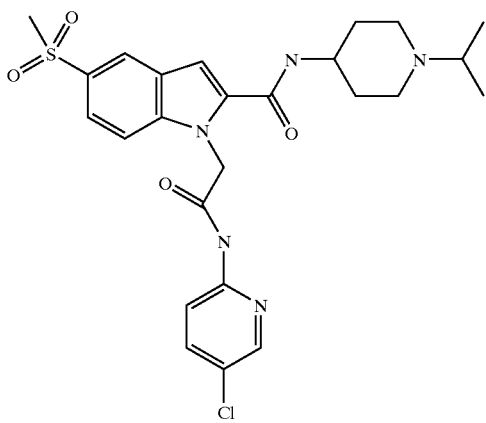

(i) 2-Bromo-N-(5-chloro-pyridin-2-yl)-acetamide.

To a solution of 5 g 5-Chloro-pyridin-2-ylamine and 1.5 ml pyridine in 30 ml toluene, 8 g bromo-acetyl bromide dissolved in 10 ml toluene was added dropwise under ice cooling. After 2 h the precipitate was isolated by filtration and recrystallized from toluene to yield a white solid. Yield: 12 g.

(ii) 1-[(5-Chloro-pyridin-2-ylcarbamoyl)-methyl]-5-methanesulfonyl-1H-indole-2-carboxylic acid.

To a solution of 1 g 5-Methanesulfonyl-1H-indole-2-carboxylic acid methyl ester in 10 ml DMF, 158 mg (60% in oil) sodium hydride were added at RT. After stirring for 10 min 985 mg 2-Bromo-N-(5-chloro-pyridin-2-yl)-acetamide were added and the mixture was stirred for 2 h. After the addition of 7 ml water the mixture was filtered through a chem elut® cartridge by elution with ethyl acetate and concentrated under reduced pressure. The residue was taken-up in 10 ml water/THF 1:2 and treated with 2 ml aqueous KOH solution (10%). After stirring for 16 h at RT the reaction mixture was acidified with hydrochloric acid (5M). The precipitate was collected by filtration and dried in vacuo to yield the product as a yellow solid. Yield: 1.1 g.

(iii) 1-[(5-Chloro-pyridin-2-ylcarbamoyl)-methyl]-5-methanesulfonyl-1H-indole-2-carboxylic acid (1-isopropyl-piperidin-4-yl)-amide.

To a solution of 500 mg 1-[(5-Chloro-pyridin-2-ylcarbamoyl)-methyl]-5-methanesulfonyl-1H-indole-2-carboxylic acid in 5 ml DMF and 0.7 ml NEt$_3$, 312 mg BOP-Cl and 264 mg 1-Isopropyl-piperidin-4-ylamine hydrochloride were added at RT and the mixture was stirred for 16 h. Subsequently the solvent was removed under reduced pressure and the residue was purified by preparative HPLC (C18 reverse phase column, elution with a H$_2$O/MeCN gradient with 0.1% TFA). The fractions containing the product were evaporated and lyophilized to give a white solid. The product was obtained as its trifluoroacetate salt.

Yield: 364 mg MS (ES$^+$): m/e=532, chloro pattern.

Example 215

1-[(4-Chloro-phenylcarbamoyl)-methyl]-5-methanesulfonyl-1H-indole-2-carboxylic acid (1-isopropyl-piperidin-4-yl)-amide

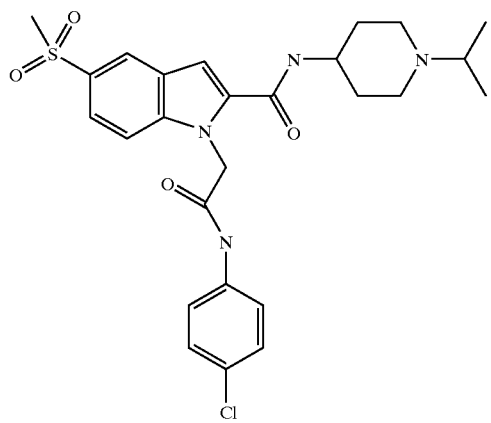

The title compound was prepared analogously to example 214 with the difference that 2-Bromo-N-(4-chloro-phenyl)-acetamide was used instead of 2-Bromo-N-(5-chloro-pyridin-2-yl)-acetamide in the alkylation step.

MS (ESI+): m/e=531, chloro pattern.

Example 216

5-Chloro-1-[(5-chloro-pyridin-2-ylcarbamoyl)-methyl]-1H-indole-2-carboxylic acid 1-isopropyl-piperidin-4-yl)-amide

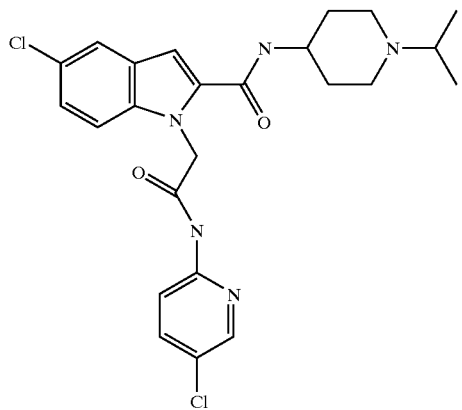

The title compound was prepared analogously to example 214 with the difference that 5-Chloro-1H-indole-2-carboxylic acid methyl ester was used instead of 5-Methanesulfonyl-1H-indole-2-carboxylic acid methyl ester.

MS (ESI+): m/e=488, chloro pattern.

Example 217

1-[(5-Chloro-pyridin-2-ylcarbamoyl)-methyl]-5-fluoro-1H-indole-2-carboxylic acid (1-isopropyl-piperidin-4-yl)-amide

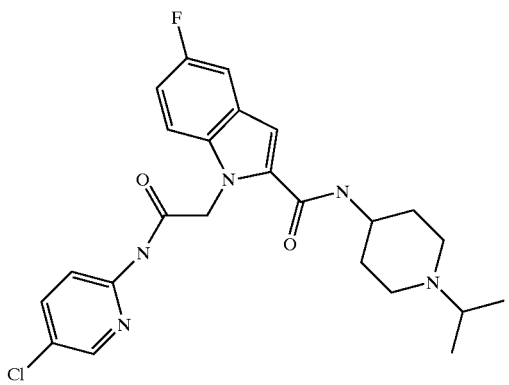

The title compound was prepared analogously to example 214 with the difference that 5-Fluoro-1H-indole-2-carboxylic acid methyl ester was used instead of 5-Methanesulfonyl-1H-indole-2-carboxylic acid methyl ester.

MS (ESI+): m/e=472, chloro pattern.

Example 218

1-[(5-Chloro-pyridin-2-ylcarbamoyl)-methyl]-5,7-difluoro-1H-indole-2-carboxylic acid (1-isopropyl-piperidin-4-yl)-amide

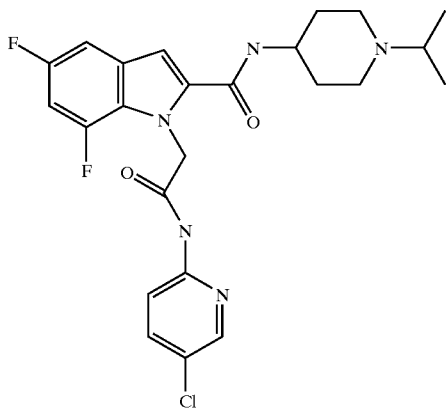

The title compound was prepared analogously to example 214 with the difference that 5,7-Difluoro-1H-indole-2-carboxylic acid methyl ester was used instead of 5-Methanesulfonyl-1H-indole-2-carboxylic acid methyl ester.

MS (ESI+): m/e=490, chloro pattern.

Example 219

S-1-[5-(5-Chloro-thiophen-2-yl)-isoxazol-3-ylmethyl]-1H-indole-2-carboxylic acid (1-ethyl-pyrrolidin-3-yl)-amide

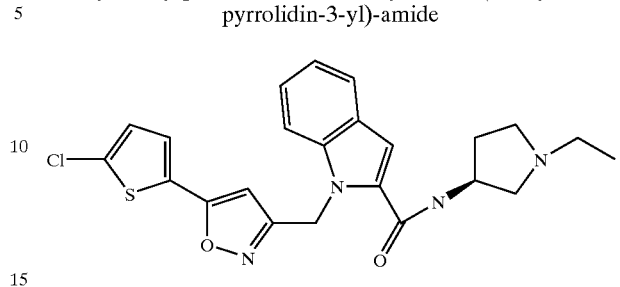

The title compound was prepared analogously to example 36 with the difference that S-3-tert.Butoxycarbonylpyrrolidine was used instead of (1-Isopropyl-piperidin-4-yl)-carbamic acid tert-butyl ester in the reductive amination step. MS (ESI+): m/e=455, chloro pattern.

Example 220

R-1-[5-(5-Chloro-thiophen-2-yl)-isoxazol-3-ylmethyl]-1H-indole-2-carboxylic acid (1-ethyl-pyrrolidin-3-yl)-amide

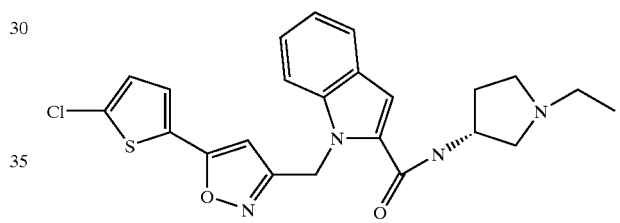

The title compound was prepared analogously to example 36 with the difference 3R-3-tert.Butoxycarbonylpyrrolidine was used instead of (1-Isopropyl-piperidin-4-yl)-carbamic acid tert-butyl ester in the reductive amination step. MS (ESI+): m/e=455, chloro pattern.

Example 221

R-1-[5-(5-Chloro-thiophen-2-yl)-isoxazol-3-ylmethyl]-1H-indole-2-carboxylic acid (1-isopropyl-pyrrolidin-3-yl)-amide

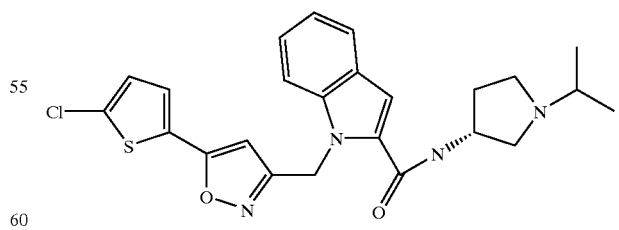

The title compound was prepared analogously to example 1 with the difference that 3R-3-tert.Butoxycarbonylpyrrolidine was used instead of (1-Isopropyl-piperidin-4-yl)-carbamic acid tert-butyl ester in the reductive amination step. MS (ESI+): m/e=469, chloro pattern.

Example 222

S-1-[5-(5-Chloro-thiophen-2-yl)-isoxazol-3-ylmethyl]-1H-indole-2-carboxylic 1-isopropyl-pyrrolidin-3-yl)-amide

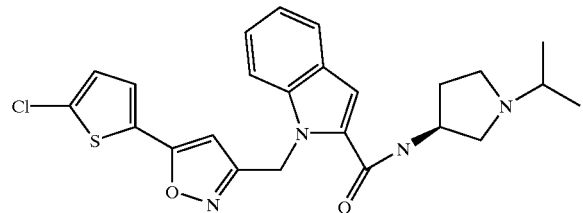

The title compound was prepared analogously to example 1 with the difference that 3S-3-tert.Butoxycarbonylpyrrolidine was used instead of (1-Isopropyl-piperidin-4-yl)-carbamic acid tert-butyl ester in the reductive amination step. MS (ESI+): m/e 469, chloro pattern.

Example 223

[{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid ethyl ester

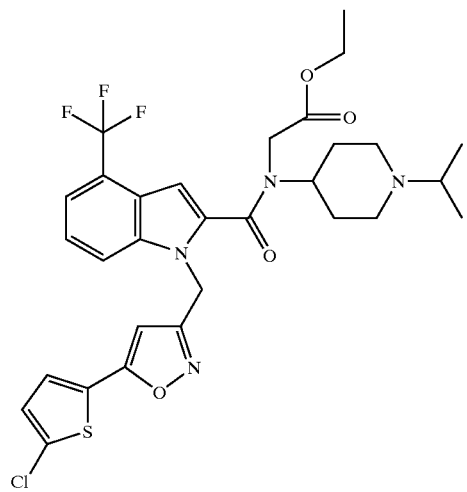

The title compound was prepared analogously to example 184 with the difference that 1-[5-(5-Chloro-thiophen-2-yl)-isoxazol-3-ylmethyl]-4-trifluoromethyl-1H-indole-2-carboxylic acid was used instead of 1-[5-(5-Chloro-thiophen-2-yl)-isoxazol-3-ylmethyl]-7-methyl-1H-indole-2-carboxylic acid. MS (ESI+): m/e=637, chloro pattern.

Example 224

[{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid ethyl ester

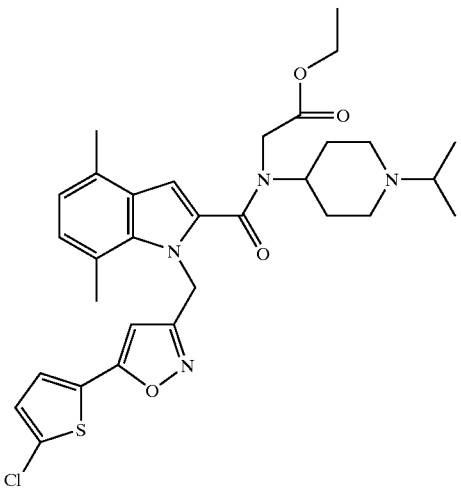

The title compound was prepared analogously to example 184 with the difference that 1-[5-(5-Chloro-thiophen-2-yl)-isoxazol-3-ylmethyl]-4,7-dimethyl-1H-indole-2-carboxylic acid was used instead of 1-[5-(5-Chloro-thiophen-2-yl)-isoxazol-3-ylmethyl]-7-methyl-1H-indole-2-carboxylic acid. MS (ESI+): m/e=, 597, chloro pattern.

Example 225

[{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid ethyl ester

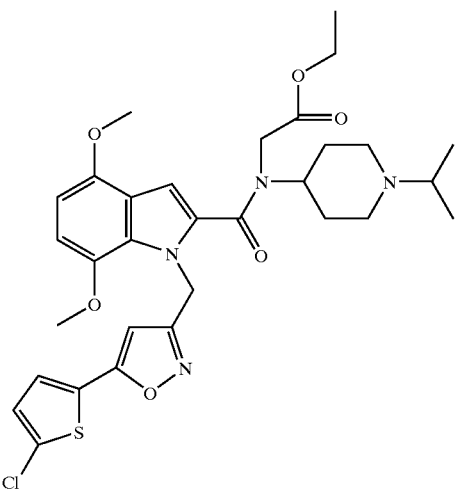

The title compound was prepared analogously to example 184 with the difference that 1-[5-(5-Chloro-thiophen-2-yl)-isoxazol-3-ylmethyl]-4,7-dimethoxy-1H-indole-2-carboxylic acid was used instead of 1-[5-(5-Chloro-thiophen-2-yl)-isoxazol-3-ylmethyl]-7-methyl-1H-indole-2-carboxylic acid. MS (ESI+): m/e=629, chloro pattern.

Example 226

[{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester

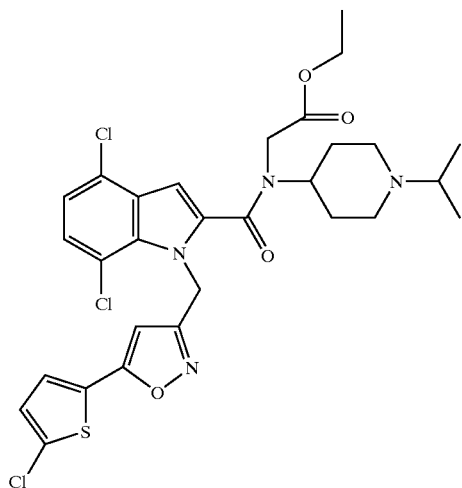

The title compound was prepared analogously to example 184 with the difference that 4,7-Dichloro-1-[5-(5-chloro-thiophen-2-yl)-isoxazol-3-ylmethyl]-1H-indole-2-carboxylic acid was used instead of 1-[5-(5-Chloro-thiophen-2-yl)-isoxazol-3-ylmethyl]-7-methyl-1H-indole-2-carboxylic acid. MS (ESI+): m/e=638, chloro pattern.

Example 227

[{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester

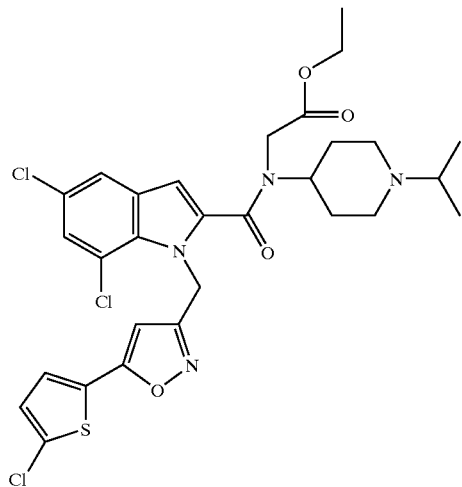

The title compound was prepared analogously to example 184 with the difference that 5,7-Dichloro-1-[5-(5-chloro-thiophen-2-yl)-isoxazol-3-ylmethyl]-1H-indole-2-carboxylic acid was used instead of 1-[5-(5-Chloro-thiophen-2-yl)-isoxazol-3-ylmethyl]-7-methyl-1H-indole-2-carboxylic acid. MS (ESI+): m/e=638, chloro pattern.

Example 228

[{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester

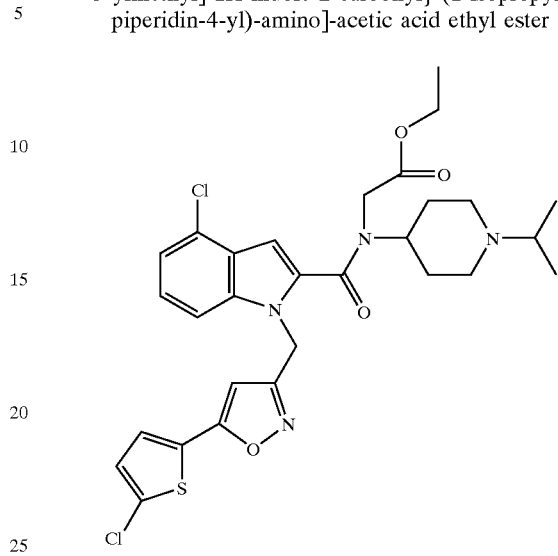

The title compound was prepared analogously to example 184 with the difference that 4-Chloro-1-[5-(5-chloro-thiophen-2-yl)-isoxazol-3-ylmethyl]-1H-indole-2-carboxylic acid was used instead of 1-[5-(5-Chloro-thiophen-2-yl)-isoxazol-3-ylmethyl]-7-methyl-1H-indole-2-carboxylic acid. MS (ESI+): m/e=603, chloro pattern.

Example 229

[{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid

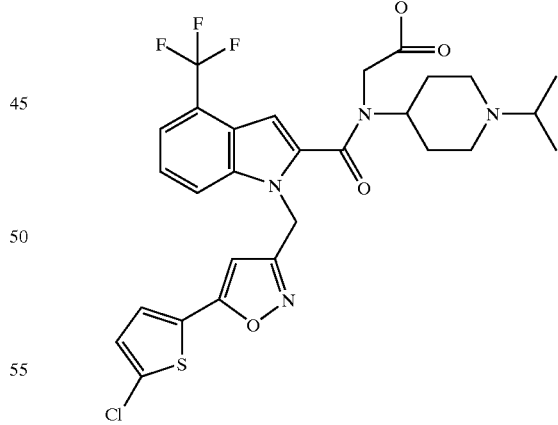

The title compound was prepared analogously to example 185 with the difference that [{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid ethyl ester was used instead of [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester. MS (ESI+): m/e=609, chloro pattern.

Example 230

[{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid

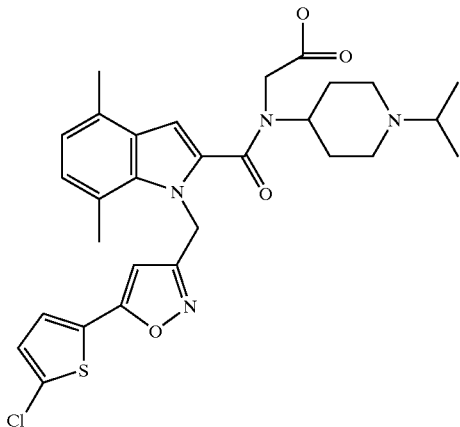

The title compound was prepared analogously to example 185 with the difference that [{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid ethyl ester was used instead of [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester. MS (ESI+): m/e=569, chloro pattern.

Example 231

[{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid

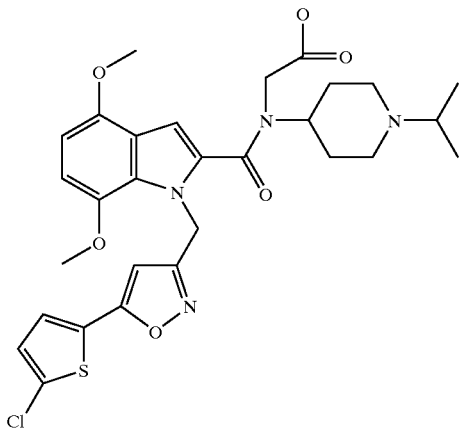

The title compound was prepared analogously to example 185 with the difference that [{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid ethyl ester was used instead of [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester. MS (ESI+): m/e=601, chloro pattern.

Example 232

[{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid

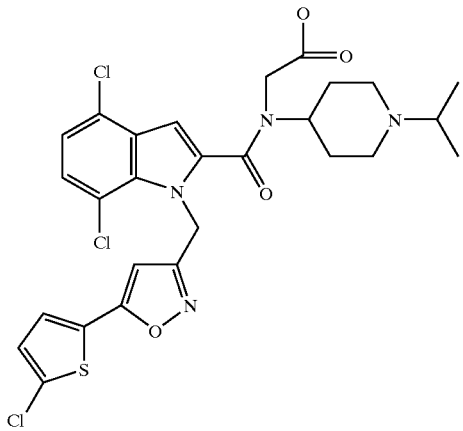

The title compound was prepared analogously to example 185 with the difference [{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester was used instead of [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester. MS (ESI+): m/e=609, chloro pattern.

Example 233

[{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid

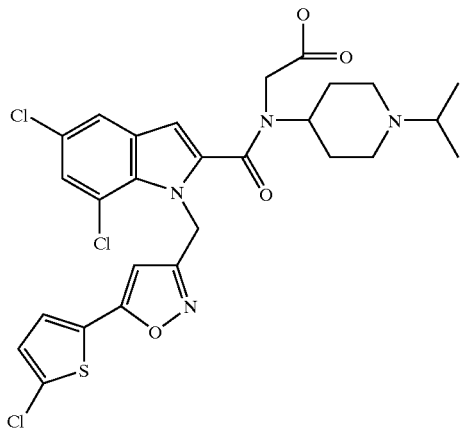

The title compound was prepared analogously to example 185 with the difference that [{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester was used instead of [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester. MS (ESI+): m/e=609, chloro pattern.

Example 234

[{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid

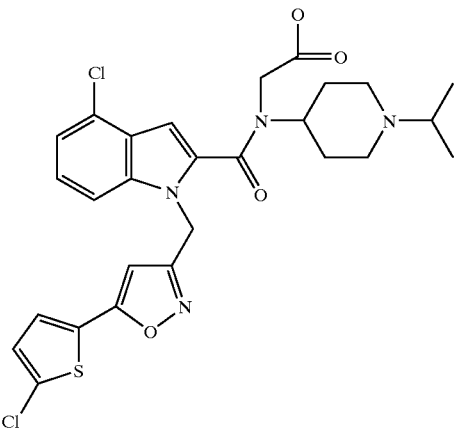

The title compound was prepared analogously to example 185 with the difference that [{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester was used instead of [{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester. MS (ESI+): m/e=575, chloro pattern.

Example 235

1-[5-(5-Chloro-thiophen-2-yl)-isoxazol-3-ylmethyl]-2-(1-isopropyl-piperidin-4-ylcarbamoyl)-1H-indole-5-carboxylic acid isopropyl ester

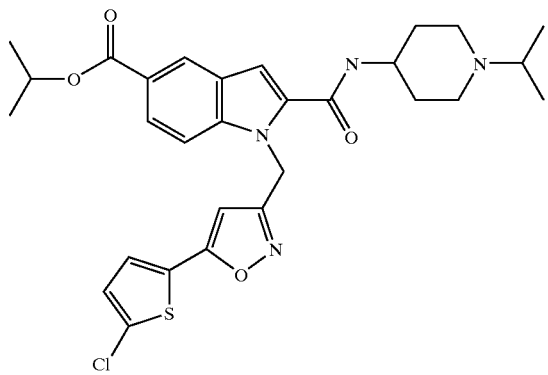

(i) 1H-Indole-2,5-dicarboxylic acid 2-ethyl ester 5-isopropyl este.

To a solution of 15.5 g AlCl$_3$ in 400 ml DCM, 10 ml oxalyl dichloride was added dropwise. Then, after 30 min 10 g 1H-Indole-2-carboxylic acid ethyl ester in 100 ml DCM were added and the reaction mixture was stirred for 2 h. The reaction mixture was poured on to crushed ice and extracted twice with 500 ml DCM. The organic layer was dried over MgSO$_4$ and the solvent removed under reduced pressure. The residue was taken-up in 300 ml Propan-2-ol and stirred for 4 h at room temperature. After concentration of the reaction mixture under reduced pressure the residue was purified by chromatography on silica gel eluting with an ethyl acetate/heptane gradient 1:10→4:1. Yield: 2.71 g.

(ii) 1-[5-(5-Chloro-thiophen-2-yl)-isoxazol-3-ylmethyl]-1H-indole-2,5-dicarboxylic acid 2-ethyl ester 5-isopropyl ester.

This compound was prepared using a procedure analogous to that described for the preparation of example 1 (iv), using 1H-Indole-2,5-dicarboxylic acid 2-ethyl ester 5-isopropyl ester as the starting material. The compound was purified by chromatography on silica gel eluting with n-heptane/ethyl acetate 6:1. Yield 6.3 g. MS (ESI+): m/e= 473 (M+) chloro pattern.

(iii) 1-[5-(5-Chloro-thiophen-2-yl)-isoxazol-3-ylmethyl]-1H-indole-2,5-dicarboxylic acid 5-isopropyl ester.

To a solution of 6.21 g 1-[5-(5-Chloro-thiophen-2-yl)-isoxazol-3-ylmethyl]-1H-indole-2,5-dicarboxylic acid 2-ethyl ester 5-isopropyl ester in 100 ml THF and 40 ml MeOH 52 ml of an aqueous 1 M LiOH solution were added and stirred for 2 h. The organic solvents were removed under reduced pressure and the residue acidified with 2 M hydrochloric acid to pH 2. The precipitated product was collected by filtration and dried over P$_2$O$_5$ in vacuo to yield a white solid. Yield: 5.77 g.

(iv) 1-[5-(5-Chloro-thiophen-2-yl)-isoxazol-3-ylmethyl]-2-(1-isopropyl-piperidin-4-ylcarbomyl)-1H-indole-5-carboxylic acid isopropyl este.

To a solution of 5.77 g 1-[5-(5-Chloro-thiophen-2-yl)-isoxazol-3-ylmethyl]-1H-indole-2,5-dicarboxylic acid 5-isopropyl ester and 2.79 g 1-Isopropyl-piperidin-4-ylamine hydrochloride in 100 ml DMF, 4.25 g TOTU and 6.6 ml DIPEA were added and the mixture was stirred for 3 h at room temperature. After removal of the solvent under reduced pressure the residue was dissolved in 200 ml ethyl acetate and washed with sat. NaHCO$_3$ solution. The organic layer was dried over MgSO$_4$. After removal of the solvent under reduced pressure the residue was purified by chromatography on silica gel eluting with DCM/MeOH/AcOH/H$_2$O 95:5:0.5:0.5. The fractions containing the product were collected and the solvent evaporated under reduced pressure. The product was obtained as its acetate salt. Yield: 6.13 g MS (ES$^+$): m/e=569, chloro pattern.

Example 236

1-[5-(5-Chloro-thiophen-2-yl)-isoxazol-3-ylmethyl]-2-(1-isopropyl-piperidin-4-ylcarbamoyl)-1H-indole-5-carboxylic acid

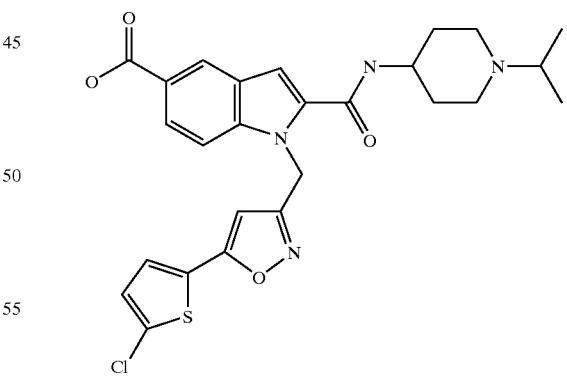

To a solution of 6.13 g 1-[5-(5-Chloro-thiophen-2-yl)-isoxazol-3-ylmethyl]-2-(1-isopropyl-piperidin-4-ylcarbamoyl)-1H-indole-5-carboxylic acid isopropyl ester in 200 ml MeOH 54 ml of a 1M aqueous LiOH solution were added and heated for 24 h to 60° C. The reaction mixture was the concentrated under reduced pressure and acidified with 2 M hydrochloric acid to pH 3. Then the mixture was extracted with ethyl acetate (2×200 ml) and the organic layer was dried over MgSO$_4$ which yielded after evaporation of the solvent under reduced pressure 5.3 g of the crude acid as a yellow solid. 600 mg of this acid were purified by preparative HPLC (C18 reverse phase column, elution with a H$_2$O/MeCN gradient with 0.1% TFA). The fractions containing the product were evaporated and lyophilized after addition of 2M hydrochloric acid to give a white solid. The product was obtained as its hydrochloride.

Yield: 280 mg MS (ES$^+$): m/e=527, chloro pattern.

Example 237

1-[5-(5-Chloro-thiophen-2-yl)-isoxazol-3-ylmethyl]-5-hydroxymethyl-1H-indole-2-carboxylic acid (1-isopropyl-piperidin-4-yl)-amide

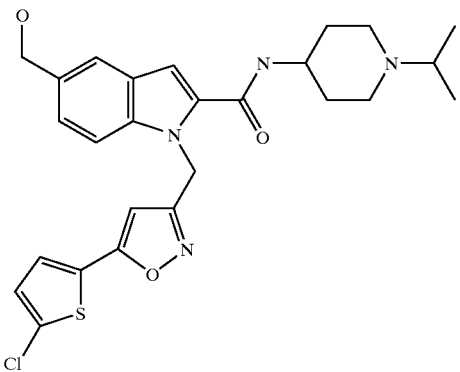

To a solution of 100 mg 1-[5-(5-Chloro-thiophen-2-yl)-isoxazol-3-ylmethyl]-2-(1-isopropyl-piperidin-4-ylcarbamoyl)-1H-indole-5-carboxylic acid and 50 µl NEt$_3$ in 4 ml THF, 17 µl ethyl chloroformate were added at −7° C. After stirring for 2 h at −7° C. the reaction mixture was filtered, the filtrate was treated with 24 mg NaBH$_4$ and warmed to room temperature. After 2 h additional 24 mg NaBH$_4$ were added and the reaction mixture stirred for 16 h. Then, 110 µl MeOH in 4 ml THF were added within 2 h and the reaction mixture was stirred for additional 4 h at room temperature. After removal of the solvents under reduced pressure the residue was purified by chromatography on silica gel eluting with DCM/MeOH 8:2. The fractions containing the product were collected and evaporated under reduced pressure.

Yield: 39 mg MS (ES$^+$): m/e=513, chloro pattern.

Example 238

1-[5-(5-Chloro-thiophen-2-yl)-isoxazol-3-ylmethyl]-2-(1-isopropyl-piperidin-4-ylcarbamoyl)-1H-indole-5-carboxylic acid ethyl ester

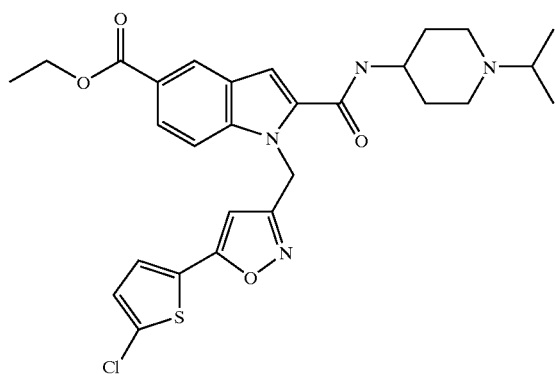

To a solution of 0.6 g 1-[5-(5-Chloro-thiophen-2-yl)-isoxazol-3-ylmethyl]-2-(1-isopropyl-piperidin-4-ylcarbamoyl)-1H-indole-5-carboxylic acid in 10 ml DMF sequentially 0.4 ml EtOH, 110 mg DMAP and 256 mg DCC were added and the reaction mixture was stirred for 16 h at room temperature. The precipitate was then filtered off and the filtrate was concentrated and purified by chromatography on silica gel eluting with DCM/MeOH/AcOH/H$_2$O 95:3:0.5:0.5. The fractions containing the product were collected and the solvent evaporated under reduced pressure.

Yield: 418 mg MS (ES$^+$): m/e=555, chloro pattern.

Example 239

1-[5-(5-Chloro-thiophen-2-yl)-isoxazol-3-ylmethyl]-2-(1-isopropyl-piperidin-4-ylcarbamoyl)-1H-indole-5-carboxylic acid methyl ester

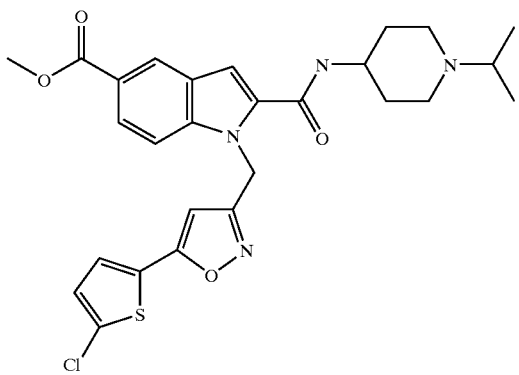

The title compound was prepared analogously to example 238 with the difference that methanol was used instead of ethanol in the esterification reaction.

MS (ESI+): m/e=541, chloro pattern.

Alternatively the title compound can be prepared by the following procedure:

(i) 1H-Indole-2,5-dicarboxylic acid 5-methyl ester.

A solution of 25 g 4-Amino-3-iodo-benzoic acid methyl ester, 19 ml 2-Oxo-propionic acid, 30.4 g 1,4-Diaza-bicyclo[2.2.2]octane and 1 g Pd(OAc)$_2$ was heated under argon to 100° C. After 5 h the reaction mixture was concentrated under reduced pressure and the residue was partitioned between 300 ml ethyl acetate and 200 ml 1 M hydrochloric acid. The organic layer was dried over MgSO$_4$ and the solvent removed under reduced pressure to yield a yellow solid (6.4 g). From the aqueous layer additional product slowly precipitated as a white solid (7.9 g) which was collected by filtration. Both fractions were combined, dried in vacuo and used in the next reaction without further purification. Yield: 14.3 g MS (ES$^+$): m/e=220.

(ii) 1H-Indole-2,5-dicarboxylic acid 2-tert-butyl ester 5-methyl ester.

To 13 g 1H-Indole-2,5-dicarboxylic acid 5-methyl ester in 300 ml toluene, 59 ml Di-tert-butoxymethyl-dimethyl-amine were added dropwise at 80° C. Then, the reaction mixture was heated under reflux for additional 6 h. After removal of the solvents under reduced pressure the residue was dissolved in 300 ml DCM and washed with sat. aqueous NaHCO$_3$ solution (2×100 ml). The organic layer was dried over MgSO$_4$ and concentrated under reduced pressure. The residue was purified by chromatography on silica gel eluting with a n-heptane/ethyl acetate gradient. The fractions containing the product were collected and concentrated under reduced pressure.

Yield: 8.3 g MS (ES$^+$): m/e=276.

(iii) 1-[5-(5-Chloro-thiophen-2-yl)-isoxazol-3-ylmethyl]-1H-indole-2,5-dicarboxylic acid 2-tert-butyl ester 5-methyl ester.

This compound was prepared using a procedure analogous to that described for the preparation of example 1 (iv), using 1H-Indole-2,5-dicarboxylic acid 2-tert-butyl ester 5-methyl ester as the starting material. The compound was chromatographed on silica gel eluting with n-heptane/ethyl acetate 6:1. Yield 9.6 g. MS (ESI+): m/e=417, chloro pattern.

(iv) 1-[5-(5-Chloro-thiophen-2-yl)-isoxazol-3-ylmethyl]-1H-indole-2,5-dicarboxylic acid 5-methyl ester.

9.5 g 1-[5-(5-Chloro-thiophen-2-yl)-isoxazol-3-ylmethyl]-1H-indole-2,5-dicarboxylic acid 2-tert-butyl ester 5-methyl ester were dissolved in 300 ml trifluoro-acetic acid and stirred for 1 h at RT. Then 200 ml toluene were added and the solvents were removed under reduced pressure. This procedure was repeated three times, then the residue was dried in vacuo. Yield: 8.4 g.

(v) 1-[5-(5-Chloro-thiophen-2-yl)-isoxazol-3-ylmethyl]-2-(1-isopropyl-piperidin-4-ylcarbamoyl)-1H-indole-5-carboxylic acid methyl ester.

This compound was prepared using a procedure analogous to that described for the preparation of example 1 (vi), using 1-[5-(5-Chloro-thiophen-2-yl)-isoxazol-3-ylmethyl]-1H-indole-2,5-dicarboxylic acid 5-methyl ester as the starting material. The compound was chromatographed on silica gel eluting with DCM/MeOH/AcOH/H$_2$O 95:3:0.5:0.5.

Yield 10 g. MS (ESI+): m/e=541, chloro pattern.

Example 240

1-[5-(5-Chloro-thiophen-2-yl)-isoxazol-3-ylmethyl]-2-(1-isopropyl-piperidin-4-ylcarbamoyl)-1H-indole-5-carboxylic acid 2,2-dimethyl-propionyloxymethyl ester

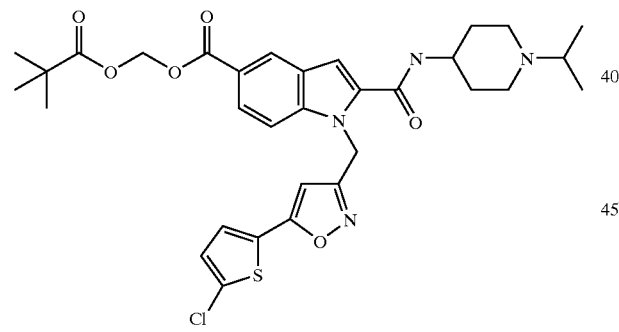

To a solution of 1.2 g 1-[5-(5-Chloro-thiophen-2-yl)-isoxazol-3-ylmethyl]-2-(1-isopropyl-piperidin-4-ylcarbamoyl)-1H-indole-5-carboxylic acid in 30 ml DMF 0,641 g 2,2-Dimethyl-propionic acid chloromethyl ester and 885 µl NEt$_3$ were added and the reaction mixture was stirred for 5 h a 60° C. Then additional 0,32 g 2,2-Dimethyl-propionic acid chloromethyl ester and 295 µl NEt$_3$ were added and the reaction mixture was stirred for 6 h at 60° C. After removal of the solvent under reduced pressure the residue was dissolved in CH$_2$Cl$_2$ and the solution was washed with water. The phases were separated and the organic phase (after drying over Na$_2$SO$_4$) was concentrated in vacuo. The residue was purified by preparative RP-HPLC eluting with a gradient of 0–100% acetonitrile in water (+0.01% trifluoroacetic acid). After addition of 1 M hydrochloric acid and lyophilization in an acetonitrile/water mixture, the product was obtained as its hydrochloride. Yield: 1,17 g MS (ESI+): m/e=641, chloro pattern.

Example 241

1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid isopropyl ester

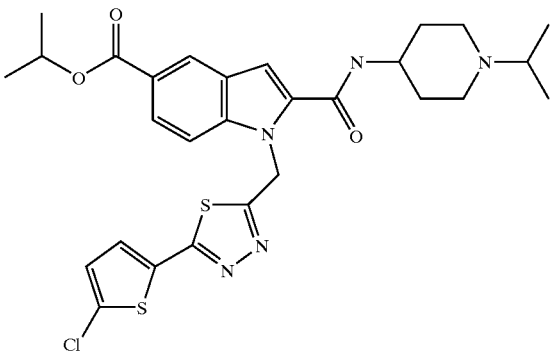

The title compound was prepared analogously to example 235 with the difference that 2-Bromomethyl-5-(5-chloro-thiophen-2-yl)-[1,3,4]thiadiazole [prepared by adopting a procedure described by Ewing, William R. et al. PCT Int. Appl. (2001), 460 pp. WO 0107436 A2] was used instead of 3-Bromomethyl-5-(5-chloro-thiophen-2-yl)-isoxazole.

MS (ESI+): m/e=586, chloro pattern.

Example 242

1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid

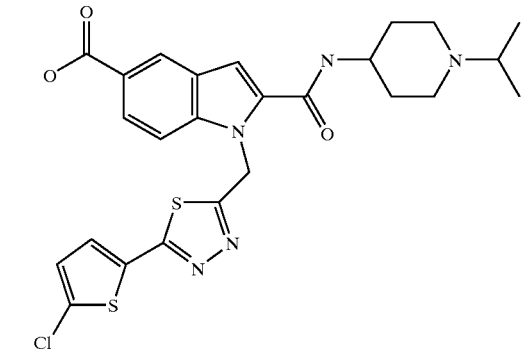

The title compound was prepared analogously to example 236 with the difference that 1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid isopropyl ester was used instead of 1-[5-(5-Chloro-thiophen-2-yl)-isoxazol-3-ylmethyl]-2-(1-isopropyl-piperidin-4-ylcarbamoyl)-1H-indole-5-carboxylic acid isopropyl ester.

MS (ESI+): m/e=544, chloro pattern.

Example 243

1-[(4-Chloro-phenylcarbamoyl)-methyl]-2-(1-isopropyl-piperidin-4-ylcarbamoyl)-1H-indole-5-carboxylic acid isopropyl ester

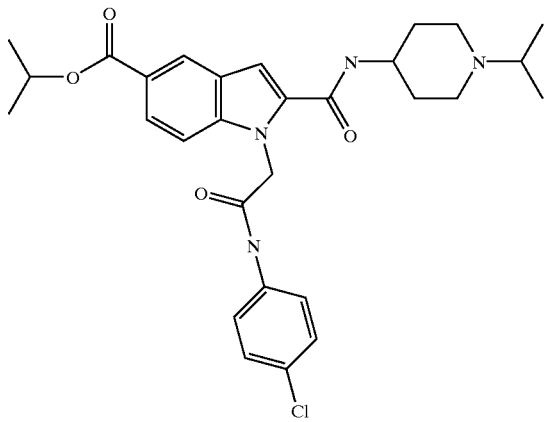

(i) 1H-Indole-2,5-dicarboxylic acid 5-isopropyl ester.

To a solution of 855 mg 1H-Indole-2,5-dicarboxylic acid 2-ethyl ester 5-isopropyl ester in 50 ml MeOH, 12.4 ml 1 M aqueous LiOH solution were added. After heating the reaction mixture at 50° C. for 1 h the organic solvents were removed under reduced pressure and the residue was acidified to pH 2 with 1 M hydrochloric acid. The precipitated product was collected by filtration and dried in vacuo. Yield: 673 mg.

(ii) 2-(1-Isopropyl-piperidin-4-ylcarbamoyl)-1H-indole-5-carboxylic acid isopropyl ester.

To a solution of 673 mg 1H-Indole-2,5-dicarboxylic acid 5-isopropyl ester and 702 mg 1-Isopropyl-piperidin-4-ylamine hydrochloride in 20 ml DMF, 1.07 g TOTU and 1.67 ml DIPEA were added and the mixture was stirred for 1 h at room temperature. After removal of the solvent under reduced pressure the residue was dissolved in 100 ml DCM and washed with sat. $NaHCO_3$ solution. The organic layer was dried over $MgSO_4$. After removal of the solvent under reduced pressure the residue was purified by chromatography on silica gel eluting with DCM/MeOH/AcOH/$H_2O$ 95:5:0.5:0.5. The fractions containing the product were collected and the solvent evaporated under reduced pressure. The product was obtained as its acetate salt.

Yield: 698 mg.

(iii) 2-Bromo-N-(4-chloro-phenyl)-acetamide.

To a solution of 5 g 4-Chloro-phenylamine and 1.5 ml pyridine in 30 ml toluene, 8 g bromo-acetyl bromide dissolved in 10 ml toluene was added dropwise under ice cooling. After 2 h the precipitate was isolated by filtration and recrystallized from toluene to yield a white solid.

Yield: 10 g.

(iv) 1-[(4-Chloro-phenylcarbamoyl)-methyl]-2-(1-isopropyl-piperidin-4-ylcarbamoyl)-1H-indole-5-carboxylic acid isopropyl ester.

To a solution of 100 mg 2-(1-Isopropyl-piperidin-4-ylcarbamoyl)-1H-indole-5-carboxylic acid isopropyl ester in 2 ml DMF, 8 mg sodium hydride (60% in oil) were added at RT. After 30 min 67 mg 2-Bromo-N-(4-chloro-phenyl)-acetamide were added and the reaction mixture was stirred for 3 h. After removal of the solvent under reduced pressure the residue was purified by preparative RP-HPLC eluting with a gradient of 0–100% acetonitrile in water (+0.01% trifluoroacetic acid). After lyophilization the product was obtained as its trifluoroacetate salt.

Yield: 66 mg MS (ESI+): m/e=539, chloro pattern.

Example 244

1-[(4-Chloro-phenylcarbamoyl)-methyl]-2-(1-isopropyl-piperidin-4-ylcarbamoyl)-1H-indole-5-carboxylic acid

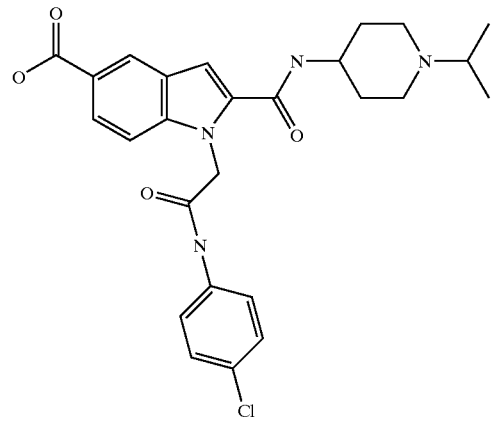

To a solution of 1.2 g 1-[(4-Chloro-phenylcarbamoyl)-methyl]-2-(1-isopropyl-piperidin-4-ylcarbamoyl)-1H-indole-5-carboxylic acid isopropyl ester in 150 ml MeOH, 11 ml of a 1 M aqueous LiOH solution were added and the reaction mixture was heated to 60° C. for 24 h. Then after concentration under reduced pressure the residue was acidified to pH 2 with 2 M hydrochloric acid. The precipitated product was collected by filtration and purified by chromatography on silica gel eluting with DCM/MeOH/AcOH/$H_2O$ 95:3:0.5:0.5. The fractions containing the product were collected and concentrated under reduced pressure. After addition of 3 ml 2 M hydrochloric acid and lyophilization the product was obtained as its hydrochloride.

Yield: 499 mg MS (ESI+): m/e=497, chloro pattern.

Example 245

1-[5-(5-Chloro-thiophen-2-yl)-isoxazol-3-ylmethyl]-2-(1-isopropyl-piperidin-4-ylcarbamoyl)-1H-indole-4-carboxylic acid methyl ester

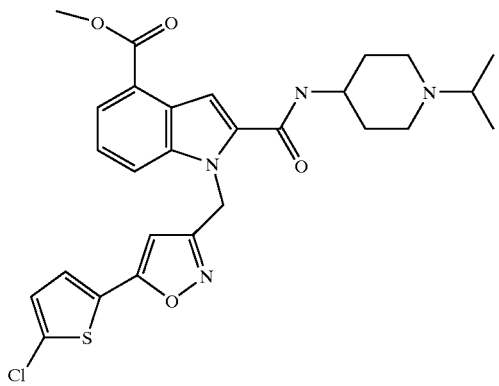

(i) 4-Bromo-1H-indole-2-carboxylic acid tert-butyl ester.

To 7 g 4-Bromo-1H-indole-2-carboxylic acid in 150 ml toluene, 28 ml Di-tert-butoxymethyl-dimethyl-amine were added dropwise at 80° C. The reaction mixture was heated under reflux for additional 12 h. After removal of the solvents under reduced pressure the residue was dissolved in 200 ml DCM and washed with sat. aqueous NaHCO$_3$ solution (2×50 ml). The organic layer was dried over MgSO$_4$ and concentrated under reduced pressure. The residue was purified by chromatography on silica gel eluting with n-heptane/ethyl acetate 9:1. The fractions containing the product were collected and concentrated under reduced pressure.

Yield: 6.5 g MS (ESI+): m/e=297.

(ii) 1H-Indole-2,4-dicarboxylic acid 2-tert-butyl ester 4-methyl ester.

To a solution of 7.3 g 4-Bromo-1H-indole-2-carboxylic acid tert-butyl ester in 100 ml DMF, 6.8 ml NEt$_3$, 276 mg Pd(OAc)$_2$, 128 mg 1,1'-Bis(diphenylphosphino)ferrocene, 12 ml MeOH were added and purged with argon for 15 min. This solution was then purged with carbon monoxide and heated to 70° C. for 4 h. The reaction mixture was concentrated under reduced pressure, the residue dissolved in 200 ml DCM and washed with 100 ml water. The organic layer was dried over MgSO$_4$ and, after removal of the solvent under reduced pressure, the residue was purified by chromatography on silica gel eluting with n-heptane/ethyl acetate 9:1. The fractions containing the product were collected and concentrated under reduced pressure.

Yield: 3.8 g MS (ESI+): m/e=276.

(iii) 1-[5-(5-Chloro-thiophen-2-yl)-isoxazol-3-ylmethyl]-1H-indole-2,4-dicarboxylic acid 2-tert-butyl ester 4-methyl ester.

This compound was prepared using a procedure analogous to that described for the preparation of example 1 (iv), using 1H-Indole-2,4-dicarboxylic acid 2-tert-butyl ester 4-methyl ester as the starting material. The compound was chromatographed on silica gel eluting n-heptane/ethyl acetate 6:1. Yield 4.1 g. MS (ESI+): m/e=473(M+) chloro pattern.

(iv) 1-[5-(5-Chloro-thiophen-2-yl)-isoxazol-3-ylmethyl]-1H-indole-2,4-dicarboxylic acid 4-methyl ester.

4.1 g 1-[5-(5-Chloro-thiophen-2-yl)-isoxazol-3-ylmethyl]-1H-indole-2,4-dicarboxylic acid 2-tert-butyl ester 4-methyl ester were dissolved in 100 ml trifluoro-acetic acid and stirred for 1 h at RT. Then 100 ml toluene was added and the solvents were removed under reduced pressure. This procedure was repeated three times, then the residue was dried in vacuo.

Yield: 3.4 g MS (ESI+): m/e=416, chloro pattern.

(v) 1-[5-(5-Chloro-thiophen-2-yl)-isoxazol-3-ylmethyl]-2-(1-isopropyl-piperidin-4-ylcarbamoyl)-1H-indole-4-carboxylic acid methyl ester.

This compound was prepared using a procedure analogous to that described for the preparation of example 235 (iv), using 1-[5-(5-Chloro-thiophen-2-yl)-isoxazol-3-ylmethyl]-1H-indole-2,4-dicarboxylic acid 4-methyl ester as the starting material. The compound was chromatographed on silica gel eluting with DCM/MeOH/AcOH/H$_2$O 95:3:0.5:0.5.

Yield 4.2 g. MS (ESI+): m/e=541, chloro pattern.

Example 246

1-[5-(5-Chloro-thiophen-2-yl)-isoxazol-3-ylmethyl]-2-(1-isopropyl-piperidin-4-ylcarbamoyl)-1H-indole-4-carboxylic acid

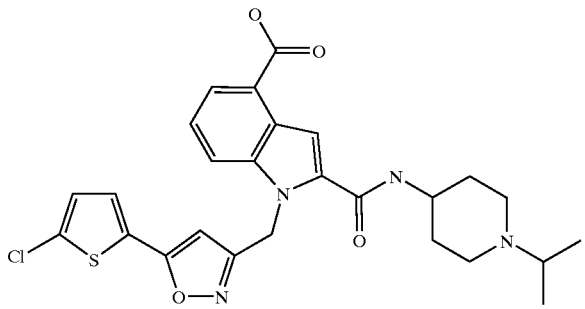

This compound was prepared using a procedure analogous to that described for the preparation of example 236, using 1-[5-(5-Chloro-thiophen-2-yl)-isoxazol-3-ylmethyl]-2-(1-isopropyl-piperidin-4-ylcarbamoyl)-1H-indole-4-carboxylic acid methyl ester as the starting material. The compound was chromatographed on silica gel eluting with DCM/MeOH/AcOH/H$_2$O 95:3:0.5:0.5.

MS (ESI+): m/e=527 (M$^+$), chloro pattern.

Example 247

1-[5-(5-Chloro-thiophen-2-yl)-isoxazol-3-ylmethyl]-1H-indole-2,5-dicarboxylic acid 5-amide 2-[(1-isopropyl-piperidin-4-yl)-amide]

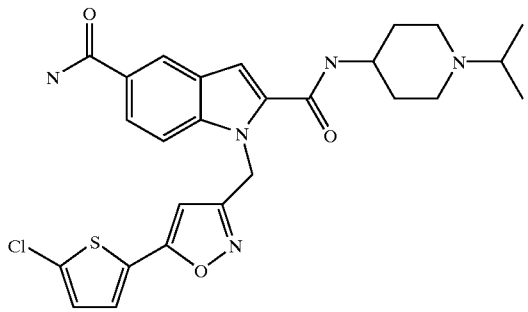

The title compound was isolated as a by-product in example 176.

MS (ES$^+$): m/e=526, chloro pattern.

Example 248

1-[(4-chloro-phenylcarbamoyl)-methyl]-1H-indole-2-carboxylic acid (1-isopropyl-piperidin-4-yl)-amide

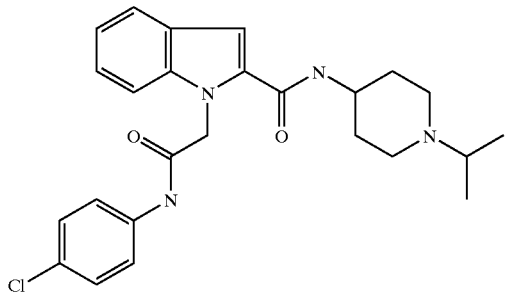

(i) 1H-Indole-2-carboxylic acid benzyl ester.

To a solution of 10.32 g 1H-indole-2-carboxylic acid in 100 ml tetrahydro-furan 10.38 g di-imidazol-1-yl-methanone were added and the mixture was stirred for 20 min at room temperature. 7.29 ml phenyl-methanol were added to the mixture and the reaction mixture was refluxed for 10 h. The mixture was allowed to cool to ambient temperature and then partitioned between 200 ml water and 200 ml dichloro-methane. The organic layer was washed with additional water and then dried over sodium sulphate. After filtration the solvent was removed under reduced pressure, a white solid was obtained. The residue was directly subjected to the subsequent reaction without further purification.

Yield: 18.8 g MS (ES$^+$): m/e=252, chloro pattern.

1H-NMR (400 MHz, DMSO/TMS): δ=7.65 (d, 1H); 7.40 (m, 7H); 7.25 (t, 1H); 7.20 (s, 1H); 7.07 (t, 1H); 5.39 (s, 2H).

(ii) 1-tert.-Butoxycarbonylmethyl-1H-indole-2-carboxylic acid benzyl ester.

To a solution of 18.80 g 1H-indole-2-carboxylic acid benzyl ester in 70 ml N,N-dimethylformamide 1.98 g sodium hydride were added at 0C. After stirring for 1 hour 15.91 ml bromo-acetic acid tert.-butyl ester were added to the mixture and the reaction mixture was stirred for 2 hours at room temperature. After removal of the solvent under reduced pressure the residue was partitioned between 300 ml water and 300 ml dichloromethane. The aqueous layer was washed twice with additional 200 ml dichloromethane. Subsequently the combined organic phases were washed with a saturated aqueous solution of sodium chloride. After filtration the solvent was removed under reduced pressure and the residue was crystallized from ethoxy-ethane/heptane. The product was obtained as a white solid.

Yield: 23.8 g MS (ES$^+$): m/e=366, chloro pattern.

1H-NMR (400 MHz, DMSO/TMS): δ=7.70 (d, 1H); 7.62 (d, 1H); 7.46 (d, 2H); 7.38 (m, 5H); 7.15 (t, 1H); 5.35 (s, 2H); 5.28 (s, 2H); 1.39 (s, 9H).

(iii) 1-tert.-Butoxycarbonyl methyl-1H-indole-2-carboxylic acid.

To a solution of 3.0 g 1-tert.-butoxycarbonylmethyl-1H-indole-2-carboxylic acid benzyl ester in a mixture of 10 ml N,N-dimethylformamide and 10 ml ethanol 0.5 g palladium, 5% an carbon were added. The reaction mixture was stirred for 2 hours under a hydrogen atmosphere. The mixture was filtered through a chem elut® cartridge and the compound was eluted with ethanol. After concentration under reduced pressure the residue was directly subjected to the subsequent reaction without further purification.

Yield: 2.2 g.

1H-NMR (400 MHz, DMSO/TMS): δ=12.50 (s, 1H); 7.68 (d, 1H); 7.59 (d, 1H); 7.31 (t, 1H); 7.25 (s, 1H); 7.13 (t, 1H); 5.26 (s, 2H); 1.40 (s, 9H).

(iv) tert.-Butyl [2-(1-isopropyl-piperidin-4-ylcarbamoyl)-indol-1-yl]-acetate.

To a solution of 0.5 g 1-tert.-butoxycarbonylmethyl-1H-indole-2-carboxylic acid and 0.91 ml N-ethylmorpholine in 3 ml dichloromethane 0.6 g O-[(ethoxycarbonyl)cyanomethylenamino]-N,N,N',N'-tetramethyluronium tetrafluoroborate were added and the mixture was stirred for 30 min at room temperature. 0.39 g 1-isopropyl-piperidin-4-ylamine hydrochloride were added to the mixture and the reaction mixture was further stirred for 1 hour. After removal of the solvent under reduced pressure the residue was partitioned between 15 ml water and 15 ml dichloromethane. The organic layer was washed with additional water and then dried over sodium sulphate. After filtration the solvent was removed under reduced pressure and a white solid was obtained. The residue was directly subjected to the subsequent reaction without further purification.

Yield: 0.51 g MS (ES$^+$): m/e=400.

1H-NMR (400 MHz, DMSO/TMS): δ=8.38 (d, 1H); 7.63 (d, 1H); 7.51 (d, 1H); 7.25 (t, 1H); 7.20 (s, 1H); 7.11 (t, 1H); 5.27 (s, 2H); 3.55 (m, 1H); 2.82 (m, 2H); 2.30 (m, 1H); 2.18 (m, 2H); 1.77 (m, 2H); 1.55 (m, 2H); 1.39 (s, 9H); 0.98 (d, 6H).

(v) [2-(1-Isopropyl-piperidin-4-ylcarbamoyl)-indol-1-yl]-acetic acid.

To 0.51 g tert.-butyl [2-(1-isopropyl-piperidin-4-ylcarbamoyl)-indol-1-yl]-acetic acid in 5 ml dichloromethane 1 ml trifluoroacetic acid was added and the mixture was stirred for 16 hours. Removal of the solvent under reduced pressure yielded a white solid, which was coevaporated twice with 15 ml toluene. The product was obtained as its trifluoroacetate salt.

Yield: 0.43 g MS (ES$^+$): m/e=344.

1H-NMR (400 MHz, DMSO/TMS): δ=12.6 (1H); 9.17 (s, 1H); 8.56 (d, 1H); 7.66 (d, 1H); 7.27 (t, 1H); 7.25 (s, 1H); 7.11 (t, 1H); 5.30 (s, 2H); 4.02 (m, 1H); 3.43 (m, 2H); 2.06 (m, 3H); 1.83 (m, 2H); 1.25 (d, 6H).

(vi) 1-[(4-Chloro-phenylcarbamoyl)-methyl]-1H-indole-2-carboxylic acid (1-isopropyl-piperidin-4-yl)-amide.

To a suspension of 50 mg [2-(1-isopropyl-piperidin-4-ylcarbamoyl)-indol-1-yl]-acetic acid, 22 mg 4-chlorophenylamine and 37 mg bis(2-oxo-3-oxazolidinyl)phosphinic chloride in 1 ml dichloro-methane 0.08 ml N-ethylmorpholine were added at room temperature and the mixture was stirred for 16 hours. After removal of the solvent under reduced pressure the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 12.6 mg MS (ES$^+$): m/e=453, chloro pattern.

1H-NMR (300 MHz, DMSO/TMS): δ=10.44 (s, 1H); 8.95 (s, 1H); 8.58 (d, 1H); 7.67 (d, 1H); 7.60 (d, 2H); 7.58 (d, 1H); 7.35 (d, 2H); 7.28 (t, 1H); 7.25 (s, 1H); 7.13 (t, 1H); 5.45 (s, 2H); 4.03 (s, 1H); 3.43 (m, 2H); 3.08 (m, 2H); 2.05 (m, 3H); 1.80 (m, 2H); 1.23 (d, 6H).

Example 249

1-[(5-chloro-thiophen-2-ylcarbamoyl)-methyl]-1H-indole-2-carboxylic acid (1-isopropyl-piperidin-4-yl)-amide

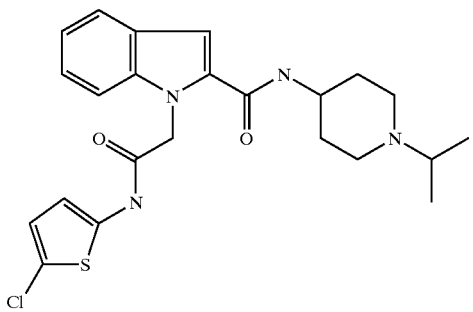

The title compound was prepared analogously to example 248 with the difference that 5-Chloro-thiophen-2-ylamine [prepared according to a procedure published in Synth. Comm. 1977, 255–256] was used instead of 4-chloro-phenylamine.

MS (ESI+): m/e=459, chloro pattern.

1H-NMR (300 MHz, DMSO/TMS): δ=11.72 (s, 1H); 8.90 (s, 1H); 8.57 (d, 1H); 7.68 (d, 1H); 7.58 (d, 1H); 7.27 (t, 1H); 7.25 (s, 1H); 7.14 (t, 1H); 6.88 (d, 1H); 6.53 (d, 1H); 5.46 (s, 2H); 4.00 (s, 1H); 3.43 (m, 2H); 3.08 (m, 2H); 2.03 (m, 3H); 1.80 (m, 2H); 1.23 (d, 6H).

Example 250

1-[(4-chloro-2-fluoro-phenylcarbamoyl)-methyl]-1H-indole-2-carboxylic acid (1-isopropyl-piperidin-4-yl)-amide

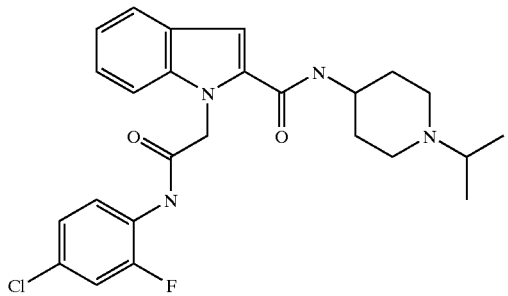

The title compound was prepared analogously to example 248 with the difference that 4-Chloro-2-fluoro-phenylamine was used instead of 4-chloro-phenylamine.

MS (ESI+): m/e=471, chloro pattern.

1H-NMR (300 MHz, DMSO/TMS): δ=10.24 (s, 1H); 8.93 (s, 1H); 8.60 (d, 1H); 7.95 (t, 1H); 7.68 (d, 1H); 7.55 (d, 1H); 7.50 (d, 1H); 7.26 (d, 1H); 7.24 (s, 1H); 7.22 (s, 1H); 7.13 (t, 1H); 5.48 (s, 2H); 4.04 (s, 1H); 3.43 (m, 2H); 3.10 (m, 2H); 2.08 (m, 3H); 1.80 (m, 2H); 1.25 (d, 6H).

Example 251

1-[(5-chloro-pyridin-2-ylcarbamoyl)-methyl]-1H-indole-2-carboxylic acid (1-isopropyl-piperidin-4-yl)-amide

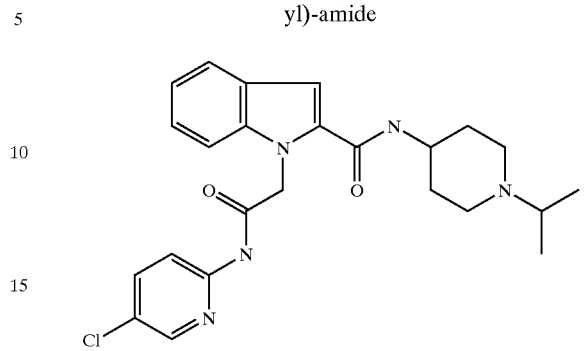

The title compound was prepared analogously to example 248 with the difference that 5-Chloro-pyridin-2-ylamine was used instead of 4-chloro-phenylamine.

MS (ESI+): m/e=454, chloro pattern.

1H-NMR (300 MHz, DMSO/TMS): δ=10.99 (s, 1H); 8.90 (s, 1H); 8.58 (d, 1H); 8.39 (d, 1H); 7.97 (d, 1H); 7.87 (dd, 1H); 7.68 (d, 1H); 7.56 (d, 1H); 7.27 (t, 1H); 7.25 (s, 1H); 7.13 (t, 1H); 5.45 (s, 2H); 4.02 (s, 1H); 3.43 (m, 2H); 3.08 (m, 2H); 2.03 (m, 3H); 1.80 (m, 2H); 1.23 (d, 6H).

Example 252

1-[(4-chloro-phenylcarbamoyl)-methyl]-1H-indole-2-carboxylic acid (3,4,5,6-tetrahydro-2H-[1,4']bipyridinyl-4-ylmethyl)-amide

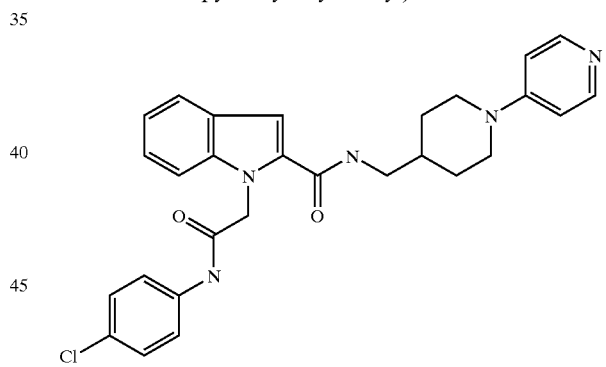

(i) 1-[(4-Chloro-phenylcarbamoyl)-methyl]-1H-indole-2-carboxylic acid ethyl ester.

To a solution of 1.0 g 1H-indole-2-carboxylic acid ethyl ester in 10 ml N,N-dimethylformamide 0.14 g sodium hydride were added at 0° C. After stirring for 30 min 1.58 g 2-bromo-N-(4-chloro-phenyl)-acetamide were added and the mixture was stirred for 2 hours at room temperature. After diluting with 15 ml water the mixture was filtered through a chem elut® cartridge and the compound was eluted with ethyl acetate. After concentration under reduced pressure the residue was directly subjected to the subsequent saponification reaction without further purification.

Yield: 1.45 g. MS (ESI+): m/e=357, chloro pattern.

(ii) 1-[(4-Chloro-phenylcarbamoyl)-methyl]-1H-indole-2-carboxylic acid.

To a solution of 1.45 g 1-[(4-chloro-phenylcarbamoyl)-methyl]-1H-indole-2-carboxylic acid ethyl ester in 100 ml tetrahydrofuran 30 ml water and 0.59 g potassium hydroxide were added. After stirring for 2 hours at room temperature the reaction mixture was acidified with 6 N hydrochloric acid. The precipitate was collected by filtration and was washed with 20 ml water. The product was obtained as a white solid which was dried under reduced pressure.

Yield: 1.37 g. MS (ESI+): m/e=329, chloro pattern.

1H-NMR (400 MHz, DMSO/TMS): δ=10.50 (s, 1H); 7.70 (d, 1H); 7.61 (d, 2H); 7.58 (d, 1H); 7.37 (d, 2H); 7.32 (t, 1H); 7.25 (s, 1H); 7.14 (t, 1H); 5.44 (s, 2H).

(iii) 1-[(4-Chloro-phenylcarbamoyl)-methyl]-1H-indole-2-carboxylic acid (3,4,5,6-tetrahydro-2H-[1,4']bipyridinyl-4-ylmethyl)-amide.

To a suspension of 50 mg 1-[(4-chloro-phenylcarbamoyl)-methyl]-1H-indole-2-carboxylic acid, 97 mg (3,4,5,6-tetrahydro-2H-[1,4']bipyridinyl-4-yl)-methylamine and 38.7 mg bis(2-oxo-3-oxazolidinyl)phosphinic chloride in 1 ml N,N-dimethylformamide 61.7 μl triethylamine were added. After stirring at room temperature for 16 hours the solvent was removed under reduced pressure and the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 6.9 mg MS (ES+): m/e=502, chloro pattern.

1H-NMR (300 MHz, DMSO/TMS): δ=13.14 (s, 1H); 10.45 (s, 1H); 8.63 (t, 1H); 8.17 (d, 2H); 7.64 (d, 1H); 7.61 (d, 2H); 7.56 (d, 1H); 7.38 (d, 2H); 7.26 (t, 1H); 7.17 (s, 1H); 7.12 (m, 3H); 5.43 (s, 2H); 4.13 (d, 2H); 3.13 (m, 4H); 1.80 (m, 2H); 1.21 (m, 3H).

Example 253

1-[(4-chloro-phenylcarbamoyl)-methyl]-1H-indole-2-carboxylic acid (3,4,5,6-tetrahydro-2H-[1,4']bipyridinyl-4-yl)-amide

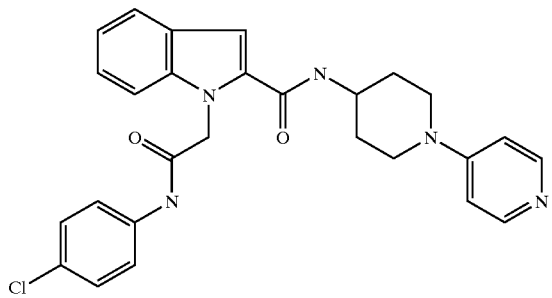

The title compound was prepared analogously to example 252 with the difference that 3,4,5,6-Tetrahydro-2H-[1,4']bipyridinyl-4-ylamine was used instead of (3,4,5,6-tetrahydro-2H-[1,4']bipyridinyl-4-yl)-methylamine.

MS (ES+): m/e=488, chloro pattern.

1H-NMR (300 MHz, DMSO/TMS): δ=13.23 (s, 1H); 10.44 (s, 1H); 8.43 (d, 1H); 8.23 (d, 2H); 7.65 (d, 1H); 7.61 (d, 2H); 7.56 (d, 1H); 7.35 (d, 2H); 7.23 (m, 4H); 7.12 (t, 1H); 5.44 (s, 2H); 4.20 (m, 3H); 3.32 (m, 2H); 1.95 (m, 2H); 1.58 (m, 2H).

Example 254

N-(4-chloro-phenyl)-2-{2-[4-(pyridin-4-ylamino)-piperidine-1-carbonyl]-indol-1-yl}-acetamide

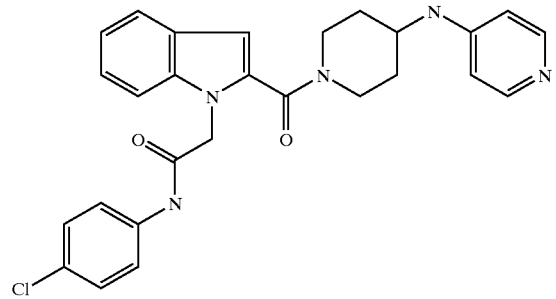

The title compound was prepared analogously to example 252 by using Piperidin-4-yl-pyridin-4-yl-amine was used instead of (3,4,5,6-tetrahydro-2H-[1,4']bipyridinyl-4-yl)-methylamine.

MS (ES+): m/e=488, chloro pattern.

1H-NMR (300 MHz, DMSO/TMS): δ=13.24 (s, 1H); 10.45 (s, 1H); 8.43 (d, 1H); 8.23 (d, 2H); 7.64 (d, 1H); 7.60 (d, 2H); 7.55 (d, 1H); 7.35 (d, 2H); 7.22 (m, 4H); 7.11 (t, 1H); 5.44 (s, 2H); 4.20 (m, 3H); 3.33 (m, 2H); 1.95 (m, 2H); 1.57 (m, 2H).

Example 255

1-[(4-chloro-phenylcarbamoyl)-methyl]-1H-indole-2-carboxylic acid (1-cyclopropyl-piperidin-4-yl)-amide

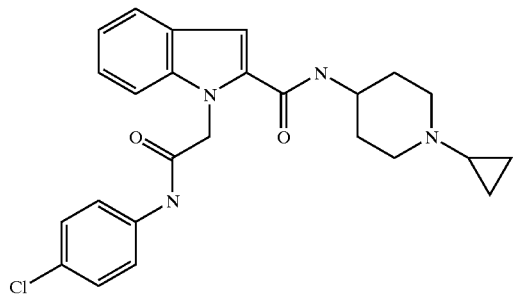

The title compound was prepared analogously to example 252 with the difference that 1-Cyclopropyl-piperidin-4-ylamine was used instead of (3,4,5,6-tetrahydro-2H-[1,4']bipyridinyl-4-yl)-methylamine. MS (ES+): m/e=451, chloro pattern.

1H-NMR (300 MHz, DMSO/TMS): δ=10.44 (s, 1H); 8.78 (s, 1H); 8.57 (d, 1H); 7.68 (d, 1H); 7.60 (d, 2H); 7.57 (d, 1H); 7.36 (d, 2H); 7.27 (t, 1H); 7.23 (s, 1H); 7.12 (t, 1H); 5.44 (s, 2H); 3.44 (m, 2H); 3.25 (m, 2H); 2.03 (m, 3H); 1.73 (m, 2H); 0.84 (m, 5H).

Example 256

N-(4-chloro-phenyl)-2-[2-(4-pyrrolidin-1-yl-piperidine-1-carbonyl)-indol-1-yl]-acetamide

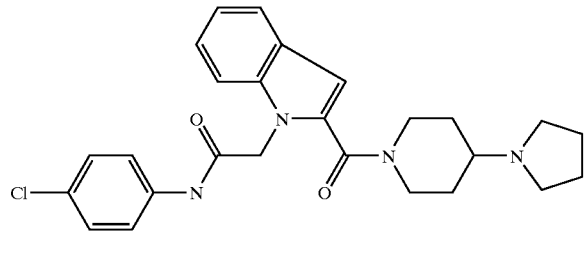

The title compound was prepared analogously to example 252 with the difference that 4-Pyrrolidin-1-yl-piperidine was used instead of (3,4,5,6-tetrahydro-2H-[1,4']bipyridinyl-4-yl)-methylamine.

MS (ES$^+$): m/e=465, chloro pattern.

1H-NMR (300 MHz, DMSO/TMS): δ=10.53 (s, 1H); 9.64 (s, 1H); 7.64 (d, 1H); 7.57 (m, 3H); 7.36 (d, 2H); 7.26 (t, 1H); 7.13 (t, 1H); 6.76 (s, 1H); 5.20 (s, 2H); 4.45 (s, 2H); 3.45 (m, 3H); 3.06 (m, 3H); 1.97 (m, 7H); 1.55 (s, 2H).

Example 257

1-[(4-chloro-phenylcarbamoyl)-methyl]-5-nitro-1H-indole-2-carboxylic acid (1-isopropyl-piperidin-4-yl)-amide

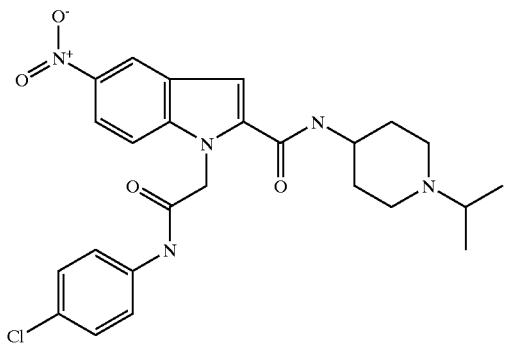

The title compound was prepared in analogy to example 248 with the difference that 5-nitro-1H-indole-2-carboxylic acid ethyl ester was used instead of the unsubstituted 1H-indole-2-carboxylic acid ethyl ester.

MS (ES$^+$): m/e=498, chloro pattern.

1H-NMR (300 MHz, DMSO/TMS): δ=10.53 (s, 1H); 8.98 (s, 1H); 8.83 (d, 1H); 8.74 (s, 1H); 8.14 (d, 1H); 7.85 (d, 1H); 7.59 (d, 2H); 7.50 (s, 1H); 7.38 (d, 2H); 5.52 (s, 2H); 4.02 (m, 1H); 3.45 (m, 2H); 3.07 (m, 2H); 2.03 (m, 3H); 1.81 (m, 2H); 1.25 (d, 6H).

Example 258

5-amino-4-chloro-1-[5-(5-chloro-thiophen-2-yl)-isoxazol-3-ylmethyl]-1H-indole-2-carboxylic acid (1-isopropyl-piperidin-4-yl)-amide

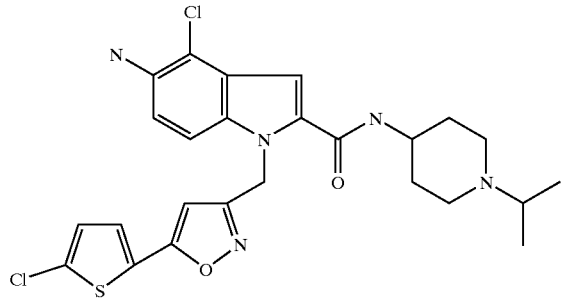

24.4 mg 1-[5-(5-chloro-thiophen-2-yl)-isoxazol-3-ylmethyl]-5-nitro-1H-indole-2-carboxylic acid (1-isopropyl-piperidin-4-yl)-amide were added to a solution of 58.5 mg tin chloride dihydrate in 1 ml ethanol. 0.5 ml 12 N aqueous hydrochloric acid was added and the mixture was stirred at room temperature for 16 hours. After cooling of the reaction mixture it was basified to pH 12 with saturated aqueous solution of sodium hydroxide and the product isolated by filtration. The product was obtained as a white solid which was dried under reduced pressure.

Yield: 10.0 mg MS (ES$^+$): m/e=532, chloro pattern.

1H-NMR (300 MHz, DMSO/TMS): δ=8.40 (d, 1H); 7.56 (d, 1H); 7.28 (d, 1H); 7.24 (d, 1H); 7.07 (s, 1H); 6.86 (d, 1H); 6.54 (s, 1H); 5.83 (s, 2H); 4.97 (s, 2H); 3.70 (m, 1H); 2.78 (m, 2H); 2.68 (m, 1H); 2.14 (m, 2H); 1.78 (m, 2H); 1.53 (m, 2H); 0.96 (d, 6H).

Example 259

1-[5-(5-chloro-thiophen-2-yl)-isoxazol-3-ylmethyl]-1H-indole-2-carboxylic acid (1-cyanomethyl-piperidin-4-yl)-amide

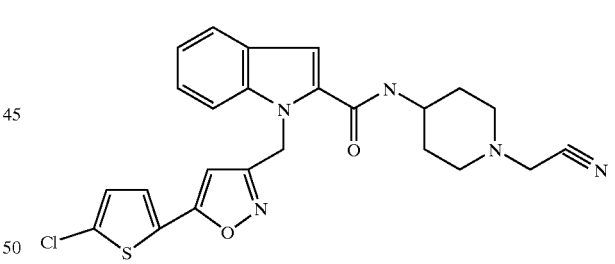

To a suspension of 50 mg 1-[5-(5-chloro-thiophen-2-yl)-isoxazol-3-ylmethyl]-1H-indole-2-carboxylic acid piperidin-4-ylamide in 1 ml ethanol 43.5 mg potassium carbonate, 14.5 μL triethylamine and 7.3 μl bromo-acetonitrile were added. After stirring at room temperature for 16 hours the solvent was removed under reduced pressure and the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 13.8 mg MS (ES$^+$): m/e=480, chloro pattern.

1H-NMR (300 MHz, DMSO/TMS): δ=8.49 (d, 1H); 7.67 (d, 1H); 7.58 (d, 1H); 7.55 (d, 1H); 7.28 (t, 1H); 7.25 (d, 1H);

7.22 (s, 1H); 7.13 (t, 1H); 6.59 (s, 1H); 5.90 (s, 2H); 3.87 (m, 3H); 3.00 (m, 2H); 2.48 (m, 2H); 1.91 (m, 2H); 1.67 (m, 2H).

Example 260

1-[5-(5-chloro-thiophen-2-yl)-isoxazol-3-ylmethyl]-1H-indole-2-carboxylic acid [1-(2-hydroxy-ethyl)-piperidin-4-yl]-amide

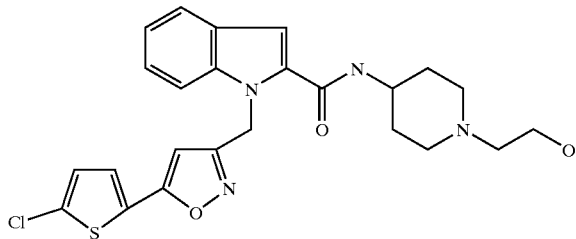

The title compound was prepared analogously to example 259 with the difference that 2-bromo-ethanol was used instead of bromo-acetonitrile.

MS (ES$^+$): m/e=485, chloro pattern

1H-NMR (300 MHz, DMSO/TMS): δ=9.35 (s, 1H); 8.63 (m, 1H); 7.68 (d, 1H); 7.61 (d, 1H); 7.55 (d, 1H); 7.30 (t, 1H); 7.25 (m, 2H); 7.14 (t, 1H); 6.59 (s, 1H); 5.90 (s, 2H); 5.33 (s, 1H); 4.04 (m, 1H); 3.76 (m, 2H); 3.56 (m, 2H); 3.33 (m, 2H); 3.12 (m, 2H); 2.02 (m, 2H); 1.87 (m, 1H); 1.73 (m, 1H).

Example 261

1-[5-(5-chloro-thiophen-2-yl)-isoxazol-3-ylmethyl]-1H-indole-2-carboxylic acid [1-(2-methoxy-ethyl)-piperidin-4-yl]-amide

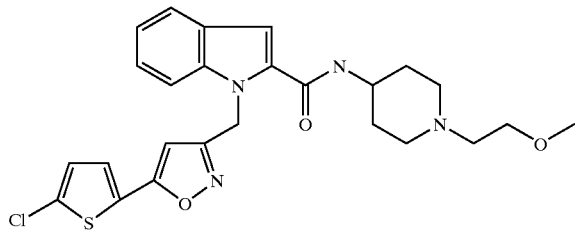

The title compound was prepared analogously to example 259 with the difference that 1-bromo-2-methoxy-ethane was used instead of bromo-acetonitrile and acetonitrile as solvent.

MS (ES$^+$): m/e=499, chloro pattern.

1H-NMR (300 MHz, DMSO/TMS): δ=9.30 (s, 1H); 8.65 (d, 1H); 7.68 (d, 1H); 7.60 (d, 1H); 7.54 (d, 1H); 7.30 (t, 1H); 7.25 (m, 2H); 7.15 (t, 1H); 6.58 (s, 1H); 5.90 (s, 2H); 4.02 (m, 1H); 3.67 (t, 2H); 3.54 (m, 2H); 3.33 (s, 3H); 3.28 (t, 2H); 3.10 (m, 2H); 2.04 (m, 2H); 1.83 (m, 2H).

Example 262

1-[5-(5-chloro-thiophen-2-yl)-isoxazol-3-ylmethyl]-1H-indole-2-carboxylic acid (1-carbamoylmethyl-piperidin-4-yl)-amide

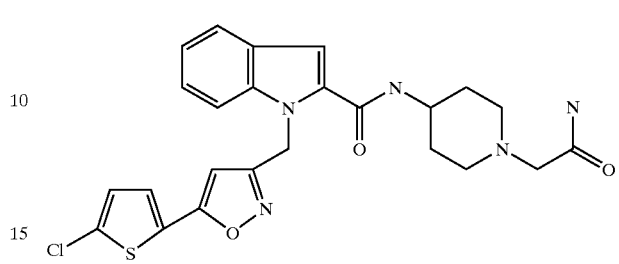

To a suspension of 50 mg 1-[5-(5-chloro-thiophen-2-yl)-isoxazol-3-ylmethyl]-1H-indole-2-carboxylic acid piperidin-4-ylamide in 1 ml acetonitrile 42.4 μl ethyl-diisopropyl-amine and 29.4 mg 2-chloro-acetamide were added. The reaction mixture was stirred at 80° C. for 3 hours. After removal of the solvent under reduced pressure the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

MS (ES$^+$): m/e=498, chloro pattern.

1H-NMR (300 MHz, DMSO/TMS): δ=9.62 (s, 1H); 8.65 (d, 1H); 7.94 (s, 1H); 7.68 (m, 2H); 7.60 (d, 1H); 7.54 (d, 1H); 7.28 (t, 1H); 7.25 (m, 2H); 7.15 (t, 1H); 6.58 (s, 1H); 5.90 (s, 2H); 4.00 (m, 1H); 3.88 (m, 2H); 3.53 (m, 2H); 3.16 (m, 2H); 2.00 (m, 4H).

Example 263

1-[5-(5-chloro-thiophen-2-yl)-isoxazol-3-ylmethyl]-1H-indole-2-carboxylic acid (1-methylcarbamoylmethyl-piperidin-4-yl)-amide

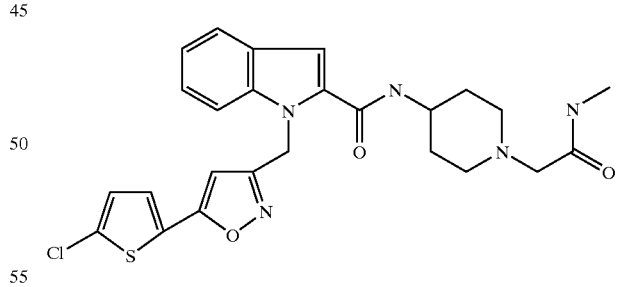

The title compound was prepared analogously to example 262 with the difference that 2-chloro-N-methyl-acetamide was used instead of 2-chloro-acetamide.

MS (ES$^+$): m/e=512, chloro pattern.

1H-NMR (300 MHz, DMSO/TMS): δ=9.74 (s, 1H); 8.65 (d, 1H); 8.45 (s, 1H); 7.68 (d, 1H); 7.60 (d, 1H); 7.53 (d, 1H); 7.29 (t, 1H); 7.25 (m, 2H); 7.14 (t, 1H); 6.56 (s, 1H); 5.90 (s, 2H); 4.00 (m, 1H); 3.88 (m, 2H); 3.53 (m, 2H); 3.16 (m, 2H); 2.69 (d, 3H); 2.04 (m, 2H); 1.92 (m, 2H).

Example 264

1-[5-(5-chloro-thiophen-2-yl)-isoxazol-3-ylmethyl]-1H-indole-2-carboxylic acid [1-(1H-imidazol-2-ylmethyl)-piperidin-4-yl]-amide

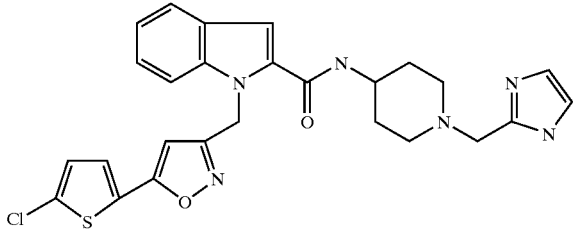

A solution of 50 mg 1-[5-(5-chloro-thiophen-2-yl)-isoxazol-3-ylmethyl]-1H-indole-2-carboxylic acid piperidin-4-ylamide in 1.5 ml 1,2-dichloro-ethane was treated with 66.76 mg sodium triacetoxyborohydride, 18 μl glacial acid and 11.1 mg 1H-imidazole-2-carbaldehyde. After stirring of the reaction mixture for 16 hours at room temperature the solvent was removed under reduced pressure. The residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

MS (ES$^+$): m/e=521, chloro pattern.

1H-NMR (300 MHz, DMSO/TMS): δ=8.54 (d, 1H); 7.68 (d, 1H); 7.58 (d, 1H); 7.53 (d, 1H); 7.45 (s, 2H); 7.29 (t, 1H); 7.25 (d, 1H); 7.22 (s, 1H); 7.14 (t, 1H); 6.57 (s, 1H); 5.90 (s, 2H); 4.13 (m, b); 3.87 (m, b); 3.18 (m, 2H); 1.95 (m, 2H); 1.75 (m, 2H).

Example 265

1-[5-(5-chloro-thiophen-2-yl)-isoxazol-3-ylmethyl]-1H-indole-2-carboxylic acid [1-(1-methyl-1H-imidazol-2-ylmethyl)-piperidin-4-yl]-amide

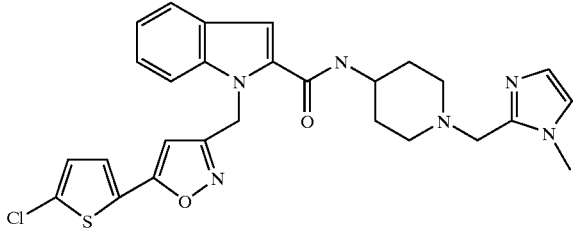

The title compound was prepared analogously to example 264 with the difference that 1-methyl-1H-imidazole-2-carbaldehyde was used instead of 1H-imidazole-2-carbaldehyde.

MS (ES$^+$): m/e=535, chloro pattern.

1H-NMR (300 MHz, DMSO/TMS): δ=8.54 (d, 1H); 7.68 (d, 1H); 7.59 (d, 1H); 7.55 (d, 1H); 7.50 (s, 1H); 7.29 (t, 1H); 7.25 (d, 1H); 7.22 (s, 1H); 7.14 (t, 1H); 6.57 (s, 1H); 5.90 (s, 2H); 4.13 (m, b); 3.93 (m, b); 3.78 (s, 3H); 3.23 (m, b); 1.95 (m, 2H); 1.75 (m, 2H).

Example 266

1-[5-(5-chloro-thiophen-2-yl)-isoxazol-3-ylmethyl]-1H-indole-2-carboxylic acid [1-(2-dimethylamino-acetyl)-piperidin-4-yl]-amide

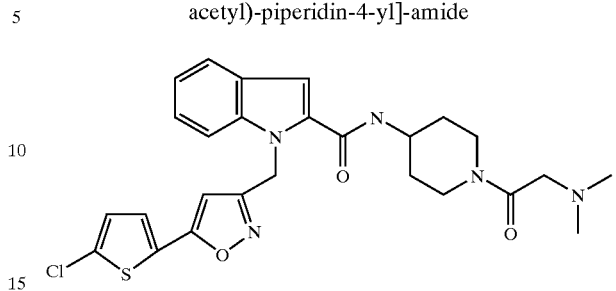

A solution of 50 mg 1-[5-(5-chloro-thiophen-2-yl)-isoxazol-3-ylmethyl]-1H-indole-2-carboxylic acid piperidin-4-ylamide in 1 ml N,N-dimethylformamide was treated with 29.0 mg potassium carbonate, 187.5 μl ethyl-diisopropyl-amine and 16.7 μl chloro-acetyl chloride. After stirring oft the reaction mixture for 15 min at room temperature 19.5 mg dimethylamine hydrochloride were added and the mixture was further stirred at room temperature for 16 hours. The solvent was removed under reduced pressure and the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt. MS (ES$^+$): m/e=526, chloro pattern.

1H-NMR (300 MHz, DMSO/TMS): characteristic protons for aromatic and amide moieties: 9.50 (s, 1H); 8.53 (d, 1H); 7.68 (d, 1H); 7.60 (d, 1H); 7.55 (d, 1H); 7.28 (t, 1H); 7.25 (d, 1H); 7.20 (s, 1H); 7.15 (t, 1H); 6.59 (s, 1H).

Example 267

1-[5-(5-chloro-thiophen-2-yl)-isoxazol-3-ylmethyl]-1H-indole-2-carboxylic acid [1-(2-amino-acetyl)-piperidin-4-yl]-amide

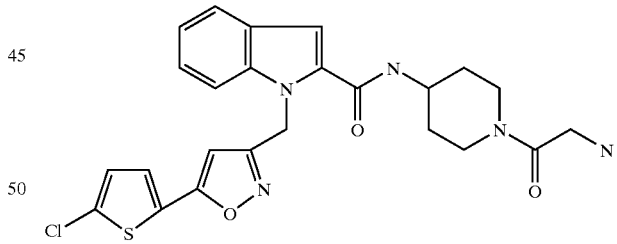

(i) {2-[4-({1-[5-(5-Chloro-thiophen-2-yl)-isoxazol-3-ylmethyl]-1H-indole-2-carbonyl}-amino)-piperidin-1-yl]-2-oxo-ethyl}-carbamic acid tert.-butyl ester To a solution of 50 mg 1-[5-(5-chloro-thiophen-2-yl)-isoxazol-3-ylmethyl]-1H-indole-2-carboxylic acid piperidin-4-ylamide and 44.1 μl N-ethylmorpholine in 1 ml dichloro-methane 28.5 mg O-[(ethoxycarbonyl)cyanomethylenamino]-N,N,N',N'-tetramethyluronium tetrafluoroborate were added and the mixture was stirred for 1 hour at room temperature. 15.2 mg tert.-butoxycarbonylamino-acetic acid were added to the mixture and the reaction mixture was further stirred for 1 hour. After removal of the solvent under reduced pressure the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 22.0 mg MS (ES+): m/e=598.

(ii) 1-[5-(5-Chloro-thiophen-2-yl)-isoxazol-3-ylmethyl]-1H-indole-2-carboxylic acid [1-(2-amino-acetyl)-piperidin-4-yl]-amide.

A solution of 22.0 mg {2-[4-({1-[5-(5-chloro-thiophen-2-yl)-isoxazol-3-ylmethyl]-1H-indole-2-carbonyl}-amino)-piperidin-1-yl]-2-oxo-ethyl}-carbamic acid tert.-butyl ester in 5 ml of a 8 N solution of hydrochloric acid in methanol) was stirred at room temperature for 16 hours. 10 ml water was added to the reaction mixture and the resulting mixture was lyophilized to yield a white solid. The product was obtained as its hydrochloride salt.

MS (ES+): m/e=498, chloro pattern.

1H-NMR (300 MHz, DMSO/TMS): δ=8.54 (d, 1H); 8.03 (m, 2H); 7.68 (d, 1H); 7.59 (d, 1H); 7.55 (d, 1H); 7.28 (t, 1H); 7.25 (d, 1H); 7.22 (s, 1H); 7.13 (t, 1H); 6.59 (s, 1H); 5.90 (s, 2H); 4.35 (m, 1H); 4.07 (m, 1H); 3.95 (m, 1H); 3.87 (m, 1H); 3.73 (m, 1H); 3.16 (m, 1H); 2.86 (m, 1H); 1.90 (m, 2H); 1.54 (m, 1H); 1.44 (m, 1H).

Example 268

1-[5-(5-Chloro-thiophen-2-yl)-isoxazol-3-ylmethyl]-2-(1-isopropyl-piperidin-4-ylcarbamoyl)-1H-indole-5-carboxylic acid 1-ethoxycarbonyloxy-ethyl ester

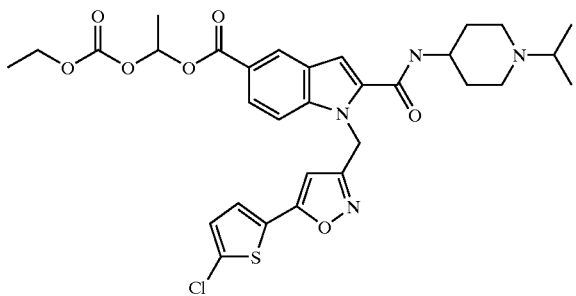

To a solution of 0.39 g 1-[5-(5-Chloro-thiophen-2-yl)-isoxazol-3-ylmethyl]-2-(1-isopropyl-piperidin-4-ylcarbamoyl)-1H-indole-5-carboxylic acid hydrochloride in 15 ml DMF 0.23 g KI, 0.383 g K₂CO₃ and 0.37 ml 1-chloroethyl-ethylcarbonate were added and the reaction mixture was stirred for 3 h at 60° C. in an argon athmosphere. After filtration and removal of the solvent under reduced pressure the residue was directly purified by preparative RP-HPLC eluting with a gradient of 0–100% acetonitrile in water (+0.01% trifluoroacetic acid). After addition of 1 M hydrochloric acid and lyophilization in an acetonitrile/water mixture, the product was obtained as its hydrochloride.

Yield: 0,33 g MS (ESI+): m/e=643, chloro pattern.

Example 269

1-[5-(5-Chloro-thiophen-2-yl)-isoxazol-3-ylmethyl]-2-(1-isopropyl-piperidin-4-ylcarbamoyl)-1H-indole-4-carboxylic acid 1-ethoxycarbonyloxy-ethyl ester

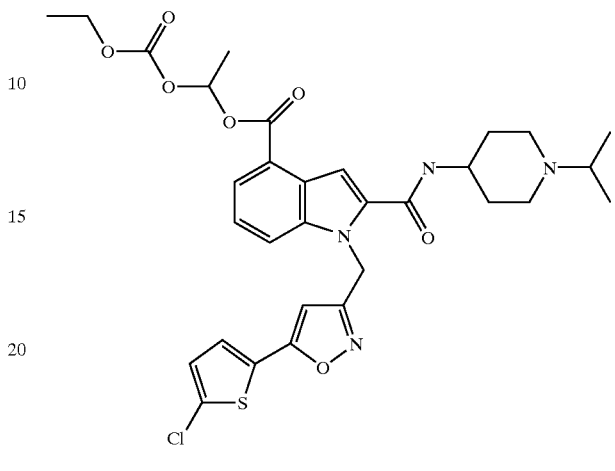

To a solution of 0.6 g 1-[5-(5-Chloro-thiophen-2-yl)-isoxazol-3-ylmethyl]-2-(1-isopropyl-piperidin-4-ylcarbamoyl)-1H-4-carboxylic acid hydrochloride in 20 ml DMF 0.679 g KI, 1.13 g K₂CO₃ and 1.094 ml 1-chloroethyl-ethylcarbonate were added and the reaction mixture was stirred for 3 h at 60° C. in an argon athmosphere. After filtration and removal of the solvent under reduced pressure the residue was directly purified by preparative RP-HPLC eluting with a gradient of 0–100% acetonitrile in water (+0.01% trifluoroacetic acid). After addition of 1 M hydrochloric acid and lyophilization in an acetonitrile/water mixture, the product was obtained as its hydrochloride.

Yield: 0,56 g MS (ESI+): m/e=643, chloro pattern.

Example 270

1-[5-(5-Chloro-thiophen-2-yl)-isoxazol-3-ylmethyl]-2-(1-isopropyl-piperidin-4-ylcarbamoyl)-1H-indole-4-carboxylic acid 2,2-dimethyl-propionyloxymethyl ester

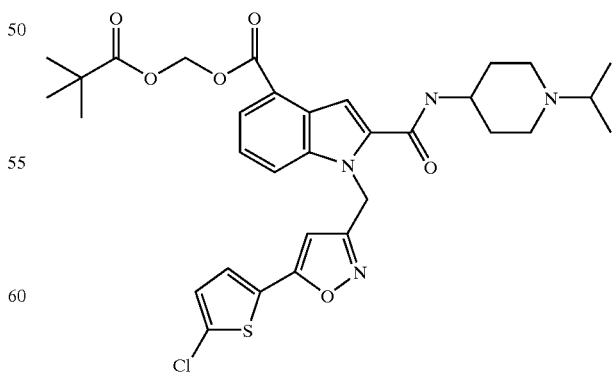

To a solution of 0,6 g 1-[5-(5-Chloro-thiophen-2-yl)-isoxazol-3-ylmethyl]-2-(1-isopropyl-piperidin-4- ylcarbamoyl)-1H-indole-4-carboxylic acid in 20 ml DMF 0,319 g 2,2-Dimethyl-propionic acid chloromethyl ester and 441 µl NEt₃ were added and the reaction mixture was stirred for 5 h at 60° C. Then additional 0,16 g 2,2-Dimethyl-propionic acid chloromethyl ester and 147 µl NEt₃ were added and the reaction mixture was stirred for 6 h at 60° C. After removal of the solvent under reduced pressure the residue was dissolved in CH₂Cl₂ and the solution was washed with water. The phases were separated and the organic phase (after drying over Na₂SO₄) was concentrated in vacuo. The residue was purified by preparative RP-HPLC eluting with a gradient of 0–100% acetonitrile in water (+0.01% trifluoroacetic acid). After addition of 1 M hydrochloric acid and lyophilization in an acetonitrile/water mixture, the product was obtained as its hydrochloride. Yield: 0,5 g MS (ESI+): m/e=641, chloro pattern.

Example 271

1-[5-(5-Chloro-thiophen-2-yl)-isoxazol-3-ylmethyl]-2-(1-isopropyl-piperidin-4-ylcarbamoyl)-1H-indole-5-carboxylic acid 1-(2,2-dimethyl-propionyloxy)-ethyl ester

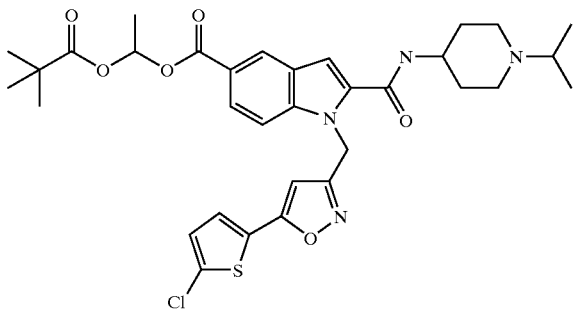

To a suspension of 0.5 g 1-[5-(5-Chloro-thiophen-2-yl)-isoxazol-3-ylmethyl]-2-(1-isopropyl-piperidin-4-ylcarbamoyl)-1H-indole-5-carboxylic acid in 30 ml acetone 531 µl DBU were added and the mixture was stirred for 15 min. at room temperature. To this solution 0,556 g 2,2-Dimethyl-propionic acid 1-bromo-ethyl ester (prepared as described by E. Defossa et al., Liebigs Ann. 1996, 1743–1749) was added and the reaction mixture stirred for 4 h at room temperature. Then additional 266 µl DBU and 0.185 g 2,2-Dimethyl-propionic acid 1-bromo-ethyl ester were added. After 16 h at room temperature the mixture was concentrated in vacuo and the residue purified by preparative RP-HPLC eluting with a gradient of 0–100% acetonitrile in water (+0.01% trifluoroacetic acid). After addition of 1 M hydrochloric acid and lyophilization in an acetonitrile/water mixture, the product was obtained as its hydrochloride.

Yield: 0,48 g MS (ESI+): m/e=655, chloro pattern.

Example 272

1-[5-(5-Chloro-thiophen-2-yl)-isoxazol-3-ylmethyl]-2-(1-isopropyl-piperidin-4-ylcarbamoyl)-1H-indole-4-carboxylic acid 1-(2,2-dimethyl-propionyloxy)-ethyl ester

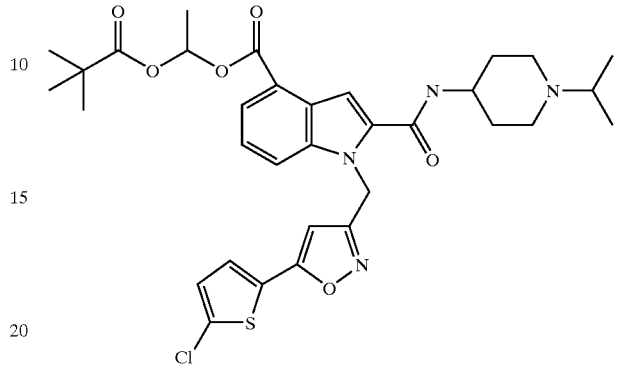

To a suspension of 0.427 g 1-[5-(5-Chloro-thiophen-2-yl)-isoxazol-3-ylmethyl]-2-(1-isopropyl-piperidin-4-ylcarbamoyl)-1H-indole-4-carboxylic acid in 30 ml acetone 453 µl DBU were added and the mixture was stirred for 15 min. at room temperature. To this solution 0,475 g 2,2-Dimethyl-propionic acid 1-bromo-ethyl ester (prepared as described by E. Defossa et al., Liebigs Ann. 1996, 1743–1749) was added and the reaction mixture stirred for 4 h at room temperature. Then additional 227 µl DBU and 0.158 g 2,2-Dimethyl-propionic acid 1-bromo-ethyl ester were added. After 16 h at room temperature the mixture was concentrated in vacuo and the residue purified by preparative RP-HPLC eluting with a gradient of 0–100% acetonitrile in water (+0.01% trifluoroacetic acid). After addition of 1 M hydrochloric acid and lyophilization in an acetonitrile/water mixture, the product was obtained as its hydrochloride.

Yield: 0,4 g MS (ESI+): m/e=655, chloro pattern.

Example 273

1-[5-(5-Chloro-thiophen-2-yl)-isoxazol-3-ylmethyl]-2-(1-isopropyl-piperidin-4-ylcarbamoyl)-1H-indole-5-carboxylic acid 5-methyl-2-oxo-[1,3]dioxol-4-ylmethyl

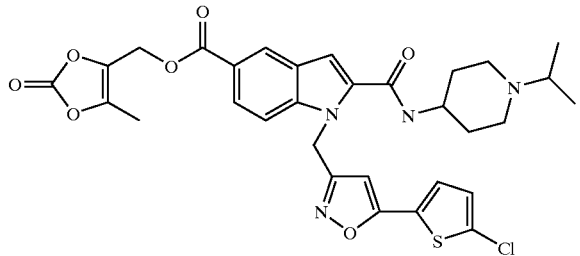

can be prepared from 1-[5-(5-Chloro-thiophen-2-yl)-isoxazol-3-ylmethyl]-2-(1-isopropyl-piperidin-4-ylcarbamoyl)-1H-indole-4-carboxylic acid and 4-Chloromethyl-5-methyl-[1,3]dioxol-2-one by the procedure described by H. Yanagisawa et al., J. Med. Chem. 1996, 39, 323–338.

Example 274

1-[5-(5-Chloro-thiophen-2-yl)-isoxazol-3-ylmethyl]-2-(1-isopropyl-piperidin-4-ylcarbamoyl)-1H-indole-4-carboxylic acid 5-methyl-2-oxo-[1,3]dioxol-4-ylmethyl

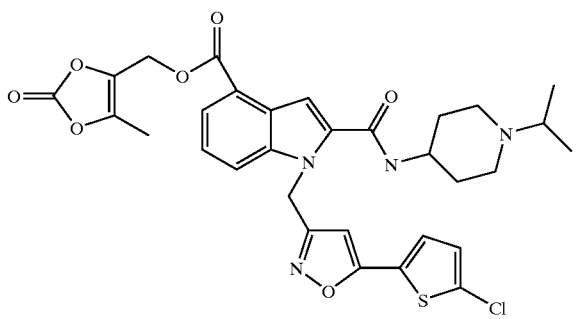

can be prepared from 1-[5-(5-Chloro-thiophen-2-yl)-isoxazol-3-ylmethyl]-2-(1-isopropyl-piperidin-4-ylcarbamoyl)-1H-indole-4-carboxylic acid and 4-Chloromethyl-5-methyl-[1,3]dioxol-2-one by the procedure described by H. Yanagisawa et al., J. Med. Chem. 1996, 39, 323–338.

Example 275

1-[5-(5-Chloro-thiophen-2-yl)-isoxazol-3-ylmethyl]-2-(1-isopropyl-piperidin-4-ylcarbamoyl)-1H-indole-5-carboxylic acid 1-cyclohexyloxycarbonyloxy-ethyl ester

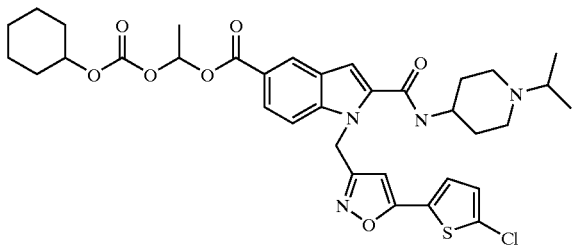

can be prepared from 1-[5-(5-Chloro-thiophen-2-yl)-isoxazol-3-ylmethyl]-2-(1-isopropyl-piperidin-4-ylcarbamoyl)-1H-indole-4-carboxylic acid and cyclohexyl 1-chloroethyl carbonate by the procedure described by K. Kubo et al., J. Med. Chem. 1993, 36, 2343–2349.

Example 276

1-[5-(5-Chloro-thiophen-2-yl)-isoxazol-3-ylmethyl]-2-(1-isopropyl-piperidin-4-ylcarbamoyl)-1H-indole-4-carboxylic acid 1-cyclohexyloxycarbonyloxy-ethyl ester

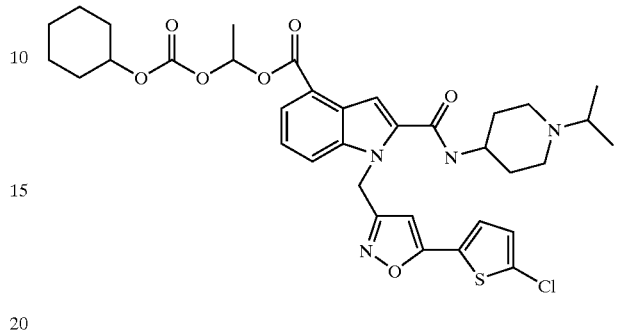

can be prepared from 1-[5-(5-Chloro-thiophen-2-yl)-isoxazol-3-ylmethyl]-2-(1-isopropyl-piperidin-4-ylcarbamoyl)-1H-indole-4-carboxylic acid and cyclohexyl 1-chloroethyl carbonate by the procedure described by K. Kubo et al., J. Med. Chem. 1993, 36, 2343–2349.

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i.e. the $IC_{50}$ value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formula 1. For calculating the inhibition constant Ki, the $IC_{50}$ value was corrected for competition with substrate using the formula $Ki=IC_{50}/\{1+(\text{substrate concentration}/Km)\}$ wherein Km is the Michaelis-Menten constant (Chen and Prusoff, Biochem. Pharmacol. 22 (1973), 3099–3108; I. H. Segal, Enzyme Kinetics, 1975, John Wiley & Sons, New York, 100–125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) $NaN_3$) was used. The $IC_{50}$ was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-P[G (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 μM.

b) Factor VIIa Assay

The inhibitory activity towards factor VIIa/tissue factor activity was determined using a chromomogenic assay essentially as described previously (J. A. Ostrem et al., Biochemistry 37 (1998) 1053–1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 μl human factor VIIa and TF (5 nM and 10 nM, respective final concentration) combined with 40 μl of inhibitor dilutions in 10% DMSO/TBS-PEG buffer (50 mM Tris, 15 mM NaCl, 5 mM CaCl$_2$, 0.05% PEG 8000, pH 8.15). Following a 15 minutes preincubation period, the assay was initiated by the addition of 35 μl of the chromogenic substrate S-2288 (D-Ile-Pro-Arg-p-nitroanilide, Pharmacia Hepar Inc., 500 μM final concentration). The results (inhibition constants Ki (FXa) for inhibition of factor Xa) are shown in Table 1.

TABLE 1

| Example | Ki(FXa) [μM] | Example | Ki(FXa) [μM] | Example | Ki(FXa) [μM] |
|---|---|---|---|---|---|
| 1 | 0.0033 | 70 | 0.114 | 215 | 0.023 |
| 2 | 0.020 | 71 | 0.277 | 216 | 0.009 |
| 3 | 0.001 | 72 | 0.167 | 217 | 0.700 |
| 4 | 0.834 | 119 | 0.040 | 218 | 0.001 |
| 5 | 0.005 | 120 | 0.004 | 219 | 0.173 |
| 6 | 0.013 | 121 | 0.003 | 220 | 0.102 |
| 7 | 0.004 | 122 | 0.002 | 221 | 0.048 |
| 8 | 0.009 | 123 | 0.002 | 222 | 0.103 |
| 9 | 0.003 | 146 | 0.44 | 223 | 0.110 |
| 10 | 0.182 | 148 | 1.930 | 224 | 0.021 |
| 11 | 0.0001 | 157 | 0.686 | 225 | 0.026 |
| 12 | 0.114 | 159 | 0.002 | 226 | 0.083 |
| 13 | 0.00025 | 160 | 0.0001 | 227 | 0.088 |
| 14 | 1.718 | 161 | 0.0001 | 228 | 0.051 |
| 15 | 0.0035 | 162 | 0.057 | 229 | 0.172 |
| 16 | 0.055 | 163 | 0.654 | 230 | 0.012 |
| 17 | 1.966 | 165 | 0.765 | 231 | 0.020 |
| 18 | 0.016 | 169 | 0.073 | 232 | 0.055 |
| 19 | 0.050 | 170 | 0.47 | 233 | 0.074 |
| 20 | 0.007 | 172 | 0.041 | 234 | 0.056 |
| 21 | 0.007 | 173 | 0.015 | 235 | 0.042 |
| 22 | 0.217 | 174 | 0.003 | 236 | 0.010 |
| 23 | 0.003 | 175 | 0.009 | 237 | 0.003 |
| 24 | 0.132 | 176 | 0.002 | 238 | 0.011 |

| Example | KI(FXa) [μM] | Example | Ki(FXa) [μM] | Example | Ki(FXa) [μM] |
|---|---|---|---|---|---|
| 25 | 0.336 | 177 | 0.015 | 239 | 0.005 |
| 26 | 0.0001 | 178 | 0.0013 | 240 | 0.035 |
| 27 | 0.0002 | 179 | 0.0055 | 242 | 0.004 |
| 28 | 0.014 | 180 | 0.024 | 243 | 0.010 |
| 29 | 0.019 | 181 | 0.014 | 244 | 0.004 |
| 30 | 0.025 | 182 | 0.005 | 246 | 0.004 |
| 31 | 0.018 | 183 | 0.076 | 247 | 0.024 |
| 32 | 0.037 | 184 | 0.013 | 248 | 0.003 |
| 33 | 0.011 | 185 | 0.005 | 249 | 0.015 |
| 34 | 2.997 | 186 | 0.220 | 250 | 0.031 |
| 35 | 0.502 | 187 | 0.040 | 251 | 0.001 |
| 36 | 0.018 | 188 | 1.031 | 252 | 0.230 |
| 37 | 0.003 | 189 | 2.020 | 253 | 0.340 |
| 38 | 0.701 | 190 | 1.075 | 254 | 0.223 |
| 39 | 2.001 | 191 | 0.136 | 255 | 0.106 |
| 41 | 1.029 | 192 | 0.763 | 256 | 0.754 |
| 43 | 0.504 | 193 | 0.199 | 257 | 0.006 |
| 46 | 0.161 | 194 | 0.095 | 258 | 0.011 |
| 47 | 0.064 | 199 | 0.142 | 259 | 0.772 |

TABLE 1-continued

| 48 | 0.027 | 200 | 0.064 | 260 | 0.131 |
|---|---|---|---|---|---|
| 50 | 0.071 | 201 | 1.782 | 261 | 0.139 |
| 51 | 0.106 | 202 | 0.020 | 262 | 0.250 |
| 52 | 0.089 | 203 | 0.028 | 263 | 0.580 |
| 55 | 1.700 | 204 | 0.074 | 264 | 0.559 |
| 61 | 0.475 | 205 | 0.034 | 265 | 0.404 |
| 66 | 0.043 | 206 | 0.012 | 267 | 0.891 |
| 67 | 0.187 | 208 | 0.001 | 268 | 0.042 |
| 69 | 0.159 | 210 | 0.079 | 269 | 0.007 |
|  |  | 211 | 0.400 | 270 | 0.013 |
|  |  | 212 | 0.810 | 271 | 0.092 |
|  |  | 213 | 2.230 | 272 | 0.017 |
|  |  | 214 | 0.052 |  |  |

What is claimed is:

1. A compound of formula I,

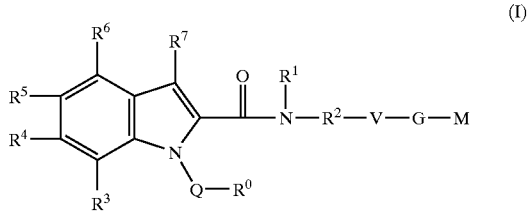

(I)

wherein

R$^0$ is selected from the group consisting of
1) monocyclic and bicyclic 6- to 14-membered aryl radicals, said aryl radicals being substituted with one two or three substituents independently selected from the R$^8$ substituents defined below, provided that at least one R$^8$ is halogen, —C(O)—NH$_2$ or —O—(C$_1$–C$_8$)-alkyl;
2) monocyclic and bicyclic 4- to 14-membered heteroaryl radicals selected from the group consisting of pyridyl, pyrimidinyl, indolyl, isoindolyl, indazolyl, phthalazinyl, quinolyl, isoquinolyl, benzothiophen, quinazolinyl and phenylpyridyl radicals, said heteroaryl radicals being unsubstituted or substituted with one two or three substituents independently selected from the R$^8$ substituents defined below;
3) monocyclic or bicyclic 4- to 14-membered heteroaryl radicals containing one, two, three or four heteroatoms selected from the group consisting of nitrogen, sulfur and oxygen, said heteroaryl radicals being unsubstituted or substituted with one two or three substituents independently selected from the R$^8$ substituents defined below, as well as by a monocyclic or bicyclic 4- to 14-membered heteroaryl, containing one, two, three or four heteroatoms selected from the group consisting of nitrogen, sulfur and oxygen, which heteroaryl radical is unsubstituted or substituted with one two or three substituents independently selected from the R$^8$ substituents defined below;

R$^8$ is selected from the group consisting of
halogen, —NO$_2$; —CN; —C(O)—NH$_2$; —OH; —NH$_2$; —OCF$_3$; monocyclic and bicyclic 4- to 14-membered aryl radicals, said aryl radicals being substituted with one, two, or three substituents independently selected from halogen and —O—(C$_1$–C$_8$)-alkyl; —(C$_1$–C$_8$)-alkyl, said alkyl being unsubstituted or substituted with up to three substituents independently selected from halogen, NH$_2$, —OH and methoxy; and —O—(C$_1$–C$_8$)-alkyl, said alkyl being unsubstituted or substituted with up to three substituents independently selected from halogen, $NH_2$, —OH and methoxy;

Q is selected from the group consisting of
a direct bond; —C(O)—; —($C_0$-$C_2$)-alkylene-C(O)—$NR^{10}$—; —$NR^{10}$—C(O)—$NR^{10}$—; —$NR^{10}$—C(O)—; —$SO_2$—; —($C_1$-$C_6$)-alkylene, wherein alkylene is unsubstituted or substituted with up to three substituents independently selected from halogen, —$NH_2$ and —OH; and ($C_3$-$C_6$)-cycloalkylene, wherein cycloalkylene is unsubstituted or substituted with up to three substituents independently selected from halogen, —$NH_2$ and —OH;

$R^1$ is selected from the group consisting of
hydrogen; —($C_1$-$C_4$)-alkyl radicals, said alkyl radicals being unsubstituted or substituted with one two or three substituents independently selected from the $R^{13}$ substituents defined below; and monocyclic or bicyclic 4- to 14-membered heteroaryl radicals said heteroaryl radical is unsubstituted or substituted with one two or three substituents independently selected from the $R^{14}$ substituents defined below;

$R^2$ is a direct bond or —($C_1$-$C_4$)-alkylene;

$R^{14}$ is selected from the group consisting of
halogen, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_1$-$C_8$)-alkylsulfonyl, —$SO_2$, —C(O)—NH—($C_1$-$C_8$)-alkyl, —C(O)—N—[($C_1$-$C_8$)-alkyl]$_2$, —$NR^{10}$—C(O)—NH—($C_1$-$C_8$)-alkyl, —C(O)—$NH_2$, —$SR^{10}$, and —$NR^{10}$—C(O)—NH—[($C_1$-$C_8$)-alkyl]$_2$, said $R^{10}$ being selected from hydrogen, —($C_1$-$C_3$)-perfluoroalkyl and —($C_1$-$C_6$)-alkyl;

V is a piperidine radical, optionally substituted with one two or three substituents independently selected from the $R^{14}$ substituents defined above;

G is selected from the group consisting of:
a direct bond, —$(CH_2)_m$—$NR^{10}$—$SO_2$—$NR^{10}$—$(CH_2)_n$—, —$(CH_2)_n$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)_m$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)_n$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— and —$(CH_2)_m$—$NR^{10}$—C(O)—O—$(CH_2)_n$—, n and m are independently selected from zero and the integers 1, 2, 3, 4, 5 and 6, $R^{10}$ is hydrogen, —($C_1$-$C_3$)-perfluoroalkyl or —($C_1$-$C_6$)-alkyl, M is selected from the group consisting of
hydrogen; —($C_1$-$C_8$)-alkyl, said alkyl being unsubstituted or substituted with one two or three substituents independently selected from the $R^{14}$ substituents defined above; —C(O)—$NR^{11}R^{12}$; —$(CH_2)_m$—$NR^{10}$; —($C_6$-$C_{14}$)-aryl, said aryl being unsubstituted or substituted with one two or three substituents independently selected from the $R^{14}$ substituents defined above; —($C_4$-$C_{14}$)-heteroaryl, said heteroaryl being unsubstituted or substituted with one two or three substituents independently selected from the $R^{14}$ substituents defined above; ($C_3$-$C_7$)-cycloalkyl, said cycloalkyl being unsubstituted or substituted with one two or three substituents independently selected from the $R^{14}$ substituents defined above; a 3- to 7-membered cyclic residue, optionally containing 1, 2, 3 or 4 heteroatoms selected from nitrogen, sulfur and oxygen, said cyclic residue being unsubstituted or substituted with one two or three substituents independently selected from the $R^{14}$ substituents defined above;

$R^{11}$ and $R^{12}$ are independently selected from the group consisting of:
hydrogen; —($C_1$-$C_6$)-alkyl, said alkyl being unsubstituted or substituted with one two or three substituents independently selected from the $R^{13}$ substituents defined below; —($C_6$-$C_{14}$)-aryl-($C_1$-$C_4$)-alkyl-, wherein said alkyl and said aryl are each independently unsubstituted or substituted with one two or three substituents independently selected from the $R^{13}$ substituents defined below;
—($C_6$-$C_{14}$)-aryl-, said aryl being unsubstituted or substituted with one two or three substituents independently selected from the $R^{13}$ substituents defined below; —($C_4$-$C_{14}$)-heteroaryl, said heteroaryl being unsubstituted or substituted with one two or three substituents independently selected from the $R^{13}$ substituents defined below; —($C_4$-$C_{14}$)-heteroaryl-($C_1$-$C_4$)-alkyl-, wherein said alkyl and said heteroaryl are each independently unsubstituted or substituted with one two or three substituents independently selected from the $R^{13}$ substituents defined below; or, alternatively, $R^{11}$ and $R^{12}$, together with the nitrogen atom to which they are bonded, form a saturated 5- to 7-membered monocyclic heterocyclic ring which, in addition to said nitrogen atom, may contain one or two identical or different ring heteroatoms selected from oxygen, sulfur and nitrogen; said heterocyclic ring being unsubstituted or substituted with one two or three substituents independently selected from the $R^{13}$ substituents defined below;

$R^{13}$ is selected from the group consisting of:
halogen; —$NO_2$; —CN; =O; —OH; —($C_1$-$C_8$)-alkyl; —($C_1$-$C_8$)-alkoxy; —$CF_3$; phenyl; phenyloxy-; —C(O)—O—$R^{11}$; phenyl-($C_1$-$C_4$)-alkoxy-; —C(O)—N—$R^{11}R^{12}$; —$NR^{11}R^{12}$; —$NR^{10}$—$SO_2$—$R^{10}$; —S—$R^{10}$; —$SO_n$—$R^{10}$; wherein n is 1 or 2; —$SO_2$—$NR^{11}R^{12}$; —C(O)—$R^{10}$; —($C_0$-$C_4$)-alkyl-C(O)—O—C($R^{15}R^{16}$)—O—C(O)—$R^{17}$; —($C_0$-$C_4$)-alkyl-C(O)—O—C($R^{15}R^{16}$)—O—C(O)O—$R^{17}$, and a residue of formula Va,

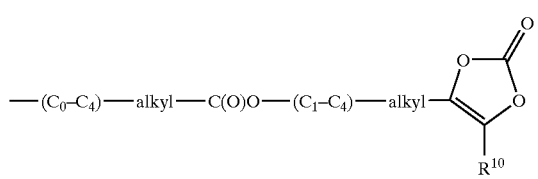

Va

—($C_0$-$C_4$)—alkyl—C(O)O—($C_1$-$C_4$)—alkyl wherein $R^{10}$, $R^{11}$, $R^{12}$ are as defined above and $R^{15}$, $R^{16}$ or $R^{17}$ are as defined below;

$R^{15}$ and $R^{16}$ are independently selected from hydrogen, and —($C_1$-$C_6$)-alkyl, or, alternatively, together with the carbon atom to which they are bonded, form a 3- to 6 membered carbocyclic ring, said carbocyclic ring being unsubstituted or substituted with one, two or three substituents independently selected from the $R^{10}$ substituents defined above;

$R^{17}$ is selected from the group consisting of —($C_1$–$C_6$)-alkyl, —($C_1$–$C_8$)-cycloalkyl, and —($C_1$–$C_6$)-alkyl-($C_1$–$C_8$)-cycloalkyl, each said cycloalkyl ring being unsubstituted or substituted with one, two or three substituents independently selected from the $R^{10}$ substituents defined above;

$R^3$, $R^4$, $R^5$, $R^6$ and $R^7$ are each independently selected from the group consisting of:

hydrogen; halogen; —($C_1$–$C_4$)-alkyl, said alkyl being unsubstituted or substituted with one two or three substituents independently selected from the $R^{13}$ substituents defined above; —($C_1$–$C_3$)-perfluoroalkyl; phenyl, said phenyl being unsubstituted or substituted with one, two or three substituents independently selected from the $R^{13}$ substituents defined above; —O—($C_1$–$C_4$)-alkyl, said alkyl being unsubstituted or substituted with one two or three substituents independently selected from the $R^{13}$ substituents defined above; —$NO_2$; —CN; —OH; phenyloxy-, said phenyloxy being unsubstituted or substituted with one two or three substituents independently selected from the $R^{13}$ substituents defined above; benzyloxy-, said benzyloxy being unsubstituted or substituted with one two or three substituents independently selected from the $R^{13}$ substituents defined above; —C(O)—O—$R^{11}$, wherein $R^{11}$ is as defined above; —C(O)—N—$R^{11}R^{12}$, wherein $R^{11}$ and $R^{12}$ are as defined above; —$NR^{11}R^{12}$, wherein $R^{11}$ and $R^{12}$ are as defined above; —$NR^{10}$—$SO_2$—$R^{10}$, wherein $R^{10}$ is as defined above; —$SR^{10}$, wherein $R^{10}$ is as defined above; —$SO_n$—$R^{10}$, wherein n is 1 or 2 and $R^{10}$ is as defined above; —$SO_2$—$NR^{11}R^{12}$, wherein $R^{11}$ and $R^{12}$ are as defined above; —C(O)—$R^{10}$, wherein $R^{10}$ is as defined above; —C(O)—O—C($R^{15}R^{16}$)—O—C(O)—$R^{17}$, wherein $R^{15}$, $R^{16}$ and $R^{17}$ are as defined above; —C(O)—O—C($R^{15}R^{16}$)—O—C(O) O—$R^{17}$, wherein $R^{15}$, $R^{16}$ and $R^{17}$ are as defined above; a residue of formula Va,

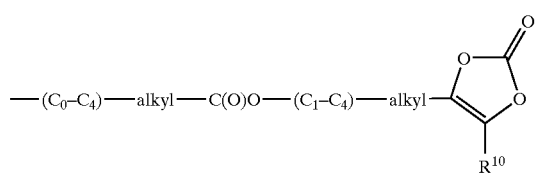

Va wherein $R^{10}$ is as defined above;
a residue of formula Vb or Vc,

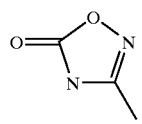

Vb

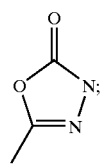

Vc

—$NR^{10}$—($C_1$–$C_4$)-alkyl, said alkyl being unsubstituted or substituted with one two or three substituents independently selected from the $R^{13}$ substituents defined above; —O—$CF_3$; and a residue selected from the group consisting of:

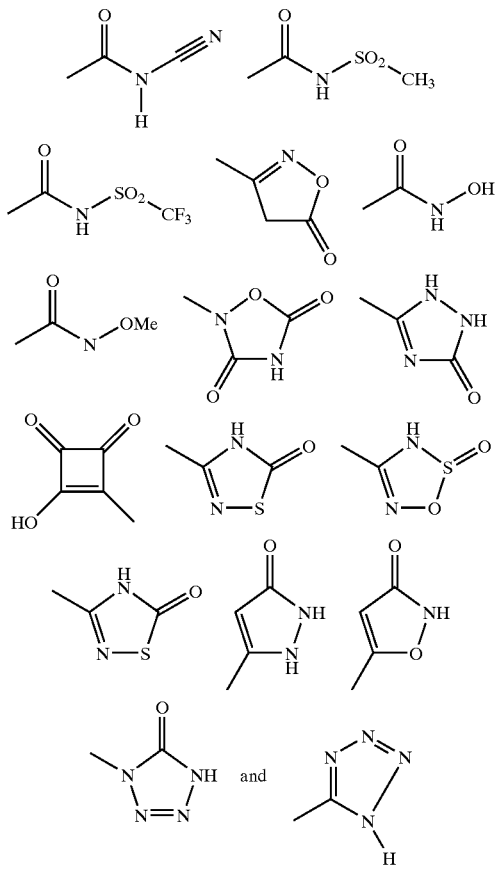

wherein $R^{10}$, $R^{11}$, $R^{12}$ and $R^{13}$ are as defined above; in all its stereoisomeric forms and mixtures thereof in any ratio, and its physiologically tolerable salts.

2. A compound of formula I, as claimed in claim 1, wherein $R^0$ is selected from the group consisting of phenyl, said phenyl being unsubstituted or substituted with one, two or three substituents independently selected from the $R^{8'}$ substituents defined below; bicyclic 5- to 14-membered heteroaryl radicals selected from the group consisting of indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, purinyl and pteridinyl, said heteroaryl radicals being unsubstituted or substituted with one, two or three substituents independently selected from the $R^{8'}$ substituents defined below; said heteroaryl radicals being optionally further substituted by an additional residue selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, triazolyl, isothiazolyl, thiadiazolyl, tetrazolyl, pyrimidinyl, pyridazinyl and pyrazinyl, said additional residue being unsubstituted or substituted with one, two or three substituents independently selected from the $R^{8'}$ substituents defined below; a monocyclic 5- to 14-membered heteroaryl radical selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, said heteroaryl radical being unsubstituted or substituted with one, two or three substituents independently selected from the $R^{8'}$ substituents defined below said heteroaryl radical being optionally further substituted by a residue selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, said residue being unsubstituted or substituted with one, two or three substituents independently selected from the $R^{8'}$ substituents defined below;

$R^{8'}$ is selected from the group consisting of:
halogen, including F, Cl, Br and I; —C(O)—NH₂; —(C₁-C₄)-alkyl, said alkyl being unsubstituted or independently substituted by one, two or three substituents selected from halogen, —OH and methoxy; and —O—(C₁-C₄)-alkyl, said alkyl being unsubstituted or independently substituted by one, two or three substituents selected from halogen and methoxy,
provided that at least one $R^{8'}$ is halogen, —C(O)—NH₂ or a —O—(C₁-C₈)-alkyl residue when $R^0$ is a monocyclic or bicyclic 6- to 14-membered aryl;

Q is selected from the group consisting of:
a direct bond; —C(O)—; —SO₂—; —(C₁-C₆)-alkylene; and —(C₀-C₂)-alkylene-C(O)—NR¹⁰—;

$R^1$ is hydrogen or —(C₁-C₂)-alkyl;

$R^2$ is a direct bond or —(C₁-C₂)-alkylene;

$R^{14}$ is halogen, —(C₁-C₄)-alkyl or —NH₂;

V is a piperidine radical, optionally substituted with one two or three substituents independently selected from the $R^{14}$ substituents defined above;

G is a direct bond, —(CH₂)ₘ—, or —(CH₂)ₘ—NR¹⁰—;

m is zero or an integer selected from 1, 2, 3 and 4;

$R^{10}$ is hydrogen, —(C₁-C₃)-perfluoroalkyl or —(C₁-C₄)-alkyl;

M is selected from the group consisting of
hydrogen; —(C₆-C₁₄)-heteroaryl, said heteroaryl being a residue selected from the group consisting of the derivatives of piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, thiadiazole and thiomorpholine, which are unsubstituted or substituted with one, two or three substituents independently selected from the $R^{14}$ substituents defined above; —(C₁-C₆)-alkyl, said alkyl being unsubstituted or substituted with one, two or three substituents independently selected from the $R^{14}$ substituents defined above; and (C₃-C₆)-cycloalkyl;

$R^3$, $R^4$, $R^5$, $R^6$ and $R^7$ are independently selected from the group consisting of
hydrogen; F; Cl; Br; —(C₁-C₄)-alkyl, said alkyl being unsubstituted or substituted by $R^{13}$ as defined below; —CF₃; phenyl, said phenyl being unsubstituted or substituted with one, two or three substituents independently selected from the $R^{13}$ substituents defined below; —O—(C₁-C₄)-alkyl, wherein alkyl is unsubstituted or substituted by $R^{13}$ as defined below; —NO₂; —CN; —OH; phenyloxy-, said phenyloxy being unsubstituted or substituted by $R^{13}$ as defined below; benzyloxy-, said benzyloxy being unsubstituted or substituted by $R^{13}$ as defined below; —C(O)—O—R¹¹; —C(O)—N—R¹¹R¹²; —NR¹¹R¹²; —NR¹⁰—SO₂—R¹⁰; —SOₙ—R¹⁰, wherein n is 1 or 2; —SO₂—NR¹¹R¹²; —C(O)—R¹⁰; —C(O)—O—C(R¹⁵R¹⁶)—O—C(O)—R¹⁷; —C(O)—O—C(R¹⁵R¹⁶)—O—C(O)O—R¹⁷; a residue of formula Va

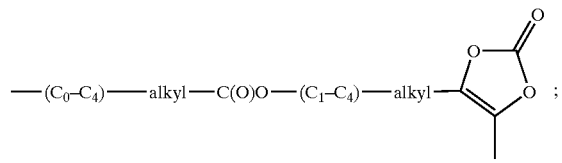

a residue of formula Vb or Vc,

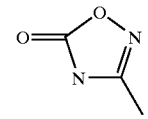

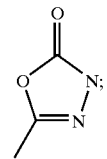

—O—CF₃; and a residue selected from the group consisting of

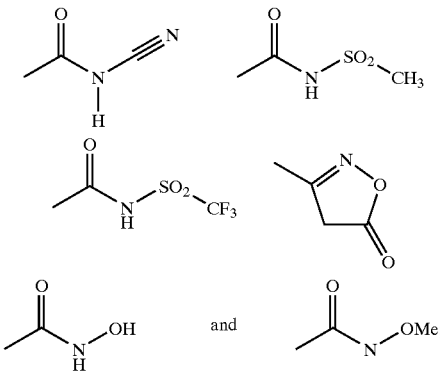

$R^{13}$ is selected from the group consisting of
halogen; —NO₂; —CN; =O; —OH; —(C₁-C₈)-alkoxy; —CF₃; —C(O)—O—R¹¹; —C(O)—N—R¹¹R¹²; —NR¹¹R¹²; —NR¹⁰—SO₂—R¹⁰; —SOₙ—

$R^{10}$, wherein n is 1 or 2; —SO$_2$—NR$^{11}$R$^{12}$; —C(O)—R$^{10}$; —(C$_0$–C$_4$)-alkyl-C(O)—O—C(R$^{15}$R$^{16}$)—O—C(O)—R$^{17}$; —(C$_0$–C$_4$)-alkyl-C(O)—O—C(R$^{15}$R$^{16}$)—O—C(O)O—R$^{17}$; and a residue of formula Va,

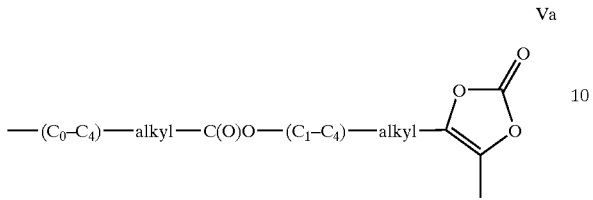

Va and R$^{10}$, R$^{11}$, R$^{12}$, R$^{15}$, R$^{16}$ and R$^{17}$ are as defined in claim 1 above, in all its stereoisomeric forms and mixtures thereof in any ratio and its physiologically tolerable salts.

3. A compound of formula I as claimed in claim 1, wherein

R$^0$ is phenyl, said phenyl being unsubstituted or substituted with one or two substituents independently selected from the R$^{8''}$ substituents defined below; or a monocyclic 4- to 14-membered heteroaryl radical selected from the group consisting of thienyl, thiadiazolyl, isoxazolyl and thiazolyl, said heteroaryl radical being substituted by a residue selected from the group consisting of thienyl, 2-thienyl and 3-thienyl, wherein said residue is unsubstituted or substituted with one or two substituents independently selected from the R$^{8''}$ substituents defined below;

R$^{8''}$ is selected from the group consisting of F, Cl, Br, —O—CH$_3$, —C(O)—NH$_2$ and —O—CF$_3$;

Q is a direct bond, —C(O)—, —SO$_2$—, methylene or ethylene;

R$^1$ is hydrogen;

R$^2$ is a direct bond or methylene;

R$^{13}$ is selected from the group consisting of —C(O)—O—R$^{11}$; —C(O)—N—R$^{11}$R$^{12}$; —NR$^{11}$R$^{12}$; —NR$^{10}$—SO$_2$—R$^{10}$; —SO$_n$—R$^{10}$, wherein n is 1 or 2; —SO$_2$—NR$^{11}$R$^{12}$; —C(O)—R$^{10}$; —(C$_0$–C$_4$)-alkyl-C(O)—O—C(R$^{15}$R$^{16}$)—O—C(O)—R$^{17}$; —(C$_0$–C$_4$)-alkyl-C(O)—O—C(R$^{15}$R$^{16}$)—O—C(O)O—R$^{17}$; and a residue of formula Va,

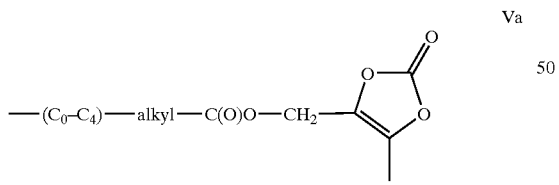

Va wherein R$^{10}$, R$^{11}$, R$^{12}$, R$^{15}$, R$^{16}$ or R$^{17}$ are as defined in claim 1 above;

R$^{14}$ is halogen, methyl, ethyl or —NH$_2$;

V is a piperidine radical, optionally substituted with one two or three substituents independently selected from the R$^{14}$ substituents defined above;

G is a direct bond, —(CH$_2$)$_m$—, or —(CH$_2$)$_m$—NR$^{10}$—, wherein m is zero, 1 or 2, and R$^{10}$ is hydrogen or —(C$_1$–C$_4$)-alkyl;

M is selected from hydrogen, (C$_2$–C$_4$)-alkyl, imidazolyl, pyrazolyl, pyrrolidinyl, tetrahydropyranyl, piperidinyl, pyridinyl, pyrimidyl, pyrazinyl, pyridazinyl, and (C$_3$–C$_6$)-cycloalkyl, which cyclic residues are unsubstituted or substituted with one or two substituents independently selected from the R$^{14}$ substituents defined above; and R$^3$, R$^4$, R$^5$, R$^6$ and R$^7$ are independently selected from the group consisting of hydrogen; F; Cl; —(C$_1$–C$_4$)-alkyl, wherein alkyl is unsubstituted or substituted by R$^{13}$, as defined above; phenyl, which is unsubstituted or substituted with one, two or three substituents independently selected from the R$^{13}$ substituents defined above; —O—(C$_1$–C$_4$)-alkyl, wherein alkyl is unsubstituted or substituted by R$^{13}$, as defined above; —C(O)—O—R$^{11}$; —C(O)—N—R$^{11}$R$^{12}$; —NR$^{11}$R$^{12}$; —NR$^{10}$—SO$_2$—R$^{10}$; —SO$_2$—NR$^{11}$R$^{12}$; —C(O)—R$^{10}$; —C(O)—O—C(R$^{15}$R$^{16}$)—O—C(O)—R$^{17}$, wherein R$^{15}$, R$^{16}$ and R$^{17}$ are as defined in claim 1 above; —C(O)—O—C(R$^{15}$R$^{16}$)—O—C(O)O—R$^{17}$, wherein R$^{15}$, R$^{16}$ and R$^{17}$ are as defined in claim 1 above; a residue of formula Va

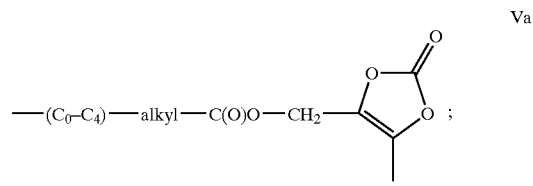

Va a residue of formula Vb or Vc,

Vb

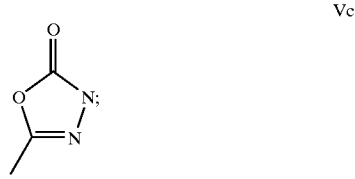

Vc and a residue selected from the group consisting of:

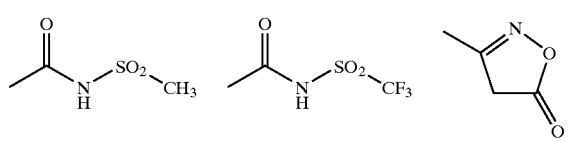

in all its stereoisomeric forms and mixtures thereof in any ratio, and its physiologically acceptable salts.

4. A compound of claim 1 selected from the group consisting of:

1-[5-(5-Chloro-thiophen-2-yl)-isoxazol-3-ylmethyl]-1H-indole-2-carboxylic acid (1-isopropyl-piperidin-4-yl)-amide;

1-[5-(5-Chloro-thiophen-2-yl)-isoxazol-3-ylmethyl]-5-methanesulfonyl-1H-indole-2-carboxylic acid (1-isopropyl-piperidin-4-yl)-amide;

1-[5-(5-Chloro-thiophen-2-yl)-isoxazol-3-ylmethyl]-5-nitro-1H-indole-2-carboxylic acid (1-isopropyl-piperidin-4-yl)-amide;

5-Benzyloxy-1-[5-(5-chloro-thiophen-2-yl)-isoxazol-3-ylmethyl]-1H-indole-2-carboxylic acid (1-isopropyl-piperidin-4-yl)-amide;

5-Chloro-1-[5-(5-chloro-thiophen-2-yl)-isoxazol-3-ylmethyl]-1H-indole-2-carboxylic acid (1-isopropyl-piperidin-4-yl)-amide;

1-[5-(5-Chloro-thiophen-2-yl)-isoxazol-3-ylmethyl]-5-methoxy-1H-indole-2-carboxylic acid (1-isopropyl-piperidin-4-yl)-amide;

1-[5-(5-Chloro-thiophen-2-yl)-isoxazol-3-ylmethyl]-6-methoxy-1H-indole-2-carboxylic acid (1-isopropyl-piperidin-4-yl)-amide;

1-[5-(5-Chloro-thiophen-2-yl)-isoxazol-3-ylmethyl]-5-methyl-1H-indole-2-carboxylic acid (1-isopropyl-piperidin-4-yl)-amide;

1-[5-(5-Chloro-thiophen-2-yl)-isoxazol-3-ylmethyl]-4,6-dimethoxy-1H-indole-2-carboxylic acid (1-isopropyl-piperidin-4-yl)-amide;

1-[5-(5-Chloro-thiophen-2-yl)-isoxazol-3-ylmethyl]-5,6-dimethoxy-1H-indole-2-carboxylic acid (1-isopropyl-piperidin-4-yl)-amide;

1-[5-(5-Chloro-thiophen-2-yl)-isoxazol-3-ylmethyl]-7-nitro-1H-indole-2-carboxylic acid (1-isopropyl-piperidin-4-yl)-amide;

1-[5-(5-Chloro-thiophen-2-yl)-isoxazol-3-ylmethyl]-5-trifluoromethoxy-1H-indole-2-carboxylic acid (1-isopropyl-piperidin-4-yl)-amide;

1-[5-(5-Chloro-thiophen-2-yl)-isoxazol-3-ylmethyl]-7-methyl-1H-indole-2-carboxylic acid (1-isopropyl-piperidin-4-yl)-amide;

1-[5-(5-Chloro-thiophen-2-yl)-isoxazol-3-ylmethyl]-7-(2,2-dimethyl-propionylamino)-1H-indole-2-carboxylic acid (1-isopropyl-piperidin-4-yl)-amide;

1-[5-(5-Chloro-thiophen-2-yl)-isoxazol-3-ylmethyl]-4-methoxy-1H-indole-2-carboxylic acid (1-isopropyl-piperidin-4-yl)-amide;

1-[5-(5-Chloro-thiophen-2-yl)-isoxazol-3-ylmethyl]-3-phenyl-1H-indole-2-carboxylic acid (1-isopropyl-piperidin-4-yl)-amide;

1-[5-(5-Chloro-thiophen-2-yl)-isoxazol-3-ylmethyl]-6-hydroxy-5-methoxy-1H-indole-2-carboxylic acid (1-isopropyl-piperidin-4-yl)-amide;

1-[5-(5-Chloro-thiophen-2-yl)-isoxazol-3-ylmethyl]-4,6-difluoro-1H-indole-2-carboxylic acid (1-isopropyl-piperidin-4-yl)-amide;

4-Benzyloxy-1-[5-(5-chloro-thiophen-2-yl)-isoxazol-3-ylmethyl]-1H-indole-2-carboxylic acid (1-isopropyl-piperidin-4-yl)-amide;

7-Chloro-1-[5-(5-chloro-thiophen-2-yl)-isoxazol-3-ylmethyl]-1H-indole-2-carboxylic acid (1-isopropyl-piperidin-4-yl)-amide;

6-Chloro-1-[5-(5-chloro-thiophen-2-yl)-isoxazol-3-ylmethyl]-1H-indole-2-carboxylic acid (1-isopropyl-piperidin-4-yl)-amide;

1-[5-(5-Chloro-thiophen-2-yl)-isoxazol-3-ylmethyl]-5-ethyl-1H-indole-2-carboxylic acid (1-isopropyl-piperidin-4-yl)-amide;

1-[5-(5-Chloro-thiophen-2-yl)-isoxazol-3-ylmethyl]-5-fluoro-1H-indole-2-carboxylic acid (1-isopropyl-piperidin-4-yl)-amide;

1-[5-(5-Chloro-thiophen-2-yl)-isoxazol-3-ylmethyl]-5-nitro-3-phenyl-1H-indole-2-carboxylic acid (1-isopropyl-piperidin-4-yl)-amide;

5-Chloro-1-[5-(5-chloro-thiophen-2-yl)-isoxazol-3-ylmethyl]-3-phenyl-1H-indole-2-carboxylic acid (1-isopropyl-piperidin-4-yl)-amide;

1-[5-(5-Chloro-thiophen-2-yl)-isoxazol-3-ylmethyl]-5,7-difluoro-1H-indole-2-carboxylic acid (1-isopropyl-piperidin-4-yl)-amide;

1-[5-(5-Chloro-thiophen-2-yl)-isoxazol-3-ylmethyl]-5,7-dinitro-1H-indole-2-carboxylic acid (1-isopropyl-piperidin-4-yl)-amide;

1-[5-(5-Chloro-thiophen-2-yl)-isoxazol-3-ylmethyl]-1H-indole-2-carboxylic acid (3,4,5,6-tetrahydro-2H-[1,4']bipyridinyl-4-yl)-amide;

1-[5-(5-Chloro-thiophen-2-yl)-isoxazol-3-ylmethyl]-7-methyl-1H-indole-2-carboxylic acid (3,4,5,6-tetrahydro-2H-[1,4']bipyridinyl-4-yl)-amide;

1-[5-(5-Chloro-thiophen-2-yl)-isoxazol-3-ylmethyl]-5-nitro-1H-indole-2-carboxylic acid (3,4,5,6-tetrahydro-2H-[1,4']bipyridinyl-4-yl)-amide;

1-[5-(5-Chloro-thiophen-2-yl)-isoxazol-3-ylmethyl]-1H-indole-2-carboxylic acid (1-ethyl-piperidin-4-yl)-amide;

1-[5-(5-Chloro-thiophen-2-yl)-isoxazol-3-ylmethyl]-7-methyl-1H-indole-2-carboxylic acid (1-ethyl-piperidin-4-yl)-amide;

1-[5-(5-Chloro-thiophen-2-yl)-isoxazol-3-ylmethyl]-1H-indole-2-carboxylic acid (1-isopropyl-piperidin-4-ylmethyl)-amide;

1-[5-(5-Chloro-thiophen-2-yl)-isoxazol-3-ylmethyl]-1H-indole-2-carboxylic acid (3,4,5,6-tetrahydro-2H-[1,4']bipyridinyl-4-ylmethyl)-amide;

1-[5-(5-Chloro-thiophen-2-yl)-isoxazol-3-ylmethyl]-1H-indole-2-carboxylic acid (1-cyclopropyl-piperidin-4-yl)-amide;

1-[5-(5-Chloro-thiophen-2-yl)-isoxazol-3-ylmethyl]-1H-indole-2-carboxylic acid [1-(tetrahydro-pyran-4-yl)-piperidin-4-yl]-amide;

1-[5-(5-Chloro-thiophen-2-yl)-isoxazol-3-ylmethyl]-1H-indole-2-carboxylic acid (1-cyclopentyl-piperidin-4-yl)-amide;

1-[5-(5-Chloro-thiophen-2-yl)-isoxazol-3-ylmethyl]-1H-indole-2-carboxylic acid (1-cyclohexyl-piperidin-4-yl)-amide;

1-(3-Methoxy-benzyl)-1H-indole-2-carboxylic acid (1-isopropyl-piperidin-4-yl)-amide;

1-(3-Methoxy-benzyl)-1H-indole-2-carboxylic acid (1-isopropyl-piperidin-4-ylmethyl)-amide;

1-(3-Methoxy-benzyl)-1H-indole-2-carboxylic acid (3,4,5,6-tetrahydro-2H-[1,4']bipyridinyl-4-ylmethyl)-amide;

1-(3-Methoxy-benzyl)-1H-indole-2-carboxylic acid (3,4,5,6-tetrahydro-2H-[1,4']bipyridinyl-4-yl)-amide;

4-Methoxy-1-(3-methoxy-benzyl)-1H-indole-2-carboxylic acid (1-isopropyl-piperidin-4-yl)-amide;

5-Chloro-1-(3-methoxy-benzyl)-1H-indole-2-carboxylic acid (1-isopropyl-piperidin-4-yl)-amide;

6-Methoxy-1-(3-methoxy-benzyl)-1H-indole-2-carboxylic acid (1-isopropyl-piperidin-4-yl)-amide;

1-(3-Methoxy-benzyl)-5-methyl-1H-indole-2-carboxylic acid (1-isopropyl-piperidin-4-yl)-amide;

5-Benzyloxy-1-(3-methoxy-benzyl)-1H-indole-2-carboxylic acid (1-isopropyl-piperidin-4-yl)-amide;

1-(3-Methoxy-benzyl)-5-nitro-1H-indole-2-carboxylic acid (1-isopropyl-piperidin-4-yl)-amide;

5-Methoxy-1-(3-methoxy-benzyl)-1H-indole-2-carboxylic acid (1-isopropyl-piperidin-4-yl)-amide;
1-(3-Methoxy-benzoyl)-1H-indole-2-carboxylic acid (1-isopropyl-piperidin-4-yl)-amide;
1-(3-Methoxy-benzenesulfonyl)-1H-indole-2-carboxylic acid (1-isopropyl-piperidin-4-yl)-amide;
1-(4-Methoxy-phenyl)-1H-indole-2-carboxylic acid (1-isopropyl-piperidin-4-yl)-amide;
1-(4-Methoxy-phenyl)-1H-indole-2-carboxylic acid (3,4,5,6-tetrahydro-2H-[1,4']bipyridinyl-4-yl)-amide;
1-(3-Methoxy-phenyl)-1H-indole-2-carboxylic acid (1-isopropyl-piperidin-4-yl)-amide;
1-(3-Chloro-phenyl)-1H-indole-2-carboxylic acid (1-isopropyl-piperidin-4-yl)-amide;
1-(3-Chloro-phenyl)-1H-indole-2-carboxylic acid (3,4,5,6-tetrahydro-2H-[1,4']bipyridinyl-4-yl)-amide;
1-(3-Chloro-phenyl)-1H-indole-2-carboxylic acid (1-isopropyl-piperidin-4-ylmethyl)-amide;
1-(3,5-Dichloro-phenyl)-1H-indole-2-carboxylic acid (1-isopropyl-piperidin-4-yl)-amide;
1-(4-Chloro-phenyl)-1H-indole-2-carboxylic acid (1-isopropyl-piperidin-4-yl)-amide;
1-(6-Chloro-benzo[b]thiophen-2-ylmethyl)-1H-indole-2-carboxylic acid (1-isopropyl-piperidin-4-yl)-amide;
1-[5-(5-Chloro-thiophen-2-yl)-[1,3,4]thiadiazol-2-ylmethyl]-1H-indole-2-carboxylic acid (1-isopropyl-piperidin-4-yl)-amide;
1-[3-(5-Chloro-thiophen-2-yl)-isoxazol-5-ylmethyl]-1H-indole-2-carboxylic acid (1-isopropyl-piperidin-4-yl)-amide;
3-Chloro-1-[5-(5-chloro-thiophen-2-yl)-isoxazol-3-ylmethyl]-1H-indole-2-carboxylic acid (1-isopropyl-piperidin-4-yl)-amide;
3-Bromo-1-[5-(5-chloro-thiophen-2-yl)-isoxazol-3-ylmethyl]-1H-indole-2-carboxylic acid (1-isopropyl-piperidin-4-yl)-amide;
1-(4-Chloro-benzyl)-1H-indole-2-carboxylic acid (1-isopropyl-piperidin-4-yl)-amide;
1-(4-Chloro-benzyl)-1H-indole-2-carboxylic acid (3,4,5,6-tetrahydro-2H-[1,4']bipyridinyl-4-yl)-amide;
1-(2,4-Dichloro-benzyl)-1H-indole-2-carboxylic acid (1-isopropyl-piperidin-4-yl)-amide;
1-(4-Methoxy-benzyl)-1H-indole-2-carboxylic acid (1-isopropyl-piperidin-4-yl)-amide;
1-(4-Trifluoromethoxy-benzyl)-1H-indole-2-carboxylic acid (1-isopropyl-piperidin-4-yl)-amide;
1-(2-Chloro-benzyl)-1H-indole-2-carboxylic acid (1-isopropyl-piperidin-4-yl)-amide;
1-(2-Chloro-benzyl)-1H-indole-2-carboxylic acid (3,4,5,6-tetrahydro-2H-[1,4']bipyridinyl-4-yl)-amide;
1-(2-Chloro-benzyl)-1H-indole-2-carboxylic acid (3,4,5,6-tetrahydro-2H-[1,4']bipyridinyl-4-ylmethyl)-amide;
1-(3,5-Dichloro-benzyl)-1H-indole-2-carboxylic acid (1-isopropyl-piperidin-4-yl)-amide;
3-Fluoro-1-[5-(5-chloro-thiophen-2-yl)-isoxazol-3-ylmethyl]-1H-indole-2-carboxylic acid (1-isopropyl-piperidin-4-yl)-amide;
1-[5-(5-Chloro-thiophen-2-yl)-isoxazol-3-ylmethyl]-3-cyano-1H-indole-2-carboxylic acid (1-isopropyl-piperidin-4-yl)-amide;
1-[5-(5-Chloro-thiophen-2-yl)-isoxazol-3-ylmethyl]-3-cyano-7-methyl-1H-indole-2-carboxylic acid (1-isopropyl-piperidin-4-yl)-amide;
1-[2-(5-Chloro-thiophen-2-yl)-thiazol-5-ylmethyl]-1H-indole-2-carboxylic acid (1-isopropyl-piperidin-4-yl)-amide;
1-(3-Chloro-benzyl)-1H-indole-2-carboxylic acid (1-isopropyl-piperidin-4-yl)-amide;
1-[2-(4-Chloro-phenyl)-ethyl]-1H-indole-2-carboxylic acid (1-isopropyl-piperidin-4-yl)-amide;
1-[2-(2,4-Dichloro-phenyl)-ethyl]-1H-indole-2-carboxylic acid (1-isopropyl-piperidin-4-yl)-amide;
1-[2-(3-Methoxy-phenyl)-ethyl]-1H-indole-2-carboxylic acid (1-isopropyl-piperidin-4-yl)-amide;
1-[2-(4-Chloro-phenyl)-ethyl]-4-methoxy-1H-indole-2-carboxylic acid (1-isopropyl-piperidin-4-yl)-amide;
4-Bromo-1-[5-(5-chloro-thiophen-2-yl)-isoxazol-3-ylmethyl]-1H-indole-2-carboxylic acid (1-isopropyl-piperidin-4-yl)-amide;
1-[5-(5-Chloro-thiophen-2-yl)-isoxazol-3-ylmethyl]-4-methyl-1H-indole-2-carboxylic acid (1-isopropyl-piperidin-4-yl)-amide;
5-Bromo-1-[5-(5-chloro-thiophen-2-yl)-isoxazol-3-ylmethyl]-1H-indole-2-carboxylic acid (1-isopropyl-piperidin-4-yl)-amide;
1-[5-(5-Chloro-thiophen-2-yl)-isoxazol-3-ylmethyl]-5-cyano-1H-indole-2-carboxylic acid (1-isopropyl-piperidin-4-yl)-amide;
1-[5-(5-Chloro-thiophen-2-yl)-isoxazol-3-ylmethyl]-4-trifluoromethyl-1H-indole-2-carboxylic acid (1-isopropyl-piperidin-4-yl)-amide;
1-[5-(5-Chloro-thiophen-2-yl)-isoxazol-3-ylmethyl]-4,7-dimethyl-1H-indole-2-carboxylic acid (1-isopropyl-piperidin-4-yl)-amide;
1-[5-(5-Chloro-thiophen-2-yl)-isoxazol-3-ylmethyl]-4,7-dimethoxy-1H-indole-2-carboxylic acid (1-isopropyl-piperidin-4-yl)-amide;
4,7-Dichloro-1-[5-(5-chloro-thiophen-2-yl)-isoxazol-3-ylmethyl]-1H-indole-2-carboxylic acid (1-isopropyl-piperidin-4-yl)-amide;
5,7-Dichloro-1-[5-(5-chloro-thiophen-2-yl)-isoxazol-3-ylmethyl]-1H-indole-2-carboxylic acid (1-isopropyl-piperidin-4-yl)-amide;
4-Chloro-1-[5-(5-chloro-thiophen-2-yl)-isoxazol-3-ylmethyl]-1H-indole-2-carboxylic acid (1-isopropyl-piperidin-4-yl)-amide;
[{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid ethyl ester;
[{1-[5-(5-Chloro-thiophen-2-yl)-isoxazol-3-ylmethyl]-7-methyl-1H-indole-2-carbonyl}-(1-isopropyl-piperidin-4-yl)-amino]-acetic acid;
1-[5-(5-Chloro-thiophen-2-yl)-isoxazol-3-ylmethyl]-1H-indole-2-carboxylic acid [1-(1-ethyl-propyl)-piperidin-4-yl]-amide;
1-[5-(5-Chloro-thiophen-2-yl)-isoxazol-3-ylmethyl]-1H-indole-2-carboxylic acid (1-methyl-piperidin-4-yl)-amide;
1-[5-(5-Chloro-thiophen-2-yl)-isoxazol-3-ylmethyl]-1H-indole-2-carboxylic acid [1-(2,2,2-trifluoro-ethyl)-piperidin-4-yl]-amide;
1-[5-(5-Chloro-thiophen-2-yl)-isoxazol-3-ylmethyl]-1H-indole-2-carboxylic acid (1-formyl-piperidin-4-yl)-amide;
1-[5-(5-Chloro-thiophen-2-yl)-isoxazol-3-ylmethyl]-1H-indole-2-carboxylic acid (1-carbamoyl-piperidin-4-yl)-amide;

1-[5-(5-Chloro-thiophen-2-yl)-isoxazol-3-ylmethyl]-1H-indole-2-carboxylic acid (1-methanesulfonyl-piperidin-4-yl)-amide;
1-[5-(5-Chloro-thiophen-2-yl)-isoxazol-3-ylmethyl]-1H-indole-2-carboxylic acid (1-acetyl-piperidin-4-yl)-amide;
1-[5-(5-Chloro-thiophen-2-yl)-isoxazol-3-ylmethyl]-1H-indole-2-carboxylic acid [1-(2-chloro-pyrimidin-4-yl)-piperidin-4-yl]-amide;
1-[5-(5-Chloro-thiophen-2-yl)-isoxazol-3-ylmethyl]-1H-indole-2-carboxylic acid (1-pyrimidin-4-yl-piperidin-4-yl)-amide;
1-[5-(5-Chloro-thiophen-2-yl)-isoxazol-3-ylmethyl]-1H-indole-2-carboxylic acid (1-isobutyl-piperidin-4-yl)-amide;
1-[5-(5-Chloro-thiophen-2-yl)-isoxazol-3-ylmethyl]-1H-indole-2-carboxylic acid (1-propyl-piperidin-4-yl)-amide;
4-({1-[5-(5-Chloro-thiophen-2-yl)-isoxazol-3-ylmethyl]-1H-indole-2-carbonyl}-amino)-piperidine-1-carboxylic acid methyl ester;
1-[5-(5-Chloro-thiophen-2-yl)-isoxazol-3-ylmethyl]-1H-indole-2-carboxylic acid pyridin-4-yl-(3,4,5,6-tetrahydro-2H-[1,4']bipyridinyl-4-yl)-amide;
1-[5-(5-Chloro-thiophen-2-yl)-isoxazol-3-ylmethyl]-5-nitro-1H-indole-2-carboxylic acid pyridin-4-yl-(3,4,5,6-tetrahydro-2H-[1,4']bipyridinyl-4-yl)-amide;
1-[5-(5-Chloro-thiophen-2-yl)-isoxazol-3-ylmethyl]-3-cyano-1H-indole-2-carboxylic acid (3,4,5,6-tetrahydro-2H-[1,4']bipyridinyl-4-yl)-amide;
1-[5-(5-Chloro-thiophen-2-yl)-isoxazol-3-ylmethyl]-3,7-diiodo-4-methoxy-1H-indole-2-carboxylic acid (1-isopropyl-piperidin-4-yl)-amide;
1-[5-(5-Chloro-thiophen-2-yl)-isoxazol-3-ylmethyl]-3,7-dicyano-4-methoxy-1H-indole-2-carboxylic acid (1-isopropyl-piperidin-4-yl)-amide;
1-[2-(4-Chloro-phenyl)-thiazol-4-ylmethyl]-1H-indole-2-carboxylic acid (1-isopropyl-piperidin-4-yl)-amide;
1-(1,7-Dichloro-isoquinolin-3-ylmethyl)-1H-indole-2-carboxylic acid (1-isopropyl-piperidin-4-yl)-amide;
1-[3-(4-Chloro-phenyl)-isoxazol-5-ylmethyl]-1H-indole-2-carboxylic acid (1-isopropyl-piperidin-4-yl)-amide;
1-[5-(4-Chloro-phenyl)-isoxazol-3-ylmethyl]-1H-indole-2-carboxylic acid (1-isopropyl-piperidin-4-yl)-amide;
1-[3-(4-Chloro-phenyl)-[1,2,4]oxadiazol-5-ylmethyl]-1H-indole-2-carboxylic acid (1-isopropyl-piperidin-4-yl)-amide;
1-[(5-Chloro-pyridin-2-ylcarbamoyl)-methyl]-5-methanesulfonyl-1H-indole-2-carboxylic acid (1-isopropyl-piperidin-4-yl)-amide;
1-[(4-Chloro-phenylcarbamoyl)-methyl]-5-methanesulfonyl-1H-indole-2-carboxylic acid (1-isopropyl-piperidin-4-yl)-amide;
5-Chloro-1-[(5-chloro-pyridin-2-ylcarbamoyl)-methyl]-1H-indole-2-carboxylic acid (1-isopropyl-piperidin-4-yl)-amide;
1-[(5-Chloro-pyridin-2-ylcarbamoyl)-methyl]-5-fluoro-1H-indole-2-carboxylic acid (1-isopropyl-piperidin-4-yl)-amide;
1-[(5-Chloro-pyridin-2-ylcarbamoyl)-methyl]-5,7-difluoro-1H-indole-2-carboxylic acid (1-isopropyl-piperidin-4-yl)-amide;
[{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid ethyl ester;
[{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid ethyl ester;
[{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid ethyl ester;
[{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester;
[{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester;
[{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid ethyl ester;
[{1-[5-(5-Chloro-thiophen-2-yl)-isoxazol-3-ylmethyl]-4-trifluoromethyl-1H-indole-2-carbonyl}-(1-isopropyl-piperidin-4-yl)-amino]-acetic acid;
[{1-[5-(5-Chloro-thiophen-2-yl)-isoxazol-3-ylmethyl]-4,7-dimethyl-1H-indole-2-carbonyl}-(1-isopropyl-piperidin-4-yl)-amino]-acetic acid;
[{1-[5-(5-Chloro-thiophen-2-yl)-isoxazol-3-ylmethyl]-4,7-dimethoxy-1H-indole-2-carbonyl}-(1-isopropyl-piperidin-4-yl)-amino]-acetic acid;
[{4,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid;
[{5,7-Dichloro-1-[5-(5-chloro-thiophen-2-yl)-isoxazol-3-ylmethyl]-1H-indole-2-carbonyl}-(1-isopropyl-piperidin-4-yl)-amino]-acetic acid;
[{4-Chloro-1-[5-(5-chloro-thiophen-2-yl)-isoxazol-3-ylmethyl]-1H-indole-2-carbonyl}-(1-isopropyl-piperidin-4-yl)-amino]-acetic acid;
1-[5-(5-Chloro-thiophen-2-yl)-isoxazol-3-ylmethyl]-2-(1-isopropyl-piperidin-4-ylcarbamoyl)-1H-indole-5-carboxylic acid isopropyl ester;
-[5-(5-Chloro-thiophen-2-yl)-isoxazol-3-ylmethyl]-2-(1-isopropyl-piperidin-4-ylcarbamoyl)-1H-indole-5-carboxylic acid;
1-[5-(5-Chloro-thiophen-2-yl)-isoxazol-3-ylmethyl]-5-hydroxymethyl-1H-indole-2-carboxylic acid (1-isopropyl-piperidin-4-yl)-amide;
1-[5-(5-Chloro-thiophen-2-yl)-isoxazol-3-ylmethyl]-2-(1-isopropyl-piperidin-4-ylcarbamoyl)-1H-indole-5-carboxylic acid ethyl ester;
1-[5-(5-Chloro-thiophen-2-yl)-isoxazol-3-ylmethyl]-2-(1-isopropyl-piperidin-4-ylcarbamoyl)-1H-indole-5-carboxylic acid methyl ester;
1-[5-(5-Chloro-thiophen-2-yl)-isoxazol-3-ylmethyl]-2-(1-isopropyl-piperidin-4-ylcarbamoyl)-1H-indole-5-carboxylic acid 2,2-dimethyl-propionyloxymethyl ester;
1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid isopropyl ester;
1-[5-(5-Chloro-thiophen-2-yl)-[1,3,4]thiadiazol-2-ylmethyl]-2-(1-isopropyl-piperidin-4-ylcarbamoyl)-1H-indole-5-carboxylic acid;
1-[(4-Chloro-phenylcarbamoyl)-methyl]-2-(1-isopropyl-piperidin-4-ylcarbamoyl)-1H-indole-5-carboxylic acid isopropyl ester;
1-[(4-Chloro-phenylcarbamoyl)-methyl]-2-(1-isopropyl-piperidin-4-ylcarbamoyl)-1H-indole-5-carboxylic acid;

1-[5-(5-Chloro-thiophen-2-yl)-isoxazol-3-ylmethyl]-2-(1-isopropyl-piperidin-4-ylcarbamoyl)-1H-indole-4-carboxylic acid methyl ester;
1-[5-(5-Chloro-thiophen-2-yl)-isoxazol-3-ylmethyl]-2-(1-isopropyl-piperidin-4-ylcarbamoyl)-1H-indole-4-carboxylic acid;
1-[5-(5-Chloro-thiophen-2-yl)-isoxazol-3-ylmethyl]-1H-indole-2,5-dicarboxylic acid 5-amide 2-[(1-isopropyl-piperidin-4-yl)-amide];
1-[(4-chloro-phenylcarbamoyl)-methyl]-1H-indole-2-carboxylic acid (1-isopropyl-piperidin-4-yl)-amide;
1-[(5-chloro-thiophen-2-ylcarbamoyl)-methyl]-1H-indole-2-carboxylic acid (1-isopropyl-piperidin-4-yl)-amide;
1-[(4-chloro-2-fluoro-phenylcarbamoyl)-methyl]-1H-indole-2-carboxylic acid (1-isopropyl-piperidin-4-yl)-amide;
1-[(5-chloro-pyridin-2-ylcarbamoyl)-methyl]-1H-indole-2-carboxylic acid (1-isopropyl-piperidin-4-yl)-amide;
1-[(4-chloro-phenylcarbamoyl)-methyl]-1H-indole-2-carboxylic acid (3,4,5,6-tetrahydro-2H-[1,4']bipyridinyl-4-ylmethyl)-amide;
1-[(4-chloro-phenylcarbamoyl)-methyl]-1H-indole-2-carboxylic acid (3,4,5,6-tetrahydro-2H-[1,4']bipyridinyl-4-yl)-amide;
N-(4-chloro-phenyl)-2-{2-[4-(pyridin-4-ylamino)-piperidine-1-carbonyl]-indol-1-yl}-acetamide;
1-[(4-chloro-phenylcarbamoyl)-methyl]-1H-indole-2-carboxylic acid (1-cyclopropyl-piperidin-4-yl)-amide;
N-(4-chloro-phenyl)-2-[2-(4-pyrrolidin-1-yl-piperidine-1-carbonyl)-indol-1-yl]-acetamide;
1-[(4-chloro-phenylcarbamoyl)-methyl]-5-nitro-1H-indole-2-carboxylic acid (1-isopropyl-piperidin-4-yl)-amide;
5-amino-4-chloro-1-[5-(5-chloro-thiophen-2-yl)-isoxazol-3-ylmethyl]-1H-indole-2-carboxylic acid (1-isopropyl-piperidin-4-yl)-amide;
1-[5-(5-chloro-thiophen-2-yl)-isoxazol-3-ylmethyl]-1H-indole-2-carboxylic acid (1-cyanomethyl-piperidin-4-yl)-amide;
1-[5-(5-chloro-thiophen-2-yl)-isoxazol-3-ylmethyl]-1H-indole-2-carboxylic acid [1-(2-hydroxy-ethyl)-piperidin-4-yl]-amide;
1-[5-(5-chloro-thiophen-2-yl)-isoxazol-3-ylmethyl]-1H-indole-2-carboxylic acid [1-(2-methoxy-ethyl)-piperidin-4-yl]-amide;
1-[5-(5-chloro-thiophen-2-yl)-isoxazol-3-ylmethyl]-1H-indole-2-carboxylic acid (1-carbamoylmethyl-piperidin-4-yl)-amide;
1-[5-(5-chloro-thiophen-2-yl)-isoxazol-3-ylmethyl]-1H-indole-2-carboxylic acid (1-methylcarbamoylmethyl-piperidin-4-yl)-amide;
1-[5-(5-chloro-thiophen-2-yl)-isoxazol-3-ylmethyl]-1H-indole-2-carboxylic acid [1-(1H-imidazol-2-ylmethyl)-piperidin-4-yl]-amide;
1-[5-(5-chloro-thiophen-2-yl)-isoxazol-3-ylmethyl]-1H-indole-2-carboxylic acid 1-(2-dimethylamino-acetyl)-piperidin-4-yl]-amide;
1-[5-(5-Chloro-thiophen-2-yl)-isoxazol-3-ylmethyl]-2-(1-isopropyl-piperidin-4-ylcarbamoyl)-1H-indole-5-carboxylic acid 1-ethoxycarbonyloxy-ethyl ester;
1-[5-(5-Chloro-thiophen-2-yl)-isoxazol-3-ylmethyl]-2-(1-isopropyl-piperidin-4-ylcarbamoyl)-1H-indole-4-carboxylic acid 1-ethoxycarbonyloxy-ethyl ester;
1-[5-(5-Chloro-thiophen-2-yl)-isoxazol-3-ylmethyl]-2-(1-isopropyl-piperidin-4-ylcarbamoyl)-1H-indole-4-carboxylic acid 2,2-dimethyl-propionyloxymethyl ester;
1-[5-(5-Chloro-thiophen-2-yl)-isoxazol-3-ylmethyl]-2-(1-isopropyl-piperidin-4-ylcarbamoyl)-1H-indole-5-carboxylic acid 1-(2,2-dimethyl-propionyloxy)-ethyl ester;
1-[5-(5-Chloro-thiophen-2-yl)-isoxazol-3-ylmethyl]-2-(1-isopropyl-piperidin-4-ylcarbamoyl)-1H-indole-4-carboxylic acid 1-(2,2-dimethyl-propionyloxy)-ethyl ester;
1-[5-(5-Chloro-thiophen-2-yl)-isoxazol-3-ylmethyl]-2-(1-isopropyl-piperidin-4-ylcarbamoyl)-1H-indole-5-carboxylic acid 5-methyl-2-oxo-[1,3]dioxol-4-ylmethyl;
1-[5-(5-Chloro-thiophen-2-yl)-isoxazol-3-ylmethyl]-2-(1-isopropyl-piperidin-4-ylcarbamoyl)-1H-indole-4-carboxylic acid 5-methyl-2-oxo-[1,3]dioxol-4-ylmethyl;
1-[5-(5-Chloro-thiophen-2-yl)-isoxazol-3-ylmethyl]-2-(1-isopropyl-piperidin-4-ylcarbamoyl)-1H-indole-5-carboxylic acid 1-cyclohexyloxycarbonyloxy-ethyl ester; and
1-[5-(5-Chloro-thiophen-2-yl)-isoxazol-3-ylmethyl]-2-(1-isopropyl-piperidin-4-ylcarbamoyl)-1H-indole-4-carboxylic acid 1-cyclohexyloxycarbonyloxy-ethyl ester.

5. A process for the preparation of a compound of formula I as claimed in claim 1, which comprises condensing a compound of formula 14

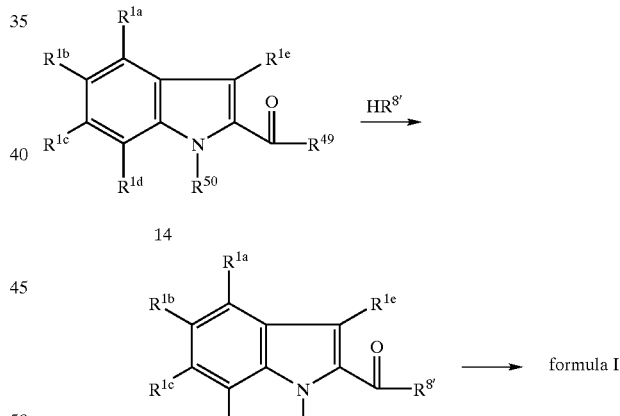

14

15 with a compound of formula $HR^{8'}$ to give a compound of formula 15 and optionally converting the compound of formula 15 into a compound of formula I, wherein the residue $R^{8'}$ is $-N(R^1)-R^2-V-G-M$, wherein each of $R^1$, $R^2$, V, G, and M are as defined in claim 1, but wherein said $R^{8'}$ functional groups can also be present in the form of precursor groups that are subsequently transformed into the final functional groups present in $-N(R^1)-R^2-V-G-M$; wherein the residue $R^{50}$ denotes the group $-Q-R^0$, as Q and $R^0$ are defined in claim 1, or a precursor group which is subsequently transformed into the group $-Q-R^0$; the group $-C(O)-R^{49}$ is a carboxylic acid group or derivative thereof; and the groups $R^{1e}$, $R^{1a}$, $R^{1b}$, $R^{1c}$ and $R^{1d}$ in the formulae 14 and 15 have the meanings corresponding to the definitions of $R^7$, $R^6$, $R^5$, $R^4$, and $R^3$, respectively, in formula I as defined above in claim 1 or contain such functional groups in protected form or in the form of precursor groups.

6. A pharmaceutical preparation, comprising a therapeuticlly effective amount of at least one compound of formula I as claimed in claim 1 and a pharmaceutically acceptable carrier.

7. A method for inhibition of thrombus formation comprising administering to a patient in need there of a therapeutically effective amount to inhibit internal blood coagulation of a,composition of claim 6.

8. The method as claimed in claim 7, wherein said inhibition is in preventing thrombosis following surgery.

* * * * *